United States Patent
Jorgensen et al.

(10) Patent No.: US 10,336,721 B2
(45) Date of Patent: Jul. 2, 2019

(54) BIARYLTRIAZOLE INHIBITORS OF MACROPHAGE MIGRATION INHIBITORY FACTOR

(71) Applicant: YALE UNIVERSITY, New Haven, CT (US)

(72) Inventors: William L. Jorgensen, Deep River, CT (US); Pawel Dziedzic, New Haven, CT (US); Jose Cisneros, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/550,573

(22) PCT Filed: Feb. 12, 2016

(86) PCT No.: PCT/US2016/017833
§ 371 (c)(1),
(2) Date: Aug. 11, 2017

(87) PCT Pub. No.: WO2016/130968
PCT Pub. Date: Aug. 18, 2016

(65) Prior Publication Data
US 2018/0179176 A1    Jun. 28, 2018

Related U.S. Application Data

(60) Provisional application No. 62/115,793, filed on Feb. 13, 2015.

(51) Int. Cl.
*C07D 401/04* (2006.01)
*C07D 403/04* (2006.01)
*C07D 471/04* (2006.01)

(52) U.S. Cl.
CPC ......... *C07D 401/04* (2013.01); *C07D 403/04* (2013.01); *C07D 471/04* (2013.01)

(58) Field of Classification Search
CPC .................................................. C07D 401/04
See application file for complete search history.

(56) References Cited

U.S. PATENT DOCUMENTS

| 2005/0222203 | A1 | 10/2005 | Letourneau et al. |
| 2010/0267714 | A1* | 10/2010 | Jorgensen ............ C07D 209/18 |
| | | | 514/230.5 |
| 2011/0263620 | A1 | 10/2011 | Hsieh et al. |
| 2012/0004261 | A1 | 1/2012 | Jorgensen et al. |

FOREIGN PATENT DOCUMENTS

WO    2012142498 A2    10/2012

OTHER PUBLICATIONS

Pillimarri "Synthesis of Novel (1,2,3)-Triazole, (1,2,3)-Thiadiazole and Isoxazole Functionalized Heterocycles of Biological Interest" Ph.D. Thesis Osmania University, Nov. 2013, Chapter II pp. 31-52, Chapter VII pp. 178-182.*
Wakefield, Basil "Fluorinated Pharmaceuticals" Innovations in Pharmaceutical Technology 2003, 74, 76-78.*
PCT International Search Report and Written Opinion for PCT International Application No. PCT/US2016/017833 dated Apr. 22, 2016.
Jorgensen, et al., "Receptor agonists of macrophage migration inhibitory factor", Bioorg Med Chem Lett. 20(23), 2010, 7033-7036.
Extended European Search Report for European Patent Application No. 16749998.7 dated Sep. 20, 2018.
Dziedzic, et al., Design, synthesis, and protein crystallography of biaryltriazoles as potent tautomerase inhibitors of macrophage migration inhibitory factor, J Am Chem Soc. 137(8) ,Mar. 2015 ,2996-3003.
Rao, et al., Synthesis of novel 2-alkyl triazole-3-alkyl substituted quinoline derivatives and their cytotoxic activity, Bioorg Med Chem Lett. 23(5) ,Mar. 2013 ,1225-1227.

* cited by examiner

*Primary Examiner* — David K O'Dell
(74) *Attorney, Agent, or Firm* — Saul Ewing Arnstein & Lehr LLP; Kathryn Doyle; Domingos J. Silva

(57) ABSTRACT

The present disclosure describes biaryl triazole compounds, as well as their compositions and methods of use. The compounds inhibit the activity of macrophage migration inhibitory factor and are useful for the treatment of diseases, e.g., inflammatory diseases and cancer.

25 Claims, 1 Drawing Sheet

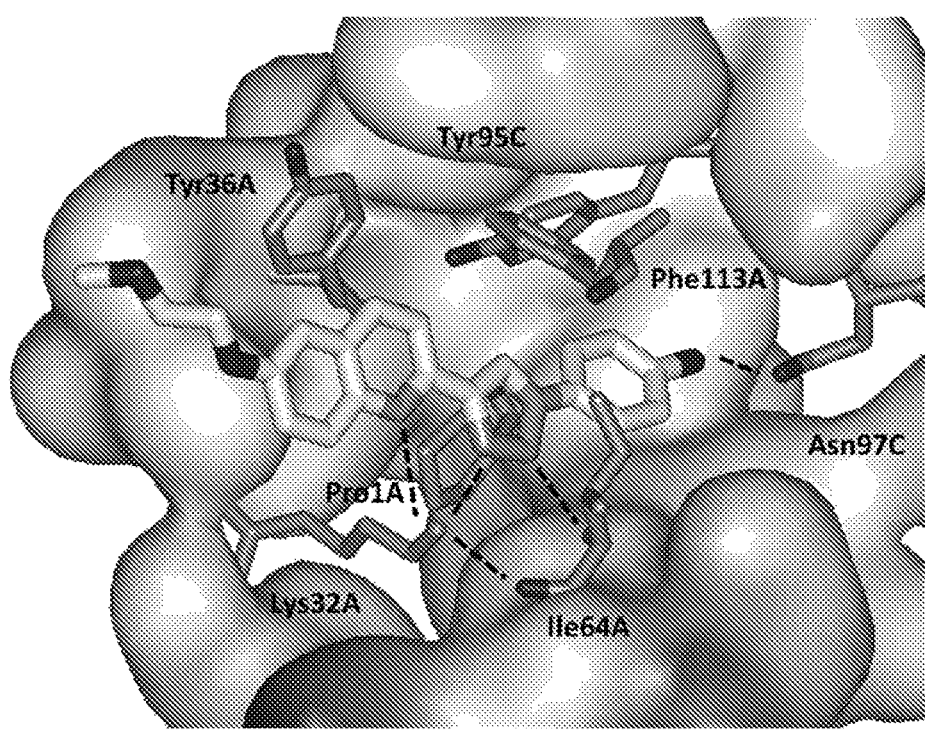

BIARYLTRIAZOLE INHIBITORS OF MACROPHAGE MIGRATION INHIBITORY FACTOR

CROSS-REFERENCE TO RELATED APPLICATIONS

This application is a 35 U.S.C. § 371 national phase application from, and claims priority to, International Application No. PCT/US2016/017833, filed Feb. 12, 2016, and published under PCT Article 21(2) in English, which claims the benefit of U.S. Provisional Application No. 62/115,793, filed Feb. 13, 2015, the entire disclosure of which is incorporated herein by reference all of which applications are incorporated herein by reference in their entireties.

RESEARCH SUPPORT

This invention was made with government support under GM032136 awarded by National Institutes of Health and under 1122492 awarded by National Science Foundation. The government has certain rights in the invention.

TECHNICAL FIELD

The present application is concerned with pharmaceutically useful compounds. The disclosure provides new compounds as well as their compositions and methods of use. The compounds inhibit the activity of macrophage migration inhibitory factor and are therefore useful in the treatment of diseases related to the activity of macrophage migration inhibitory including, e.g., inflammatory diseases and cancer.

BACKGROUND

Macrophage migration inhibitory factor (MIF) is a cytokine that plays a central role in numerous inflammatory diseases (Morand et al., *Nature Rev. Drug. Disc.* 2006, 5, 399-410; Greven et al., *Expert Opin. Ther. Targets*, 2010, 14, 253-264; Asare et al., *Thromb. Haemost.* 2013, 109, 391-398). MIF is widely expressed in both immune and non-immune cells including macrophages, endothelial cells, and T-cells. Upon activation the cells release MIF, which promotes the release of other inflammatory cytokines such as TNF-α and IL-1. Excessive or chronic inflammatory response is associated with tissue damage and autoimmune diseases such as rheumatoid arthritis, Crohn's disease, and lupus erythematosus. The connection between inflammatory disease and cancer is also well-established, and MIF has been shown to enhance cell proliferation by inhibiting accumulation of the tumor suppressor p53 and by promotion of angiogenesis (Conroy et al., *Q. J. Med.* 2010, 103, 831-836). MIF is over-expressed in many cancer cells and can serve as a marker for disease progression. Furthermore, MIF in cancer cells is protected from degradation by Hsp90, which has led to proposed targeting of Hsp90 as an indirect way of inhibiting MIF function (Schulz et al., *Curr. Opin. Oncol.*, 2014, 26, 108-113). Disruption of the inflammatory cascade and restoration of normal p53 levels have clear implications for the potential therapeutic value of inhibitors of MIF signaling. Indeed, immunoneutralization of MIF or deletion of the MIF gene is known to suppress inflammatory response, tumor growth, and angiogenesis. At the molecular level, what is needed is interference with the interaction between MIF and its cell-surface receptor CD74.

MIF is a toroid-shaped, trimeric protein with a total of 342 amino acid residues. Besides its role as a cytokine, MIF is a keto-enol tautomerase. Though the enzymatic activity appears to be vestigial in humans, there are three tautomerase active sites at the interfaces of the monomer units opening to the outside of the toroid. The presence of the tautomerase sites presents an opportunity for complexation of a tautomerase inhibitor that may also interfere with MIF/CD74 binding. This notion has been supported by many studies that show correlation between the inhibition of the enzymatic and biological activities of MIF (Senter et al., *Proc. Natl. Acad. Sci. U.S.A.*, 2002, 99, 144-149). For example, this has been demonstrated through assay results for tautomerase activity, MIF/CD74 binding, and MIF-induced phosphorylation of ERK1/2 in inflamed cells, production of interleukins, glucocorticoid overriding ability, and macrophage chemotactic migration (Senter et al; Cournia et al., *J. Med. Chem.* 2009, 52, 416-424; Hare et al., *Bioorg. Med. Chem. Lett.* 2010, 20, 5811-5814; Jorgensen et al., *Bioorg. Med. Chem. Lett.* 2010, 20, 7033-7036; Orita et al., *Curr. Pharm. Des.* 2002, 8, 1297-1317; Garai et al., *Curr. Med. Chem.* 2009, 16, 1091-1114; Xu et al., *Drug Disc. Today* 2013, 18, 592-600; Xu et al., *J. Med. Chem.* 2014, 57, 3737-3745; Tsai et al., *J. Biomol. Screen.* 2014, 19, 1116-1123).

SUMMARY

The present disclosure provides, inter alia, a compound of Formula (I):

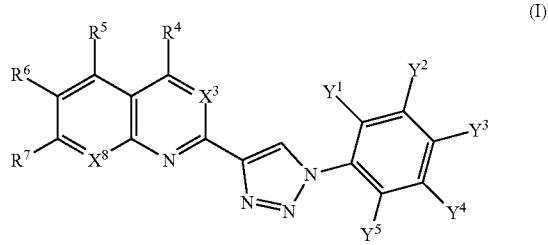

or a pharmaceutically acceptable salt thereof; wherein the variables are as defined below.

The present disclosure also provides a composition comprising a compound of Formula (I), or a pharmaceutically acceptable salt thereof, and at least one pharmaceutically acceptable carrier.

The present disclosure also provides methods of treating inflammatory diseases, cancer, and other diseases comprising administering to a patient a therapeutically effective amount of a compound of Formula (I), or a pharmaceutically acceptable salt thereof.

The details of one or more embodiments are set forth in the description below. Other features, objects and advantages will be apparent from the description and from the claims.

DESCRIPTION OF THE FIGURES

FIG. 1 is a rendering of compound 3b bound to human MIF from a 1.81-Å crystal structure. Carbon atoms of 3b are shown in yellow; some residues have been removed for clarity. Hydrogen bonds are highlighted with dashed lines.

DETAILED DESCRIPTION

For the terms "e.g." and "such as," and grammatical equivalents thereof, the phrase "and without limitation" is understood to follow unless explicitly stated otherwise.

As used herein, the singular forms "a," "an," and "the" include plural referents unless the context clearly dictates otherwise.

As used herein, the term "about" means "approximately" (e.g., plus or minus approximately 10% of the indicated value).

I. Compounds

The present disclosure provides, inter alia, a compound of Formula (I):

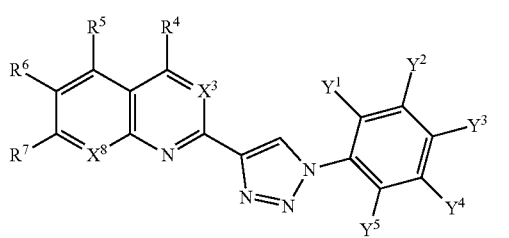

or a pharmaceutically acceptable salt thereof, wherein:

$X^3$ is $CR^3$ or N;

$X^8$ is $CR^8$ or N;

$R^3$ is selected from the group consisting of H, halogen, $C_{1-6}$ alkyl, and $C_{1-6}$ haloalkyl;

$R^4$ is selected from the group consisting of H, halogen $C_{1-6}$ alkyl, and $C_{1-6}$ haloalkyl;

$R^5$, $R^6$, $R^7$ and $R^8$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)_2R^{b1}$, $NR^{c1}S(O)_2R^{b1}$ and $S(O)_2NR^{c1}R^{d1}$; wherein each of said $C_{1-6}$ alkyl, $C_{2-6}$ alkenyl, and $C_{2-6}$ alkynyl, forming $R^5$, $R^6$, $R^7$ or $R^8$ is independently unsubstituted or substituted with 1, 2, 3, 4 or 5 substituents independently selected from halogen, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$ and $S(O)_2NR^{c2}R^{d2}$ and each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $R^5$, $R^6$, $R^7$ or $R^8$ is independently unsubstituted or substituted with 1, 2, 3, 4 or 5 substituents independently selected from $C_{1-6}$ alkyl, halogen, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$ and $S(O)_2NR^{c2}R^{d2}$;

or any one of $R^5$, $R^6$, $R^7$, and $R^8$ may represent a group of formula $Ar^5$;

or $R^5$ is a water solubilizing group;

or $R^6$ and $R^7$ in combination with the atoms to which they are attached may form a 5-7 membered carbocyclic or heterocyclic ring that is unsubstituted or substituted by 1, 2 or 3 substituents each independently selected from $R^9$;

or $R^6$ or $R^7$ or both may be each be independently selected from water solubilizing groups;

each $R^9$ is independently selected from halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)_2R^{b1}$, $NR^{c1}S(O)_2R^{b1}$ and $S(O)_2NR^{c1}R^{d1}$; wherein each of said $C_{1-6}$ alkyl, $C_{2-6}$ alkenyl, and $C_{2-6}$ alkynyl forming $R^9$ is independently unsubstituted or substituted with 1, 2, 3, 4 or 5 substituents independently selected from halogen, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, $S(O)_2NR^{c2}R^{d2}$; and each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $R^9$ is independently unsubstituted or substituted with 1, 2, 3, 4 or 5 substituents independently selected from $C_{1-6}$ alkyl, halogen, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, $S(O)_2NR^{c2}R^{d2}$, and water solubilizing groups;

$Y^1$, $Y^2$, $Y^3$, $Y^4$, and $Y^5$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)_2R^{b3}$, $NR^{c3}S(O)_2R^{b3}$ and $S(O)_2NR^{c3}R^{d3}$; wherein each of said $C_{1-6}$ alkyl, $C_{2-6}$ alkenyl, and $C_{2-6}$ alkynyl forming $Y^1$, $Y^2$, $Y^3$, $Y^4$ or $Y^5$ is independently unsubstituted or substituted with 1, 2, 3, 4 or 5 substituents independently selected from halogen, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $C(O)R^{b4}$, $S(O)_2R^{b4}$, $NR^{c4}S(O)_2R^{b4}$ and $S(O)_2NR^{c4}R^{d4}$; and each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $Y^1$, $Y^2$, $Y^3$, $Y^4$ or $Y^5$ is independently unsubstituted or substituted with 1, 2, 3, 4 or 5 substituents independently selected from $C_{1-6}$ alkyl, halogen, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)_2R^{b4}$, $NR^{c4}S(O)_2R^{b4}$ and $S(O)_2NR^{c4}R^{d4}$; or $Y^3$ is NH, and $Y^2$ and $Y^3$ or $Y^3$ and $Y^4$, in combination with the carbon atoms to which they are attached, forms a 5-membered fused heteroaromatic ring that is unsubstituted or substituted by 1 or 2 substituents independently selected from $Y^6$;

each $Y^6$ is independently selected from the group consisting of halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)_2R^{b3}$, $NR^{c3}S(O)_2R^{b3}$ and $S(O)_2NR^{c1}R^{d1}$; wherein each of said $C_{1-6}$ alkyl, $C_{2-6}$ alkenyl, and $C_{2-6}$ alkynyl forming $Y^6$ is independently unsubstituted or substituted with 1, 2, 3, 4 or 5 substituents independently selected from halogen, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)_2R^{b4}$, $NR^{c4}S(O)_2R^{b4}$ and $S(O)_2NR^{c4}R^{d4}$; and each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $Y^6$ is independently unsubstituted or substituted with 1, 2, 3, 4 or 5 substituents independently selected from $C_{1-6}$ alkyl, halogen, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)_2R^{b4}$, $NR^{c4}S(O)_2R^{b4}$ and $S(O)_2NR^{c4}R^{d4}$;

each $Ar^S$ is:

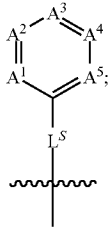

$A^1$ is N or $CZ^1$;
$A^2$ is N or $CZ^2$;
$A^3$ is N or $CZ^3$;
$A^4$ is N or $CZ^4$;
$A^5$ is N or $CZ^5$;

provided that 0, 1 or 2 of $Z^1$, $Z^2$, $Z^3$, $Z^4$, and $Z^5$ are nitrogen;

$Z^1$, $Z^2$, $Z^3$, $Z^4$, and $Z^5$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)_2R^{b5}$, $NR^{c5}S(O)_2R^{b5}$ and $S(O)_2NR^{c5}R^{d5}$; wherein each of said $C_{1-6}$ alkyl, $C_{2-6}$ alkenyl, and $C_{2-6}$ alkynyl forming $Z^1$, $Z^2$, $Z^3$, $Z^4$, or $Z^5$ is independently unsubstituted or substituted with 1, 2, 3, 4 or 5 substituents independently selected from halogen, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}(C(O)R^{b6}$, $NR^{c6}C(O)NR^{c6}R^{d6}NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)_2R^{b6}$, $NR^{c6}S(O)_2R^{b6}$ and $S(O)_2NR^{c6}R^{d6}$; and each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $Z^1$, $Z^2$, $Z^3$, $Z^4$, or $Z^5$ is independently unsubstituted or substituted with 1, 2, 3, 4 or 5 substituents independently selected from $C_{1-6}$ alkyl, halogen, $C_{1-6}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)_2R^{b6}$, $NR^{c6}S(O)_2R^{b6}$ and $S(O)_2NR^{c6}R^{d6}$;

or wherein any one or two of $Z^1$, $Z^2$, $Z^3$, $Z^4$, and $Z^5$ is independently selected from water solubilizing groups;

$L^S$ is a bond, O, $NR^{c6}$, $C_{1-4}$ alkylene, $C(O)$, $NR^{c6}C(O)$ or $C(O)NR^{c6}$;

$R^{a1}$, $R^{b1}$, $R^{a2}$, $R^{b2}$, $R^{a3}$, $R^{b3}$, $R^{a4}$, $R^{b4}$, $R^{a5}$, $R^{b5}$, $R^{a6}$ and $R^{b6}$ are each independently selected from the group consisting of hydrogen, $C_{1-4}$ alkyl, $C_{2-4}$ alkenyl, $C_{2-4}$ alkynyl, $C_{6-10}$ aryl, 5-10 membered heteroaryl, $C_{3-7}$ cycloalkyl, 5-10 membered heterocycloalkyl, $C_{6-10}$ aryl-$C_{1-4}$ alkylene, $C_{3-7}$ cycloalkyl-$C_{1-4}$ alkylene, 5-10 membered heteroaryl-$C_{1-4}$ alkylene, 5-10 membered heterocycloalkyl-$C_{1-4}$ alkylene, and $C_{1-4}$ alkoxy-$C_{1-4}$ alkylene, wherein each of said $C_{1-4}$ alkyl, $C_{2-4}$ alkenyl, $C_{2-4}$ alkynyl, and $C_{1-4}$ alkoxy-$C_{1-4}$ alkylene forming $R^{a1}$, $R^{b1}$, $R^{a2}$, $R^{b2}$, $R^{a3}$, $R^{b3}$, $R^{a4}$, $R^{b4}$, $R^{a5}$, $R^{b5}$, $R^{a6}$ or $R^{b6}$ is independently unsubstituted or substituted by 1, 2, 3, 4 or 5 groups independently selected from halogen, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$ and $S(O)_2NR^{c7}R^{d7}$ and wherein said $C_{6-10}$ aryl, 5-10 membered heteroaryl, $C_{3-7}$ cycloalkyl, 5-10 membered heterocycloalkyl, $C_{6-10}$ aryl-$C_{1-4}$ alkylene, $C_{3-7}$ cycloalkyl-$C_{1-4}$ alkylene, 5-10 membered heteroaryl-$C_{1-4}$ alkylene, and 5-10 membered heterocycloalkyl-$C_{1-4}$ alkylene, forming $R^{a1}$, $R^{b1}$, $R^{a2}$, $R^{b2}$, $R^{a3}$, $R^{b3}$, $R^{a4}$ or $R^{b4}$ is independently unsubstituted or substituted by 1, 2, 3, 4 or 5 groups independently selected from $C_{1-6}$ alkyl, halogen, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$ and $S(O)_2NR^{c7}R^{d7}$;

$R^{c1}$, $R^{d1}$, $R^{c2}$, $R^{d2}$, $R^{c3}$, $R^{d3}$, $R^{c4}$, $R^{d4}$, $R^{c5}$, $R^{d5}$, $R^{c6}$, and $R^{d6}$ are each independently selected from the group consisting of hydrogen, $C_{1-4}$ alkyl, $C_{2-4}$ alkenyl, $C_{2-4}$ alkynyl, $C_{6-10}$ aryl, 5-10 membered heteroaryl, $C_{3-7}$ cycloalkyl, 5-10 membered heterocycloalkyl, $C_{6-10}$ aryl-$C_{1-4}$ alkylene, $C_{3-7}$ cycloalkyl-$C_{1-4}$ alkylene, 5-10 membered heteroaryl-$C_{1-4}$ alkylene, 5-10 membered heterocycloalkyl-$C_{1-4}$ alkylene, and $C_{1-4}$ alkoxy-$C_{1-4}$ alkylene, wherein each of said $C_{1-4}$ alkyl, $C_{2-4}$ alkenyl, $C_{2-4}$ alkynyl, and $C_{1-4}$ alkoxy-$C_{1-4}$ alkylene forming $R^{c1}$, $R^{d1}$, $R^{c2}$, $R^{d2}$, $R^{c3}$, $R^{d3}$, $R^{c4}$, $R^{d4}$, $R^{c5}$, $R^{d5}$, $R^{c6}$, or $R^{d6}$ is independently unsubstituted or substituted by 1, 2, 3, 4 or 5 groups independently selected from halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C$ (=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$ and S(O)$_2$NR$^{c7}$R$^{d7}$ and wherein each of said C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, and 5-10 membered heterocycloalkyl-C$_{1-4}$ alkylene, forming R$^{c1}$, R$^{d1}$, R$^{c2}$, R$^{d2}$, R$^{c3}$, R$^{d3}$, R$^{c4}$, R$^{d4}$, R$^{c5}$, R$^{d5}$, R$^{c6}$, or R$^{d6}$ is independently unsubstituted or substituted by 1, 2, 3, 4 or 5 groups independently selected from C$_{1-6}$ alkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$ and S(O)$_2$NR$^{c7}$R$^{d7}$;

or R$^{c1}$ and R$^{d1}$, R$^{c2}$ and R$^{d2}$, R$^{c3}$ and R$^{d3}$, R$^{c4}$ and R$^{d4}$, R$^{c5}$ and R$^{d5}$, or R$^{c6}$ and R$^{d6}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$ and S(O)$_2$NR$^{c7}$R$^{d7}$;

R$^{a7}$, R$^{b7}$, R$^{c7}$ and R$^{d7}$ are each independently selected from H, C$_{1-6}$ alkyl, C$_{1-6}$ haloalkyl, C$_{2-6}$ alkenyl, C$_{2-6}$ alkynyl, C$_{6-10}$ aryl, 5-10 membered heteroaryl, C$_{3-7}$ cycloalkyl, 4-10 membered heterocycloalkyl, C$_{6-10}$ aryl-C$_{1-4}$ alkylene, 5-10 membered heteroaryl-C$_{1-4}$ alkylene, C$_{3-7}$ cycloalkyl-C$_{1-4}$ alkylene and 4-10 membered heterocycloalkyl-C$_{1-3}$ alkylene, wherein said C$_{1-6}$ alkyl, C$_{1-6}$ haloalkyl, C$_{2-6}$ alkenyl, C$_{2-6}$ alkynyl, C$_{6-10}$ aryl, 5-10 membered heteroaryl, C$_{3-7}$ cycloalkyl, 4-10 membered heterocycloalkyl, C$_{6-10}$ aryl-C$_{1-4}$ alkylene, 5-10 membered heteroaryl-C$_{1-4}$ alkylene, C$_{3-7}$ cycloalkyl-C$_{1-4}$ alkylene and 4-10 membered heterocycloalkyl-C$_{1-3}$ alkylene forming R$^{a7}$, R$^{b7}$, R$^{c7}$ and R$^{d7}$ are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$haloalkoxy;

or R$^{c7}$ and R$^{d7}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$haloalkyl and C$_{1-6}$haloalkoxy; and R$^{e1}$, R$^{e2}$, R$^{e3}$, R$^{e4}$, R$^{e6}$ and R$^{e7}$ are each independently selected from H, C$_{1-4}$ alkyl, OH, and C$_{1-4}$ alkoxy.

In some embodiments, when Y$^1$, Y$^2$, Y$^4$, Y$^5$, and R$^4$ are each H, Y$^3$ is F, and X$^3$ is H or C$_{1-6}$ alkyl, then at least one of R$^5$, R$^6$, and R$^7$ is not H.

In some embodiments, when Y$^1$, Y$^2$, Y$^4$, Y$^5$, and R$^4$ are each H, Y$^3$ is halogen, and X$^3$ is H or C$_{1-6}$ alkyl, then at least one of R$^5$, R$^6$, and R$^7$ is not H.

In some embodiments, at least one of Y$^1$, Y$^2$, Y$^4$, Y$^5$, and R$^4$ is other than H, Y$^3$ is other than halogen, or X$^3$ is other than H or C$_{1-6}$ alkyl.

In some embodiments, at least one of R$^5$, R$^6$, R$^7$ and R$^8$ is not H.

In some embodiments, at least one of R$^5$, R$^6$ and R$^7$ is not H.

In some embodiments, X$^3$ is CR$^3$.

In some embodiments, R$^3$ is H, fluoro, or C$_{1-6}$ alkyl (e.g., methyl or ethyl). In some embodiments, R$^3$ is H, methyl, or ethyl. In some embodiments, R$^3$ is H.

In some embodiments, X$^3$ is N.

In some embodiments, R$^4$ is H, fluoro, or C$_{1-6}$ alkyl. In some embodiments, R$^4$ is H or methyl, or ethyl. In some embodiments, R$^4$ is H.

In some embodiments, R$^5$ is H, C$_{6-10}$ aryl, or OR$^{a1}$, wherein the C$_{6-10}$ aryl forming R$^5$ is unsubstituted or substituted with 1, 2, or 3 substituents independently selected from C$_{1-6}$ alkyl, halogen, and OR$^{a2}$.

In some embodiments, R$^5$ is H, unsubstituted phenyl, phenyl substituted with 1 substituent selected from C$_{1-6}$ alkyl, halogen, and C$_{1-6}$ alkoxy, or OR$^{a2}$, wherein R$^{a2}$ is unsubstituted phenyl or phenyl substituted with 1 group independently selected from OR$^{a5}$, and C(O)OR$^{a5}$. In some embodiments, R$^5$ is H, 4-methoxyphenyl, 4-(2-methoxy (ethoxy))phenyl, 4-carboxyphenyl or phenoxy. In some embodiments, R$^5$ is H.

In some embodiments, R$^5$ is a water solubilizing group. In some embodiments, R$^5$ is a water solubilizing group selected from the groups listed in Table 2.

In some embodiments, R$^5$ is a group of the following formula:

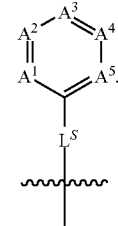

In some embodiments, one and only one of A$^1$, A$^2$, A$^3$, A$^4$ and A$^5$ is N. In some embodiments, two of A$^1$, A$^2$, A$^3$, A$^4$ and A$^5$ is N.

In some embodiments, R$^5$ is a group of any of the following formulae:

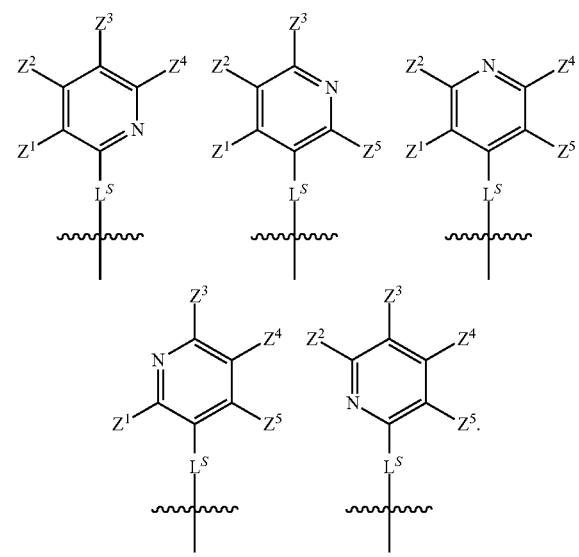

In some embodiments, R$^5$ is a group of the following formula:

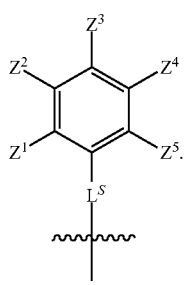

In some embodiments, $R^5$ is a group of the following formula:

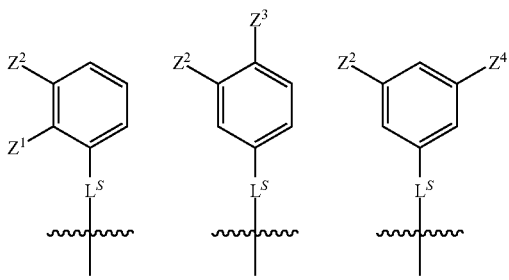

In some embodiments, $Z^1$, $Z^2$, $Z^3$, $Z^4$, and $Z^5$ are each independently selected from H, $C_{1-6}$ alkyl, halogen, and $C_{1-6}$ alkoxy, or wherein any one or two of $Z^1$, $Z^2$, $Z^3$, $Z^4$, and $Z^5$ is independently selected from water solubilizing groups.

In some embodiments, any one or two of $Z^1$, $Z^2$, $Z^3$, $Z^4$, and $Z^5$ is independently selected from water solubilizing groups and the remainder of of $Z^1$, $Z^2$, $Z^3$, $Z^4$, and $Z^5$ are hydrogen.

In some embodiments, any one $Z^1$, $Z^2$, $Z^3$, $Z^4$, and $Z^5$ is a water solubilizing group and the remainder of of $Z^1$, $Z^2$, $Z^3$, $Z^4$, and $Z^5$ are hydrogen.

In some embodiments, the water solubilizing group forming $Z^1$, $Z^2$, $Z^3$, $Z^4$, or $Z^5$ is a water solubilizing group independently selected from the groups listed in Table 2.

In some embodiments, $Z^1$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^1$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy) methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy) ethyl, 2-(carboxymethoxy)ethoxy, 2-carboxyethoxymethyl, or 2-(2-caroxyethoxy)ethoxy.

In some embodiments, $Z^1$ is a water solubilizing group selected from the groups listed in Table 2.

In some embodiments, $Z^2$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^2$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy) methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy) ethyl, 2-(carboxymethoxy)ethoxy, 2-carboxyethoxymethyl, or 2-(2-caroxyethoxy)ethoxy.

In some embodiments, $Z^2$ is a water solubilizing group selected from the groups listed in Table 2.

In some embodiments, $Z^3$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^3$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $Z^3$ is a water solubilizing group selected from the groups listed in Table 2.

In some embodiments, $Z^4$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^4$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $Z^4$ is a water solubilizing group selected from the groups listed in Table 2.

In some embodiments, $Z^5$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^5$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $Z^5$ is a water solubilizing group selected from the groups listed in Table 2.

In some embodiments, $L^S$ is O.

In some embodiments, $L^S$ is NH.

In some embodiments, $R^6$ is H, $OR^{a1}$, or $C_{1-6}$ alkyl substituted with one or more substituents selected from $OR^{a2}$, $C(O)OR^{a2}$, and $NR^{c2}R^{d2}$.

In some embodiments, $R^6$ is H or $OR^{a1}$.

In some embodiments, $R^6$ is H.

In some embodiments, $R^6$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^6$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $R^6$ is a group of formula $Ar^S$.

In some embodiments, $R^6$ is a water solubilizing group. In some embodiments, $R^6$ is a water solubilizing group selected from the groups listed in Table 2.

In some embodiments, $R^7$ is H, $OR^{a1}$, or $C_{1-6}$ alkyl substituted with one or more substituent selected from $OR^{a2}$, $C(O)OR^{a2}$, and $NR^{c2}R^{d2}$.

In some embodiments, $R^7$ is H or $OR^{a1}$.

In some embodiments, $R^7$ is H.

In some embodiments, $R^7$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered heterocycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^7$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $R^7$ is a group of formula $Ar^S$.

In some embodiments, $R^7$ is a water solubilizing group. In some embodiments, $R^7$ is a water solubilizing group selected from the groups listed in Table 2.

In some embodiments, $R^6$ and $R^7$ are each independently selected from water solubilizing groups.

In some embodiments, $R^6$ and $R^7$ are each independently selected from $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered heterocycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^6$ and $R^7$ are each independently selected from methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, and 2-(2-caroxyethoxy)ethoxy.

In some embodiments, $R^6$ and $R^7$ are each independently selected from water solubilizing groups selected from the groups listed in Table 2.

In some embodiments, $X^8$ is $CR^8$.

In some embodiments, $R^8$ is H, halogen, $C_{6-10}$ aryl, or $OR^{a1}$, wherein each $C_{6-10}$ aryl forming $R^8$ is independently unsubstituted or substituted with 1, 2, or 3 substituents independently selected from $C_{1-6}$ alkyl, halogen, and $OR^{a2}$.

In some embodiments, $R^8$ is H, halogen, $C_{6-10}$ aryl, or $OR^{a1}$, wherein each $C_{6-10}$ aryl forming $R^8$ is independently unsubstituted or substituted with 1, 2, or 3 substituents independently selected from $C_{1-6}$ alkyl, halogen, and $OR^{a2}$.

In some embodiments, $R^8$ is H, halogen, unsubstituted phenyl, phenyl substituted with 1 substituent selected from $C_{1-6}$ alkyl, halogen, and $C_{1-6}$ alkoxy, or $OR^{a2}$, wherein $R^{a2}$ is $C_{1-6}$ alkoxy, $C_{1-6}$ alkoxy-$C_{1-4}$ alkoxy or unsubstituted phenyl.

In some embodiments, $R^8$ is H, chloro, methoxy, 2-(methoxy)ethoxy, 4-methoxyphenyl, or phenoxy. In some embodiments, $R^8$ is H.

In some embodiments, $R^8$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^8$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $R^8$ is a group of formula $Ar^S$.

In some embodiments, $R^8$ is a water solubilizing group. In some embodiments, $R^8$ is a water solubilizing group selected from the groups listed in Table 2.

In some embodiments, $R^8$ is a group of the following formula:

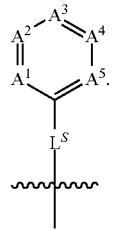

wherein each of $A^1$, $A^2$, $A^3$, $A^4$ and $A^5$ is independently defined as described above (or for any of the embodiments thereof).

In some embodiments, $R^8$ is a group of any of the following formulae:

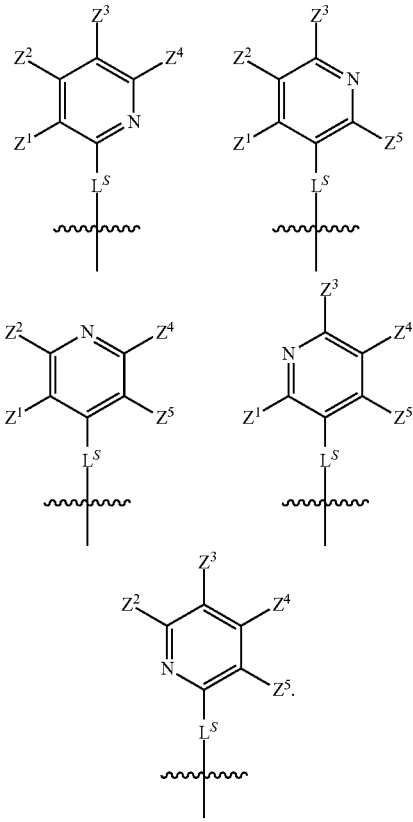

wherein each of $Z^1$, $Z^2$, $Z^3$, $Z^4$ and $Z^5$ is independently defined as described above (or for any of the embodiments thereof).

In some embodiments, $R^8$ is a group of the following formula:

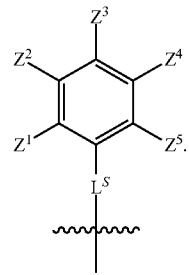

In some embodiments, $R^8$ is a group of any one of the following formulae:

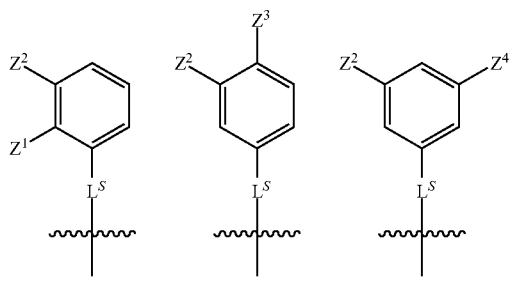

In some embodiments, $X^8$ is N.

In some embodiments, $Y^1$ is H or halogen. In some embodiments, $Y^1$ is H. In some embodiments, $Y^1$ is F.

In some embodiments, $Y^2$ is H, halogen, $C_{1-6}$ alkyl, or $OR^{a3}$. In some embodiments, $Y^2$ is H, F, methyl or methoxy. In some embodiments, $Y^2$ is H or F. In some embodiments, $Y^2$ is H.

In some embodiments, $Y^3$ is OH, halogen, CN, $OR^{a3}$, $NR^{c3}R^{d3}$, or $C(O)NR^{c3}R^{d3}$. In some embodiments, $Y^3$ is OH, Cl, or F. In some embodiments, $Y^3$ is OH. In some embodiments, $Y^4$ is H or halo. In some embodiments, $Y^4$ is H or F. In some embodiments, $Y^4$ is H.

In some embodiments, $Y^5$ is H or F. In some embodiments, $Y^5$ is H.

In some embodiments, one of $R^5$, $R^6$, $R^7$, and $R^8$ represents a group of formula $Ar^S$.

In some embodiments, one and only one of $A^1$, $A^2$, $A^3$, $A^4$ and $A^5$ is N.

In some embodiments, two of $A^1$, $A^2$, $A^3$, $A^4$ and $A^5$ is N.

In some embodiments, $Ar^S$ is a group of the following formulae:

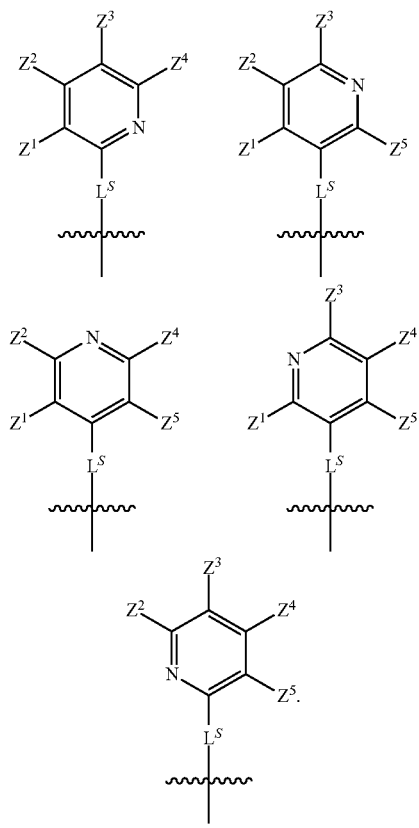

In some embodiments, $Ar^S$ is a group of the following formula:

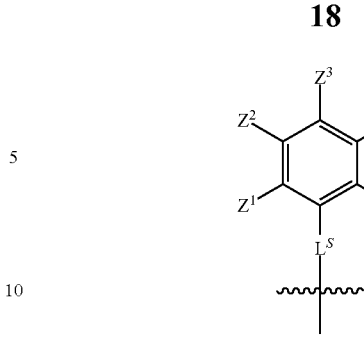

Each of $Z^1$, $Z^2$, $Z^3$, $Z^4$ and $Z^5$ can independently be defined as described above (or for any of the embodiments thereof).

In some embodiments, $Z^1$, $Z^2$, $Z^3$, $Z^4$, and $Z^5$ are each independently selected from H, $C_{1-6}$ alkyl, halogen, and $C_{1-6}$ alkoxy, or wherein any one or two of $Z^1$, $Z^2$, $Z^3$, $Z^4$, and $Z^5$ is independently selected from water solubilizing groups.

In some embodiments, any one or two of $Z^1$, $Z^2$, $Z^3$, $Z^4$, and $Z^5$ is independently selected from water solubilizing groups and the remainder of of $Z^1$, $Z^2$, $Z^3$, $Z^4$ and $Z^5$ are hydrogen.

In some embodiments, any one $Z^1$, $Z^2$, $Z^3$, $Z^4$, and $Z^5$ is a water solubilizing group and the remainder of of $Z^1$, $Z^2$, $Z^3$, $Z^4$, and $Z^5$ are hydrogen.

In some embodiments, the water solubilizing group forming $Z^1$, $Z^2$, $Z^3$, $Z^4$, or $Z^5$ is a water solubilizing group independently selected from the groups listed in Table 2.

In some embodiments, $Ar^S$ is a group of any one of the following formulae:

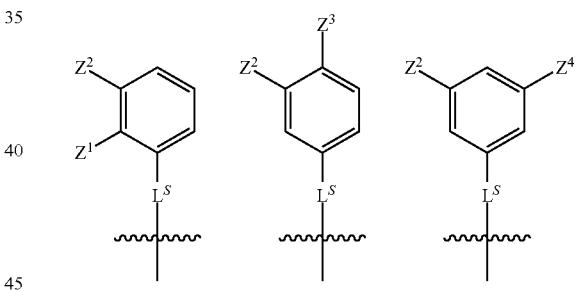

In some embodiments:
$X^3$ is $CR^3$ or N;
$X^8$ is $CR^8$ or N;
$R^3$ is selected from the group consisting of H, halogen, $C_{1-6}$ alkyl, and $C_{1-6}$ haloalkyl;
$R^4$ is selected from the group consisting of H, halogen $C_{1-6}$ alkyl, and $C_{1-6}$ haloalkyl;
$R^5$, $R^6$, $R^7$ and $R^8$ are each independently selected from the group consisting of H, halogen, $C_{1-6}$ alkyl, $C_{2-6}$ alkenyl, $C_{2-6}$ alkynyl, $C_{6-10}$ aryl, and $OR^{a1}$, wherein each $C_{6-10}$ aryl forming $R^5$, $R^6$, $R^7$ or $R^8$ is independently unsubstituted or substituted with 1, 2, 3, 4 or 5 substituents independently selected from $C_{1-6}$ alkyl, halogen, and $OR^{a2}$;
$Y^1$, $Y^2$, $Y^3$, $Y^4$, and $Y^5$ are each independently selected from the group consisting of H, halogen, $C_{1-6}$ alkyl, $C_{2-6}$ alkenyl, $C_{2-6}$ alkynyl, CN, $OR^{a3}$, $NR^{c3}R^{d3}$ and $C(O)NR^{c3}R^{d3}$;
$R^{a1}$, $R^{a2}$, and $R^{a3}$ are each independently selected from the group consisting of hydrogen, $C_{1-4}$ alkyl, and $C_{6-10}$ aryl, wherein each said $C_{1-4}$ alkyl forming $R^{a1}$, $R^{a2}$, or $R^{a3}$ is independently unsubstituted or substituted by 1, 2, or 3 groups independently selected from halo and $OR^{a5}$ and wherein each said $C_{6-10}$ aryl forming $R^{a1}$, $R^{a2}$, and $R^{a3}$ is independently unsubstituted or substituted by 1, 2, or 3, groups independently selected from $C_{1-6}$ alkyl, halo, $OR^{a5}$, and $C(O)OR^{a5}$;

$R^{c3}$ and $R^{d3}$ are each independently selected from the group consisting of hydrogen and $C_{1-4}$ alkyl;

each $R^{a5}$ is independently selected from H and $C_{1-6}$ alkyl, wherein said $C_{1-6}$ alkyl, forming $R^{a5}$ is optionally substituted with 1, 2 or 3 substituents independently selected from OH, amino, $NH(C_{1-6}$ alkyl), $N(C_{1-6}$ alkyl)$_2$, $C_{1-6}$ alkoxy and 4-10 membered heterocycloalkyl-$C_{1-3}$ alkylene; and $R^{c5}$ and $R^{d5}$ are each independently selected from H and $C_{1-6}$ alkyl.

In some embodiments:
$X^3$ is $CR^8$;
$X^8$ is $CR^8$ or N;
$R^3$ is H or $C_{1-6}$ alkyl;
$R^4$ is H or $C_{1-6}$ alkyl;
$R^5$ is H, $C_{6-10}$ aryl, or $OR^{a1}$, wherein each $C_{6-10}$ aryl forming $R^5$ is independently unsubstituted or substituted with 1, 2, or 3 substituents independently selected from $C_{1-6}$ alkyl, halogen, and $OR^{a2}$;
$R^6$ is H or $OR^{a1}$,
$R^7$ is H;
$R^8$ is H, halogen, $C_{6-10}$ aryl, or $OR^{a1}$, wherein each $C_{6-10}$ aryl forming $R^8$ is independently unsubstituted or substituted with 1, 2, or 3 substituents independently selected from $C_{1-6}$ alkyl, halogen, and $OR^{a2}$;
$Y^1$ is H;
$Y^2$ is H, halogen, $C_{1-6}$ alkyl, or $OR^{a3}$;
$Y^3$ is OH, halogen, CN, $OR^{a3}$, $NR^{c3}R^{d3}$, or $C(O)NR^{c3}R^{d3}$;
$Y^4$ is H;
$Y^5$ is H;
$R^{a1}$, $R^{a2}$, and $R^{a2}$ are each independently selected from the group consisting of hydrogen, $C_{1-4}$ alkyl, and $C_{6-10}$ aryl, wherein each said $C_{1-4}$ alkyl forming $R^{a1}$, $R^{a2}$, or $R^{a3}$ is independently unsubstituted or substituted by 1, 2, or 3 groups independently selected from halo and $OR^{a5}$ and wherein each said $C_{6-10}$ aryl forming $R^{a1}$, $R^{a2}$, and $R^{a3}$ is independently unsubstituted or substituted by 1, 2, or 3, groups independently selected from $C_{1-6}$ alkyl, halo, $OR^{a5}$, and $C(O)OR^{a5}$;

$R^{c3}$ and $R^{d3}$ are each independently selected from the group consisting of hydrogen and $C_{1-4}$ alkyl;

each $R^{a5}$ is independently selected from H and $C_{1-6}$ alkyl, wherein said $C_{1-6}$ alkyl, forming $R^{a5}$ is optionally substituted with 1, 2 or 3 substituents independently selected from OH, amino, $NH(C_{1-6}$ alkyl), $N(C_{1-6}$ alkyl)$_2$, $C_{1-6}$ alkoxy and 4-10 membered heterocycloalkyl-$C_{1-4}$ alkyl; and $R^{c5}$ and $R^{d5}$ are each independently selected from H and $C_{1-6}$ alkyl.

In some embodiments:
$X^3$ is $CR^3$ or N;
$X^8$ is $CR^8$ or N;
$R^3$ is selected from the group consisting of H, F, methyl and ethyl;
$R^4$ is selected from the group consisting of H, F, methyl and ethyl;
$R^5$ is selected from the group consisting of H, $Ar^S$; and water solubilizing groups;
$R^6$ is selected from the group consisting of H, $Ar^S$; and water solubilizing groups;
$R^7$ is selected from the group consisting of H, $Ar^S$; and water solubilizing groups;
$R^8$ is selected from the group consisting of H, $Ar^S$; and water solubilizing groups;
$Y^1$, $Y^2$, $Y^4$, and $Y^5$ are each independently selected from the group consisting of H and F; and
$Y^3$ is selected from the group consisting of H, F, Cl and OH.

In some such embodiments, at least one of $R^5$, $R^6$, $R^7$ and $R^8$ is selected from $Ar^S$. In some such embodiments, the other of $R^5$, $R^6$, $R^7$ and $R^8$ are H. In some such embodiments, $Ar^S$ is substituted by one or by one or more water solubilizing groups.

In some such embodiments, one and only one of $R^5$, $R^6$, $R^7$ and $R^8$ is selected from $Ar^S$. In some such embodiments, the other of $R^5$, $R^6$, $R^7$ and $R^8$ are H.

In some such embodiments, at least one of $R^5$, $R^6$, $R^7$ and $R^8$ is selected from water solubilizing groups. In some such embodiments, the other of $R^5$, $R^6$, $R^7$ and $R^8$ are H. In some such embodiments, $Ar^S$ is substituted by one or by one or more water solubilizing groups.

In some such embodiments, one and only one of $R^5$, $R^6$, $R^7$ and $R^8$ is selected from water solubilizing groups. In some such embodiments, the other of $R^5$, $R^6$, $R^7$ and $R^8$ are H.

In some embodiments, preferred water solubilizing groups as $R^5$, $R^6$, $R^7$ or $R^8$ or as substituents of $Ar^S$ include H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl) amino-$C_{1-6}$ alkoxy-$C_{1-6}$ alkyl, 4-10 membered hetercycloalkyl-$C_{1-6}$ alkyl, 4-10 membered heterocycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered heterocycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, preferred water solubilizing groups as $R^5$, $R^6$, $R^7$ or $R^8$ or as substituents of $Ar^S$ include H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, preferred water solubilizing groups as $R^5$, $R^6$, $R^7$ or $R^8$ or as substituents of $Ar^S$ include those listed in Table 2.

In some embodiments, the compound of Formula (I), or a pharmaceutically acceptable salt thereof, is a compound of Formula (II), (III) or (IV):

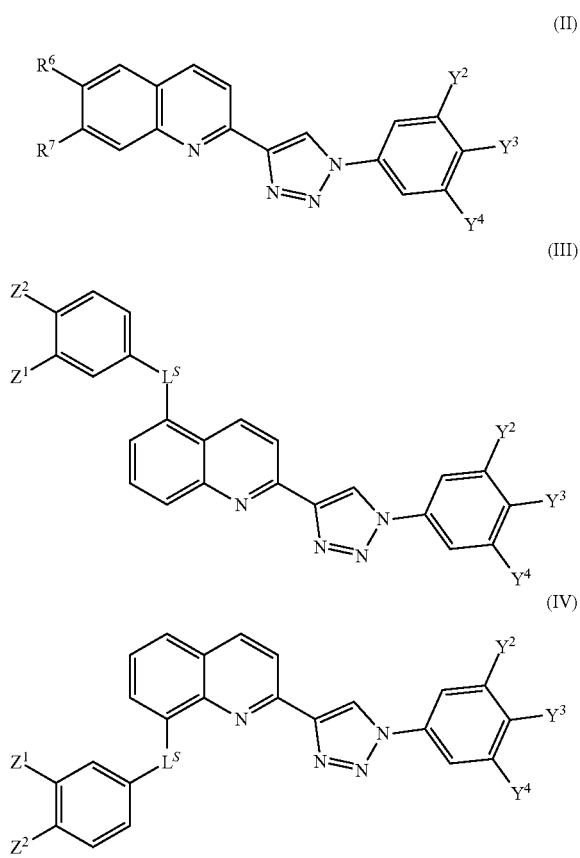

or a pharmaceutically acceptable salt thereof.

In some embodiments, the compound of Formula (I), or a pharmaceutically acceptable salt thereof, is a compound of Formula (II), or a pharmaceutically acceptable salt thereof.

In some embodiments, the compound of Formula (I), or a pharmaceutically acceptable salt thereof, is a compound of Formula (III), or a pharmaceutically acceptable salt thereof.

In some embodiments, $L^S$ is NH.

In some embodiments, $L^S$ is O.

In some embodiments, $Y^2$ is H, halogen, $C_{1-6}$ alkyl, or $OR^{a3}$. In some embodiments, $Y^2$ is H or halogen. In some embodiments, $Y^2$ is H, F, methyl or methoxy. In some embodiments, $Y^2$ is H or F. In some embodiments, $Y^2$ is H.

In some embodiments, $Y^3$ is OH, halogen, CN, $OR^{a3}$, $NR^{c3}R^{d3}$, or $C(O)NR^{c3}R^{d3}$. In some embodiments, $Y^3$ is OH, Cl, or F. In some embodiments, $Y^3$ is OH or F.

In some embodiments, $Y^4$ is H or halogen. In some embodiments, $Y^4$ is H or F. In some embodiments, $Y^4$ is H.

In some embodiments, $R^6$ is H, $OR^{a1}$, or $C_{1-6}$ alkyl substituted with a substituent selected from $OR^{a2}$, $C(O)OR^{a2}$, and $NR^{c2}R^{d2}$. In some embodiments, $R^6$ is H or $OR^{a1}$. In some embodiments, $R^6$ is H.

In some embodiments, $R^6$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^6$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $R^6$ is a water solubilizing group. In some embodiments, $R^6$ is a water solubilizing group selected from the groups listed in Table 2.

In some embodiments, $R^7$ is H, $OR^{a1}$, or $C_{1-6}$ alkyl substituted with a substituent selected from $OR^{a2}$, $C(O)OR^{a2}$, and $NR^{c2}R^{d2}$. In some embodiments, $R^7$ is H or $OR^{a1}$. In some embodiments, $R^7$ is H.

In some embodiments, $R^7$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $R^7$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $R^7$ is a water solubilizing group. In some embodiments, $R^7$ is a water solubilizing group selected from the groups listed in Table 2.

In some embodiments, $R^6$ and $R^7$ are each independently selected from water solubilizing groups. In some embodiments, $R^6$ and $R^7$ are each independently selected from water solubilizing groups selected from the groups listed in Table 2.

In some embodiments, $Z^1$ and $Z^2$ are each independently selected from H, $C_{1-6}$ alkyl, halogen, and $C_{1-6}$ alkoxy, or wherein $Z^1$ or $Z^2$ or $Z^1$ and $Z^2$ are independently selected from water solubilizing groups.

In some embodiments, $Z^1$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^1$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $Z^1$ is a water solubilizing group selected from the groups listed in Table 2.

In some embodiments, $Z^2$ is H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl)amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-$C_{1-6}$ alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, or carboxy-$C_{1-6}$-alkoxy, carboxy-$C_{1-6}$-alkyl-$C_{1-6}$-alkoxy, or carboxy-$C_{1-6}$-alkoxy-$C_{1-6}$-alkoxy.

In some embodiments, $Z^2$ is H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl)ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy)ethoxy, 2-carboxyethoxymethyl, or 2-(2-caroxyethoxy)ethoxy.

In some embodiments, $Z^2$ is a water solubilizing group selected from the groups listed in Table 2. In some embodiments, $Z^1$ is a water solubilizing group and $Z^2$ is a water solubilizing group.

In some embodiments, $Z^1$ is a water solubilizing group and $Z^2$ is hydrogen.

In some embodiments, $Z^2$ is a water solubilizing group and $Z^1$ is hydrogen.

In some embodiments, the water solubilizing group or groups are each independently selected from the groups listed in Table 2.

The compounds of Formula (I) include the following compounds, and pharmaceutically acceptable salts thereof: 4-(4-(quinolin-2-yl)-1H-1,2,3-triazol-1-yl)phenol (3a) 4-(4-(6-(2-methoxyethoxy)quinolin-2-yl)-1H-1,2,3-triazol-1-yl)phenol (3b); 4-(4-(6-(2-(2-aminoethoxy)ethoxy)quinolin-2-yl)-1H-1,2,3-triazol-1-yl)phenol (3c); 2-(1-(4-fluorophenyl)-1H-1,2,3-triazol-4-yl)-6-(2-methoxy ethoxy)quinoline (3d); 2-(1-(4-chlorophenyl)-1H-1,2,3-triazol-4-yl)-6-(2-methoxy ethoxy)quinoline (3e); 4-(4-(6-(2-methoxyethoxy)quinolin-2-yl)-1H-1,2,3-triazol-1-yl)aniline (3f) 2-(1-(4-methoxyphenyl)-1H-1,2,3-triazol-4-yl)-6-(2-methoxyethoxy)quinoline (3g); 4-(4-(6-(2-methoxyethoxy)quinolin-2-yl)-1H-1,2,3-triazol-1-yl)benzonitrile (3h); 4-(4-(6-(2-methoxyethoxy)quinolin-2-yl)-1H-1,2,3-triazol-1-yl)benzamide (3i); 4-(4-(6-(2-methoxyethoxy)quinolin-2-yl)-1H-1,2,3-triazol-1-yl)-2-methylphenol (3j); 2-methoxy-4-(4-(6-(2-methoxy ethoxy)quinolin-2-yl)-1H-1,2,3-triazol-1-yl)phenol (3k); 4-(4-(3-methylquinolin-2-yl)-1H-1,2,3-triazol-1-yl)phenol (3l); 4-(4-(4-methylquinolin-2-yl)-1H-1,2,3-triazol-1-yl)phenol (3m); 4-(4-(8-chloroquinolin-2-yl)-1H-1,2,3-triazol-1-yl)phenol (3n); 2-(1-(4-fluorophenyl)-1H-1,2,3-triazol-4-yl)-8-methoxyquinoline (3o) 2-(1-(4-fluorophenyl)-1H-1,2,3-triazol-4-yl)-8-(2-methoxy ethoxy)

quinoline (3p); 4-(4-(8-(4-methoxyphenoxy)quinolin-2-yl)-1H-1,2,3-triazol-1-yl)phenol (3q); 2-(1-(4-fluorophenyl)-1H-1,2,3-triazol-4-yl)-8-phenoxyquinoline (3r); 2-(1-(4-fluorophenyl)-1H-1,2,3-triazol-4-yl)-5-phenoxyquinoline (3s); 4-(4-(6-(3-morpholinopropoxy)quinolin-2-yl)-1H-1,2,3-triazol-1-yl)phenol (3t); 4-(4-(3-methyl-6-(3-morpholinopropoxy)quinolin-2-yl)-1H-1,2,3-triazol-1-yl)phenol (3u); 4-(4-(6-(2-(2-morpholinoethoxy)ethoxy)quinolin-2-yl)-1H-1,2,3-triazol-1-yl)phenol (3v); 2-fluoro-4-(4-(6-(2-(2-morpholinoethoxy)ethoxy)quinolin-2-yl)-1H-1,2,3-triazol-1-yl)phenol (3w); 4-(2-(2-((2-(1-(4-fluorophenyl)-1H-1,2,3-triazol-4-yl)quinolin-6-yl)oxy)ethoxy)ethyl)morpholine (3x); 4-(2-(2-((2-(1-(4-fluorophenyl)-1H-1,2,3-triazol-4-yl)quinolin-6-yl)oxy)ethoxy)ethyl)morpholine (3y); 2-fluoro-4-(4-(5-(3-(2-methoxyethoxy)phenoxy)quinolin-2-yl)-1H-1,2,3-triazol-1-yl)phenol (3z); 4-((2-(1-(3-fluoro-4-hydroxyphenyl)-1H-1,2,3-triazol-4-yl)quinolin-5-yl)oxy)benzoic acid (3aa); 4-(4-(1,8-naphthyridin-2-yl)-1H-1,2,3-triazol-1-yl)phenol (4a); 2-(1-(4-chlorophenyl)-1H-1,2,3-triazol-4-yl)-1,8-naphthyridine (4b); 4-(4-(7-(2-(2-morpholinoethoxy)ethoxy)quinolin-2-yl)-1H-1,2,3-triazol-1-yl)phenol; 4-(4-(6-(2-methoxyethoxy)quinazolin-2-yl)-1H-1,2,3-triazol-1-yl)phenol; 3-((2-(1-(3-fluoro-4-hydroxyphenyl)-1H-1,2,3-triazol-4-yl)quinolin-5-yl)oxy)benzoic acid (3bb); 3-((2-(1-(4-hydroxyphenyl)-1H-1,2,3-triazol-4-yl)quinolin-5-yl)oxy)benzoic acid; 4-((2-(1-(4-hydroxyphenyl)-1H-1,2,3-triazol-4-yl)quinolin-5-yl)oxy)benzoic acid; 4-(4-(5-(3-(aminomethyl)phenoxy)quinolin-2-yl)-1H-1,2,3-triazol-1-yl)phenol; 4-(4-(5-(4-(aminomethyl)phenoxy)quinolin-2-yl)-1H-1,2,3-triazol-1-yl)phenol; 4-(4-(5-(4-(2-methoxyethoxy)phenoxy)quinolin-2-yl)-1H-1,2,3-triazol-1-yl)phenol; 4-(4-(5-(3-(2-methoxyethoxy)phenoxy)quinolin-2-yl)-1H-1,2,3-triazol-1-yl)phenol; 4-(4-(5-(3-(2-(2-morpholinoethoxy)ethoxy)phenoxy)quinolin-2-yl)-1H-1,2,3-triazol-1-yl)phenol; 4-(4-(5-(4-(2-(2-morpholinoethoxy)ethoxy)phenoxy)quinolin-2-yl)-1H-1,2,3-triazol-1-yl)phenol; 4-(1-(isoquinolin-4-yl)-1H-1,2,3-triazol-4-yl)phenol; 2-(1-(4-hydroxyphenyl)-1H-1,2,3-triazol-4-yl)-7-methyl-1,7-naphthyridin-8(7H)-one; 4-(4-(6-(2-(2-aminoethoxy)ethoxy)quinolin-2-yl)-1H-1,2,3-triazol-1-yl)-2-fluorophenol; 4-(4-(6-(2-(2-aminoethoxy)ethoxy)quinolin-2-yl)-1H-1,2,3-triazol-1-yl)-2,6-difluorophenol; 2-fluoro-4-(4-(5-(2-(2-morpholinoethoxy)ethoxy)quinolin-2-yl)-1H-1,2,3-triazol-1-yl)phenol; 2-fluoro-4-(4-(7-(2-(2-morpholinoethoxy)ethoxy)quinolin-2-yl)-1H-1,2,3-triazol-1-yl)phenol; 2-fluoro-4-(4-(6-(2-(2-(pyridin-2-yl)ethoxy)ethoxy)quinolin-2-yl)-1H-1,2,3-triazol-1-yl)phenol; 2-fluoro-4-(4-(6-(2-(2-(piperidin-1-yl)ethoxy)ethoxy)quinolin-2-yl)-1H-1,2,3-triazol-1-yl)phenol; 4-(4-(6-(2-(2-(1H-imidazol-1-yl)ethoxy)ethoxy)quinolin-2-yl)-1H-1,2,3-triazol-1-yl)-2-fluorophenol; 2-fluoro-4-(4-(6-(2-(2-(4-methylpiperazin-1-yl)ethoxy)ethoxy)quinolin-2-yl)-1H-1,2,3-triazol-1-yl)phenol; 2-((2-(1-(3-fluoro-4-hydroxyphenyl)-1H-1,2,3-triazol-4-yl)quinolin-6-yl)oxy)acetic acid; N-(2-(diethylamino)ethyl)-2-(1-(3-fluoro-4-hydroxyphenyl)-1H-1,2,3-triazol-4-yl)quinoline-6-carboxamide; 4-((2-(1-(3-fluoro-4-hydroxyphenyl)-1H-1,2,3-triazol-4-yl)quinolin-6-yl)oxy)benzoic acid; 2-(2-(1-(3-fluoro-4-hydroxyphenyl)-1H-1,2,3-triazol-4-yl)quinolin-6-yl)acetic acid; 2,6-difluoro-4-(4-(6-(2-(2-morpholinoethoxy)ethoxy)quinolin-2-yl)-1H-1,2,3-triazol-1-yl)phenol; 2-fluoro-5-((2-(1-(3-fluoro-4-hydroxyphenyl)-1H-1,2,3-triazol-4-yl)quinolin-5-yl)oxy)benzoic acid; 3-fluoro-5-((2-(1-(3-fluoro-4-hydroxyphenyl)-1H-1,2,3-triazol-4-yl)quinolin-5-yl)oxy)benzoic acid; 3-((2-(1-(3,4-difluorophenyl)-1H-1,2,3-triazol-4-yl)quinolin-5-yl)oxy)benzoic acid; 4-(4-(5-(3-(aminomethyl)phenoxy)quinolin-2-yl)-1H-1,2,3-triazol-1-yl)-2-fluorophenol; 2-fluoro-4-(4-(5-(3-(2-(2-morpholinoethoxy)ethoxy)phenoxy)quinolin-2-yl)-1H-1,2,3-triazol-1-yl)phenol; 4-((2-(1-(3-fluoro-4-hydroxyphenyl)-1H-1,2,3-triazol-4-yl)quinolin-8-yl)oxy)benzoic acid; 3-((2-(1-(3-fluoro-4-hydroxyphenyl)-1H-1,2,3-triazol-4-yl)quinolin-8-yl)oxy)benzoic acid; 2-((2-(1-(3-fluoro-4-hydroxyphenyl)-1H-1,2,3-triazol-4-yl)quinolin-7-yl)oxy)acetic acid; 4-((2-(1-(3-fluoro-4-hydroxyphenyl)-1H-1,2,3-triazol-4-yl)quinolin-7-yl)oxy)butanoic acid; 4-((2-(1-(3-fluoro-4-hydroxyphenyl)-1H-1,2,3-triazol-4-yl)quinolin-6-yl)oxy)butanoic acid; and 2-(2-((2-(1-(3-fluoro-4-hydroxyphenyl)-1H-1,2,3-triazol-4-yl)quinolin-6-yl)oxy)ethoxy)acetic acid.

In some embodiments, the compound of Formula (I) is 2-(2-((2-(1-(3-fluoro-4-hydroxyphenyl)-1H-1,2,3-triazol-4-yl)quinolin-6-yl)oxy)ethoxy)acetic acid, or a pharmaceutically acceptable salt thereof. In some embodiments, the compound of Formula (I) is 2-(2-((2-(1-(3-fluoro-4-hydroxyphenyl)-1H-1,2,3-triazol-4-yl)quinolin-6-yl)oxy)ethoxy)acetic acid.

In some embodiments, the compounds of Formula (I) include compounds of the formulae (II), (III) and the following formulae (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51) and (D-52) and pharmaceutically acceptable salts thereof:

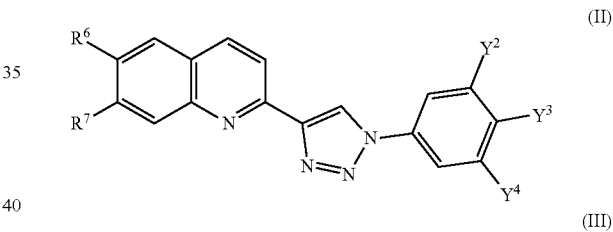

(II)

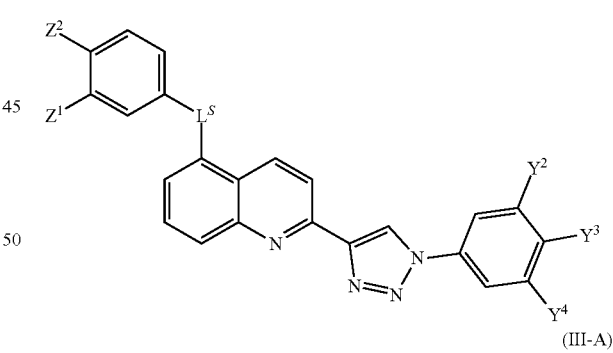

(III)

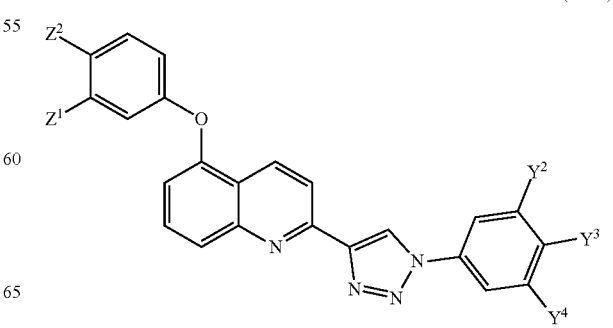

(III-A)

(III-B)
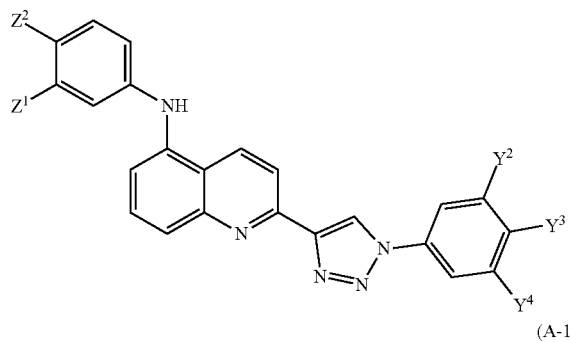
(A-1)
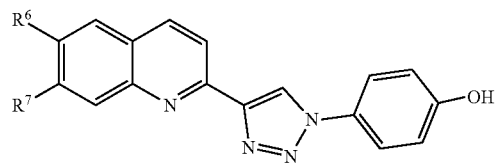
(A-2)
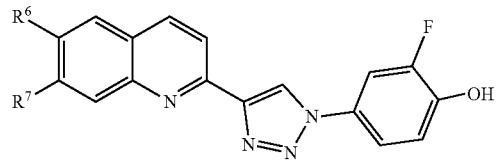
(A-3)
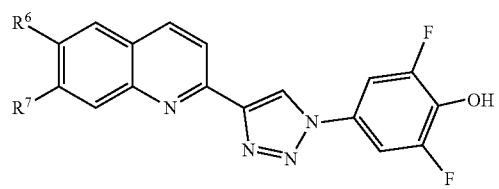
(A-4)
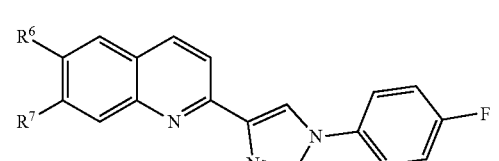
(A-5)
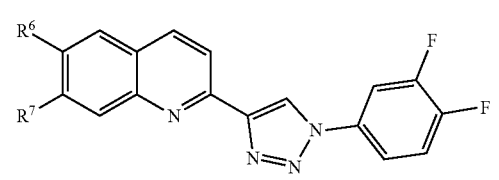
(B-1)
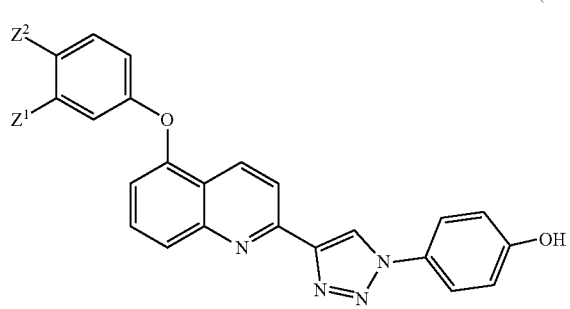
(B-2)
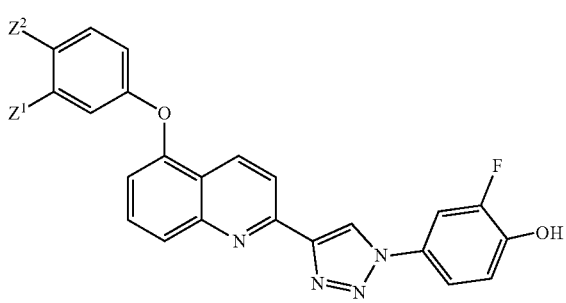
(B-3)
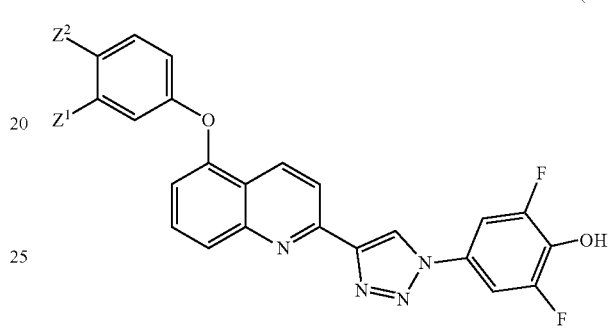
(B-4)
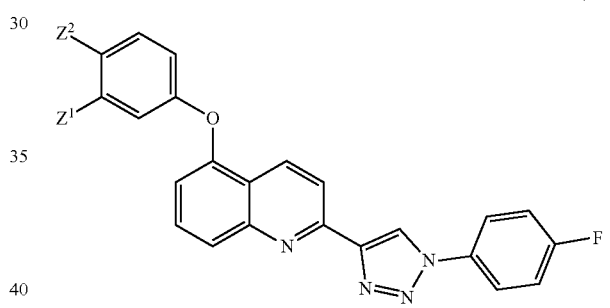
(B-5)
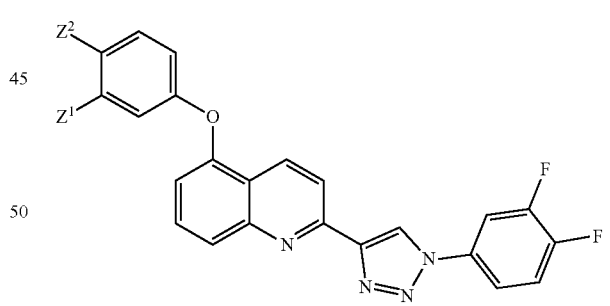
(B-6)
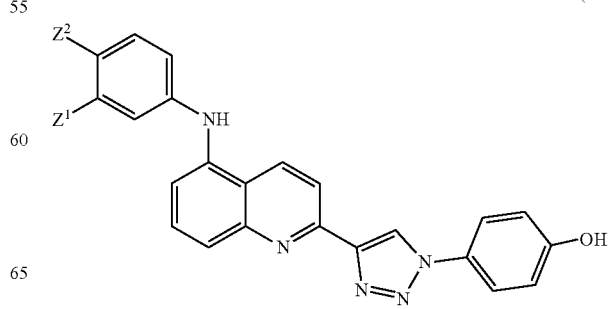

(B-7)
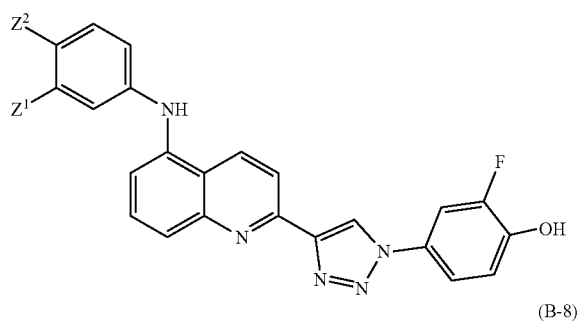
(B-8)
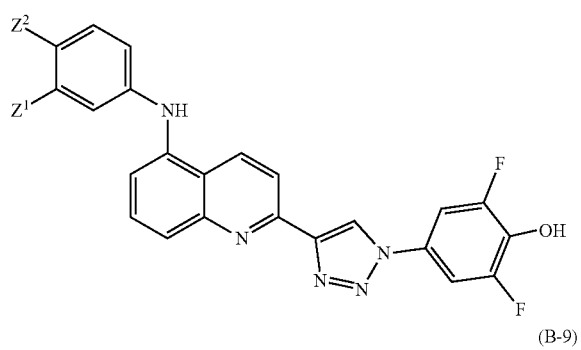
(B-9)
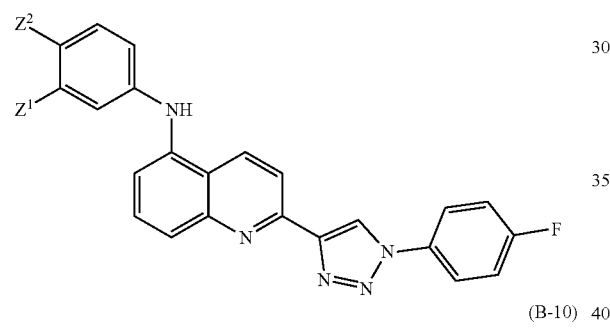
(B-10)
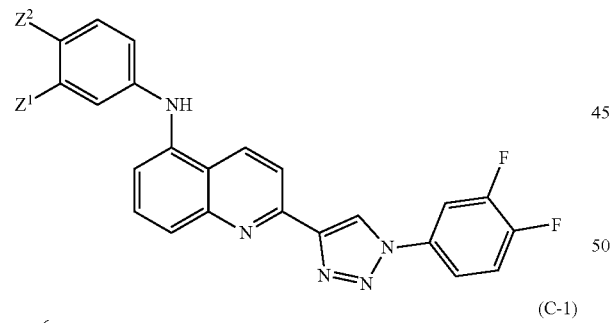
(C-1)
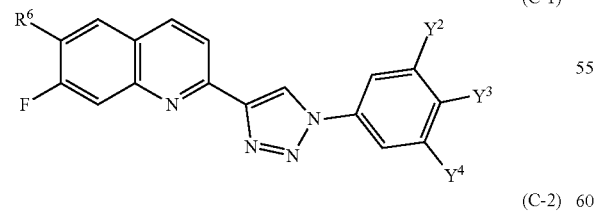
(C-2)
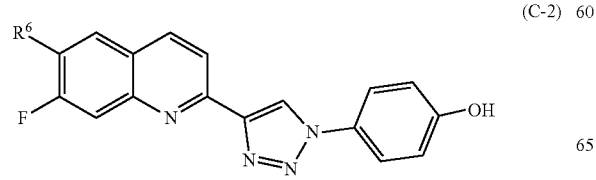
(C-3)
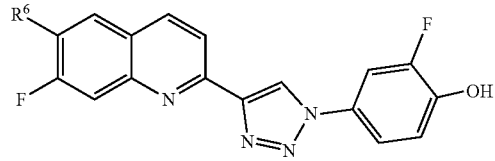
(C-4)
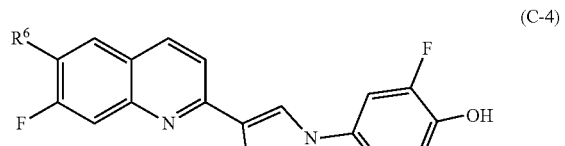
(C-5)
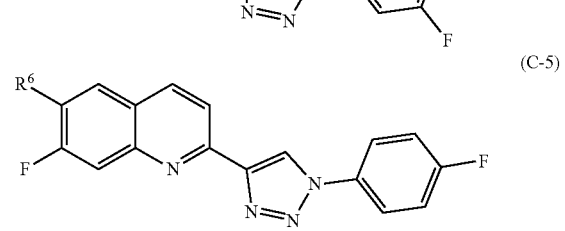
(C-6)
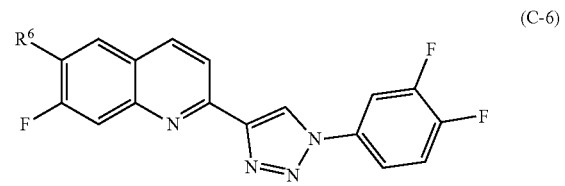
(C-7)
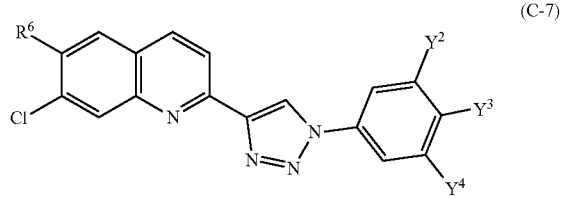
(C-8)
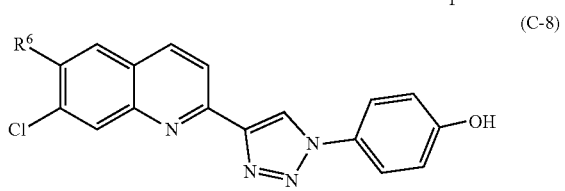
(C-9)
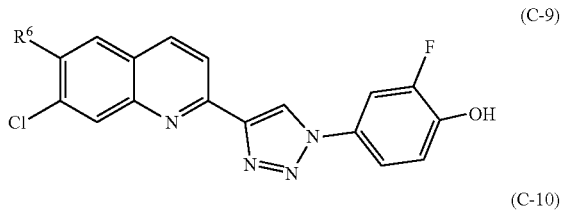
(C-10)
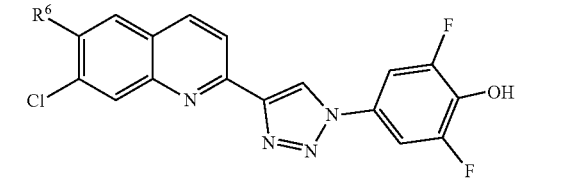
(C-11)
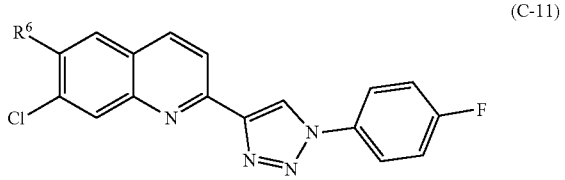

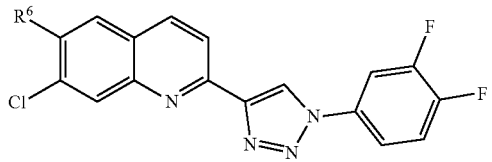
(C-12)
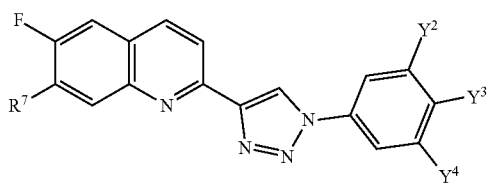
(C-13)
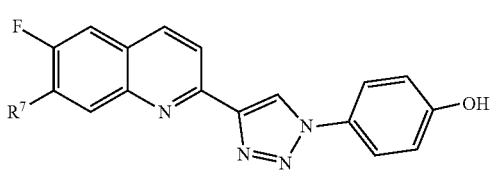
(C-14)

(C-15)
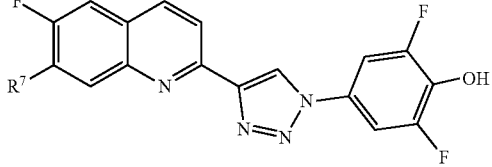
(C-16)
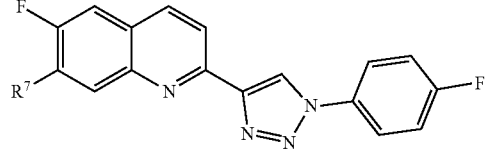
(C-17)
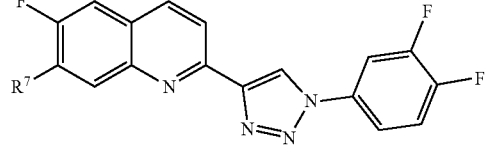
(C-18)
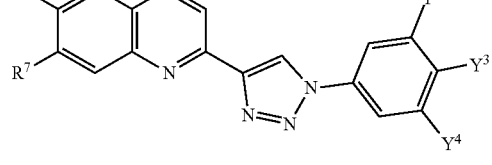
(C-19)
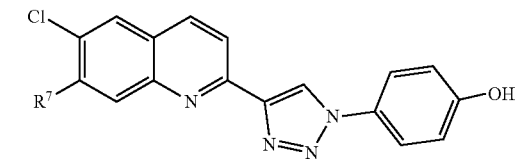
(C-20)
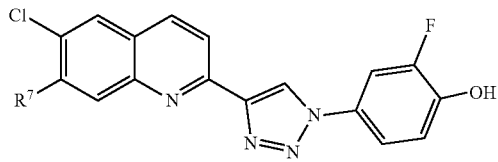
(C-21)
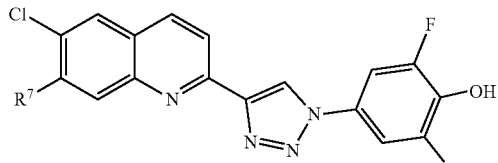
(C-22)
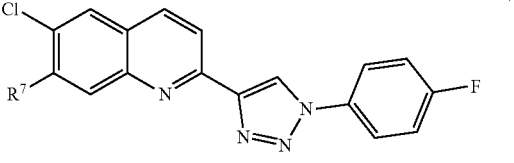
(C-23)
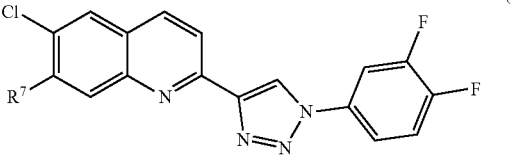
(C-24)
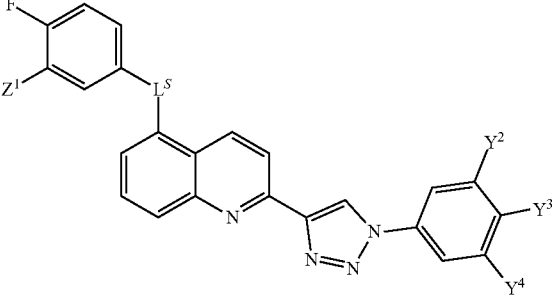
(D-1)
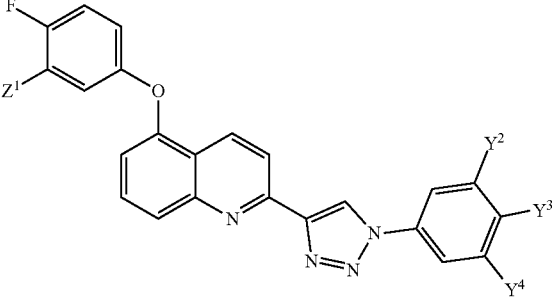
(D-2)

(D-3)
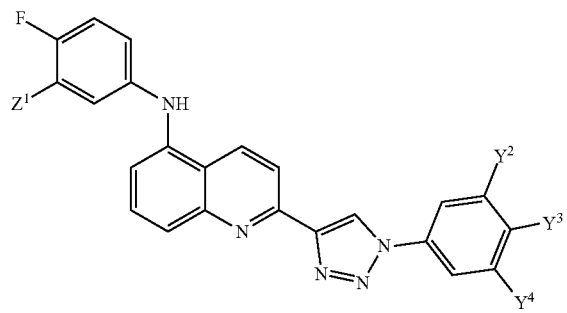
(D-4)
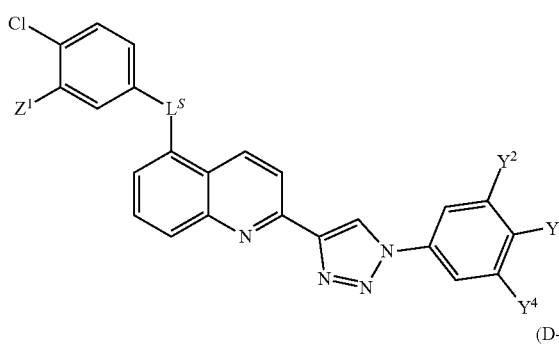
(D-5)
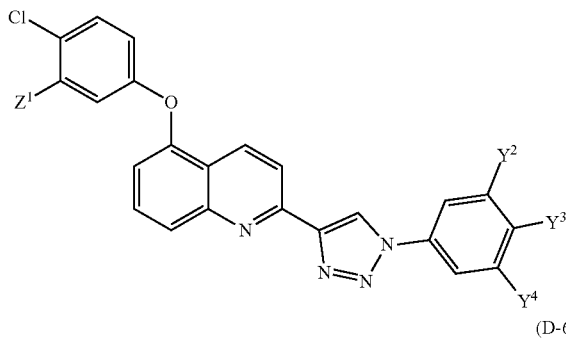
(D-6)
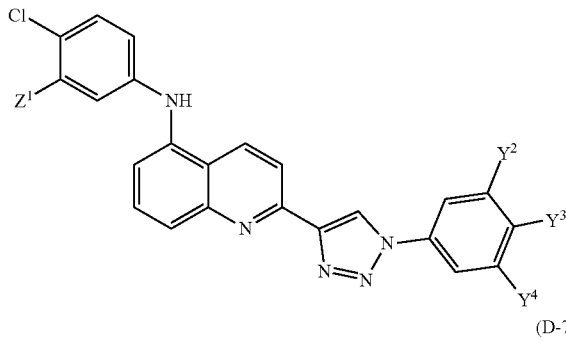
(D-7)
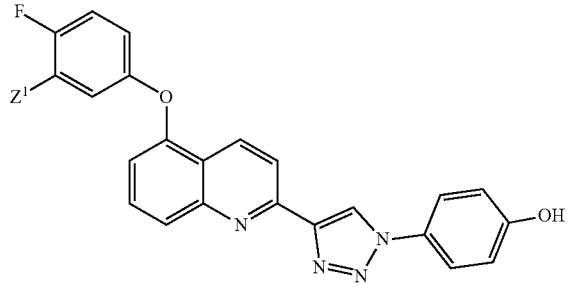
(D-8)
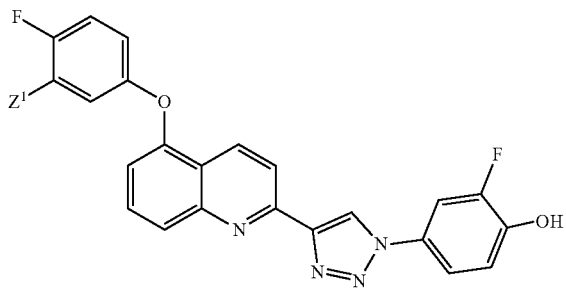
(D-9)
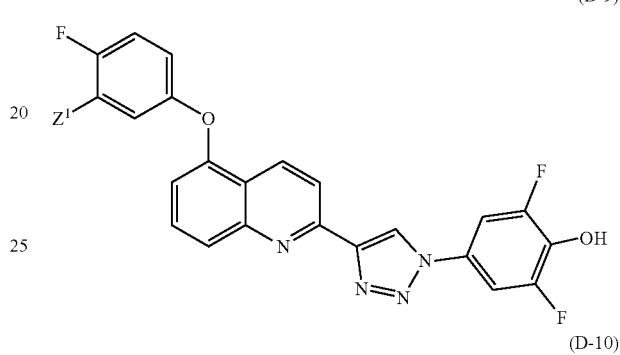
(D-10)

(D-11)
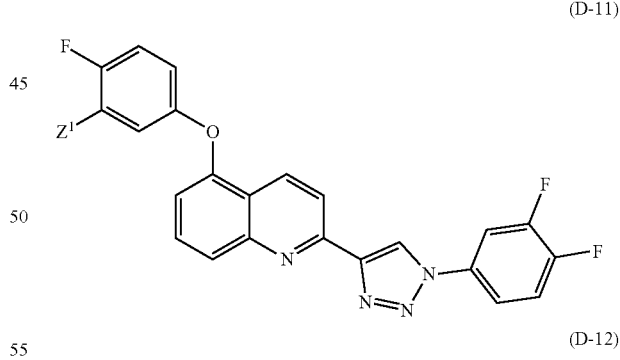
(D-12)

(D-13)
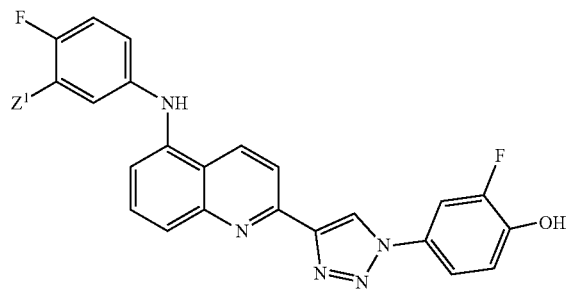
(D-14)
(D-15)
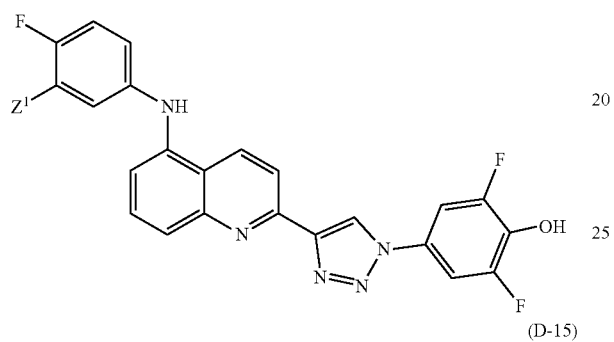
(D-16)
(D-17)
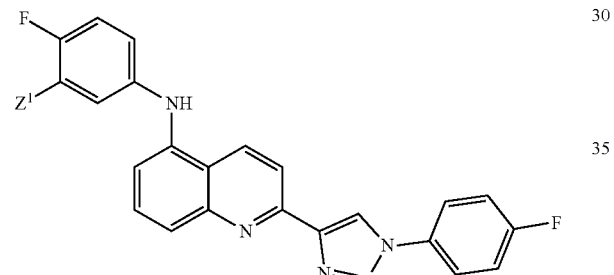
(D-18)
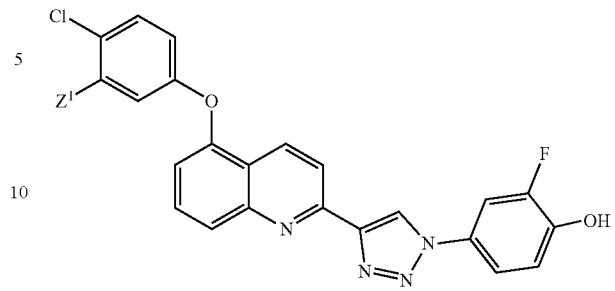
(D-19)
(D-20)
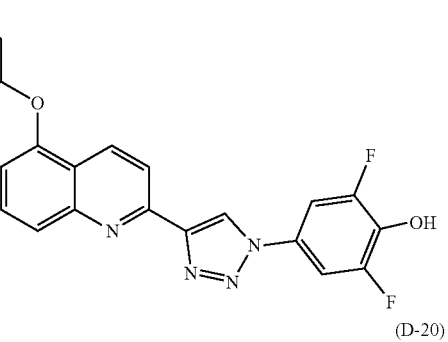
(D-21)
(D-21)
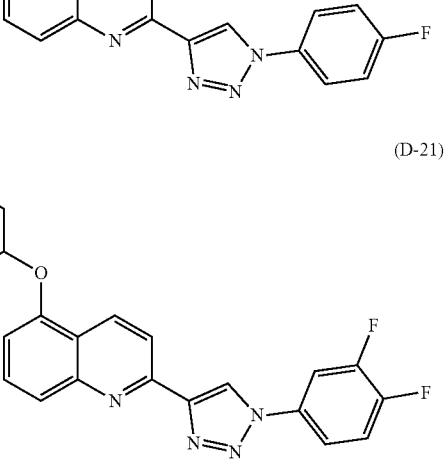

-continued
(D-23)
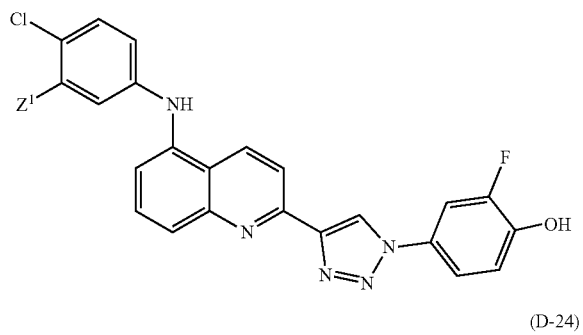
(D-24)
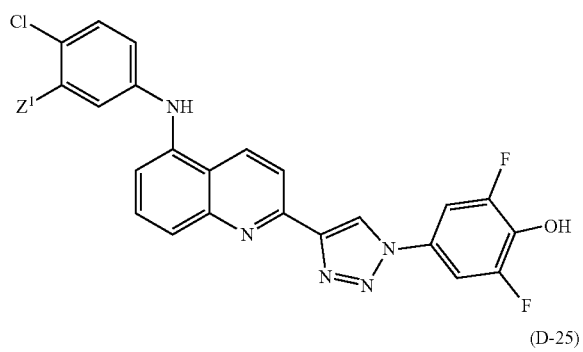
(D-25)
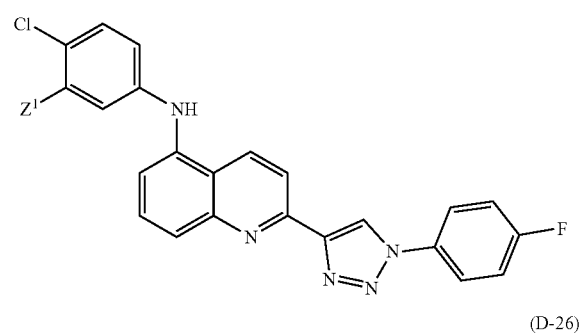
(D-26)
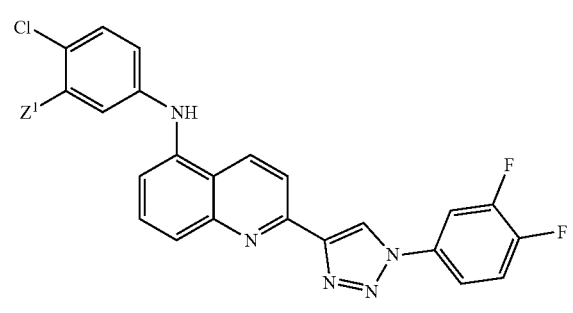
(D-27)
-continued
(D-28)
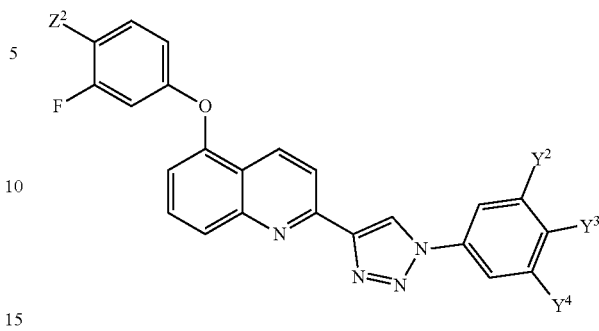
(D-29)
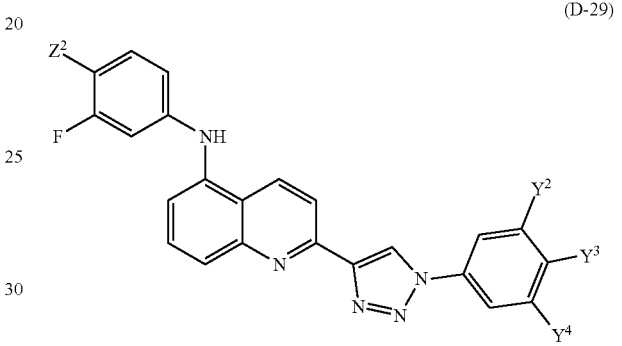
(D-30)
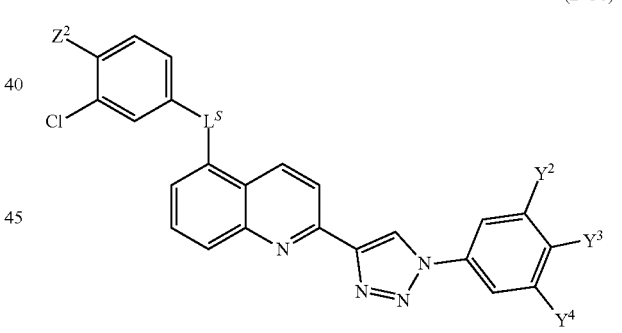
(D-31)
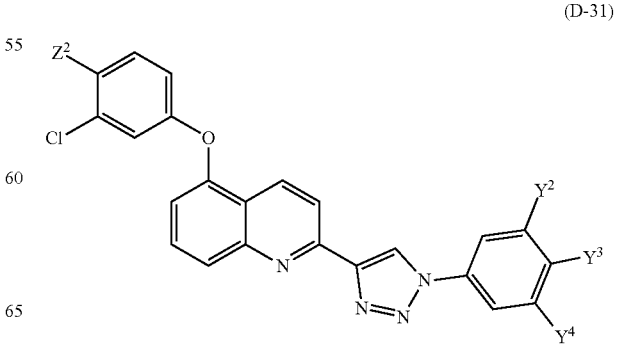

(D-32)
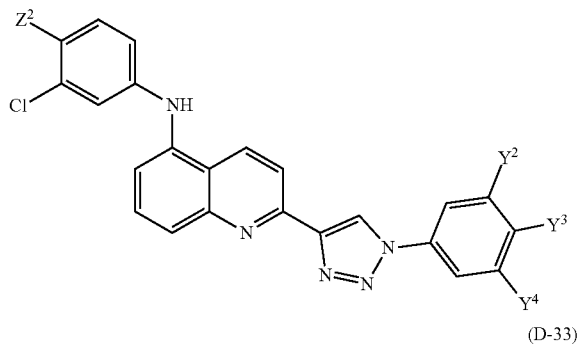
(D-33)
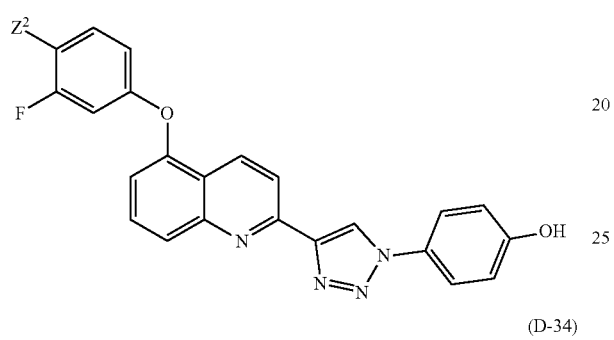
(D-34)
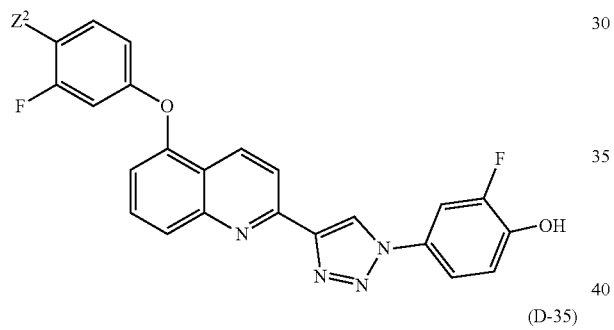
(D-35)
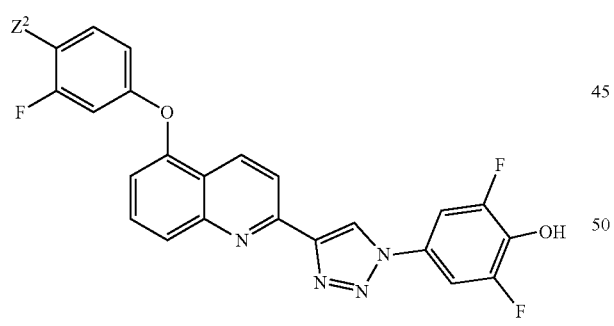
(D-36)
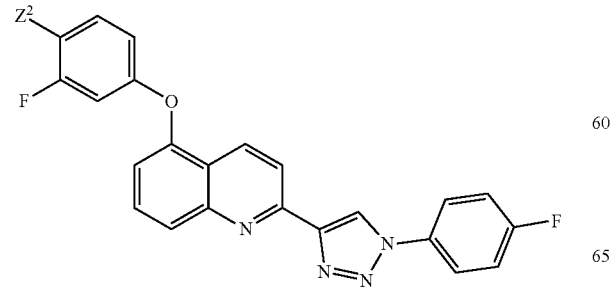
(D-37)
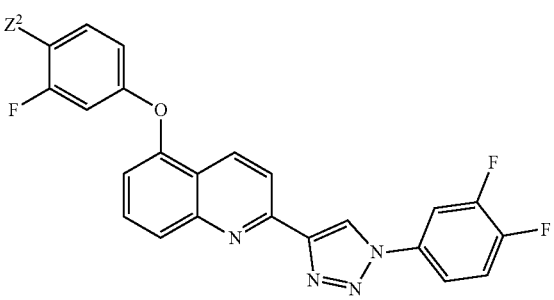
(D-38)
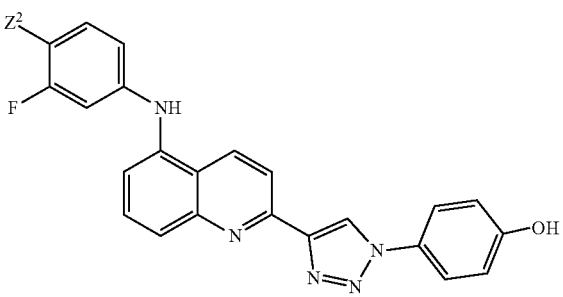
(D-39)
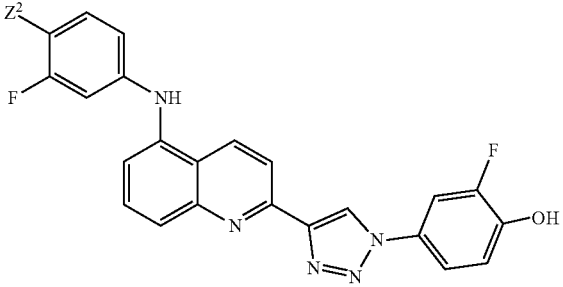
(D-40)
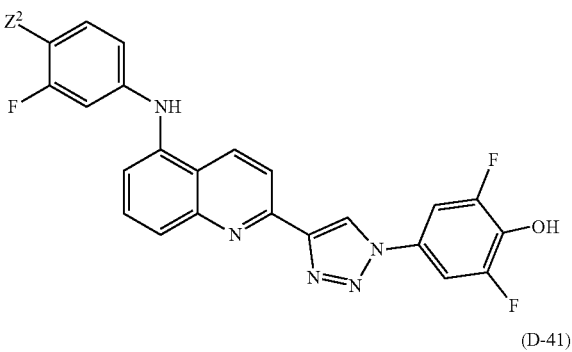

(D-42)
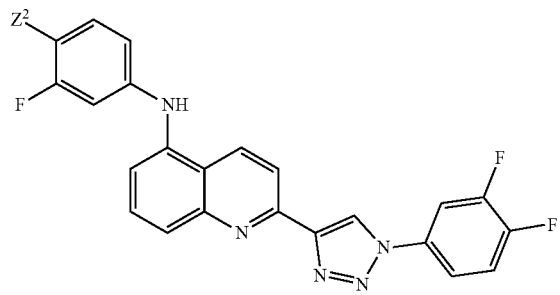
(D-43)
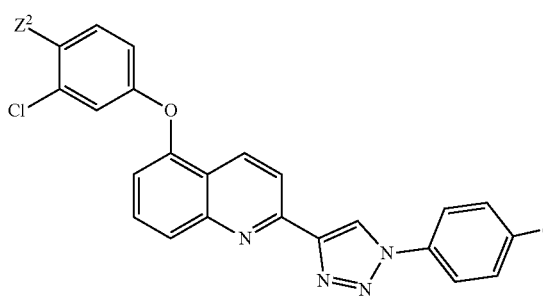
(D-44)
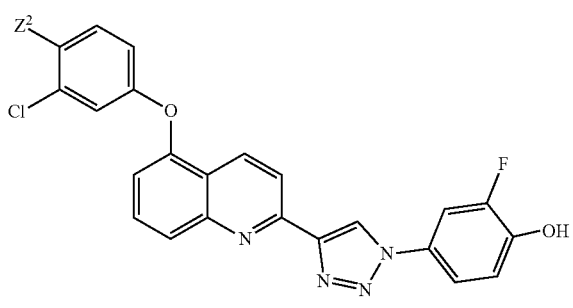
(D-45)
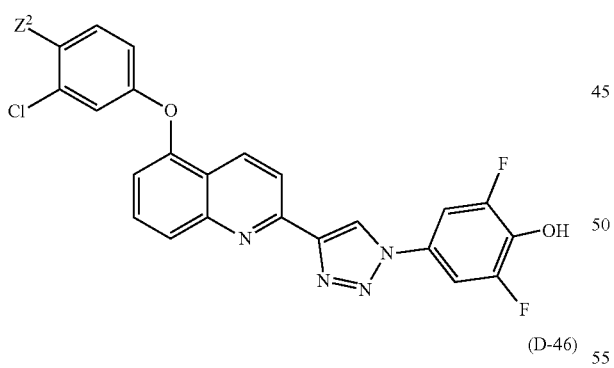
(D-46)
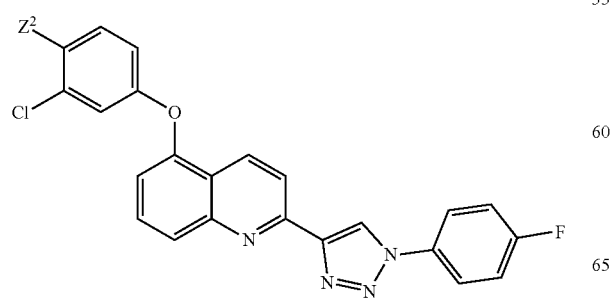
(D-47)
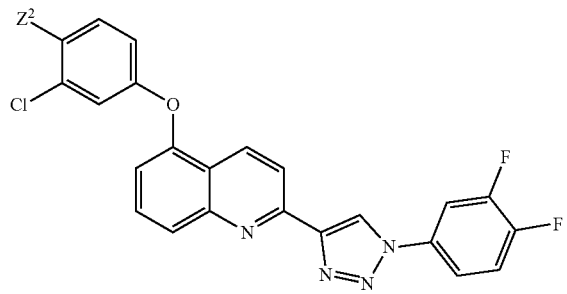
(D-48)
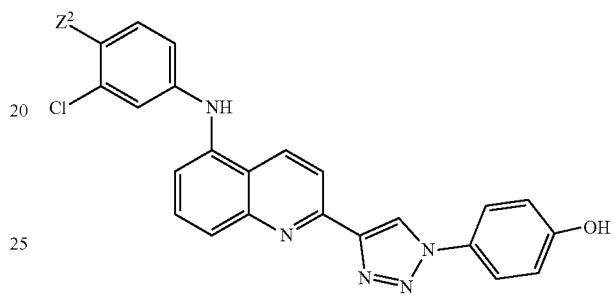
(D-49)
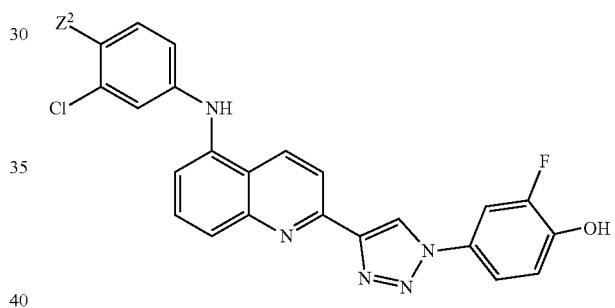
(D-50)
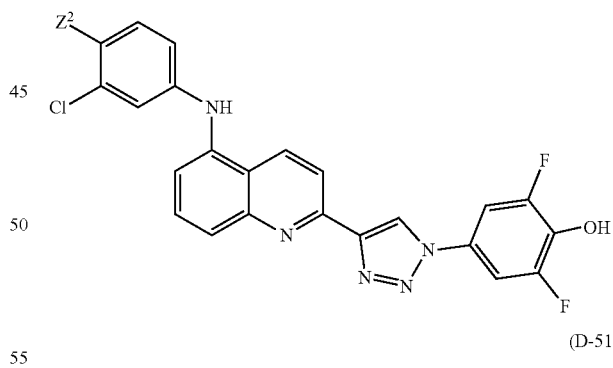
(D-51)
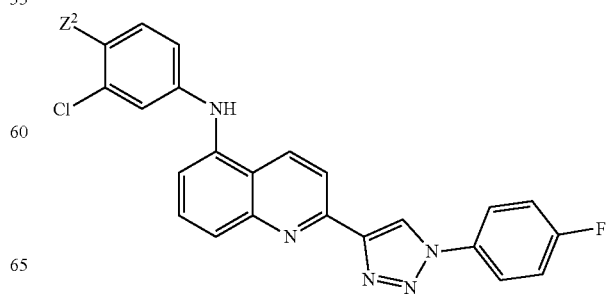

(D-52)
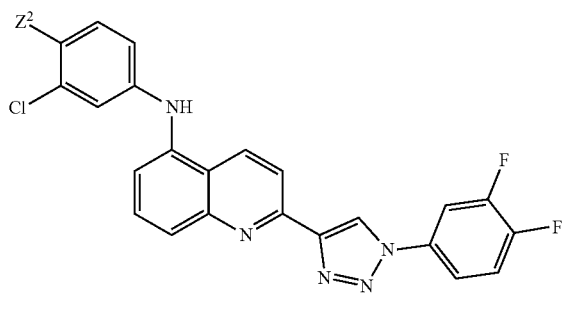
(D-56)
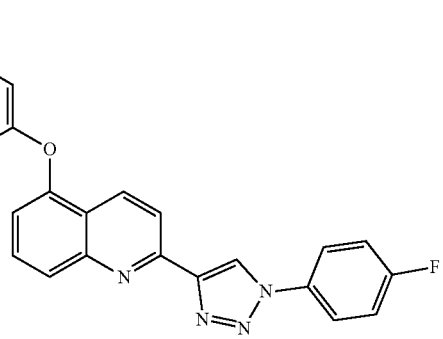
(D-53)
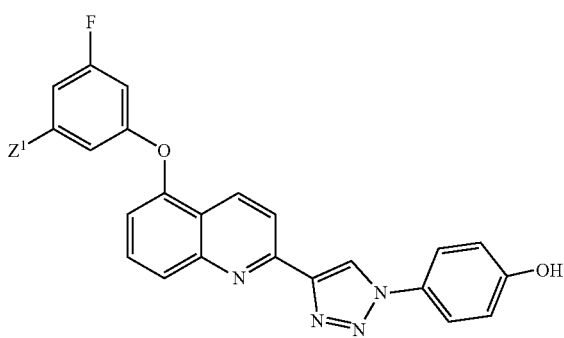
(D-57)
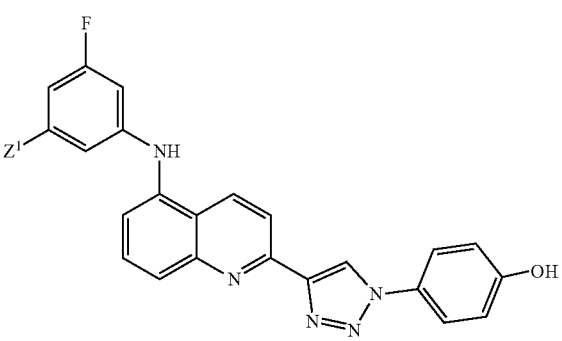
(D-54)
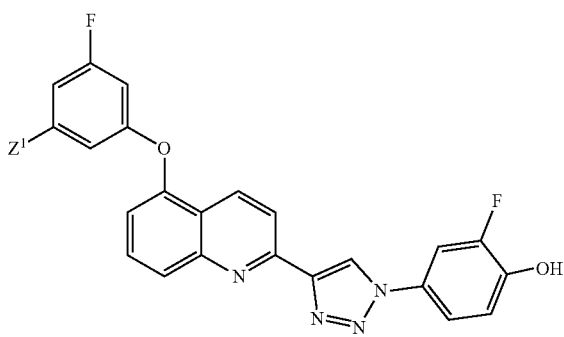
(D-58)
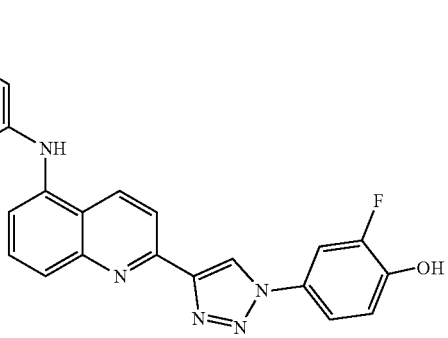
(D-55)
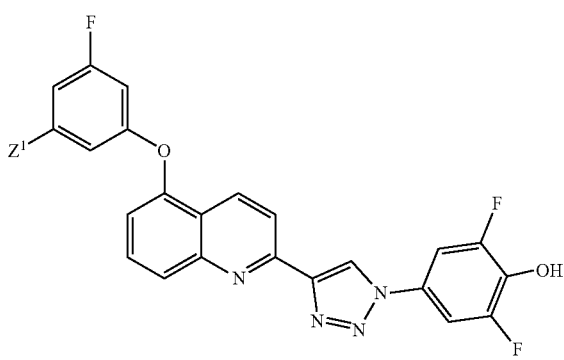
(D-59)

(D-60)
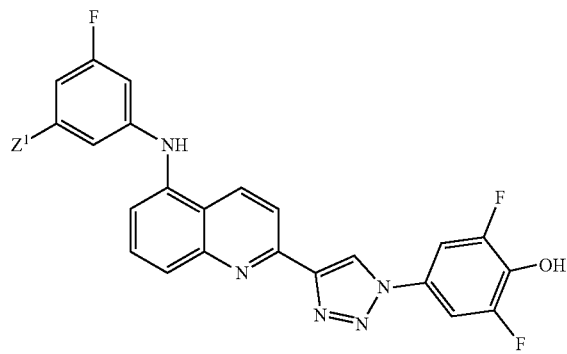
(D-64)
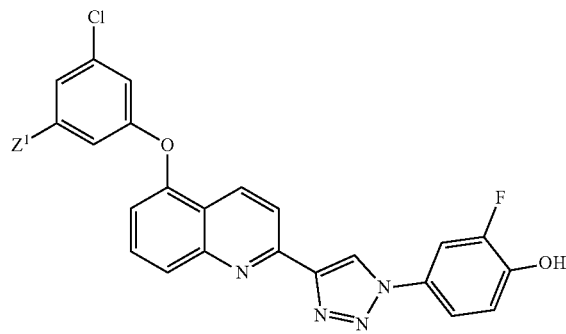
(D-61)
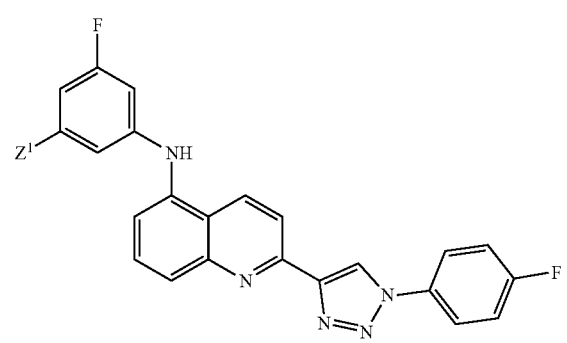
(D-65)
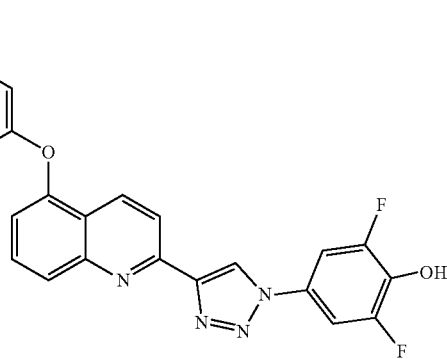
(D-62)
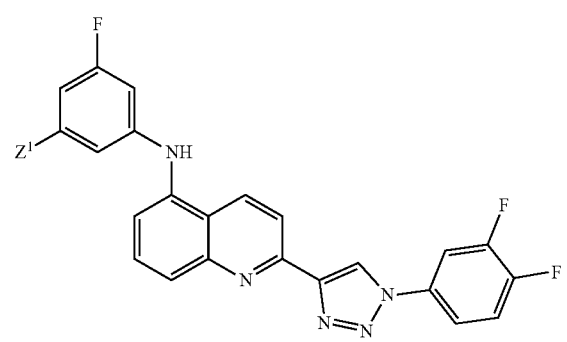
(D-66)
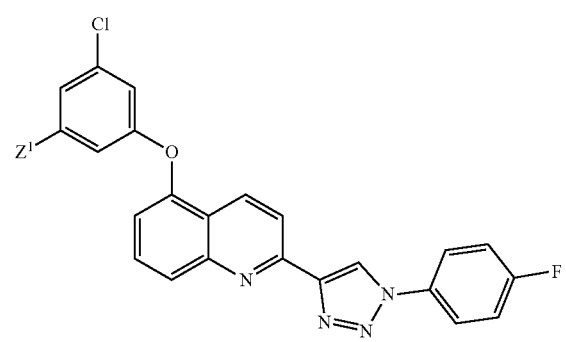
(D-63)
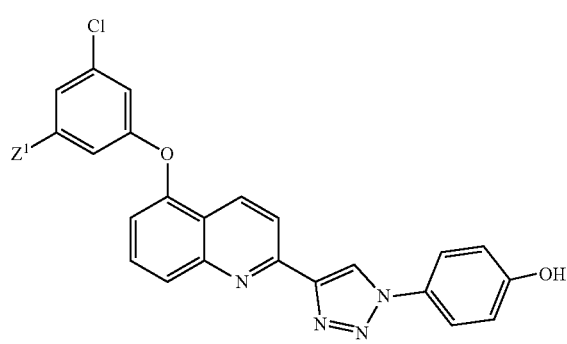
(D-67)
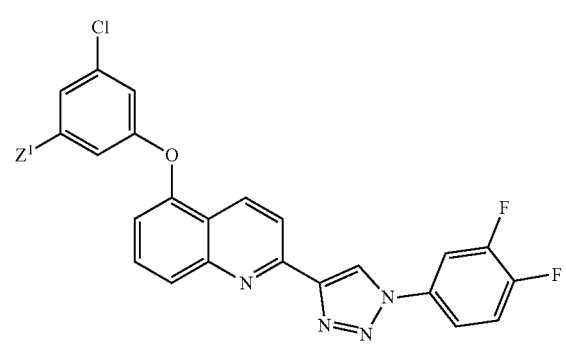

(D-68)

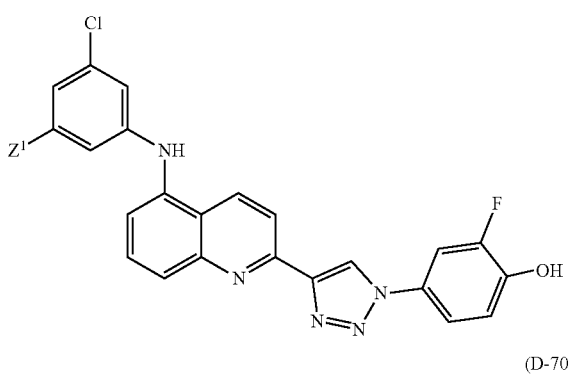
(D-69)

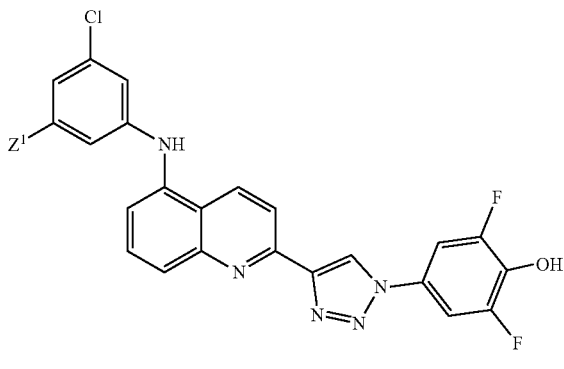
(D-70)

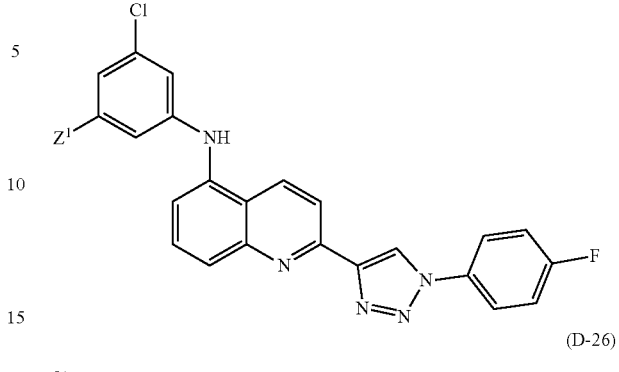
(D-71)

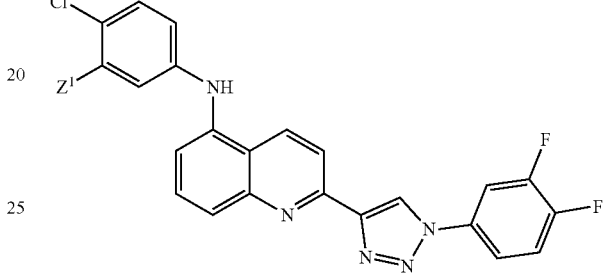
(D-26)

In the compounds of formulae (II), (III), (III-A), (III-B), (C-1), (C-7), (C-13), (C-19), (D-1) to (D-6) and (D-27) to (D-32), the variables $L^S$, $Y^2$, $Y^3$ and $Y^4$ can be as defined above for the compounds of Formula (I) or any of the embodiments thereof. In particular embodiments of the compounds of each of the formulae (II), (III), (III-A), (III-B), (A-1), (A-2), (A-3), (A-4), (A-5), (B-1), (B-2), (B-3), (B-4), (B-5), (B-6), (B-7), (B-8), (B-9), and (B-10) the variables $R^6$ and $R^7$ (in formulae (II), (A-1), (A-2), (A-3), (A-4), (A-5)) and the variables $Z^1$ and $Z^2$ (in formulae (III), (III-A), (III-B), (B-1), (B-2), (B-3), (B-4), (B-5), (B-6), (B-7), (B-8), (B-9), and (B-10)) can have the values shown in Table 1. The variable $R^6$ in formulae (C-1) to (C-12) and the variable $Z^1$ in formulae (D-1) to (D-26) and (D-53) to (D-72), can have the values shown in Entries 1-406 of Table 1. The variable $R^7$ in formulae (C-13) to (C-24) and the variable $Z^2$ in formulae (D-27) to (D-52), can have the values shown in Entries 407-812 of Table 1.

TABLE 1

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1 | —OH | H |
| 2 | —OMe | H |
| 3 | —OEt | H |
| 4 | —OPr | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 5 | —OiPr | H |
| 6 | —OcPr | H |
| 7 | —OcBu | H |
| 8 | —OcPn | H |
| 9 | —OcHex | H |
| 10 | —OCH$_2$CH$_2$OH | H |
| 11 | —OCH$_2$CH$_2$OMe | H |
| 12 | —OCH$_2$CH$_2$OEt | H |
| 13 | —OCH$_2$CH$_2$NH$_2$ | H |
| 14 | —OCH$_2$CH$_2$NHMe | H |
| 15 | —OCH$_2$CH$_2$NMe$_2$ | H |
| 16 | pyrrolidin-1-yl-CH$_2$CH$_2$O— | H |
| 17 | piperidin-1-yl-CH$_2$CH$_2$O— | H |
| 18 | piperazin-1-yl-CH$_2$CH$_2$O— | H |
| 19 | 4-methylpiperazin-1-yl-CH$_2$CH$_2$O— | H |
| 20 | morpholin-4-yl-CH$_2$CH$_2$O— | H |
| 21 | —OCH$_2$CH$_2$CH$_2$OH | H |
| 22 | —OCH$_2$CH$_2$CH$_2$OMe | H |
| 23 | —OCH$_2$CH$_2$CH$_2$OEt | H |
| 24 | —OCH$_2$CH$_2$CH$_2$NH$_2$ | H |
| 25 | —OCH$_2$CH$_2$CH$_2$NHMe | H |
| 26 | —OCH$_2$CH$_2$CH$_2$NMe$_2$ | H |
| 27 | pyrrolidin-1-yl-CH$_2$CH$_2$CH$_2$O— | H |
| 28 | piperidin-1-yl-CH$_2$CH$_2$CH$_2$O— | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 29 | piperazinyl-propyl-O- | H |
| 30 | 4-methylpiperazinyl-propyl-O- | H |
| 31 | morpholinyl-propyl-O- | H |
| 32 | —OCH$_2$CH$_2$OCH$_2$CH$_2$OH | H |
| 33 | —OCH$_2$CH$_2$OCH$_2$CH$_2$OMe | H |
| 34 | —OCH$_2$CH$_2$OCH$_2$CH$_2$OEt | H |
| 35 | —OCH$_2$CH$_2$OCH$_2$CH$_2$NH$_2$ | H |
| 36 | —OCH$_2$CH$_2$OCH$_2$CH$_2$NHMe | H |
| 37 | —OCH$_2$CH$_2$OCH$_2$CH$_2$NMe$_2$ | H |
| 38 | pyrrolidinyl-ethyl-O-ethyl-O- | H |
| 39 | piperidinyl-ethyl-O-ethyl-O- | H |
| 40 | piperazinyl-ethyl-O-ethyl-O- | H |
| 41 | 4-methylpiperazinyl-ethyl-O-ethyl-O- | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ in formulae (III), (III-A), (III-B), and B-1 to B-10) or $R^7$ in formulae (C-13) to (C-24) or $Z^2$ in formulae (D-27) to (D-52) |
|---|---|---|
| 42 | morpholine-CH$_2$CH$_2$-O-CH$_2$CH$_2$-O- | H |
| 43 | —OCH$_2$CH$_2$OCH$_2$CH$_2$CH$_2$OH | H |
| 44 | —OCH$_2$CH$_2$OCH$_2$CH$_2$CH$_2$OMe | H |
| 45 | —OCH$_2$CH$_2$OCH$_2$CH$_2$CH$_2$OEt | H |
| 46 | —OCH$_2$CH$_2$OCH$_2$CH$_2$CH$_2$NH$_2$ | H |
| 47 | —OCH$_2$CH$_2$OCH$_2$CH$_2$CH$_2$NHMe | H |
| 48 | —OCH$_2$CH$_2$OCH$_2$CH$_2$CH$_2$NMe$_2$ | H |
| 49 | pyrrolidine-CH$_2$CH$_2$CH$_2$-O-CH$_2$CH$_2$-O- | H |
| 50 | piperidine-CH$_2$CH$_2$CH$_2$-O-CH$_2$CH$_2$-O- | H |
| 51 | HN-piperazine-CH$_2$CH$_2$CH$_2$-O-CH$_2$CH$_2$-O- | H |
| 52 | MeN-piperazine-CH$_2$CH$_2$CH$_2$-O-CH$_2$CH$_2$-O- | H |
| 53 | morpholine-CH$_2$CH$_2$CH$_2$-O-CH$_2$CH$_2$-O- | H |
| 54 | —OCH$_2$CH$_2$CH$_2$OCH$_2$CH$_2$OH | H |
| 55 | —OCH$_2$CH$_2$CH$_2$OCH$_2$CH$_2$OMe | H |
| 56 | —OCH$_2$CH$_2$CH$_2$OCH$_2$CH$_2$OEt | H |
| 57 | —OCH$_2$CH$_2$CH$_2$OCH$_2$CH$_2$NH$_2$ | H |
| 58 | —OCH$_2$CH$_2$CH$_2$OCH$_2$CH$_2$NHMe | H |
| 59 | —OCH$_2$CH$_2$CH$_2$OCH$_2$CH$_2$NMe$_2$ | H |
| 60 | pyrrolidine-CH$_2$CH$_2$-O-CH$_2$CH$_2$CH$_2$-O- | H |
| 61 | piperidine-CH$_2$CH$_2$-O-CH$_2$CH$_2$CH$_2$-O- | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 62 | piperazinyl-CH₂CH₂-O-CH₂CH₂CH₂-O- | H |
| 63 | 4-methylpiperazinyl-CH₂CH₂-O-CH₂CH₂CH₂-O- | H |
| 64 | morpholinyl-CH₂CH₂-O-CH₂CH₂CH₂-O- | H |
| 65 | —OCH₂CH₂CH₂OCH₂CH₂CH₂OH | H |
| 66 | —OCH₂CH₂CH₂OCH₂CH₂CH₂OMe | H |
| 67 | —OCH₂CH₂CH₂OCH₂CH₂CH₂OEt | H |
| 68 | —OCH₂CH₂CH₂OCH₂CH₂CH₂NH₂ | H |
| 69 | —OCH₂CH₂CH₂OCH₂CH₂CH₂NHMe | H |
| 70 | —OCH₂CH₂CH₂OCH₂CH₂CH₂NMe₂ | H |
| 71 | pyrrolidinyl-CH₂CH₂CH₂-O-CH₂CH₂CH₂-O- | H |
| 72 | piperidinyl-CH₂CH₂CH₂-O-CH₂CH₂CH₂-O- | H |
| 73 | piperazinyl-CH₂CH₂CH₂-O-CH₂CH₂CH₂-O- | H |
| 74 | 4-methylpiperazinyl-CH₂CH₂CH₂-O-CH₂CH₂CH₂-O- | H |
| 75 | morpholinyl-CH₂CH₂CH₂-O-CH₂CH₂CH₂-O- | H |
| 76 | —OCH₂CH₂NHCH₂CH₂OH | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 77 | —OCH$_2$CH$_2$NHCH$_2$CH$_2$OMe | H |
| 78 | —OCH$_2$CH$_2$NHCH$_2$CH$_2$OEt | H |
| 79 | —OCH$_2$CH$_2$NHCH$_2$CH$_2$NH$_2$ | H |
| 80 | —OCH$_2$CH$_2$NHCH$_2$CH$_2$NHMe | H |
| 81 | —OCH$_2$CH$_2$NHCH$_2$CH$_2$NMe$_2$ | H |
| 82 | pyrrolidinyl-CH$_2$CH$_2$-NH-CH$_2$CH$_2$-O- | H |
| 83 | piperidinyl-CH$_2$CH$_2$-NH-CH$_2$CH$_2$-O- | H |
| 84 | piperazinyl-CH$_2$CH$_2$-NH-CH$_2$CH$_2$-O- | H |
| 85 | 4-methylpiperazinyl-CH$_2$CH$_2$-NH-CH$_2$CH$_2$-O- | H |
| 86 | morpholinyl-CH$_2$CH$_2$-NH-CH$_2$CH$_2$-O- | H |
| 87 | —OCH$_2$CH$_2$NHCH$_2$CH$_2$CH$_2$OH | H |
| 88 | —OCH$_2$CH$_2$NHCH$_2$CH$_2$CH$_2$OMe | H |
| 89 | —OCH$_2$CH$_2$NHCH$_2$CH$_2$CH$_2$OEt | H |
| 90 | —OCH$_2$CH$_2$NHCH$_2$CH$_2$CH$_2$NH$_2$ | H |
| 91 | —OCH$_2$CH$_2$NHCH$_2$CH$_2$CH$_2$NHMe | H |
| 92 | —OCH$_2$CH$_2$NHCH$_2$CH$_2$CH$_2$NMe$_2$ | H |
| 93 | pyrrolidinyl-CH$_2$CH$_2$CH$_2$-NH-CH$_2$CH$_2$-O- | H |
| 94 | piperidinyl-CH$_2$CH$_2$CH$_2$-NH-CH$_2$CH$_2$-O- | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 95 | 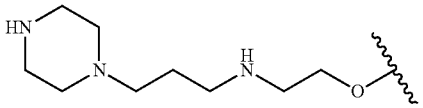 [SMILES: *OCCNCCCN1CCNCC1] | H |
| 96 | 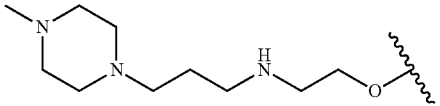 | H |
| 97 | 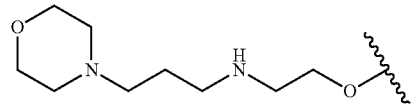 | H |
| 98 | —OCH$_2$CH$_2$CH$_2$NHCH$_2$CH$_2$OH | H |
| 99 | —OCH$_2$CH$_2$CH$_2$NHCH$_2$CH$_2$OMe | H |
| 100 | —OCH$_2$CH$_2$CH$_2$NHCH$_2$CH$_2$OEt | H |
| 101 | —OCH$_2$CH$_2$CH$_2$NHCH$_2$CH$_2$NH$_2$ | H |
| 102 | —OCH$_2$CH$_2$CH$_2$NHCH$_2$CH$_2$NHMe | H |
| 103 | —OCH$_2$CH$_2$CH$_2$NHCH$_2$CH$_2$NMe$_2$ | H |
| 104 | 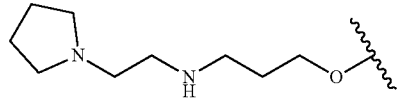 [SMILES: *OCCCNCCN1CCCC1] | H |
| 105 | 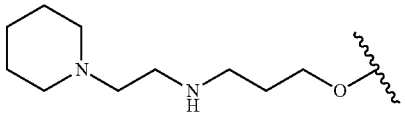 [SMILES: *OCCCNCCN1CCCCC1] | H |
| 106 | 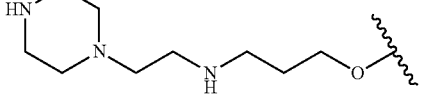 | H |
| 107 | 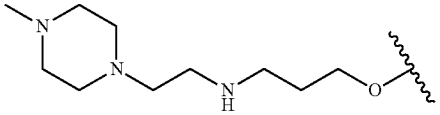 [SMILES: *OCCCNCCN1CCN(C)CC1] | H |
| 108 | 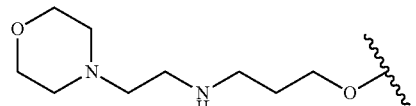 | H |
| 109 | —OCH$_2$CH$_2$CH$_2$NHCH$_2$CH$_2$CH$_2$OH | H |
| 110 | —OCH$_2$CH$_2$CH$_2$NHCH$_2$CH$_2$CH$_2$OMe | H |
| 111 | —OCH$_2$CH$_2$CH$_2$NHCH$_2$CH$_2$CH$_2$OEt | H |
| 112 | —OCH$_2$CH$_2$CH$_2$NHCH$_2$CH$_2$CH$_2$NH$_2$ | H |
| 113 | —OCH$_2$CH$_2$CH$_2$NHCH$_2$CH$_2$CH$_2$NHMe | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 114 | —OCH$_2$CH$_2$CH$_2$NHCH$_2$CH$_2$CH$_2$NMe$_2$ | H |
| 115 | pyrrolidine-N-(CH$_2$)$_3$-NH-(CH$_2$)$_3$-O— | H |
| 116 | piperidine-N-(CH$_2$)$_3$-NH-(CH$_2$)$_3$-O— | H |
| 117 | piperazine-N-(CH$_2$)$_3$-NH-(CH$_2$)$_3$-O— | H |
| 118 | 4-methylpiperazine-N-(CH$_2$)$_3$-NH-(CH$_2$)$_3$-O— | H |
| 119 | morpholine-N-(CH$_2$)$_3$-NH-(CH$_2$)$_3$-O— | H |
| 120 | —OCH$_2$CH$_2$N(CH$_2$CH$_2$OH)$_2$ | H |
| 121 | —OCH$_2$CH$_2$N(CH$_2$CH$_2$OMe)$_2$ | H |
| 122 | —OCH$_2$CH$_2$N(CH$_2$CH$_2$OEt)$_2$ | H |
| 123 | —OCH$_2$CH$_2$N(CH$_2$CH$_2$NH$_2$)$_2$ | H |
| 124 | —OCH$_2$CH$_2$N(CH$_2$CH$_2$NHMe)$_2$ | H |
| 125 | —OCH$_2$CH$_2$N(CH$_2$CH$_2$NMe$_2$)$_2$ | H |
| 126 | —OCH$_2$CH$_2$N(CH$_2$CH$_2$CH$_2$OH)$_2$ | H |
| 127 | —OCH$_2$CH$_2$N(CH$_2$CH$_2$CH$_2$OMe)$_2$ | H |
| 128 | —OCH$_2$CH$_2$N(CH$_2$CH$_2$CH$_2$OEt)$_2$ | H |
| 129 | —OCH$_2$CH$_2$CH$_2$(HCH$_2$CH$_2$OH)$_2$ | H |
| 130 | —OCH$_2$CH$_2$CH$_2$N(CH$_2$CH$_2$OMe)$_2$ | H |
| 131 | —OCH$_2$CH$_2$CH$_2$N(CH$_2$CH$_2$OEt)$_2$ | H |
| 132 | —OCH$_2$CH$_2$CH$_2$N(CH$_2$CH$_2$CH$_2$OH)$_2$ | H |
| 133 | —OCH$_2$CH$_2$CH$_2$N(CH$_2$CH$_2$CH$_2$OMe)$_2$ | H |
| 134 | —OCH$_2$CH$_2$CH$_2$N(CH$_2$CH$_2$CH$_2$OEt)$_2$ | H |
| 135 | —OCH$_2$CH$_2$NMeCH$_2$CH$_2$OH | H |
| 136 | —OCH$_2$CH$_2$NMeCH$_2$CH$_2$OMe | H |
| 137 | —OCH$_2$CH$_2$NMeCH$_2$CH$_2$OEt | H |
| 138 | —OCH$_2$CH$_2$NMeCH$_2$CH$_2$NH$_2$ | H |
| 139 | —OCH$_2$CH$_2$NMeCH$_2$CH$_2$NHMe | H |
| 140 | —OCH$_2$CH$_2$NMeCH$_2$CH$_2$NMe$_2$ | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 141 | [pyrrolidine-CH2CH2-N(Me)-CH2CH2-O-] | H |
| 142 | [piperidine-CH2CH2-N(Me)-CH2CH2-O-] | H |
| 143 | [HN-piperazine-CH2CH2-N(Me)-CH2CH2-O-] | H |
| 144 | [N-methylpiperazine-CH2CH2-N(Me)-CH2CH2-O-] | H |
| 145 | [morpholine-CH2CH2-N(Me)-CH2CH2-O-] | H |
| 146 | —OCH$_2$CH$_2$NMeCH$_2$CH$_2$CH$_2$OH | H |
| 147 | —OCH$_2$CH$_2$NMeCH$_2$CH$_2$CH$_2$OMe | H |
| 148 | —OCH$_2$CH$_2$NMeCH$_2$CH$_2$CH$_2$OEt | H |
| 149 | —OCH$_2$CH$_2$NMeCH$_2$CH$_2$CH$_2$NH$_2$ | H |
| 150 | —OCH$_2$CH$_2$NMeCH$_2$CH$_2$CH$_2$NHMe | H |
| 151 | —OCH$_2$CH$_2$NMeCH$_2$CH$_2$CH$_2$NMe$_2$ | H |
| 152 | [pyrrolidine-CH2CH2CH2-N(Me)-CH2CH2-O-] | H |
| 153 | [piperidine-CH2CH2CH2-N(Me)-CH2CH2-O-] | H |
| 154 | [HN-piperazine-CH2CH2CH2-N(Me)-CH2CH2-O-] | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 155 | [structure: 4-methylpiperazine-N-CH2CH2CH2-N(Me)-CH2CH2-O-] | H |
| 156 | [structure: morpholine-N-CH2CH2CH2-N(Me)-CH2CH2-O-] | H |
| 157 | —OCH$_2$CH$_2$CH$_2$NMeCH$_2$CH$_2$OH | H |
| 158 | —OCH$_2$CH$_2$CH$_2$NMeCH$_2$CH$_2$OMe | H |
| 159 | —OCH$_2$CH$_2$CH$_2$NMeCH$_2$CH$_2$OEt | H |
| 160 | —OCH$_2$CH$_2$CH$_2$NMeCH$_2$CH$_2$NH$_2$ | H |
| 161 | —OCH$_2$CH$_2$CH$_2$NMeCH$_2$CH$_2$NHMe | H |
| 162 | —OCH$_2$CH$_2$CH$_2$NMeCH$_2$CH$_2$NMe$_2$ | H |
| 163 | [structure: pyrrolidine-N-CH2CH2-N(Me)-CH2CH2CH2-O-] | H |
| 164 | [structure: piperidine-N-CH2CH2-N(Me)-CH2CH2CH2-O-] | H |
| 165 | [structure: piperazine(HN)-N-CH2CH2-N(Me)-CH2CH2CH2-O-] | H |
| 166 | [structure: 4-methylpiperazine-N-CH2CH2-N(Me)-CH2CH2CH2-O-] | H |
| 167 | [structure: morpholine-N-CH2CH2-N(Me)-CH2CH2CH2-O-] | H |
| 168 | —OCH$_2$CH$_2$CH$_2$NMeCH$_2$CH$_2$CH$_2$OH | H |
| 169 | —OCH$_2$CH$_2$CH$_2$NMeCH$_2$CH$_2$CH$_2$OMe | H |
| 170 | —OCH$_2$CH$_2$CH$_2$NMeCH$_2$CH$_2$CH$_2$OEt | H |
| 171 | —OCH$_2$CH$_2$CH$_2$NMeCH$_2$CH$_2$CH$_2$NH$_2$ | H |
| 172 | —OCH$_2$CH$_2$CH$_2$NMeCH$_2$CH$_2$CH$_2$NHMe | H |
| 173 | —OCH$_2$CH$_2$CH$_2$NMeCH$_2$CH$_2$CH$_2$NMe$_2$ | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 174 | pyrrolidine-N-(CH₂)₃-N(Me)-(CH₂)₃-O- | H |
| 175 | piperidine-N-(CH₂)₃-N(Me)-(CH₂)₃-O- | H |
| 176 | HN-piperazine-N-(CH₂)₃-N(Me)-(CH₂)₃-O- | H |
| 177 | MeN-piperazine-N-(CH₂)₃-N(Me)-(CH₂)₃-O- | H |
| 178 | morpholine-N-(CH₂)₃-N(Me)-(CH₂)₃-O- | H |
| 179 | —CH₂OH | H |
| 180 | —CH₂OMe | H |
| 181 | —CH₂OEt | H |
| 182 | —CH₂NH₂ | H |
| 183 | —CH₂NHMe | H |
| 184 | —CH₂NMe₂ | H |
| 185 | pyrrolidine-N-CH₂- | H |
| 186 | piperidine-N-CH₂- | H |
| 187 | HN-piperazine-N-CH₂- | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 188 | N-methylpiperazinyl-CH(CH3)- | H |
| 189 | morpholinyl-CH(CH3)- | H |
| 190 | —CH$_2$CH$_2$OH | H |
| 191 | —CH$_2$CH$_2$OMe | H |
| 192 | —CH$_2$CH$_2$OEt | H |
| 193 | —CH$_2$CH$_2$NH$_2$ | H |
| 194 | —CH$_2$CH$_2$NHMe | H |
| 195 | —CH$_2$CH$_2$NMe$_2$ | H |
| 196 | pyrrolidinyl-CH$_2$CH$_2$-CH(CH3)- | H |
| 197 | piperidinyl-CH$_2$CH$_2$-CH(CH3)- | H |
| 198 | piperazinyl-CH$_2$CH$_2$-CH(CH3)- | H |
| 199 | N-methylpiperazinyl-CH$_2$CH$_2$-CH(CH3)- | H |
| 200 | morpholinyl-CH$_2$CH$_2$-CH(CH3)- | H |
| 201 | —CH$_2$CH$_2$CH$_2$OH | H |
| 202 | —CH$_2$CH$_2$CH$_2$OMe | H |
| 203 | —CH$_2$CH$_2$CH$_2$OEt | H |
| 204 | —CH$_2$CH$_2$CH$_2$NH$_2$ | H |
| 205 | —CH$_2$CH$_2$CH$_2$NHMe | H |
| 206 | —CH$_2$CH$_2$CH$_2$NMe$_2$ | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 207 | pyrrolidinyl-(CH₂)₃– | H |
| 208 | piperidinyl-(CH₂)₃– | H |
| 209 | piperazinyl-(CH₂)₃– | H |
| 210 | 4-methylpiperazinyl-(CH₂)₃– | H |
| 211 | morpholinyl-(CH₂)₃– | H |
| 212 | —CH₂CH₂CH₂CH₂OH | H |
| 213 | —CH₂CH₂CH₂CH₂OMe | H |
| 214 | —CH₂CH₂CH₂CH₂OEt | H |
| 215 | —CH₂CH₂CH₂CH₂NH₂ | H |
| 216 | —CH₂CH₂CH₂CH₂NHMe | H |
| 217 | —CH₂CH₂CH₂CH₂NMe₂ | H |
| 218 | pyrrolidinyl-(CH₂)₄– | H |
| 219 | piperidinyl-(CH₂)₄– | H |
| 220 | piperazinyl-(CH₂)₄– | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10), or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 221 | 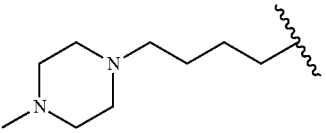 [SMILES: *CCCCN1CCN(C)CC1] | H |
| 222 | 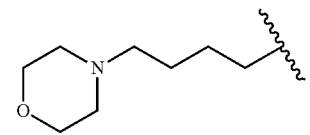 [SMILES: *CCCCN1CCOCC1] | H |
| 223 | —CH$_2$OCH$_2$CH$_2$OH | H |
| 224 | —CH$_2$OCH$_2$CH$_2$OMe | H |
| 225 | —CH$_2$OCH$_2$CH$_2$OEt | H |
| 226 | —CH$_2$OCH$_2$CH$_2$NH$_2$ | H |
| 227 | —CH$_2$OCH$_2$CH$_2$NHMe | H |
| 228 | —CH$_2$OCH$_2$CH$_2$NMe$_2$ | H |
| 229 | 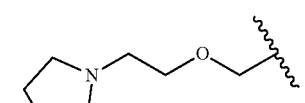 | H |
| 230 | 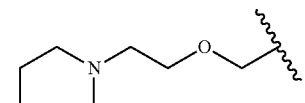 | H |
| 231 | 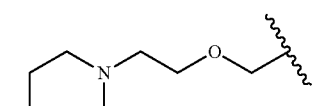 | H |
| 232 | 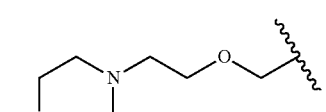 | H |
| 233 | 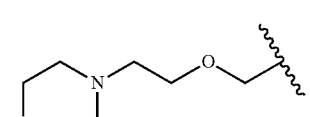 | H |
| 234 | —CH$_2$NHCH$_2$CH$_2$OH | H |
| 235 | —CH$_2$NHCH$_2$CH$_2$OMe | H |
| 236 | —CH$_2$NHCH$_2$CH$_2$OEt | H |
| 237 | —CH$_2$NHCH$_2$CH$_2$NH$_2$ | H |
| 238 | —CH$_2$NHCH$_2$CH$_2$NHMe | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 239 | —CH$_2$NHCH$_2$CH$_2$NMe$_2$ | H |
| 240 | pyrrolidin-1-yl-CH$_2$CH$_2$NH— | H |
| 241 | piperidin-1-yl-CH$_2$CH$_2$NH— | H |
| 242 | piperazin-1-yl-CH$_2$CH$_2$NH— | H |
| 243 | 4-methylpiperazin-1-yl-CH$_2$CH$_2$NH— | H |
| 244 | morpholin-4-yl-CH$_2$CH$_2$NH— | H |
| 245 | —CH$_2$N(CH$_2$CH$_2$OH)$_2$ | H |
| 246 | —CH$_2$N(CH$_2$CH$_2$OMe)$_2$ | H |
| 247 | —CH$_2$N(CH$_2$CH$_2$OEt)$_2$ | H |
| 248 | —CH$_2$NMeCH$_2$CH$_2$OH | H |
| 249 | —CH$_2$NMeCH$_2$CH$_2$OMe | H |
| 250 | —CH$_2$NMeCH$_2$CH$_2$OEt | H |
| 251 | —CH$_2$NMeCH$_2$CH$_2$NH$_2$ | H |
| 252 | —CH$_2$NMeCH$_2$CH$_2$NHMe | H |
| 253 | —CH$_2$NMeCH$_2$CH$_2$NMe$_2$ | H |
| 254 | pyrrolidin-1-yl-CH$_2$CH$_2$N(Me)— | H |
| 255 | piperidin-1-yl-CH$_2$CH$_2$N(Me)— | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 256 | 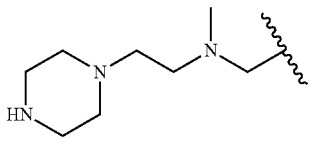 [SMILES: *CN(C)CCN1CCNCC1] | H |
| 257 | 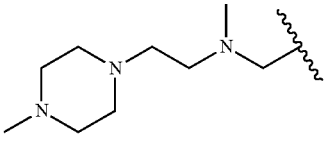 [SMILES: *CN(C)CCN1CCN(C)CC1] | H |
| 258 | 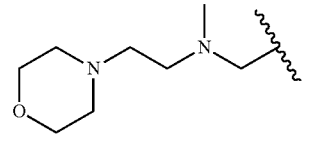 [SMILES: *CN(C)CCN1CCOCC1] | H |
| 259 | —CH$_2$CH$_2$OCH$_2$CH$_2$OH | H |
| 260 | —CH$_2$CH$_2$OCH$_2$CH$_2$OMe | H |
| 261 | —CH$_2$CH$_2$OCH$_2$CH$_2$OEt | H |
| 262 | —CH$_2$CH$_2$OCH$_2$CH$_2$NH$_2$ | H |
| 263 | —CH$_2$CH$_2$OCH$_2$CH$_2$NHMe | H |
| 264 | —CH$_2$CH$_2$OCH$_2$CH$_2$NMe$_2$ | H |
| 265 | 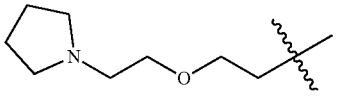 [SMILES: *CCOCCN1CCCC1] | H |
| 266 | 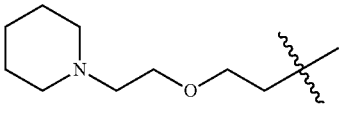 [SMILES: *CCOCCN1CCCCC1] | H |
| 267 | 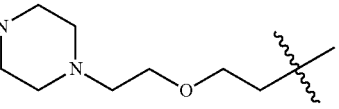 | H |
| 268 | 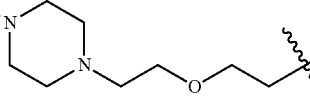 | H |
| 269 | 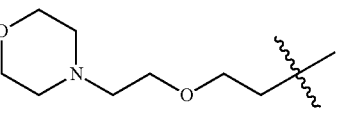 | H |
| 270 | —CH$_2$CH$_2$NHCH$_2$CH$_2$OH | H |
| 271 | —CH$_2$CH$_2$NHCH$_2$CH$_2$OMe | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 272 | —CH$_2$CH$_2$NHCH$_2$CH$_2$OEt | H |
| 273 | —CH$_2$CH$_2$NHCH$_2$CH$_2$NH$_2$ | H |
| 274 | —CH$_2$CH$_2$NHCH$_2$CH$_2$NHMe | H |
| 275 | —CH$_2$CH$_2$NHCH$_2$CH$_2$NMe$_2$ | H |
| 276 | pyrrolidinyl-CH$_2$CH$_2$-NH-CH$_2$CH$_2$- | H |
| 277 | piperidinyl-CH$_2$CH$_2$-NH-CH$_2$CH$_2$- | H |
| 278 | HN-piperazinyl-CH$_2$CH$_2$-NH-CH$_2$CH$_2$- | H |
| 279 | N-methylpiperazinyl-CH$_2$CH$_2$-NH-CH$_2$CH$_2$- | H |
| 280 | morpholinyl-CH$_2$CH$_2$-NH-CH$_2$CH$_2$- | H |
| 281 | —CH$_2$CH$_2$N(CH$_2$CH$_2$OH)$_2$ | H |
| 282 | —CH$_2$CH$_2$N(CH$_2$CH$_2$OMe)$_2$ | H |
| 283 | —CH$_2$CH$_2$N(CH$_2$CH$_2$OEt)$_2$ | H |
| 284 | —CH$_2$CH$_2$NMeCH$_2$CH$_2$OH | H |
| 285 | —CH$_2$CH$_2$NMeCH$_2$CH$_2$OMe | H |
| 286 | —CH$_2$CH$_2$NMeCH$_2$CH$_2$OEt | H |
| 287 | —CH$_2$CH$_2$NMeCH$_2$CH$_2$NH$_2$ | H |
| 288 | —CH$_2$CH$_2$NMeCH$_2$CH$_2$NHMe | H |
| 289 | —CH$_2$CH$_2$NMeCH$_2$CH$_2$NMe$_2$ | H |
| 290 | pyrrolidinyl-CH$_2$CH$_2$-NMe-CH$_2$CH$_2$- | H |
| 291 | piperidinyl-CH$_2$CH$_2$-NMe-CH$_2$CH$_2$- | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 292 | piperazine-CH₂CH₂-N(Me)- group | H |
| 293 | 4-methylpiperazine-CH₂CH₂-N(Me)- group | H |
| 294 | morpholine-CH₂CH₂-N(Me)- group | H |
| 295 | —NH | H |
| 296 | —NHMe | H |
| 297 | —NMe₂ | H |
| 298 | —NHEt | H |
| 299 | —NHPr | H |
| 300 | —NHiPr | H |
| 301 | —NHcPr | H |
| 302 | —NHcBu | H |
| 303 | —NHcPn | H |
| 304 | —NHcHex | H |
| 305 | —NHCH₂CH₂OH | H |
| 306 | —NHCH₂CH₂OMe | H |
| 307 | —NHCH₂CH₂OEt | H |
| 308 | —NHCH₂CH₂NH₂ | H |
| 309 | —NHCH₂CH₂NHMe | H |
| 310 | —NHCH₂CH₂NMe₂ | H |
| 311 | pyrrolidine-CH₂CH₂-NH- group | H |
| 312 | piperidine-CH₂CH₂-NH- group | H |
| 313 | piperazine-CH₂CH₂-NH- group | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 314 | 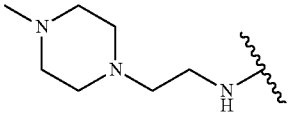 [SMILES: *NCCN1CCN(C)CC1] | H |
| 315 | 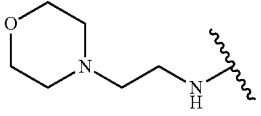 | H |
| 316 | —NHCH$_2$CH$_2$CH$_2$OH | H |
| 317 | —NHCH$_2$CH$_2$CH$_2$OMe | H |
| 318 | —NHCH$_2$CH$_2$CH$_2$OEt | H |
| 319 | —NHCH$_2$CH$_2$CH$_2$NH$_2$ | H |
| 320 | —NHCH$_2$CH$_2$CH$_2$NHMe | H |
| 321 | —NHCH$_2$CH$_2$CH$_2$NMe$_2$ | H |
| 322 | 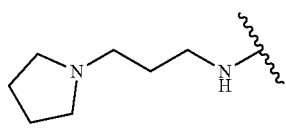 [SMILES: *NCCCN1CCCC1] | H |
| 323 | 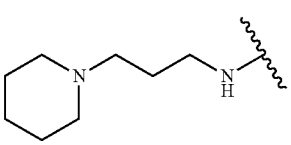 [SMILES: *NCCCN1CCCCC1] | H |
| 324 | 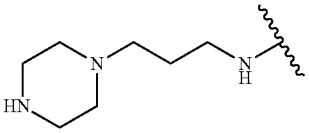 | H |
| 325 | 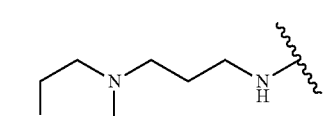 | H |
| 326 | 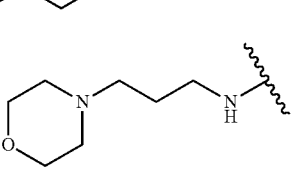 | H |
| 327 | —NHCH$_2$CH$_2$OCH$_2$CH$_2$OH | H |
| 328 | —NHCH$_2$CH$_2$OCH$_2$CH$_2$OMe | H |
| 329 | —NHCH$_2$CH$_2$OCH$_2$CH$_2$OEt | H |
| 330 | —NHCH$_2$CH$_2$OCH$_2$CH$_2$NH$_2$ | H |
| 331 | —NHCH$_2$CH$_2$OCH$_2$CH$_2$NHMe | H |
| 332 | —NHCH$_2$CH$_2$OCH$_2$CH$_2$NMe$_2$ | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 333 | —N(CH$_2$CH$_2$OH)$_2$ | H |
| 334 | —N(CH$_2$CH$_2$OMe)$_2$ | H |
| 335 | —N(CH$_2$CH$_2$OEt)$_2$ | H |
| 336 | —N(CH$_2$CH$_2$CH$_2$OH)$_2$ | H |
| 337 | —N(CH$_2$CH$_2$CH$_2$OMe)$_2$ | H |
| 338 | —N(CH$_2$CH$_2$CH$_2$OEt)$_2$ | H |
| 339 | 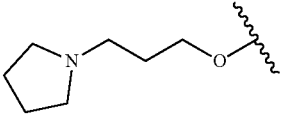 [SMILES: *OCCCN1CCCC1] | H |
| 340 | —N(CH$_2$CH$_2$OCH$_2$CH$_2$OH)$_2$ | H |
| 341 | —N(CH$_2$CH$_2$OCH$_2$CH$_2$OMe)$_2$ | H |
| 342 | —N(CH$_2$CH$_2$OCH$_2$CH$_2$OEt)$_2$ | H |
| 343 | —NMeCH$_2$CH$_2$OH | H |
| 344 | —NMeCH$_2$CH$_2$OMe | H |
| 345 | —NMeCH$_2$CH$_2$OEt | H |
| 346 | —NMeCH$_2$CH$_2$NH$_2$ | H |
| 347 | —NMeCH$_2$CH$_2$NHMe | H |
| 348 | —NMeCH$_2$CH$_2$NMe$_2$ | H |
| 349 | 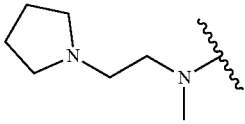 [SMILES: *N(C)CCN1CCCC1] | H |
| 350 | 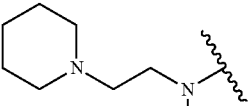 | H |
| 351 | 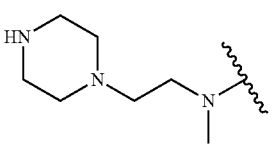 [SMILES: *N(C)CCN1CCNCC1] | H |
| 352 | 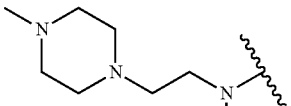 | H |
| 353 | 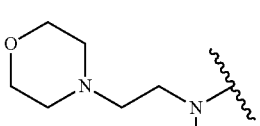 | H |
| 354 | —NMeCH$_2$CH$_2$CH$_2$OH | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 355 | —NMeCH$_2$CH$_2$CH$_2$OMe | H |
| 356 | —NMeCH$_2$CH$_2$CH$_2$OEt | H |
| 357 | —NMeCH$_2$CH$_2$CH$_2$NH$_2$ | H |
| 358 | —NMeCH$_2$CH$_2$CH$_2$NHMe | H |
| 359 | —NMeCH$_2$CH$_2$CH$_2$NMe$_2$ | H |
| 360 | 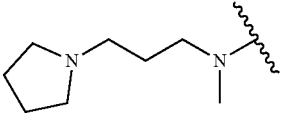 [SMILES: *N(C)CCCN1CCCC1] | H |
| 361 | 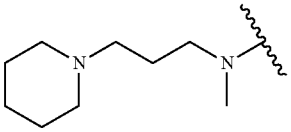 [SMILES: *N(C)CCCN1CCCCC1] | H |
| 362 | 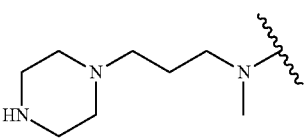 | H |
| 363 | 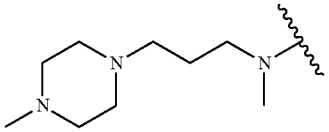 [SMILES: *N(C)CCCN1CCN(C)CC1] | H |
| 364 | 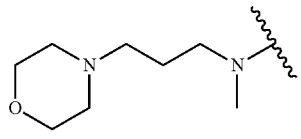 [SMILES: *N(C)CCCN1CCOCC1] | H |
| 365 | —NMeCH$_2$CH$_2$OCH$_2$CH$_2$OH | H |
| 366 | —NMeCH$_2$CH$_2$OCH$_2$CH$_2$OMe | H |
| 367 | —NMeCH$_2$CH$_2$OCH$_2$CH$_2$OEt | H |
| 368 | —NMeCH$_2$CH$_2$OCH$_2$CH$_2$NH$_2$ | H |
| 369 | —NMeCH$_2$CH$_2$OCH$_2$CH$_2$NHMe | H |
| 370 | —NMeCH$_2$CH$_2$OCH$_2$CH$_2$NMe$_2$ | H |
| 371 | —O(C=O)OMe | H |
| 372 | —O(C=O)OEt | H |
| 373 | —O(C=O)OnPr | H |
| 374 | —O(C=O)OiPr | H |
| 375 | —O(C=O)OcPr | H |
| 376 | —O(C=O)OcBu | H |
| 377 | —O(C=O)OcPn | H |
| 378 | —O(C=O)OcHex | H |
| 379 | —COOH | H |
| 380 | —CH$_2$(C=O)OH | H |
| 381 | —CH$_2$(C=O)OMe | H |
| 382 | —CH$_2$(C=O)OEt | H |
| 383 | —CH$_2$(C=O)OnPr | H |
| 384 | —CH$_2$(C=O)OiPr | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 385 | —CH₂(C═O)OcPn | H |
| 386 | —CH₂(C═O)OcBu | H |
| 387 | —CH₂(C═O)OcPn | H |
| 388 | —CH₂(C═O)OcHex | H |
| 389 | —OCH₂(C═O)OH | H |
| 390 | —OCH₂(C═O)OMe | H |
| 391 | —OCH₂(C═O)OEt | H |
| 392 | —OCH₂(C═O)OnPr | H |
| 393 | —OCH₂(C═O)OiPr | H |
| 394 | —OCH₂(C═O)OcPr | H |
| 395 | —OCH₂(C═O)OcBu | H |
| 396 | —OCH₂(C═O)OcPn | H |
| 397 | —OCH₂(C═O)OcHex | H |
| 398 | —NHCH₂(C═O)OH | H |
| 399 | —NHCH₂(C═O)OMe | H |
| 400 | —NHCH₂(C═O)OEt | H |
| 401 | —NHCH₂(C═O)OnPr | H |
| 402 | —NHCH₂(C═O)OiPr | H |
| 403 | —NHCH₂(C═O)OcPr | H |
| 404 | —NHCH₂(C═O)OcBu | H |
| 405 | —NHCH₂(C═O)OcPn | H |
| 406 | —NHCH₂(C═O)OcHex | H |
| 407 | H | —OH |
| 408 | H | —OMe |
| 409 | H | —OEt |
| 410 | H | —OPr |
| 411 | H | —OiPr |
| 412 | H | —OcPr |
| 413 | H | —OcBu |
| 414 | H | —OcPn |
| 415 | H | —OcHex |
| 416 | H | —OCH₂CH₂OH |
| 417 | H | —OCH₂CH₂OMe |
| 418 | H | —OCH₂CH₂OEt |
| 419 | H | —OCH₂CH₂NH₂ |
| 420 | H | —OCH₂CH₂NHMe |
| 421 | H | —OCH₂CH₂NMe₂ |
| 422 | H | 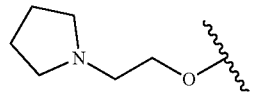 |
| 423 | H | 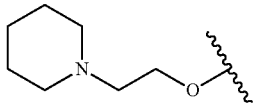 |
| 424 | H | 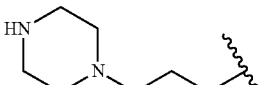 |
| 425 | H | 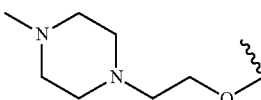 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 426 | H | 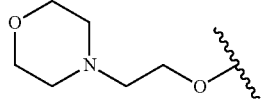 [SMILES: *OCCN1CCOCC1] |
| 427 | H | —OCH$_2$CH$_2$CH$_2$OH |
| 428 | H | —OCH$_2$CH$_2$CH$_2$OMe |
| 429 | H | —OCH$_2$CH$_2$CH$_2$OEt |
| 430 | H | —OCH$_2$CH$_2$CH$_2$NH$_2$ |
| 431 | H | —OCH$_2$CH$_2$CH$_2$NHMe |
| 432 | H | —OCH$_2$CH$_2$CH$_2$NMe$_2$ |
| 433 | H | 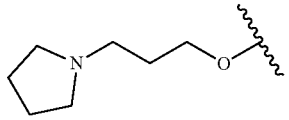 [SMILES: *OCCCN1CCCC1] |
| 434 | H | 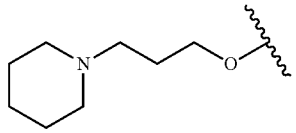 [SMILES: *OCCCN1CCCCC1] |
| 435 | H | 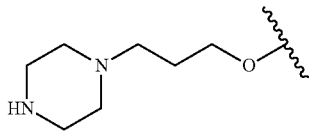 [SMILES: *OCCCN1CCNCC1] |
| 436 | H | 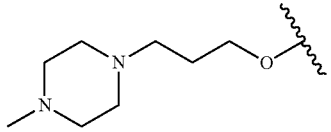 [SMILES: *OCCCN1CCN(C)CC1] |
| 437 | H | 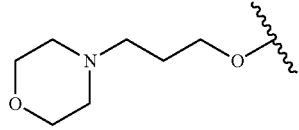 [SMILES: *OCCCN1CCOCC1] |
| 438 | H | —OCH$_2$CH$_2$OCH$_2$CH$_2$OH |
| 439 | H | —OCH$_2$CH$_2$OCH$_2$CH$_2$OMe |
| 440 | H | —OCH$_2$CH$_2$OCH$_2$CH$_2$OEt |
| 441 | H | —OCH$_2$CH$_2$OCH$_2$CH$_2$NH$_2$ |
| 442 | H | —OCH$_2$CH$_2$OCH$_2$CH$_2$NHMe |
| 443 | H | —OCH$_2$CH$_2$OCH$_2$CH$_2$NMe$_2$ |
| 444 | H | 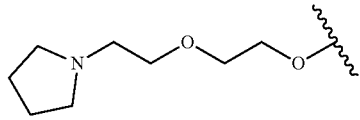 [SMILES: *OCCOCCN1CCCC1] |

US 10,336,721 B2

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 445 | H | 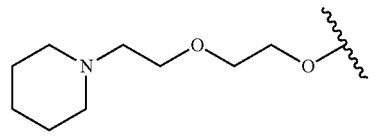 [SMILES: *OCCOCCN1CCCCC1] |
| 446 | H | 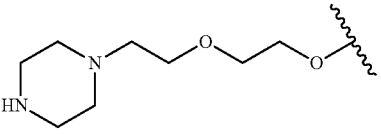 |
| 447 | H | 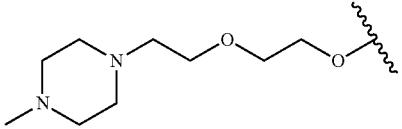 [SMILES: *OCCOCCN1CCN(C)CC1] |
| 448 | H | 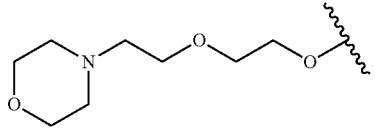 [SMILES: *OCCOCCN1CCOCC1] |
| 449 | H | —OCH$_2$CH$_2$OCH$_2$CH$_2$CH$_2$OH |
| 450 | H | —OCH$_2$CH$_2$OCH$_2$CH$_2$CH$_2$OMe |
| 451 | H | —OCH$_2$CH$_2$OCH$_2$CH$_2$CH$_2$OEt |
| 452 | H | —OCH$_2$CH$_2$OCH$_2$CH$_2$CH$_2$NH$_2$ |
| 453 | H | —OCH$_2$CH$_2$OCH$_2$CH$_2$CH$_2$NHMe |
| 454 | H | —OCH$_2$CH$_2$OCH$_2$CH$_2$CH$_2$NMe$_2$ |
| 455 | H | 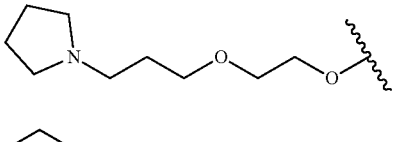 |
| 456 | H | 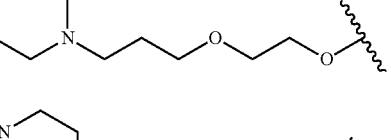 |
| 457 | H | 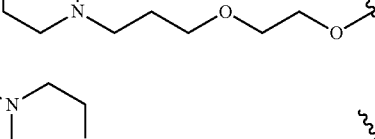 |
| 458 | H | 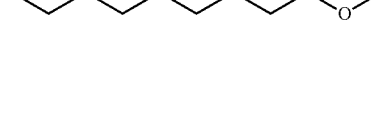 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68, (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 459 | H | 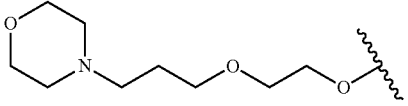 |
| 460 | H | —OCH$_2$CH$_2$CH$_2$OCH$_2$CH$_2$OH |
| 461 | H | —OCH$_2$CH$_2$CH$_2$OCH$_2$CH$_2$OMe |
| 462 | H | —OCH$_2$CH$_2$CH$_2$OCH$_2$CH$_2$OEt |
| 463 | H | —OCH$_2$CH$_2$CH$_2$OCH$_2$CH$_2$NH$_2$ |
| 464 | H | —OCH$_2$CH$_2$CH$_2$OCH$_2$CH$_2$NHMe |
| 465 | H | —OCH$_2$CH$_2$CH$_2$OCH$_2$CH$_2$NMe$_2$ |
| 466 | H | 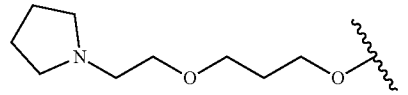 [SMILES: *OCCCOCCN1CCCC1] |
| 467 | H | 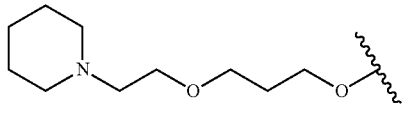 [SMILES: *OCCCOCCN1CCCCC1] |
| 468 | H | 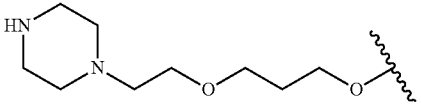 [SMILES: *OCCCOCCN1CCNCC1] |
| 469 | H | 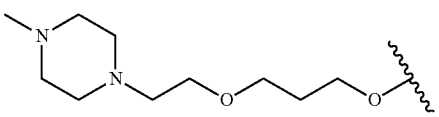 [SMILES: *OCCCOCCN1CCN(C)CC1] |
| 470 | H | 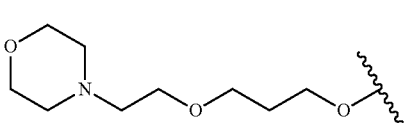 [SMILES: *OCCCOCCN1CCOCC1] |
| 471 | H | —OCH$_2$CH$_2$CH$_2$OCH$_2$CH$_2$CH$_2$OH |
| 472 | H | —OCH$_2$CH$_2$CH$_2$OCH$_2$CH$_2$CH$_2$OMe |
| 473 | H | —OCH$_2$CH$_2$CH$_2$OCH$_2$CH$_2$CH$_2$OEt |
| 474 | H | —OCH$_2$CH$_2$CH$_2$OCH$_2$CH$_2$CH$_2$NH$_2$ |
| 475 | H | —OCH$_2$CH$_2$CH$_2$OCH$_2$CH$_2$CH$_2$NHMe |
| 476 | H | —OCH$_2$CH$_2$CH$_2$OCH$_2$CH$_2$CH$_2$NMe$_2$ |
| 477 | H | 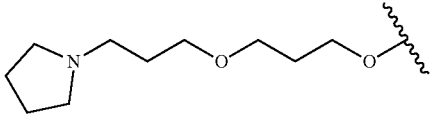 [SMILES: *OCCCOCCCN1CCCC1] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 478 | H | 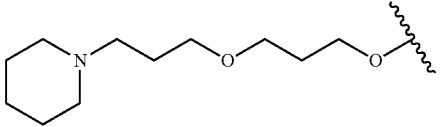 [SMILES: *OCCCOCCCN1CCCCC1] |
| 479 | H | 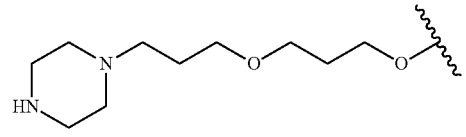 [SMILES: *OCCCOCCCN1CCNCC1] |
| 480 | H | 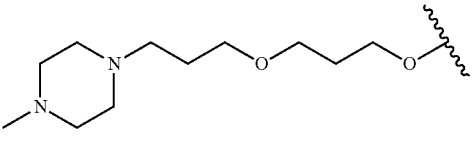 [SMILES: *OCCCOCCCN1CCN(C)CC1] |
| 481 | H | 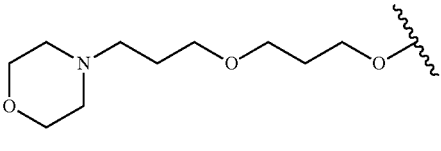 [SMILES: *OCCCOCCCN1CCOCC1] |
| 482 | H | —OCH$_2$CH$_2$NHCH$_2$CH$_2$OH |
| 483 | H | —OCH$_2$CH$_2$NHCH$_2$CH$_2$OMe |
| 484 | H | —OCH$_2$CH$_2$NHCH$_2$CH$_2$OEt |
| 485 | H | —OCH$_2$CH$_2$NHCH$_2$CH$_2$NH$_2$ |
| 486 | H | —OCH$_2$CH$_2$NHCH$_2$CH$_2$NHMe |
| 487 | H | —OCH$_2$CH$_2$NHCH$_2$CH$_2$NMe$_2$ |
| 488 | H | 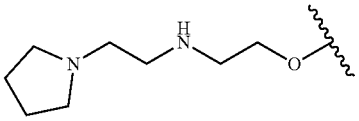 [SMILES: *OCCNCCN1CCCC1] |
| 489 | H | 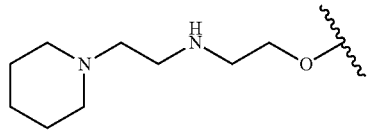 [SMILES: *OCCNCCN1CCCCC1] |
| 490 | H | 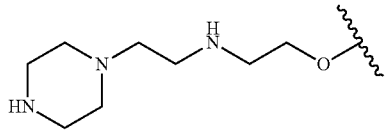 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 491 | H | [structure: N-methylpiperazine-CH2CH2-NH-CH2CH2-O-] |
| 492 | H | [structure: morpholine-CH2CH2-NH-CH2CH2-O-] |
| 493 | H | —OCH₂CH₂NHCH₂CH₂CH₂OH |
| 494 | H | —OCH₂CH₂NHCH₂CH₂CH₂OMe |
| 495 | H | —OCH₂CH₂NHCH₂CH₂CH₂OEt |
| 496 | H | —OCH₂CH₂NHCH₂CH₂CH₂NH₂ |
| 497 | H | —OCH₂CH₂NHCH₂CH₂CH₂NHMe |
| 498 | H | —OCH₂CH₂NHCH₂CH₂CH₂NMe₂ |
| 499 | H | [structure: pyrrolidine-CH2CH2CH2-NH-CH2CH2-O-] |
| 500 | H | [structure: piperidine-CH2CH2CH2-NH-CH2CH2-O-] |
| 501 | H | [structure: piperazine(NH)-CH2CH2CH2-NH-CH2CH2-O-] |
| 502 | H | [structure: N-methylpiperazine-CH2CH2CH2-NH-CH2CH2-O-] |
| 503 | H | [structure: morpholine-CH2CH2CH2-NH-CH2CH2-O-] |
| 504 | H | —OCH₂CH₂CH₂NHCH₂CH₂OH |
| 505 | H | —OCH₂CH₂CH₂NHCH₂CH₂OMe |
| 506 | H | —OCH₂CH₂CH₂NHCH₂CH₂OEt |
| 507 | H | —OCH₂CH₂CH₂NHCH₂CH₂NH₂ |
| 508 | H | —OCH₂CH₂CH₂NHCH₂CH₂NHMe |
| 509 | H | —OCH₂CH₂CH₂NHCH₂CH₂NMe₂ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 510 | H | [pyrrolidine-N-CH₂CH₂-NH-CH₂CH₂CH₂-O-] |
| 511 | H | [piperidine-N-CH₂CH₂-NH-CH₂CH₂CH₂-O-] |
| 512 | H | [piperazine-N-CH₂CH₂-NH-CH₂CH₂CH₂-O-] |
| 513 | H | [N-methylpiperazine-N-CH₂CH₂-NH-CH₂CH₂CH₂-O-] |
| 514 | H | [morpholine-N-CH₂CH₂-NH-CH₂CH₂CH₂-O-] |
| 515 | H | —OCH$_2$CH$_2$CH$_2$NHCH$_2$CH$_2$CH$_2$OH |
| 516 | H | —OCH$_2$CH$_2$CH$_2$NHCH$_2$CH$_2$CH$_2$OMe |
| 517 | H | —OCH$_2$CH$_2$CH$_2$NHCH$_2$CH$_2$CH$_2$OEt |
| 518 | H | —OCH$_2$CH$_2$CH$_2$NHCH$_2$CH$_2$CH$_2$NH$_2$ |
| 519 | H | —OCH$_2$CH$_2$CH$_2$NHCH$_2$CH$_2$CH$_2$NHMe |
| 520 | H | —OCH$_2$CH$_2$CH$_2$NHCH$_2$CH$_2$CH$_2$NMe$_2$ |
| 521 | H | [pyrrolidine-N-CH₂CH₂CH₂-NH-CH₂CH₂CH₂-O-] |
| 522 | H | [piperidine-N-CH₂CH₂CH₂-NH-CH₂CH₂CH₂-O-] |
| 523 | H | [piperazine-N-CH₂CH₂CH₂-NH-CH₂CH₂CH₂-O-] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 524 | H | [structure: 4-methylpiperazinyl-propyl-NH-propyl-O-] |
| 525 | H | [structure: morpholinyl-propyl-NH-propyl-O-] |
| 526 | H | —OCH$_2$CH$_2$N(CH$_2$CH$_2$OH)$_2$ |
| 527 | H | —OCH$_2$CH$_2$N(CH$_2$CH$_2$OMe)$_2$ |
| 528 | H | —OCH$_2$CH$_2$N(CH$_2$CH$_2$OEt)$_2$ |
| 529 | H | —OCH$_2$CH$_2$N(CH$_2$CH$_2$NH$_2$)$_2$ |
| 530 | H | —OCH$_2$CH$_2$N(CH$_2$CH$_2$NHMe)$_2$ |
| 531 | H | —OCH$_2$CH$_2$N(CH$_2$CH$_2$NMe$_2$)$_2$ |
| 532 | H | —OCH$_2$CH$_2$N(CH$_2$CH$_2$CH$_2$OH)$_2$ |
| 533 | H | —OCH$_2$CH$_2$N(CH$_2$CH$_2$CH$_2$OMe)$_2$ |
| 534 | H | —OCH$_2$CH$_2$N(CH$_2$CH$_2$CH$_2$OEt)$_2$ |
| 535 | H | —OCH$_2$CH$_2$CH$_2$(HCH$_2$CH$_2$OH)$_2$ |
| 536 | H | —OCH$_2$CH$_2$CH$_2$N(CH$_2$CH$_2$OMe)$_2$ |
| 537 | H | —OCH$_2$CH$_2$CH$_2$N(CH$_2$CH$_2$OEt)$_2$ |
| 538 | H | —OCH$_2$CH$_2$CH$_2$N(CH$_2$CH$_2$CH$_2$OH)$_2$ |
| 539 | H | —OCH$_2$CH$_2$CH$_2$N(CH$_2$CH$_2$CH$_2$OMe)$_2$ |
| 540 | H | —OCH$_2$CH$_2$CH$_2$N(CH$_2$CH$_2$CH$_2$OEt)$_2$ |
| 541 | H | —OCH$_2$CH$_2$NMeCH$_2$CH$_2$OH |
| 542 | H | —OCH$_2$CH$_2$NMeCH$_2$CH$_2$OMe |
| 543 | H | —OCH$_2$CH$_2$NMeCH$_2$CH$_2$OEt |
| 544 | H | —OCH$_2$CH$_2$NMeCH$_2$CH$_2$NH$_2$ |
| 545 | H | —OCH$_2$CH$_2$NMeCH$_2$CH$_2$NHMe |
| 546 | H | —OCH$_2$CH$_2$NMeCH$_2$CH$_2$NMe$_2$ |
| 547 | H | [structure: pyrrolidinyl-ethyl-N(Me)-ethyl-O-] |
| 548 | H | [structure: piperidinyl-ethyl-N(Me)-ethyl-O-] |
| 549 | H | [structure: piperazinyl-ethyl-N(Me)-ethyl-O-] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 550 | H | [structure: N-methylpiperazine-CH2CH2-N(Me)-CH2CH2-O-] |
| 551 | H | [structure: morpholine-CH2CH2-N(Me)-CH2CH2-O-] |
| 552 | H | —OCH$_2$CH$_2$NMeCH$_2$CH$_2$CH$_2$OH |
| 553 | H | —OCH$_2$CH$_2$NMeCH$_2$CH$_2$CH$_2$OMe |
| 554 | H | —OCH$_2$CH$_2$NMeCH$_2$CH$_2$CH$_2$OEt |
| 555 | H | —OCH$_2$CH$_2$NMeCH$_2$CH$_2$CH$_2$NH$_2$ |
| 556 | H | —OCH$_2$CH$_2$NMeCH$_2$CH$_2$CH$_2$NHMe |
| 557 | H | —OCH$_2$CH$_2$NMeCH$_2$CH$_2$CH$_2$NMe$_2$ |
| 558 | H | [structure: pyrrolidine-CH2CH2CH2-N(Me)-CH2CH2-O-] |
| 559 | H | [structure: piperidine-CH2CH2CH2-N(Me)-CH2CH2-O-] |
| 560 | H | [structure: piperazine(NH)-CH2CH2CH2-N(Me)-CH2CH2-O-] |
| 561 | H | [structure: N-methylpiperazine-CH2CH2CH2-N(Me)-CH2CH2-O-] |
| 562 | H | [structure: morpholine-CH2CH2CH2-N(Me)-CH2CH2-O-] |
| 563 | H | —OCH$_2$CH$_2$CH$_2$NMeCH$_2$CH$_2$OH |
| 564 | H | —OCH$_2$CH$_2$CH$_2$NMeCH$_2$CH$_2$OMe |
| 565 | H | —OCH$_2$CH$_2$CH$_2$NMeCH$_2$CH$_2$OEt |
| 566 | H | —OCH$_2$CH$_2$CH$_2$NMeCH$_2$CH$_2$NH$_2$ |
| 567 | H | —OCH$_2$CH$_2$CH$_2$NMeCH$_2$CH$_2$NHMe |
| 568 | H | —OCH$_2$CH$_2$CH$_2$NMeCH$_2$CH$_2$NMe$_2$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 569 | H | [pyrrolidine-N-CH$_2$CH$_2$-N(Me)-CH$_2$CH$_2$CH$_2$-O~] |
| 570 | H | [piperidine-N-CH$_2$CH$_2$-N(Me)-CH$_2$CH$_2$CH$_2$-O~] |
| 571 | H | [HN-piperazine-N-CH$_2$CH$_2$-N(Me)-CH$_2$CH$_2$CH$_2$-O~] |
| 572 | H | [MeN-piperazine-N-CH$_2$CH$_2$-N(Me)-CH$_2$CH$_2$CH$_2$-O~] |
| 573 | H | [morpholine-N-CH$_2$CH$_2$-N(Me)-CH$_2$CH$_2$CH$_2$-O~] |
| 574 | H | —OCH$_2$CH$_2$CH$_2$NMeCH$_2$CH$_2$CH$_2$OH |
| 575 | H | —OCH$_2$CH$_2$CH$_2$NMeCH$_2$CH$_2$CH$_2$OMe |
| 576 | H | —OCH$_2$CH$_2$CH$_2$NMeCH$_2$CH$_2$CH$_2$OEt |
| 577 | H | —OCH$_2$CH$_2$CH$_2$NMeCH$_2$CH$_2$CH$_2$NH$_2$ |
| 578 | H | —OCH$_2$CH$_2$CH$_2$NMeCH$_2$CH$_2$CH$_2$NHMe |
| 579 | H | —OCH$_2$CH$_2$CH$_2$NMeCH$_2$CH$_2$CH$_2$NMe$_2$ |
| 580 | H | [pyrrolidine-N-CH$_2$CH$_2$CH$_2$-N(Me)-CH$_2$CH$_2$CH$_2$-O~] |
| 581 | H | [piperidine-N-CH$_2$CH$_2$CH$_2$-N(Me)-CH$_2$CH$_2$CH$_2$-O~] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 582 | H | 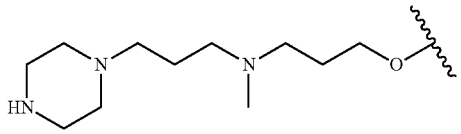 [SMILES: *OCCCN(C)CCCN1CCNCC1] |
| 583 | H | 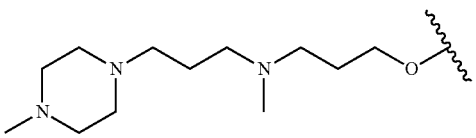 [SMILES: *OCCCN(C)CCCN1CCN(C)CC1] |
| 584 | H | 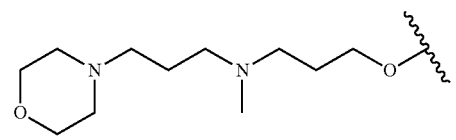 [SMILES: *OCCCN(C)CCCN1CCOCC1] |
| 585 | H | —CH$_2$OH |
| 586 | H | —CH$_2$OMe |
| 587 | H | —CH$_2$OEt |
| 588 | H | —CH$_2$NH$_2$ |
| 589 | H | —CH$_2$NHMe |
| 590 | H | —CH$_2$NMe$_2$ |
| 591 | H | 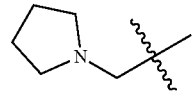 [SMILES: *CN1CCCC1] |
| 592 | H | 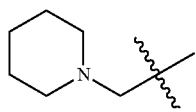 [SMILES: *CN1CCCCC1] |
| 593 | H | 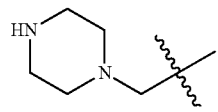 [SMILES: *CN1CCNCC1] |
| 594 | H | 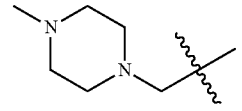 [SMILES: *CN1CCN(C)CC1] |
| 595 | H | 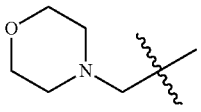 [SMILES: *CN1CCOCC1] |
| 596 | H | —CH$_2$CH$_2$OH |
| 597 | H | —CH$_2$CH$_2$OMe |
| 598 | H | —CH$_2$CH$_2$OEt |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 599 | H | —CH$_2$CH$_2$NH$_2$ |
| 600 | H | —CH$_2$CH$_2$NHMe |
| 601 | H | —CH$_2$CH$_2$NMe$_2$ |
| 602 | H | pyrrolidin-1-yl-propyl |
| 603 | H | piperidin-1-yl-propyl |
| 604 | H | piperazin-1-yl-propyl |
| 605 | H | 4-methylpiperazin-1-yl-propyl |
| 606 | H | morpholin-4-yl-propyl |
| 607 | H | —CH$_2$CH$_2$CH$_2$OH |
| 608 | H | —CH$_2$CH$_2$CH$_2$OMe |
| 609 | H | —CH$_2$CH$_2$CH$_2$OEt |
| 610 | H | —CH$_2$CH$_2$CH$_2$NH$_2$ |
| 611 | H | —CH$_2$CH$_2$CH$_2$NHMe |
| 612 | H | —CH$_2$CH$_2$CH$_2$NMe$_2$ |
| 613 | H | pyrrolidin-1-yl-butyl |
| 614 | H | piperidin-1-yl-butyl |

US 10,336,721 B2

113                                                               114

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 615 | H | 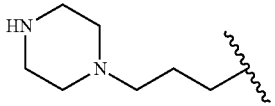 |
| 616 | H | 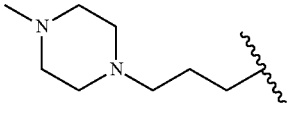 [SMILES: *CCCN1CCN(C)CC1] |
| 617 | H | 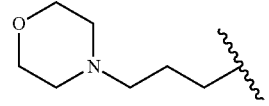 [SMILES: *CCCN1CCOCC1] |
| 618 | H | —$CH_2CH_2CH_2CH_2OH$ |
| 619 | H | —$CH_2CH_2CH_2CH_2OMe$ |
| 620 | H | —$CH_2CH_2CH_2CH_2OEt$ |
| 621 | H | —$CH_2CH_2CH_2CH_2NH_2$ |
| 622 | H | —$CH_2CH_2CH_2CH_2NHMe$ |
| 623 | H | —$CH_2CH_2CH_2CH_2NMe_2$ |
| 624 | H | 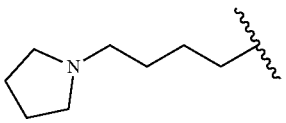 |
| 625 | H | 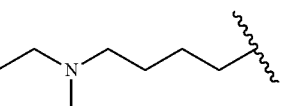 |
| 626 | H | 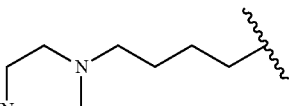 |
| 627 | H | 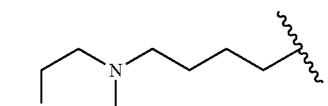 |
| 628 | H | 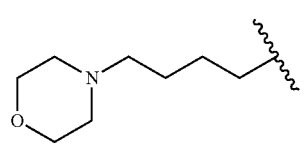 [SMILES: *CCCCN1CCOCC1] |
| 629 | H | —$CH_2OCH_2CH_2OH$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 630 | H | —CH$_2$OCH$_2$CH$_2$OMe |
| 631 | H | —CH$_2$OCH$_2$CH$_2$OEt |
| 632 | H | —CH$_2$OCH$_2$CH$_2$NH$_2$ |
| 633 | H | —CH$_2$OCH$_2$CH$_2$NHMe |
| 634 | H | —CH$_2$OCH$_2$CH$_2$NMe$_2$ |
| 635 | H | 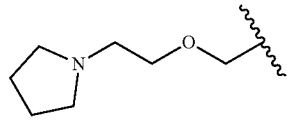 [SMILES: *COCCN1CCCC1] |
| 636 | H | 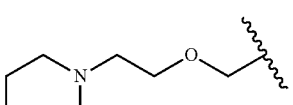 |
| 637 | H | 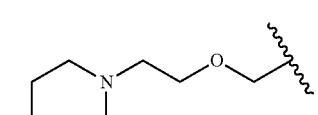 |
| 638 | H | 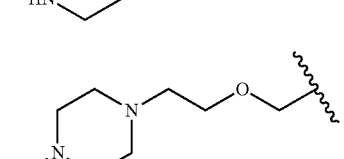 |
| 639 | H | 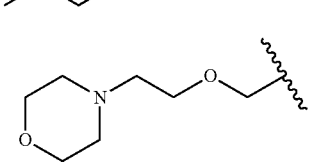 |
| 640 | H | —CH$_2$NHCH$_2$CH$_2$OH |
| 641 | H | —CH$_2$NHCH$_2$CH$_2$OMe |
| 642 | H | —CH$_2$NHCH$_2$CH$_2$OEt |
| 643 | H | —CH$_2$NHCH$_2$CH$_2$NH$_2$ |
| 644 | H | —CH$_2$NHCH$_2$CH$_2$NHMe |
| 645 | H | —CH$_2$NHCH$_2$CH$_2$NMe$_2$ |
| 646 | H | 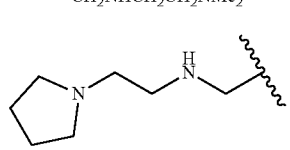 |
| 647 | H | 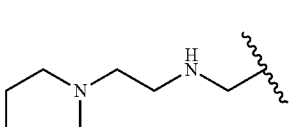 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 648 | H | [piperazinyl-ethyl-NH- structure] |
| 649 | H | [4-methylpiperazinyl-ethyl-NH- structure] |
| 650 | H | [morpholinyl-ethyl-NH- structure] |
| 651 | H | —CH$_2$N(CH$_2$CH$_2$OH)$_2$ |
| 652 | H | —CH$_2$N(CH$_2$CH$_2$OMe)$_2$ |
| 653 | H | —CH$_2$N(CH$_2$CH$_2$OEt)$_2$ |
| 654 | H | —CH$_2$NMeCH$_2$CH$_2$OH |
| 655 | H | —CH$_2$NMeCH$_2$CH$_2$OMe |
| 656 | H | —CH$_2$NMeCH$_2$CH$_2$OEt |
| 657 | H | —CH$_2$NMeCH$_2$CH$_2$NH$_2$ |
| 658 | H | —CH$_2$NMeCH$_2$CH$_2$NHMe |
| 659 | H | —CH$_2$NMeCH$_2$CH$_2$NMe$_2$ |
| 660 | H | [pyrrolidinyl-ethyl-NMe- structure] |
| 661 | H | [piperidinyl-ethyl-NMe- structure] |
| 662 | H | [piperazinyl-ethyl-NMe- structure] |
| 663 | H | [4-methylpiperazinyl-ethyl-NMe- structure] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 664 | H | 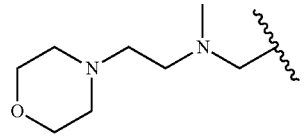 [SMILES: *CN(C)CCN1CCOCC1] |
| 665 | H | —CH$_2$CH$_2$OCH$_2$CH$_2$OH |
| 666 | H | —CH$_2$CH$_2$OCH$_2$CH$_2$OMe |
| 667 | H | —CH$_2$CH$_2$OCH$_2$CH$_2$OEt |
| 668 | H | —CH$_2$CH$_2$OCH$_2$CH$_2$NH$_2$ |
| 669 | H | —CH$_2$CH$_2$OCH$_2$CH$_2$NHMe |
| 670 | H | —CH$_2$CH$_2$OCH$_2$CH$_2$NMe$_2$ |
| 671 | H | 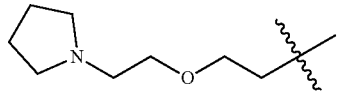 [SMILES: *CCOCCN1CCCC1] |
| 672 | H | 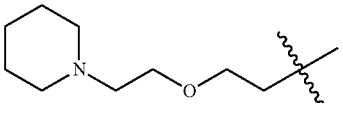 [SMILES: *CCOCCN1CCCCC1] |
| 673 | H | 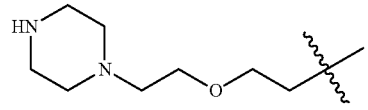 [SMILES: *CCOCCN1CCNCC1] |
| 674 | H | 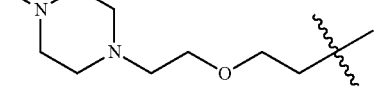 |
| 675 | H | 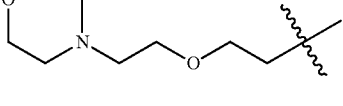 |
| 676 | H | —CH$_2$CH$_2$NHCH$_2$CH$_2$OH |
| 677 | H | —CH$_2$CH$_2$NHCH$_2$CH$_2$OMe |
| 678 | H | —CH$_2$CH$_2$NHCH$_2$CH$_2$OEt |
| 679 | H | —CH$_2$CH$_2$NHCH$_2$CH$_2$NH$_2$ |
| 680 | H | —CH$_2$CH$_2$NHCH$_2$CH$_2$NHMe |
| 681 | H | —CH$_2$CH$_2$NHCH$_2$CH$_2$NMe$_2$ |
| 682 | H | 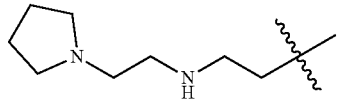 [SMILES: *CCNCCN1CCCC1] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 683 | H | 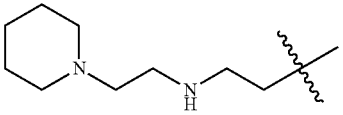 |
| 684 | H | 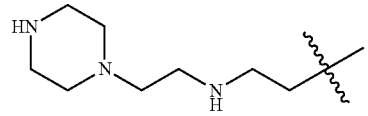 [SMILES: *CCNCCN1CCNCC1] |
| 685 | H | 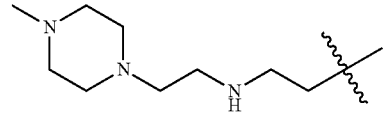 [SMILES: *CCNCCN1CCN(C)CC1] |
| 686 | H | 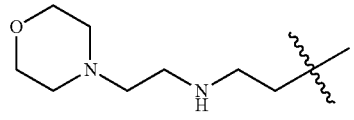 [SMILES: *CCNCCN1CCOCC1] |
| 687 | H | —CH$_2$CH$_2$N(CH$_2$CH$_2$OH)$_2$ |
| 688 | H | —CH$_2$CH$_2$N(CH$_2$CH$_2$OMe)$_2$ |
| 689 | H | —CH$_2$CH$_2$N(CH$_2$CH$_2$OEt)$_2$ |
| 690 | H | —CH$_2$CH$_2$NMeCH$_2$CH$_2$OH |
| 691 | H | —CH$_2$CH$_2$NMeCH$_2$CH$_2$OMe |
| 692 | H | —CH$_2$CH$_2$NMeCH$_2$CH$_2$OEt |
| 693 | H | —CH$_2$CH$_2$NMeCH$_2$CH$_2$NH$_2$ |
| 694 | H | —CH$_2$CH$_2$NMeCH$_2$CH$_2$NHMe |
| 695 | H | —CH$_2$CH$_2$NMeCH$_2$CH$_2$NMe$_2$ |
| 696 | H | 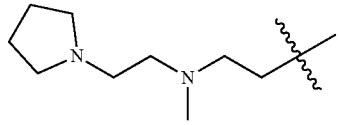 [SMILES: *CCN(C)CCN1CCCC1] |
| 697 | H | 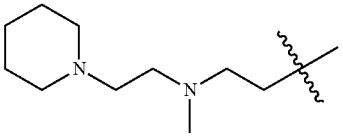 [SMILES: *CCN(C)CCN1CCCCC1] |
| 698 | H | 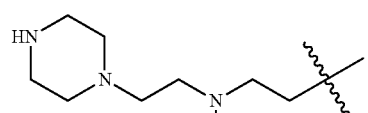 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 699 | H | ![structure: N-methylpiperazine-CH2CH2-N(Me)- attachment] |
| 700 | H | ![structure: morpholine-CH2CH2-N(Me)- attachment] |
| 701 | H | —NH |
| 702 | H | —NHMe |
| 703 | H | —NMe$_2$ |
| 704 | H | —NHEt |
| 705 | H | —NHPr |
| 706 | H | —NHiPr |
| 707 | H | —NHcPr |
| 708 | H | —NHcBu |
| 709 | H | —NHcPn |
| 710 | H | —NHcHex |
| 711 | H | —NHCH$_2$CH$_2$OH |
| 712 | H | —NHCH$_2$CH$_2$OMe |
| 713 | H | —NHCH$_2$CH$_2$OEt |
| 714 | H | —NHCH$_2$CH$_2$NH$_2$ |
| 715 | H | —NHCH$_2$CH$_2$NHMe |
| 716 | H | —NHCH$_2$CH$_2$NMe$_2$ |
| 717 | H | ![structure: pyrrolidine-CH2CH2-NH- attachment] |
| 718 | H | ![structure: piperidine-CH2CH2-NH- attachment] |
| 719 | H | ![structure: piperazine-CH2CH2-NH- attachment] |
| 720 | H | ![structure: N-methylpiperazine-CH2CH2-NH- attachment] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 721 | H | morpholine-N-CH$_2$CH$_2$-NH- |
| 722 | H | —NHCH$_2$CH$_2$CH$_2$OH |
| 723 | H | —NHCH$_2$CH$_2$CH$_2$OMe |
| 724 | H | —NHCH$_2$CH$_2$CH$_2$OEt |
| 725 | H | —NHCH$_2$CH$_2$CH$_2$NH$_2$ |
| 726 | H | —NHCH$_2$CH$_2$CH$_2$NHMe |
| 727 | H | —NHCH$_2$CH$_2$CH$_2$NMe$_2$ |
| 728 | H | pyrrolidine-N-CH$_2$CH$_2$CH$_2$-NH- |
| 729 | H | piperidine-N-CH$_2$CH$_2$CH$_2$-NH- |
| 730 | H | piperazine-N-CH$_2$CH$_2$CH$_2$-NH- |
| 731 | H | 4-methylpiperazine-N-CH$_2$CH$_2$CH$_2$-NH- |
| 732 | H | morpholine-N-CH$_2$CH$_2$CH$_2$-NH- |
| 733 | H | —NHCH$_2$CH$_2$OCH$_2$CH$_2$OH |
| 734 | H | —NHCH$_2$CH$_2$OCH$_2$CH$_2$OMe |
| 735 | H | —NHCH$_2$CH$_2$OCH$_2$CH$_2$OEt |
| 736 | H | —NHCH$_2$CH$_2$OCH$_2$CH$_2$NH$_2$ |
| 737 | H | —NHCH$_2$CH$_2$OCH$_2$CH$_2$NHMe |
| 738 | H | —NHCH$_2$CH$_2$OCH$_2$CH$_2$NMe$_2$ |
| 739 | H | —N(CH$_2$CH$_2$OH)$_2$ |
| 740 | H | —N(CH$_2$CH$_2$OMe)$_2$ |
| 741 | H | —N(CH$_2$CH$_2$OEt)$_2$ |
| 742 | H | —N(CH$_2$CH$_2$CH$_2$OH)$_2$ |
| 743 | H | —N(CH$_2$CH$_2$CH$_2$OMe)$_2$ |
| 744 | H | —N(CH$_2$CH$_2$CH$_2$OEt)$_2$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 745 | H | 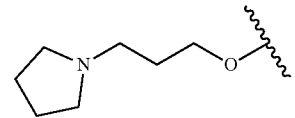 [SMILES: *OCCCN1CCCC1] |
| 746 | H | —N(CH$_2$CH$_2$OCH$_2$CH$_2$OH)$_2$ |
| 747 | H | —N(CH$_2$CH$_2$OCH$_2$CH$_2$OMe)$_2$ |
| 748 | H | —N(CH$_2$CH$_2$OCH$_2$CH$_2$OEt)$_2$ |
| 749 | H | —NMeCH$_2$CH$_2$OH |
| 750 | H | —NMeCH$_2$CH$_2$OMe |
| 751 | H | —NMeCH$_2$CH$_2$OEt |
| 752 | H | —NMeCH$_2$CH$_2$NH$_2$ |
| 753 | H | —NMeCH$_2$CH$_2$NHMe |
| 754 | H | —NMeCH$_2$CH$_2$NMe$_2$ |
| 755 | H | 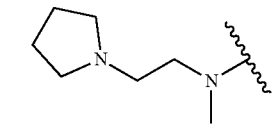 [SMILES: *N(C)CCN1CCCC1] |
| 756 | H | 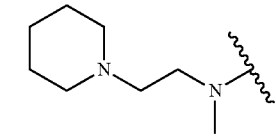 [SMILES: *N(C)CCN1CCCCC1] |
| 757 | H | 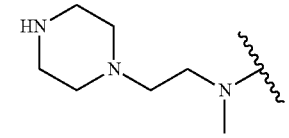 |
| 758 | H | 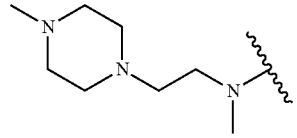 [SMILES: *N(C)CCN1CCN(C)CC1] |
| 759 | H | 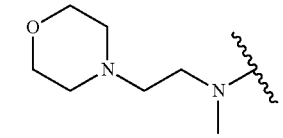 [SMILES: *N(C)CCN1CCOCC1] |
| 760 | H | —NMeCH$_2$CH$_2$CH$_2$OH |
| 761 | H | —NMeCH$_2$CH$_2$CH$_2$OMe |
| 762 | H | —NMeCH$_2$CH$_2$CH$_2$OEt |
| 763 | H | —NMeCH$_2$CH$_2$CH$_2$NH$_2$ |
| 764 | H | —NMeCH$_2$CH$_2$CH$_2$NHMe |
| 765 | H | —NMeCH$_2$CH$_2$CH$_2$NMe$_2$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 766 | H | [pyrrolidinyl-propyl-N(Me)- structure] |
| 767 | H | [piperidinyl-propyl-N(Me)- structure] |
| 768 | H | [piperazinyl-propyl-N(Me)- structure] |
| 769 | H | [N-methylpiperazinyl-propyl-N(Me)- structure] |
| 770 | H | [morpholinyl-propyl-N(Me)- structure] |
| 771 | H | —NMeCH$_2$CH$_2$OCH$_2$CH$_2$OH |
| 772 | H | —NMeCH$_2$CH$_2$OCH$_2$CH$_2$OMe |
| 773 | H | —NMeCH$_2$CH$_2$OCH$_2$CH$_2$OEt |
| 774 | H | —NMeCH$_2$CH$_2$OCH$_2$CH$_2$NH$_2$ |
| 775 | H | —NMeCH$_2$CH$_2$OCH$_2$CH$_2$NHMe |
| 776 | H | —NMeCH$_2$CH$_2$OCH$_2$CH$_2$NMe$_2$ |
| 777 | H | —O(C═O)OMe |
| 778 | H | —O(C═O)OEt |
| 779 | H | —O(C═O)OnPr |
| 780 | H | —O(C═O)OiPr |
| 781 | H | —O(C═O)OcPr |
| 782 | H | —O(C═O)OcBu |
| 783 | H | —O(C═O)OcPn |
| 784 | H | —O(C═O)OcHex |
| 785 | H | —COOH |
| 786 | H | —CH$_2$(C═O)OH |
| 787 | H | —CH$_2$(C═O)OMe |
| 788 | H | —CH$_2$(C═O)OEt |
| 789 | H | —CH$_2$(C═O)OnPr |
| 790 | H | —CH$_2$(C═O)OiPr |
| 791 | H | —CH$_2$(C═O)OcPn |
| 792 | H | —CH$_2$(C═O)OcBu |
| 793 | H | —CH$_2$(C═O)OcPn |
| 794 | H | —CH$_2$(C═O)OcHex |
| 795 | H | —OCH$_2$(C═O)OH |
| 796 | H | —OCH$_2$(C═O)OMe |

US 10,336,721 B2

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 797 | H | —OCH$_2$(C=O)OEt |
| 798 | H | —OCH$_2$(C=O)OnPr |
| 799 | H | —OCH$_2$(C=O)OiPr |
| 800 | H | —OCH$_2$(C=O)OcPr |
| 801 | H | —OCH$_2$(C=O)OcBu |
| 802 | H | —OCH$_2$(C=O)OcPn |
| 803 | H | —OCH$_2$(C=O)OcHex |
| 804 | H | —NHCH$_2$(C=O)OH |
| 805 | H | —NHCH$_2$(C=O)OMe |
| 806 | H | —NHCH$_2$(C=O)OEt |
| 807 | H | —NHCH$_2$(C=O)OnPr |
| 808 | H | —NHCH$_2$(C=O)OiPr |
| 809 | H | —NHCH$_2$(C=O)OcPr |
| 810 | H | —NHCH$_2$(C=O)OcBu |
| 811 | H | —NHCH$_2$(C=O)OcPn |
| 812 | H | —NHCH$_2$(C=O)OcHex |
| 813 | H | H |
| 814 | —OMe | —OMe |
| 815 | —OEt | —OEt |
| 816 | —OPr | —OPr |
| 817 | —OiPr | —OiPr |
| 818 | —OcPr | —OcPr |
| 819 | —OcBu | —OcBu |
| 820 | —OcPn | —OcPn |
| 821 | —OcHex | —OcHex |
| 822 | —OCH$_2$CH$_2$OH | —OCH$_2$CH$_2$OH |
| 823 | —OCH$_2$CH$_2$OMe | —OCH$_2$CH$_2$OMe |
| 824 | —OCH$_2$CH$_2$OEt | —OCH$_2$CH$_2$OEt |
| 825 | —OCH$_2$CH$_2$NH$_2$ | —OCH$_2$CH$_2$NH$_2$ |
| 826 | —OCH$_2$CH$_2$NHMe | —OCH$_2$CH$_2$NHMe |
| 827 | —OCH$_2$CH$_2$NMe$_2$ | —OCH$_2$CH$_2$NMe$_2$ |
| 828 | 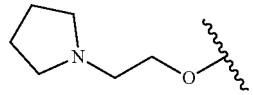 [SMILES: *OCCN1CCCC1] | 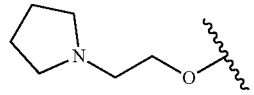 [SMILES: *OCCN1CCCC1] |
| 829 | 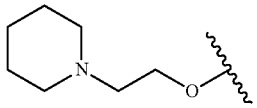 | 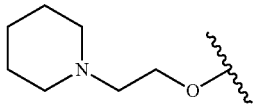 |
| 830 | 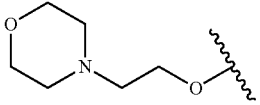 [SMILES: *OCCN1CCOCC1] | 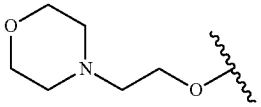 [SMILES: *OCCN1CCOCC1] |
| 831 | —OCH$_2$CH$_2$CH$_2$OH | —OCH$_2$CH$_2$CH$_2$OH |
| 832 | —OCH$_2$CH$_2$CH$_2$OMe | —OCH$_2$CH$_2$CH$_2$OMe |
| 833 | —OCH$_2$CH$_2$CH$_2$OEt | —OCH$_2$CH$_2$CH$_2$OEt |
| 834 | —OCH$_2$CH$_2$CH$_2$NH$_2$ | —OCH$_2$CH$_2$CH$_2$NH$_2$ |
| 835 | —OCH$_2$CH$_2$CH$_2$NHMe | —OCH$_2$CH$_2$CH$_2$NHMe |
| 836 | —OCH$_2$CH$_2$CH$_2$NMe$_2$ | —OCH$_2$CH$_2$CH$_2$NMe$_2$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 837 | 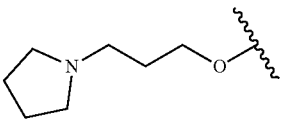 [SMILES: *OCCCN1CCCC1] | 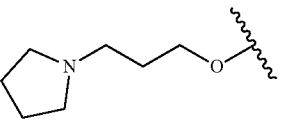 [SMILES: *OCCCN1CCCC1] |
| 838 | 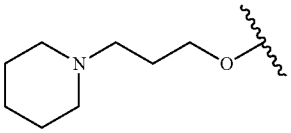 [SMILES: *OCCCN1CCCCC1] | 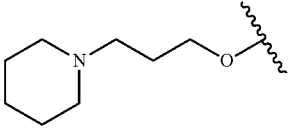 |
| 839 | 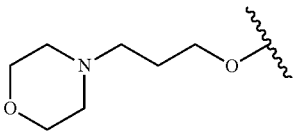 | 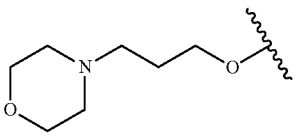 [SMILES: *OCCCN1CCOCC1] |
| 840 | —OCH$_2$CH$_2$OCH$_2$CH$_2$OH | —OCH$_2$CH$_2$OCH$_2$CH$_2$OH |
| 841 | —OCH$_2$CH$_2$OCH$_2$CH$_2$OMe | —OCH$_2$CH$_2$OCH$_2$CH$_2$OMe |
| 842 | —OCH$_2$CH$_2$OCH$_2$CH$_2$OEt | —OCH$_2$CH$_2$OCH$_2$CH$_2$OEt |
| 843 | —OCH$_2$CH$_2$OCH$_2$CH$_2$NH$_2$ | —OCH$_2$CH$_2$OCH$_2$CH$_2$NH$_2$ |
| 844 | —OCH$_2$CH$_2$OCH$_2$CH$_2$NHMe | —OCH$_2$CH$_2$OCH$_2$CH$_2$NHMe |
| 845 | —OCH$_2$CH$_2$OCH$_2$CH$_2$NMe$_2$ | —OCH$_2$CH$_2$OCH$_2$CH$_2$NMe$_2$ |
| 846 | 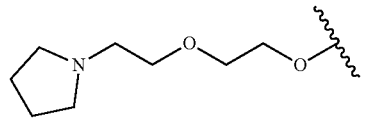 [SMILES: *OCCOCCN1CCCC1] | 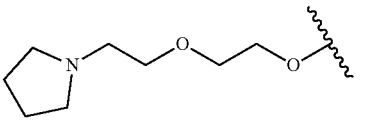 [SMILES: *OCCOCCN1CCCC1] |
| 847 | 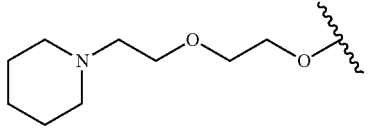 [SMILES: *OCCOCCN1CCCCC1] | 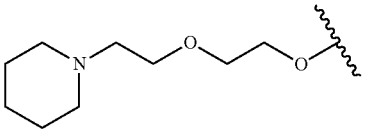 [SMILES: *OCCOCCN1CCCCC1] |
| 848 | 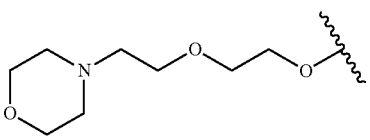 | 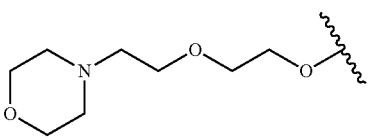 [SMILES: *OCCOCCN1CCOCC1] |
| 849 | —OCH$_2$CH$_2$OCH$_2$CH$_2$CH$_2$OH | —OCH$_2$CH$_2$OCH$_2$CH$_2$CH$_2$OH |
| 850 | —OCH$_2$CH$_2$OCH$_2$CH$_2$CH$_2$OMe | —OCH$_2$CH$_2$OCH$_2$CH$_2$CH$_2$OMe |
| 851 | —OCH$_2$CH$_2$OCH$_2$CH$_2$CH$_2$OEt | —OCH$_2$CH$_2$OCH$_2$CH$_2$CH$_2$OEt |
| 852 | —OCH$_2$CH$_2$OCH$_2$CH$_2$CH$_2$NH$_2$ | —OCH$_2$CH$_2$OCH$_2$CH$_2$CH$_2$NH$_2$ |
| 853 | —OCH$_2$CH$_2$OCH$_2$CH$_2$CH$_2$NHMe | —OCH$_2$CH$_2$OCH$_2$CH$_2$CH$_2$NHMe |
| 854 | —OCH$_2$CH$_2$OCH$_2$CH$_2$CH$_2$NMe$_2$ | —OCH$_2$CH$_2$OCH$_2$CH$_2$CH$_2$NMe$_2$ |
| 855 | 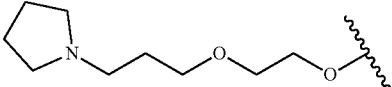 [SMILES: *OCCOCCCN1CCCC1] | 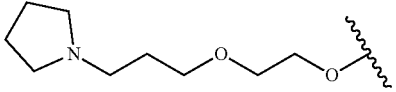 |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 856 | piperidine-N-CH₂CH₂CH₂-O-CH₂CH₂-O- | piperidine-N-CH₂CH₂CH₂-O-CH₂CH₂-O- |
| 857 | morpholine-N-CH₂CH₂CH₂-O-CH₂CH₂-O- | morpholine-N-CH₂CH₂CH₂-O-CH₂CH₂-O- |
| 858 | —OCH₂CH₂CH₂OCH₂CH₂OH | —OCH₂CH₂CH₂OCH₂CH₂OH |
| 859 | —OCH₂CH₂CH₂OCH₂CH₂OMe | —OCH₂CH₂CH₂OCH₂CH₂OMe |
| 860 | —OCH₂CH₂CH₂OCH₂CH₂OEt | —OCH₂CH₂CH₂OCH₂CH₂OEt |
| 861 | —OCH₂CH₂CH₂OCH₂CH₂NH₂ | —OCH₂CH₂CH₂OCH₂CH₂NH₂ |
| 862 | —OCH₂CH₂CH₂OCH₂CH₂NHMe | —OCH₂CH₂CH₂OCH₂CH₂NHMe |
| 863 | —OCH₂CH₂CH₂OCH₂CH₂NMe₂ | —OCH₂CH₂CH₂OCH₂CH₂NMe₂ |
| 864 | pyrrolidine-N-CH₂CH₂-O-CH₂CH₂CH₂-O- | pyrrolidine-N-CH₂CH₂-O-CH₂CH₂CH₂-O- |
| 865 | piperidine-N-CH₂CH₂-O-CH₂CH₂CH₂-O- | piperidine-N-CH₂CH₂-O-CH₂CH₂CH₂-O- |
| 866 | morpholine-N-CH₂CH₂-O-CH₂CH₂CH₂-O- | morpholine-N-CH₂CH₂-O-CH₂CH₂CH₂-O- |
| 867 | —OCH₂CH₂CH₂OCH₂CH₂CH₂OH | —OCH₂CH₂CH₂OCH₂CH₂CH₂OH |
| 868 | —OCH₂CH₂CH₂OCH₂CH₂CH₂OMe | —OCH₂CH₂CH₂OCH₂CH₂CH₂OMe |
| 869 | —OCH₂CH₂CH₂OCH₂CH₂CH₂OEt | —OCH₂CH₂CH₂OCH₂CH₂CH₂OEt |
| 870 | —OCH₂CH₂CH₂OCH₂CH₂CH₂NH₂ | —OCH₂CH₂CH₂OCH₂CH₂CH₂NH₂ |
| 871 | —OCH₂CH₂CH₂OCH₂CH₂CH₂NHMe | —OCH₂CH₂CH₂OCH₂CH₂CH₂NHMe |
| 872 | —OCH₂CH₂CH₂OCH₂CH₂CH₂NMe₂ | —OCH₂CH₂CH₂OCH₂CH₂CH₂NMe₂ |
| 873 | pyrrolidine-N-CH₂CH₂CH₂-O-CH₂CH₂CH₂-O- | pyrrolidine-N-CH₂CH₂CH₂-O-CH₂CH₂CH₂-O- |
| 874 | piperidine-N-CH₂CH₂CH₂-O-CH₂CH₂CH₂-O- | piperidine-N-CH₂CH₂CH₂-O-CH₂CH₂CH₂-O- |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 875 | 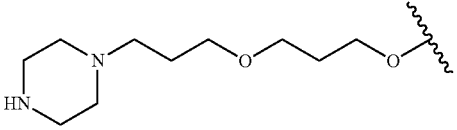 [SMILES: *OCCCOCCCN1CCNCC1] | 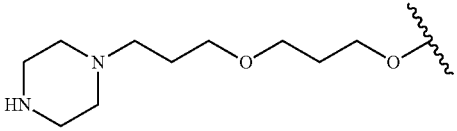 |
| 876 | 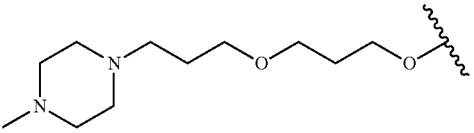 [SMILES: *OCCCOCCCN1CCN(C)CC1] | 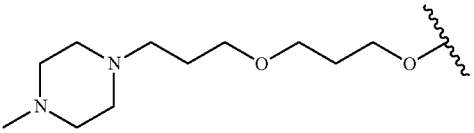 [SMILES: *OCCCOCCCN1CCN(C)CC1] |
| 877 | 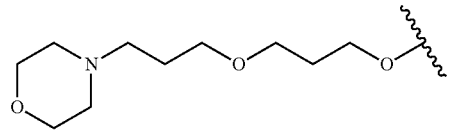 [SMILES: *OCCCOCCCN1CCOCC1] | 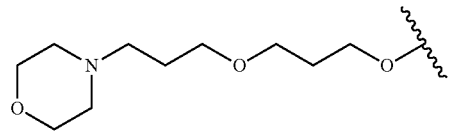 [SMILES: *OCCCOCCCN1CCOCC1] |
| 878 | —OCH$_2$CH$_2$NHCH$_2$CH$_2$OH | —OCH$_2$CH$_2$NHCH$_2$CH$_2$OH |
| 879 | —OCH$_2$CH$_2$NHCH$_2$CH$_2$OMe | —OCH$_2$CH$_2$NHCH$_2$CH$_2$OMe |
| 880 | —OCH$_2$CH$_2$NHCH$_2$CH$_2$OEt | —OCH$_2$CH$_2$NHCH$_2$CH$_2$OEt |
| 881 | —OCH$_2$CH$_2$NHCH$_2$CH$_2$CH$_2$OH | —OCH$_2$CH$_2$NHCH$_2$CH$_2$CH$_2$OH |
| 882 | —OCH$_2$CH$_2$NHCH$_2$CH$_2$CH$_2$OMe | —OCH$_2$CH$_2$NHCH$_2$CH$_2$CH$_2$OMe |
| 883 | —OCH$_2$CH$_2$NHCH$_2$CH$_2$CH$_2$OEt | —OCH$_2$CH$_2$NHCH$_2$CH$_2$CH$_2$OEt |
| 884 | —OCH$_2$CH$_2$CH$_2$NHCH$_2$CH$_2$OH | —OCH$_2$CH$_2$CH$_2$NHCH$_2$CH$_2$OH |
| 885 | —OCH$_2$CH$_2$CH$_2$NHCH$_2$CH$_2$OMe | —OCH$_2$CH$_2$CH$_2$NHCH$_2$CH$_2$OMe |
| 886 | —OCH$_2$CH$_2$CH$_2$NHCH$_2$CH$_2$OEt | —OCH$_2$CH$_2$CH$_2$NHCH$_2$CH$_2$OEt |
| 887 | —OCH$_2$CH$_2$CH$_2$NHCH$_2$CH$_2$CH$_2$OH | —OCH$_2$CH$_2$CH$_2$NHCH$_2$CH$_2$CH$_2$OH |
| 888 | —OCH$_2$CH$_2$CH$_2$NHCH$_2$CH$_2$CH$_2$OMe | —OCH$_2$CH$_2$CH$_2$NHCH$_2$CH$_2$CH$_2$OMe |
| 889 | —OCH$_2$CH$_2$CH$_2$NHCH$_2$CH$_2$CH$_2$OEt | —OCH$_2$CH$_2$CH$_2$NHCH$_2$CH$_2$CH$_2$OEt |
| 890 | —OCH$_2$CH$_2$N(CH$_2$CH$_2$OH)$_2$ | —OCH$_2$CH$_2$N(CH$_2$CH$_2$OH)$_2$ |
| 891 | —OCH$_2$CH$_2$N(CH$_2$CH$_2$OMe)$_2$ | —OCH$_2$CH$_2$N(CH$_2$CH$_2$OMe)$_2$ |
| 892 | —OCH$_2$CH$_2$N(CH$_2$CH$_2$OEt)$_2$ | —OCH$_2$CH$_2$N(CH$_2$CH$_2$OEt)$_2$ |
| 893 | —OCH$_2$CH$_2$N(CH$_2$CH$_2$CH$_2$OH)$_2$ | —OCH$_2$CH$_2$N(CH$_2$CH$_2$CH$_2$OH)$_2$ |
| 894 | —OCH$_2$CH$_2$N(CH$_2$CH$_2$CH$_2$OMe)$_2$ | —OCH$_2$CH$_2$N(CH$_2$CH$_2$CH$_2$OMe)$_2$ |
| 895 | —OCH$_2$CH$_2$N(CH$_2$CH$_2$CH$_2$OEt)$_2$ | —OCH$_2$CH$_2$N(CH$_2$CH$_2$CH$_2$OEt)$_2$ |
| 896 | —OCH$_2$CH$_2$CH$_2$(HCH$_2$CH$_2$OH)$_2$ | —OCH$_2$CH$_2$CH$_2$(HCH$_2$CH$_2$OH)$_2$ |
| 897 | —OCH$_2$CH$_2$CH$_2$N(CH$_2$CH$_2$OMe)$_2$ | —OCH$_2$CH$_2$CH$_2$N(CH$_2$CH$_2$OMe)$_2$ |
| 898 | —OCH$_2$CH$_2$CH$_2$N(CH$_2$CH$_2$OEt)$_2$ | —OCH$_2$CH$_2$CH$_2$N(CH$_2$CH$_2$OEt)$_2$ |
| 899 | —OCH$_2$CH$_2$CH$_2$N(CH$_2$CH$_2$CH$_2$OH)$_2$ | —OCH$_2$CH$_2$CH$_2$N(CH$_2$CH$_2$CH$_2$OH)$_2$ |
| 900 | —OCH$_2$CH$_2$CH$_2$N(CH$_2$CH$_2$CH$_2$OMe)$_2$ | —OCH$_2$CH$_2$CH$_2$N(CH$_2$CH$_2$CH$_2$OMe)$_2$ |
| 901 | —OCH$_2$CH$_2$CH$_2$N(CH$_2$CH$_2$CH$_2$OEt)$_2$ | —OCH$_2$CH$_2$CH$_2$N(CH$_2$CH$_2$CH$_2$OEt)$_2$ |
| 902 | —OCH$_2$CH$_2$NMeCH$_2$CH$_2$OH | —OCH$_2$CH$_2$NMeCH$_2$CH$_2$OH |
| 903 | —OCH$_2$CH$_2$NMeCH$_2$CH$_2$OMe | —OCH$_2$CH$_2$NMeCH$_2$CH$_2$OMe |
| 904 | —OCH$_2$CH$_2$NMeCH$_2$CH$_2$OEt | —OCH$_2$CH$_2$NMeCH$_2$CH$_2$OEt |
| 905 | —OCH$_2$CH$_2$NMeCH$_2$CH$_2$CH$_2$OH | —OCH$_2$CH$_2$NMeCH$_2$CH$_2$CH$_2$OH |
| 906 | —OCH$_2$CH$_2$NMeCH$_2$CH$_2$CH$_2$OMe | —OCH$_2$CH$_2$NMeCH$_2$CH$_2$CH$_2$OMe |
| 907 | —OCH$_2$CH$_2$NMeCH$_2$CH$_2$CH$_2$OEt | —OCH$_2$CH$_2$NMeCH$_2$CH$_2$CH$_2$OEt |
| 908 | —OCH$_2$CH$_2$CH$_2$NMeCH$_2$CH$_2$OH | —OCH$_2$CH$_2$CH$_2$NMeCH$_2$CH$_2$OH |
| 909 | —OCH$_2$CH$_2$CH$_2$NMeCH$_2$CH$_2$OMe | —OCH$_2$CH$_2$CH$_2$NMeCH$_2$CH$_2$OMe |
| 910 | —OCH$_2$CH$_2$CH$_2$NMeCH$_2$CH$_2$OEt | —OCH$_2$CH$_2$CH$_2$NMeCH$_2$CH$_2$OEt |
| 911 | —OCH$_2$CH$_2$CH$_2$NMeCH$_2$CH$_2$CH$_2$OH | —OCH$_2$CH$_2$CH$_2$NMeCH$_2$CH$_2$CH$_2$OH |
| 912 | —OCH$_2$CH$_2$CH$_2$NMeCH$_2$CH$_2$CH$_2$OMe | —OCH$_2$CH$_2$CH$_2$NMeCH$_2$CH$_2$CH$_2$OMe |
| 913 | —OCH$_2$CH$_2$CH$_2$NMeCH$_2$CH$_2$CH$_2$OEt | —OCH$_2$CH$_2$CH$_2$NMeCH$_2$CH$_2$CH$_2$OEt |
| 914 | —CH$_2$OH | —CH$_2$OH |
| 915 | —CH$_2$OMe | —CH$_2$OMe |
| 916 | —CH$_2$OEt | —CH$_2$OEt |
| 917 | —CH$_2$NH$_2$ | —CH$_2$NH$_2$ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 918 | —CH$_2$NHMe | —CH$_2$NHMe |
| 919 | —CH$_2$NMe$_2$ | —CH$_2$NMe$_2$ |
| 920 | pyrrolidinyl-CH< | pyrrolidinyl-CH< |
| 921 | piperidinyl-CH< | piperidinyl-CH< |
| 922 | morpholinyl-CH< | morpholinyl-CH< |
| 923 | —CH$_2$CH$_2$OH | —CH$_2$CH$_2$OH |
| 924 | —CH$_2$CH$_2$OMe | —CH$_2$CH$_2$OMe |
| 925 | —CH$_2$CH$_2$OEt | —CH$_2$CH$_2$OEt |
| 926 | —CH$_2$CH$_2$NH$_2$ | —CH$_2$CH$_2$NH$_2$ |
| 927 | —CH$_2$CH$_2$NHMe | —CH$_2$CH$_2$NHMe |
| 928 | —CH$_2$CH$_2$NMe$_2$ | —CH$_2$CH$_2$NMe$_2$ |
| 929 | pyrrolidinyl-CH$_2$CH< | pyrrolidinyl-CH$_2$CH< |
| 930 | piperidinyl-CH$_2$CH< | piperidinyl-CH$_2$CH< |
| 931 | morpholinyl-CH$_2$CH< | morpholinyl-CH$_2$CH< |
| 932 | —CH$_2$CH$_2$CH$_2$OH | —CH$_2$CH$_2$CH$_2$OH |
| 933 | —CH$_2$CH$_2$CH$_2$OMe | —CH$_2$CH$_2$CH$_2$OMe |
| 934 | —CH$_2$CH$_2$CH$_2$OEt | —CH$_2$CH$_2$CH$_2$OEt |
| 935 | —CH$_2$CH$_2$CH$_2$NH$_2$ | —CH$_2$CH$_2$CH$_2$NH$_2$ |
| 936 | —CH$_2$CH$_2$CH$_2$NHMe | —CH$_2$CH$_2$CH$_2$NHMe |
| 937 | —CH$_2$CH$_2$CH$_2$NMe$_2$ | —CH$_2$CH$_2$CH$_2$NMe$_2$ |
| 938 | pyrrolidinyl-CH$_2$CH$_2$CH< | pyrrolidinyl-CH$_2$CH$_2$CH< |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 939 | piperidinyl-(CH₂)₃– | piperidinyl-(CH₂)₃– |
| 940 | morpholinyl-(CH₂)₃– | morpholinyl-(CH₂)₃– |
| 941 | —CH₂CH₂CH₂CH₂OH | —CH₂CH₂CH₂CH₂OH |
| 942 | —CH₂CH₂CH₂CH₂OMe | —CH₂CH₂CH₂CH₂OMe |
| 943 | —CH₂CH₂CH₂CH₂OEt | —CH₂CH₂CH₂CH₂OEt |
| 944 | —CH₂CH₂CH₂CH₂NH₂ | —CH₂CH₂CH₂CH₂NH₂ |
| 945 | —CH₂CH₂CH₂CH₂NHMe | —CH₂CH₂CH₂CH₂NHMe |
| 946 | —CH₂CH₂CH₂CH₂NMe₂ | —CH₂CH₂CH₂CH₂NMe₂ |
| 947 | pyrrolidinyl-(CH₂)₄– | pyrrolidinyl-(CH₂)₄– |
| 948 | piperidinyl-(CH₂)₄– | piperidinyl-(CH₂)₄– |
| 949 | morpholinyl-(CH₂)₄– | morpholinyl-(CH₂)₄– |
| 950 | —CH₂OCH₂CH₂OH | —CH₂OCH₂CH₂OH |
| 951 | —CH₂OCH₂CH₂OMe | —CH₂OCH₂CH₂OMe |
| 952 | —CH₂OCH₂CH₂OEt | —CH₂OCH₂CH₂OEt |
| 953 | —CH₂OCH₂CH₂NH₂ | —CH₂OCH₂CH₂NH₂ |
| 954 | —CH₂OCH₂CH₂NHMe | —CH₂OCH₂CH₂NHMe |
| 955 | —CH₂OCH₂CH₂NMe₂ | —CH₂OCH₂CH₂NMe₂ |
| 956 | pyrrolidinyl-CH₂CH₂-O-CH₂– | pyrrolidinyl-CH₂CH₂-O-CH₂– |
| 957 | piperidinyl-CH₂CH₂-O-CH₂– | piperidinyl-CH₂CH₂-O-CH₂– |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 958 | morpholine-N-CH$_2$CH$_2$-O-CH$_2$- | morpholine-N-CH$_2$CH$_2$-O-CH$_2$- |
| 959 | —CH$_2$NHCH$_2$CH$_2$OH | —CH$_2$NHCH$_2$CH$_2$OH |
| 960 | —CH$_2$NHCH$_2$CH$_2$OMe | —CH$_2$NHCH$_2$CH$_2$OMe |
| 961 | —CH$_2$NHCH$_2$CH$_2$OEt | —CH$_2$NHCH$_2$CH$_2$OEt |
| 962 | —CH$_2$N(CH$_2$CH$_2$OH)$_2$ | —CH$_2$N(CH$_2$CH$_2$OH)$_2$ |
| 963 | —CH$_2$N(CH$_2$CH$_2$OMe)$_2$ | —CH$_2$N(CH$_2$CH$_2$OMe)$_2$ |
| 964 | —CH$_2$N(CH$_2$CH$_2$OEt)$_2$ | —CH$_2$N(CH$_2$CH$_2$OEt)$_2$ |
| 965 | —CH$_2$NMeCH$_2$CH$_2$OH | —CH$_2$NMeCH$_2$CH$_2$OH |
| 966 | —CH$_2$NMeCH$_2$CH$_2$OMe | —CH$_2$NMeCH$_2$CH$_2$OMe |
| 967 | —CH$_2$NMeCH$_2$CH$_2$OEt | —CH$_2$NMeCH$_2$CH$_2$OEt |
| 968 | —CH$_2$CH$_2$OCH$_2$CH$_2$OH | —CH$_2$CH$_2$OCH$_2$CH$_2$OH |
| 969 | —CH$_2$CH$_2$OCH$_2$CH$_2$OMe | —CH$_2$CH$_2$OCH$_2$CH$_2$OMe |
| 970 | —CH$_2$CH$_2$OCH$_2$CH$_2$OEt | —CH$_2$CH$_2$OCH$_2$CH$_2$OEt |
| 971 | —CH$_2$CH$_2$OCH$_2$CH$_2$NH$_2$ | —CH$_2$CH$_2$OCH$_2$CH$_2$NH$_2$ |
| 972 | —CH$_2$CH$_2$OCH$_2$CH$_2$NHMe | —CH$_2$CH$_2$OCH$_2$CH$_2$NHMe |
| 973 | —CH$_2$CH$_2$OCH$_2$CH$_2$NMe$_2$ | —CH$_2$CH$_2$OCH$_2$CH$_2$NMe$_2$ |
| 974 | pyrrolidine-N-CH$_2$CH$_2$-O-CH$_2$- | pyrrolidine-N-CH$_2$CH$_2$-O-CH$_2$- |
| 975 | piperidine-N-CH$_2$CH$_2$-O-CH$_2$- | piperidine-N-CH$_2$CH$_2$-O-CH$_2$- |
| 976 | morpholine-N-CH$_2$CH$_2$-O-CH$_2$- | morpholine-N-CH$_2$CH$_2$-O-CH$_2$- |
| 977 | —CH$_2$CH$_2$NHCH$_2$CH$_2$OH | —CH$_2$CH$_2$NHCH$_2$CH$_2$OH |
| 978 | —CH$_2$CH$_2$NHCH$_2$CH$_2$OMe | —CH$_2$CH$_2$NHCH$_2$CH$_2$OMe |
| 979 | —CH$_2$CH$_2$NHCH$_2$CH$_2$OEt | —CH$_2$CH$_2$NHCH$_2$CH$_2$OEt |
| 980 | —CH$_2$CH$_2$N(CH$_2$CH$_2$OH)$_2$ | —CH$_2$CH$_2$N(CH$_2$CH$_2$OH)$_2$ |
| 981 | —CH$_2$CH$_2$N(CH$_2$CH$_2$OMe)$_2$ | —CH$_2$CH$_2$N(CH$_2$CH$_2$OMe)$_2$ |
| 982 | —CH$_2$CH$_2$N(CH$_2$CH$_2$OEt)$_2$ | —CH$_2$CH$_2$N(CH$_2$CH$_2$OEt)$_2$ |
| 983 | —CH$_2$CH$_2$NMeCH$_2$CH$_2$OH | —CH$_2$CH$_2$NMeCH$_2$CH$_2$OH |
| 984 | —CH$_2$CH$_2$NMeCH$_2$CH$_2$OMe | —CH$_2$CH$_2$NMeCH$_2$CH$_2$OMe |
| 985 | —CH$_2$CH$_2$NMeCH$_2$CH$_2$OEt | —CH$_2$CH$_2$NMeCH$_2$CH$_2$OEt |
| 986 | —NHCH$_2$CH$_2$OH | —NHCH$_2$CH$_2$OH |
| 987 | —NHCH$_2$CH$_2$OMe | —NHCH$_2$CH$_2$OMe |
| 988 | —NHCH$_2$CH$_2$OEt | —NHCH$_2$CH$_2$OEt |
| 989 | —NHCH$_2$CH$_2$NH$_2$ | —NHCH$_2$CH$_2$NH$_2$ |
| 990 | —NHCH$_2$CH$_2$NHMe | —NHCH$_2$CH$_2$NHMe |
| 991 | —NHCH$_2$CH$_2$NMe$_2$ | —NHCH$_2$CH$_2$NMe$_2$ |
| 992 | pyrrolidine-N-CH$_2$CH$_2$-NH- | pyrrolidine-N-CH$_2$CH$_2$-NH- |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52, (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 993 | piperidine-CH₂CH₂-NH- structure | piperidine-CH₂CH₂-NH- structure |
| 994 | —NHCH₂CH₂CH₂OH | —NHCH₂CH₂CH₂OH |
| 995 | —NHCH₂CH₂CH₂OMe | —NHCH₂CH₂CH₂OMe |
| 996 | —NHCH₂CH₂CH₂OEt | —NHCH₂CH₂CH₂OEt |
| 997 | —NHCH₂CH₂CH₂NH₂ | —NHCH₂CH₂CH₂NH₂ |
| 998 | —NHCH₂CH₂CH₂NHMe | —NHCH₂CH₂CH₂NHMe |
| 999 | —NHCH₂CH₂CH₂NMe₂ | —NHCH₂CH₂CH₂NMe₂ |
| 1000 | pyrrolidine-CH₂CH₂CH₂-NH- structure | pyrrolidine-CH₂CH₂CH₂-NH- structure |
| 1001 | piperidine-CH₂CH₂CH₂-NH- structure | piperidine-CH₂CH₂CH₂-NH- structure |
| 1002 | —NHCH₂CH₂OCH₂CH₂OH | —NHCH₂CH₂OCH₂CH₂OH |
| 1003 | —NHCH₂CH₂OCH₂CH₂OMe | —NHCH₂CH₂OCH₂CH₂OMe |
| 1004 | —NHCH₂CH₂OCH₂CH₂OEt | —NHCH₂CH₂OCH₂CH₂OEt |
| 1005 | —NHCH₂CH₂OCH₂CH₂NH₂ | —NHCH₂CH₂OCH₂CH₂NH₂ |
| 1006 | —NHCH₂CH₂OCH₂CH₂NHMe | —NHCH₂CH₂OCH₂CH₂NHMe |
| 1007 | —NHCH₂CH₂OCH₂CH₂NMe₂ | —NHCH₂CH₂OCH₂CH₂NMe₂ |
| 1008 | —N(CH₂CH₂OH)₂ | —N(CH₂CH₂OH)₂ |
| 1009 | —N(CH₂CH₂OMe)₂ | —N(CH₂CH₂OMe)₂ |
| 1010 | —N(CH₂CH₂OEt)₂ | —N(CH₂CH₂OEt)₂ |
| 1011 | —N(CH₂CH₂CH₂OH)₂ | —N(CH₂CH₂CH₂OH)₂ |
| 1012 | —N(CH₂CH₂CH₂OMe)₂ | —N(CH₂CH₂CH₂OMe)₂ |
| 1013 | —N(CH₂CH₂CH₂OEt)₂ | —N(CH₂CH₂CH₂OEt)₂ |
| 1014 | pyrrolidine-CH₂CH₂CH₂-O- structure | pyrrolidine-CH₂CH₂CH₂-O- structure |
| 1015 | —N(CH₂CH₂OCH₂CH₂OH)₂ | —N(CH₂CH₂OCH₂CH₂OH)₂ |
| 1016 | —N(CH₂CH₂OCH₂CH₂OMe)₂ | —N(CH₂CH₂OCH₂CH₂OMe)₂ |
| 1017 | —N(CH₂CH₂OCH₂CH₂OEt)₂ | —N(CH₂CH₂OCH₂CH₂OEt)₂ |
| 1018 | —NMeCH₂CH₂OH | —NMeCH₂CH₂OH |
| 1019 | —NMeCH₂CH₂OMe | —NMeCH₂CH₂OMe |
| 1020 | —NMeCH₂CH₂OEt | —NMeCH₂CH₂OEt |
| 1021 | —NMeCH₂CH₂NH₂ | —NMeCH₂CH₂NH₂ |
| 1022 | —NMeCH₂CH₂NHMe | —NMeCH₂CH₂NHMe |
| 1023 | —NMeCH₂CH₂NMe₂ | —NMeCH₂CH₂NMe₂ |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1024 | 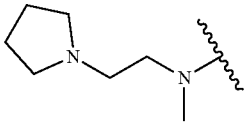 [SMILES: *N(C)CCN1CCCC1] | 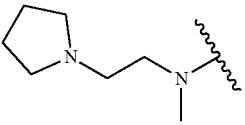 |
| 1025 | 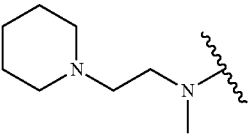 [SMILES: *N(C)CCN1CCCCC1] | 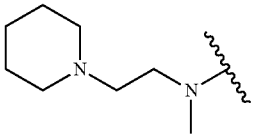 [SMILES: *N(C)CCN1CCCCC1] |
| 1026 | 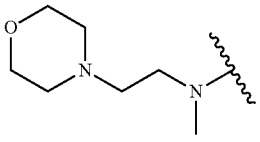 [SMILES: *N(C)CCN1CCOCC1] | 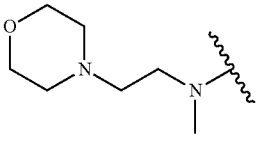 [SMILES: *N(C)CCN1CCOCC1] |
| 1027 | —NMeCH$_2$CH$_2$CH$_2$OH | —NMeCH$_2$CH$_2$CH$_2$OH |
| 1028 | —NMeCH$_2$CH$_2$CH$_2$OMe | —NMeCH$_2$CH$_2$CH$_2$OMe |
| 1029 | —NMeCH$_2$CH$_2$CH$_2$OEt | —NMeCH$_2$CH$_2$CH$_2$OEt |
| 1030 | —NMeCH$_2$CH$_2$CH$_2$NH$_2$ | —NMeCH$_2$CH$_2$CH$_2$NH$_2$ |
| 1031 | —NMeCH$_2$CH$_2$CH$_2$NHMe | —NMeCH$_2$CH$_2$CH$_2$NHMe |
| 1032 | —NMeCH$_2$CH$_2$CH$_2$NMe$_2$ | —NMeCH$_2$CH$_2$CH$_2$NMe$_2$ |
| 1033 | 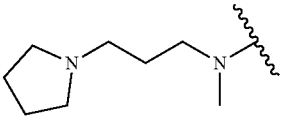 [SMILES: *N(C)CCCN1CCCC1] | 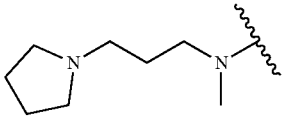 [SMILES: *N(C)CCCN1CCCC1] |
| 1034 | 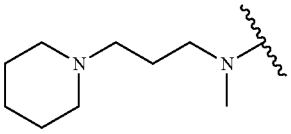 | 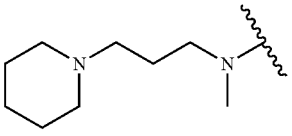 [SMILES: *N(C)CCCN1CCCCC1] |
| 1035 | 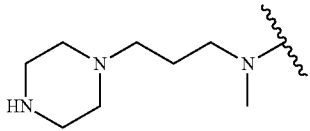 [SMILES: *N(C)CCCN1CCNCC1] | 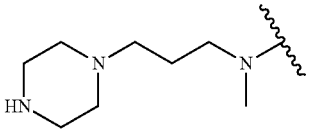 [SMILES: *N(C)CCCN1CCNCC1] |
| 1036 | 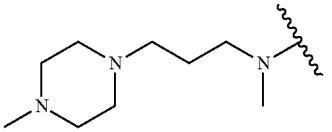 [SMILES: *N(C)CCCN1CCN(C)CC1] | 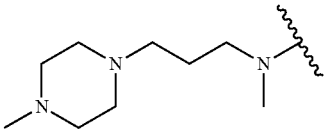 [SMILES: *N(C)CCCN1CCN(C)CC1] |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72))

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1037 | 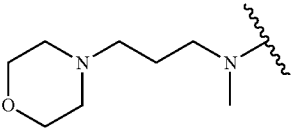 | 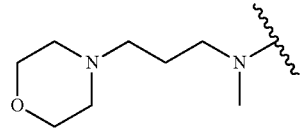 [SMILES: *N(C)CCCN1CCOCC1] |
| 1038 | —NMeCH$_2$CH$_2$OCH$_2$CH$_2$OH | —NMeCH$_2$CH$_2$OCH$_2$CH$_2$OH |
| 1039 | —NMeCH$_2$CH$_2$OCH$_2$CH$_2$OMe | —NMeCH$_2$CH$_2$OCH$_2$CH$_2$OMe |
| 1040 | —NMeCH$_2$CH$_2$OCH$_2$CH$_2$OEt | —NMeCH$_2$CH$_2$OCH$_2$CH$_2$OEt |
| 1041 | —NMeCH$_2$CH$_2$OCH$_2$CH$_2$NH$_2$ | —NMeCH$_2$CH$_2$OCH$_2$CH$_2$NH$_2$ |
| 1042 | —NMeCH$_2$CH$_2$OCH$_2$CH$_2$NHMe | —NMeCH$_2$CH$_2$OCH$_2$CH$_2$NHMe |
| 1043 | —NMeCH$_2$CH$_2$OCH$_2$CH$_2$NMe$_2$ | —NMeCH$_2$CH$_2$OCH$_2$CH$_2$NMe$_2$ |
| 1044 | —COOH | —COOH |
| 1045 | —CH$_2$(C=O)OH | —CH$_2$(C=O)OH |
| 1046 | —OCH$_2$(C=O)OH | —OCH$_2$(C=O)OH |
| 1047 | —NHCH$_2$(C=O)OH | —NHCH$_2$(C=O)OH |
| 1048 | —CH$_2$CH$_2$(C=O)OH | H |
| 1049 | —CH$_2$OCH$_2$(C=O)OH | H |
| 1050 | —OCH$_2$CH$_2$(C=O)OH | H |
| 1051 | —CH$_2$CH$_2$CH$_2$(C=O)OH | H |
| 1052 | —CH$_2$CH$_2$OCH$_2$(C=O)OH | H |
| 1053 | —CH$_2$OCH$_2$CH$_2$(C=O)OH | H |
| 1054 | —OCH$_2$CH$_2$CH$_2$(C=O)OH | H |
| 1055 | —OCH$_2$CH$_2$OCH$_2$(C=O)OH | H |
| 1056 | —CH$_2$CH$_2$CH$_2$CH$_2$(C=O)OH | H |
| 1057 | —CH$_2$CH$_2$CH$_2$OCH$_2$(C=O)OH | H |
| 1058 | —CH$_2$CH$_2$OCH$_2$CH$_2$(C=O)OH | H |
| 1059 | —CH$_2$OCH$_2$CH$_2$CH$_2$(C=O)OH | H |
| 1060 | —OCH$_2$CH$_2$CH$_2$CH$_2$(C=O)OH | H |
| 1061 | —CH$_2$OCH$_2$CH$_2$OCH$_2$(C=O)OH | H |
| 1062 | —OCH$_2$CH$_2$CH$_2$OCH$_2$(C=O)OH | H |
| 1063 | —OCH$_2$CH$_2$OCH$_2$CH$_2$(C=O)OH | H |
| 1064 | —CH$_2$OCH$_2$CH$_2$CH$_2$(C=O)OH | H |
| 1065 | —CH$_2$CH$_2$CH$_2$CH$_2$CH$_2$(C=O)OH | H |
| 1066 | —CH$_2$CH$_2$CH$_2$CH$_2$OCH$_2$(C=O)OH | H |
| 1067 | —CH$_2$CH$_2$CH$_2$OCH$_2$CH$_2$(C=O)OH | H |
| 1068 | —CH$_2$CH$_2$OCH$_2$CH$_2$CH$_2$(C=O)OH | H |
| 1069 | —CH$_2$OCH$_2$CH$_2$CH$_2$CH$_2$(C=O)OH | H |
| 1070 | —OCH$_2$CH$_2$CH$_2$CH$_2$CH$_2$(C=O)OH | H |
| 10710 | —CH$_2$CH$_2$OCH$_2$CH$_2$OCH$_2$(C=O)OH | H |
| 1072 | —CH$_2$OCH$_2$CH$_2$CH$_2$OCH$_2$(C=O)OH | H |
| 1073 | —OCH$_2$CH$_2$CH$_2$CH$_2$OCH$_2$(C=O)OH | H |
| 1074 | —CH$_2$OCH$_2$CH$_2$OCH$_2$CH$_2$(C=O)OH | H |
| 1075 | —OCH$_2$CH$_2$CH$_2$OCH$_2$CH$_2$(C=O)OH | H |
| 1076 | —OCH$_2$CH$_2$OCH$_2$CH$_2$CH$_2$(C=O)OH | H |
| 1077 | —OCH$_2$CH$_2$OCH$_2$CH$_2$OCH$_2$(C=O)OH | H |
| 1078 | —CH$_2$CH$_2$CH$_2$CH$_2$CH$_2$CH$_2$(C=O)OH | H |
| 1079 | —CH$_2$CH$_2$CH$_2$CH$_2$CH$_2$OCH$_2$(C=O)OH | H |
| 1080 | —CH$_2$CH$_2$OCH$_2$CH$_2$OCH$_2$(C=O)OH | H |
| 1081 | —CH$_2$OCH$_2$CH$_2$OCH$_2$CH$_2$OCH$_2$C(O)OH | H |
| 1082 | —OCH$_2$CH$_2$CH$_2$OCH$_2$CH$_2$OCH$_2$C(O)OH | H |
| 1083 | —CH$_2$CH$_2$CH$_2$CH$_2$OCH$_2$CH$_2$(C=O)OH | H |
| 1084 | —CH$_2$CH$_2$OCH$_2$CH$_2$OCH$_2$CH$_2$(C=O)OH | H |
| 1085 | —CH$_2$OCH$_2$CH$_2$CH$_2$CH$_2$CH$_2$(C=O)OH | H |
| 1086 | —OCH$_2$CH$_2$CH$_2$CH$_2$CH$_2$CH$_2$(C=O)OH | H |
| 1087 | —OCH$_2$CH$_2$OCH$_2$CH$_2$OCH$_2$CH$_2$(CO)OH | H |
| 1088 | —CH$_2$CH$_2$CH$_2$OCH$_2$CH$_2$CH$_2$(C=O)OH | H |
| 1089 | —CH$_2$OCH$_2$CH$_2$CH$_2$CH$_2$CH$_2$(C=O)OH | H |
| 1090 | —OCH$_2$CH$_2$CH$_2$CH$_2$CH$_2$CH$_2$(C=O)OH | H |
| 1091 | —CH$_2$CH$_2$OCH$_2$CH$_2$CH$_2$CH$_2$(C=O)OH | H |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1092 | —OCH$_2$CH$_2$OCH$_2$CH$_2$CH$_2$(C=O)OH | H |
| 1093 | —CH$_2$OCH$_2$CH$_2$CH$_2$CH$_2$(C=O)OH | H |
| 1094 | —OCH$_2$CH$_2$CH$_2$CH$_2$CH$_2$(C=O)OH | H |
| 1095 | —NHCH$_2$CH$_2$(C=O)OH | H |
| 1096 | —NMeCH$_2$CH$_2$(C=O)OH | H |
| 1097 | —N(CH$_2$CH$_2$(C=O)OH)$_2$ | H |
| 1098 | —NHCH$_2$CH$_2$OCH$_2$(C=O)OH | H |
| 1099 | —NMeCH$_2$CH$_2$OCH$_2$(C=O)OH | H |
| 1100 | —N(CH$_2$CH$_2$OCH$_2$(C=O)OH)$_2$ | H |
| 1101 | —NHCH$_2$CH$_2$CH$_2$(C=O)OH | H |
| 1102 | —NMeCH$_2$CH$_2$CH$_2$(C=O)OH | H |
| 1103 | —N(CH$_2$CH$_2$CH$_2$(C=O)OH)$_2$ | H |
| 1104 | —NHCH$_2$CH$_2$OCH$_2$(C=O)OH | H |
| 1105 | —NMeCH$_2$CH$_2$OCH$_2$(C=O)OH | H |
| 1106 | —N(CH$_2$CH$_2$OCH$_2$(C=O)OH)$_2$ | H |
| 1107 | —NHCH$_2$OCH$_2$CH$_2$(C=O)OH | H |
| 1108 | —NMeCH$_2$OCH$_2$CH$_2$(C=O)OH | H |
| 1109 | —N(CH$_2$CH$_2$OCH$_2$CH$_2$(C=O)OH)$_2$ | H |
| 1110 | —NHCH$_2$CH$_2$CH$_2$CH$_2$(C=O)OH | H |
| 1111 | —NMeCH$_2$CH$_2$CH$_2$CH$_2$(C=O)OH | H |
| 1112 | —N(CH$_2$CH$_2$CH$_2$CH$_2$(C=O)OH)$_2$ | H |
| 1113 | —NHCH$_2$CH$_2$CH$_2$OCH$_2$(C=O)OH | H |
| 1114 | —NMeCH$_2$CH$_2$CH$_2$OCH$_2$(C=O)OH | H |
| 1115 | —N(CH$_2$CH$_2$CH$_2$OCH$_2$(C=O)OH)$_2$ | H |
| 1116 | —NHCH$_2$CH$_2$OCH$_2$CH$_2$(C=O)OH | H |
| 1117 | —NMeCH$_2$CH$_2$OCH$_2$CH$_2$(C=O)OH | H |
| 1118 | —N(CH$_2$CH$_2$CH$_2$OCH$_2$CH$_2$(C=O)OH)$_2$ | H |
| 1119 | —NHCH$_2$OCH$_2$CH$_2$CH$_2$(C=O)OH | H |
| 1120 | —NMeCH$_2$OCH$_2$CH$_2$CH$_2$(C=O)OH | H |
| 1121 | —N(CH$_2$CH$_2$OCH$_2$CH$_2$(C=O)OH)$_2$ | H |
| 1122 | —NHCH$_2$CH$_2$OCH$_2$CH$_2$OCH$_2$(C=O)OH | H |
| 1123 | —NMeCH$_2$CH$_2$OCH$_2$CH$_2$OCH$_2$(C=O)OH | H |
| 1124 | —N(CH$_2$CH$_2$OCH$_2$CH$_2$OCH$_2$(C=O)OH)$_2$ | H |
| 1125 | —NHCH$_2$CH$_2$CH$_2$OCH$_2$CH$_2$OCH$_2$CO$_2$H | H |
| 1126 | —NMeCH$_2$CH$_2$CH$_2$OCH$_2$CH$_2$OCH$_2$CO$_2$H | H |
| 1127 | —N(CH$_2$CH$_2$CH$_2$OCH$_2$CH$_2$OCH$_2$CO$_2$H)$_2$ | H |
| 1128 | —NHCH$_2$CH$_2$CH$_2$CH$_2$OCH$_2$CH$_2$CO$_2$H | H |
| 1129 | —NMeCH$_2$CH$_2$CH$_2$CH$_2$OCH$_2$CH$_2$CO$_2$H | H |
| 1130 | —N(CH$_2$CH$_2$CH$_2$CH$_2$OCH$_2$CH$_2$CO$_2$H)$_2$ | H |
| 1131 | —NHCH$_2$OCH$_2$CH$_2$CH$_2$OCH$_2$CH$_2$CO$_2$H | H |
| 1132 | —NMeCH$_2$CH$_2$OCH$_2$CH$_2$OCH$_2$CH$_2$CO$_2$H | H |
| 1133 | —N(CH$_2$CH$_2$OCH$_2$CH$_2$OCH$_2$CH$_2$CO$_2$H)$_2$ | H |
| 1134 | —NHCH$_2$CH$_2$CH$_2$OCH$_2$CH$_2$CH$_2$CO$_2$H | H |
| 1135 | —NMeCH$_2$CH$_2$CH$_2$OCH$_2$CH$_2$CH$_2$CO$_2$H | H |
| 1136 | —N(CH$_2$CH$_2$CH$_2$OCH$_2$CH$_2$CH$_2$CO$_2$H)$_2$ | H |
| 1137 | —NHCH$_2$OCH$_2$CH$_2$CH$_2$CH$_2$CO$_2$H | H |
| 1138 | —NMeCH$_2$OCH$_2$CH$_2$CH$_2$CH$_2$CO$_2$H | H |
| 1139 | —N(CH$_2$CH$_2$OCH$_2$CH$_2$CH$_2$CH$_2$CO$_2$H)$_2$ | H |
| 1140 | —NHCH$_2$CH$_2$CH$_2$CH$_2$CH$_2$CO$_2$H | H |
| 1141 | —NMeCH$_2$CH$_2$CH$_2$CH$_2$CH$_2$CO$_2$H | H |
| 1142 | —N(CH$_2$CH$_2$CH$_2$CH$_2$CH$_2$CO$_2$H)$_2$ | H |
| 1143 | H | —CH$_2$CH$_2$(C=O)OH |
| 1144 | H | —CH$_2$OCH$_2$(C=O)OH |
| 1145 | H | —OCH$_2$CH$_2$(C=O)OH |
| 1146 | H | —CH$_2$CH$_2$CH$_2$(C=O)OH |
| 1147 | H | —CH$_2$CH$_2$OCH$_2$(C=O)OH |
| 1148 | H | —CH$_2$OCH$_2$CH$_2$(C=O)OH |
| 1149 | H | —OCH$_2$CH$_2$CH$_2$(C=O)OH |
| 1150 | H | —OCH$_2$CH$_2$OCH$_2$(C=O)OH |
| 1151 | H | —CH$_2$CH$_2$CH$_2$CH$_2$(C=O)OH |
| 1152 | H | —CH$_2$CH$_2$CH$_2$OCH$_2$(C=O)OH |
| 1153 | H | —CH$_2$CH$_2$OCH$_2$CH$_2$(C=O)OH |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ in formulae (III), (III-A), (III-B), and B-1 to B-10) or $R^7$ in formulae (C-13) to (C-24) or $Z^2$ in formulae (D-27) to (D-52) |
|---|---|---|
| 1154 | H | —CH$_2$OCH$_2$CH$_2$CH$_2$(C=O)OH |
| 1155 | H | —OCH$_2$CH$_2$CH$_2$CH$_2$(C=O)OH |
| 1156 | H | —CH$_2$OCH$_2$CH$_2$OCH$_2$(C=O)OH |
| 1157 | H | —OCH$_2$CH$_2$CH$_2$OCH$_2$(C=O)OH |
| 1158 | H | —OCH$_2$CH$_2$OCH$_2$CH$_2$(C=O)OH |
| 1159 | H | —CH$_2$OCH$_2$CH$_2$CH$_2$(C=O)OH |
| 1160 | H | —CH$_2$CH$_2$CH$_2$CH$_2$(C=O)OH |
| 1161 | H | —CH$_2$CH$_2$CH$_2$CH$_2$OCH$_2$(C=O)OH |
| 1162 | H | —CH$_2$CH$_2$CH$_2$OCH$_2$CH$_2$(C=O)OH |
| 1163 | H | —CH$_2$CH$_2$OCH$_2$CH$_2$CH$_2$(C=O)OH |
| 1164 | H | —CH$_2$OCH$_2$CH$_2$CH$_2$CH$_2$(C=O)OH |
| 1165 | H | —OCH$_2$CH$_2$CH$_2$CH$_2$CH$_2$(C=O)OH |
| 1166 | H | —CH$_2$CH$_2$OCH$_2$CH$_2$OCH$_2$(C=O)OH |
| 1167 | H | —CH$_2$OCH$_2$CH$_2$CH$_2$OCH$_2$(C=O)OH |
| 1168 | H | —OCH$_2$CH$_2$CH$_2$OCH$_2$CH$_2$(C=O)OH |
| 1169 | H | —CH$_2$OCH$_2$CH$_2$OCH$_2$CH$_2$(C=O)OH |
| 1170 | H | —OCH$_2$CH$_2$CH$_2$OCH$_2$CH$_2$(C=O)OH |
| 11711 | H | —OCH$_2$CH$_2$OCH$_2$CH$_2$CH$_2$(C=O)OH |
| 1172 | H | —OCH$_2$CH$_2$OCH$_2$CH$_2$OCH$_2$(C=O)OH |
| 1173 | H | —CH$_2$CH$_2$CH$_2$CH$_2$CH$_2$CH$_2$(C=O)OH |
| 1174 | H | —CH$_2$CH$_2$CH$_2$CH$_2$OCH$_2$(C=O)OH |
| 1175 | H | —CH$_2$CH$_2$CH$_2$OCH$_2$CH$_2$OCH$_2$(C=O)OH |
| 1176 | H | —CH$_2$OCH$_2$CH$_2$OCH$_2$CH$_2$OCH$_2$C(O)OH |
| 1177 | H | —OCH$_2$CH$_2$OCH$_2$CH$_2$OCH$_2$C(O)OH |
| 1178 | H | —CH$_2$CH$_2$CH$_2$CH$_2$OCH$_2$CH$_2$(C=O)OH |
| 1179 | H | —CH$_2$CH$_2$OCH$_2$CH$_2$OCH$_2$CH$_2$(C=O)OH |
| 1180 | H | —CH$_2$OCH$_2$CH$_2$OCH$_2$CH$_2$CH$_2$(C=O)OH |
| 1181 | H | —OCH$_2$CH$_2$OCH$_2$CH$_2$CH$_2$CH$_2$(C=O)OH |
| 1182 | H | —OCH$_2$CH$_2$OCH$_2$CH$_2$OCH$_2$CH$_2$(CO)OH |
| 1183 | H | —CH$_2$CH$_2$CH$_2$OCH$_2$CH$_2$CH$_2$(C=O)OH |
| 1184 | H | —CH$_2$OCH$_2$CH$_2$OCH$_2$CH$_2$CH$_2$(C=O)OH |
| 1185 | H | —OCH$_2$CH$_2$OCH$_2$CH$_2$CH$_2$CH$_2$(C=O)OH |
| 1186 | H | —CH$_2$CH$_2$OCH$_2$CH$_2$CH$_2$CH$_2$(C=O)OH |
| 1187 | H | —OCH$_2$CH$_2$OCH$_2$CH$_2$CH$_2$CH$_2$(C=O)OH |
| 1188 | H | —CH$_2$OCH$_2$CH$_2$CH$_2$CH$_2$CH$_2$(C=O)OH |
| 1189 | H | —OCH$_2$CH$_2$CH$_2$CH$_2$CH$_2$CH$_2$(C=O)OH |
| 1190 | H | —NHCH$_2$(C=O)OH |
| 1191 | H | —NMeCH$_2$(C=O)OH |
| 1192 | H | —N(CH$_2$CH$_2$(C=O)OH)$_2$ |
| 1193 | H | —NHCH$_2$CH$_2$OCH$_2$(C=O)OH |
| 1194 | H | —NMeCH$_2$CH$_2$OCH$_2$(C=O)OH |
| 1195 | H | —N(CH$_2$CH$_2$OCH$_2$(C=O)OH)$_2$ |
| 1196 | H | —NHCH$_2$CH$_2$CH$_2$CH$_2$(C=O)OH |
| 1197 | H | —NMeCH$_2$CH$_2$CH$_2$CH$_2$(C=O)OH |
| 1198 | H | —N(CH$_2$CH$_2$CH$_2$CH$_2$(C=O)OH)$_2$ |
| 1199 | H | —NHCH$_2$CH$_2$CH$_2$OCH$_2$(C=O)OH |
| 1200 | H | —NMeCH$_2$CH$_2$CH$_2$OCH$_2$(C=O)OH |
| 1201 | H | —N(CH$_2$CH$_2$CH$_2$OCH$_2$(C=O)OH)$_2$ |
| 1202 | H | —NHCH$_2$CH$_2$OCH$_2$CH$_2$(C=O)OH |
| 1203 | H | —NMeCH$_2$CH$_2$OCH$_2$CH$_2$(C=O)OH |
| 1204 | H | —N(CH$_2$CH$_2$OCH$_2$CH$_2$(C=O)OH)$_2$ |
| 1205 | H | —NHCH$_2$CH$_2$CH$_2$CH$_2$CH$_2$(C=O)OH |
| 1206 | H | —NMeCH$_2$CH$_2$CH$_2$CH$_2$CH$_2$(C=O)OH |
| 1207 | H | —N(CH$_2$CH$_2$CH$_2$CH$_2$CH$_2$(C=O)OH)$_2$ |
| 1208 | H | —NHCH$_2$CH$_2$CH$_2$CH$_2$OCH$_2$(C=O)OH |
| 1209 | H | —NMeCH$_2$CH$_2$CH$_2$CH$_2$OCH$_2$(C=O)OH |
| 1210 | H | —N(CH$_2$CH$_2$CH$_2$CH$_2$OCH$_2$(C=O)OH)$_2$ |
| 1211 | H | —NHCH$_2$CH$_2$CH$_2$OCH$_2$CH$_2$(C=O)OH |
| 1212 | H | —NMeCH$_2$CH$_2$CH$_2$OCH$_2$CH$_2$(C=O)OH |
| 1213 | H | —N(CH$_2$CH$_2$CH$_2$OCH$_2$CH$_2$(C=O)OH)$_2$ |
| 1214 | H | —NHCH$_2$CH$_2$OCH$_2$CH$_2$CH$_2$(C=O)OH |
| 1215 | H | —NMeCH$_2$CH$_2$OCH$_2$CH$_2$CH$_2$(C=O)OH |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1216 | H | —N(CH$_2$CH$_2$OCH$_2$CH$_2$C(=O)OH)$_2$ |
| 1217 | H | —NHCH$_2$CH$_2$OCH$_2$CH$_2$OCH$_2$C(=O)OH |
| 1218 | H | —NMeCH$_2$CH$_2$OCH$_2$CH$_2$OCH$_2$C(=O)OH |
| 1219 | H | —N(CH$_2$CH$_2$OCH$_2$CH$_2$OCH$_2$C(=O)OH)$_2$ |
| 1220 | H | —NHCH$_2$CH$_2$CH$_2$OCH$_2$CH$_2$OCH$_2$CO$_2$H |
| 1221 | H | —NMeCH$_2$CH$_2$CH$_2$OCH$_2$CH$_2$OCH$_2$CO$_2$H |
| 1222 | H | —N(CH$_2$CH$_2$CH$_2$OCH$_2$CH$_2$OCH$_2$CO$_2$H)$_2$ |
| 1223 | H | —NHCH$_2$CH$_2$CH$_2$OCH$_2$CH$_2$CO$_2$H |
| 1224 | H | —NMeCH$_2$CH$_2$CH$_2$OCH$_2$CH$_2$CO$_2$H |
| 1225 | H | —N(CH$_2$CH$_2$CH$_2$CH$_2$OCH$_2$CH$_2$CO$_2$H)$_2$ |
| 1226 | H | —NHCH$_2$CH$_2$OCH$_2$CH$_2$CH$_2$CO$_2$H |
| 1227 | H | —NMeCH$_2$CH$_2$OCH$_2$CH$_2$CH$_2$CO$_2$H |
| 1228 | H | —N(CH$_2$CH$_2$OCH$_2$CH$_2$OCH$_2$CH$_2$CO$_2$H)$_2$ |
| 1229 | H | —NHCH$_2$CH$_2$CH$_2$OCH$_2$CH$_2$CH$_2$CO$_2$H |
| 1230 | H | —NMeCH$_2$CH$_2$CH$_2$OCH$_2$CH$_2$CH$_2$CO$_2$H |
| 1231 | H | —N(CH$_2$CH$_2$CH$_2$OCH$_2$CH$_2$CH$_2$CO$_2$H)$_2$ |
| 1232 | H | —NHCH$_2$OCH$_2$CH$_2$CH$_2$CH$_2$CO$_2$H |
| 1233 | H | —NMeCH$_2$OCH$_2$CH$_2$CH$_2$CH$_2$CO$_2$H |
| 1234 | H | —N(CH$_2$OCH$_2$CH$_2$CH$_2$CH$_2$CO$_2$H)$_2$ |
| 1235 | H | —NHCH$_2$CH$_2$CH$_2$CH$_2$CH$_2$CH$_2$CO$_2$H |
| 1236 | H | —NMeCH$_2$CH$_2$CH$_2$CH$_2$CH$_2$CH$_2$CO$_2$H |
| 1237 | H | —N(CH$_2$CH$_2$CH$_2$CH$_2$CH$_2$CH$_2$CO$_2$H)$_2$ |
| 1238 | —CH$_2$CH$_2$C(=O)OH | —CH$_2$CH$_2$C(=O)OH |
| 1239 | —CH$_2$OCH$_2$C(=O)OH | —CH$_2$OCH$_2$C(=O)OH |
| 1240 | —OCH$_2$CH$_2$C(=O)OH | —OCH$_2$CH$_2$C(=O)OH |
| 1241 | —CH$_2$CH$_2$CH$_2$C(=O)OH | —CH$_2$CH$_2$CH$_2$C(=O)OH |
| 1242 | —CH$_2$CH$_2$OCH$_2$C(=O)OH | —CH$_2$CH$_2$OCH$_2$C(=O)OH |
| 1243 | —CH$_2$OCH$_2$CH$_2$C(=O)OH | —CH$_2$OCH$_2$CH$_2$C(=O)OH |
| 1244 | —OCH$_2$CH$_2$CH$_2$C(=O)OH | —OCH$_2$CH$_2$CH$_2$C(=O)OH |
| 1245 | —OCH$_2$CH$_2$OCH$_2$C(=O)OH | —OCH$_2$CH$_2$OCH$_2$C(=O)OH |
| 1246 | —CH$_2$CH$_2$CH$_2$CH$_2$C(=O)OH | —CH$_2$CH$_2$CH$_2$CH$_2$C(=O)OH |
| 1247 | —CH$_2$CH$_2$CH$_2$OCH$_2$C(=O)OH | —CH$_2$CH$_2$CH$_2$OCH$_2$C(=O)OH |
| 1248 | —CH$_2$CH$_2$OCH$_2$CH$_2$C(=O)OH | —CH$_2$CH$_2$OCH$_2$CH$_2$C(=O)OH |
| 1249 | —CH$_2$OCH$_2$CH$_2$CH$_2$C(=O)OH | —CH$_2$OCH$_2$CH$_2$CH$_2$C(=O)OH |
| 1250 | —OCH$_2$CH$_2$CH$_2$CH$_2$C(=O)OH | —OCH$_2$CH$_2$CH$_2$CH$_2$C(=O)OH |
| 1251 | —CH$_2$OCH$_2$CH$_2$OCH$_2$C(=O)OH | —CH$_2$OCH$_2$CH$_2$OCH$_2$C(=O)OH |
| 1252 | —OCH$_2$CH$_2$CH$_2$OCH$_2$C(=O)OH | —OCH$_2$CH$_2$CH$_2$OCH$_2$C(=O)OH |
| 1253 | —OCH$_2$CH$_2$OCH$_2$CH$_2$C(=O)OH | —OCH$_2$CH$_2$OCH$_2$CH$_2$C(=O)OH |
| 1254 | —CH$_2$OCH$_2$CH$_2$CH$_2$C(=O)OH | —CH$_2$OCH$_2$CH$_2$CH$_2$C(=O)OH |
| 1255 | —CH$_2$CH$_2$CH$_2$CH$_2$CH$_2$C(=O)OH | —CH$_2$CH$_2$CH$_2$CH$_2$CH$_2$C(=O)OH |
| 1256 | —CH$_2$CH$_2$CH$_2$CH$_2$OCH$_2$C(=O)OH | —CH$_2$CH$_2$CH$_2$CH$_2$OCH$_2$C(=O)OH |
| 1257 | —CH$_2$CH$_2$CH$_2$OCH$_2$CH$_2$C(=O)OH | —CH$_2$CH$_2$CH$_2$OCH$_2$CH$_2$C(=O)OH |
| 1258 | —CH$_2$CH$_2$OCH$_2$CH$_2$CH$_2$C(=O)OH | —CH$_2$CH$_2$OCH$_2$CH$_2$CH$_2$C(=O)OH |
| 1259 | —CH$_2$OCH$_2$CH$_2$CH$_2$CH$_2$C(=O)OH | —CH$_2$OCH$_2$CH$_2$CH$_2$CH$_2$C(=O)OH |
| 1260 | —OCH$_2$CH$_2$CH$_2$CH$_2$CH$_2$C(=O)OH | —OCH$_2$CH$_2$CH$_2$CH$_2$CH$_2$C(=O)OH |
| 1261 | —CH$_2$CH$_2$OCH$_2$CH$_2$OCH$_2$C(=O)OH | —CH$_2$CH$_2$OCH$_2$CH$_2$OCH$_2$C(=O)OH |
| 1262 | —CH$_2$OCH$_2$CH$_2$CH$_2$OCH$_2$C(=O)OH | —CH$_2$OCH$_2$CH$_2$CH$_2$OCH$_2$C(=O)OH |
| 1263 | —OCH$_2$CH$_2$CH$_2$CH$_2$OCH$_2$C(=O)OH | —OCH$_2$CH$_2$CH$_2$CH$_2$OCH$_2$C(=O)OH |
| 1264 | —CH$_2$OCH$_2$CH$_2$OCH$_2$CH$_2$C(=O)OH | —CH$_2$OCH$_2$CH$_2$OCH$_2$CH$_2$C(=O)OH |
| 1265 | —OCH$_2$CH$_2$CH$_2$OCH$_2$CH$_2$C(=O)OH | —OCH$_2$CH$_2$CH$_2$OCH$_2$CH$_2$C(=O)OH |
| 1266 | —OCH$_2$CH$_2$OCH$_2$CH$_2$CH$_2$C(=O)OH | —OCH$_2$CH$_2$OCH$_2$CH$_2$CH$_2$C(=O)OH |
| 1267 | —OCH$_2$CH$_2$OCH$_2$CH$_2$OCH$_2$C(=O)OH | —OCH$_2$CH$_2$OCH$_2$CH$_2$OCH$_2$C(=O)OH |
| 1268 | —CH$_2$CH$_2$CH$_2$CH$_2$CH$_2$CH$_2$C(=O)OH | —CH$_2$CH$_2$CH$_2$CH$_2$CH$_2$CH$_2$C(=O)OH |
| 1269 | —CH$_2$CH$_2$CH$_2$CH$_2$CH$_2$OCH$_2$C(=O)OH | —CH$_2$CH$_2$CH$_2$CH$_2$CH$_2$OCH$_2$C(=O)OH |
| 1270 | —CH$_2$CH$_2$CH$_2$OCH$_2$CH$_2$OCH$_2$C(=O)OH | —CH$_2$CH$_2$CH$_2$OCH$_2$CH$_2$OCH$_2$C(=O)OH |
| 12712 | —CH$_2$OCH$_2$CH$_2$OCH$_2$CH$_2$OCH$_2$C(O)OH | —CH$_2$OCH$_2$CH$_2$OCH$_2$CH$_2$OCH$_2$C(O)OH |
| 1272 | —OCH$_2$CH$_2$OCH$_2$CH$_2$OCH$_2$CH$_2$C(O)OH | —OCH$_2$CH$_2$OCH$_2$CH$_2$OCH$_2$CH$_2$C(O)OH |
| 1273 | —CH$_2$CH$_2$CH$_2$CH$_2$OCH$_2$CH$_2$C(=O)OH | —CH$_2$CH$_2$CH$_2$CH$_2$OCH$_2$CH$_2$C(=O)OH |
| 1274 | —CH$_2$CH$_2$OCH$_2$CH$_2$OCH$_2$CH$_2$C(=O)OH | —CH$_2$CH$_2$OCH$_2$CH$_2$OCH$_2$CH$_2$C(=O)OH |
| 1275 | —CH$_2$OCH$_2$CH$_2$OCH$_2$CH$_2$CH$_2$C(=O)OH | —CH$_2$OCH$_2$CH$_2$OCH$_2$CH$_2$CH$_2$C(=O)OH |
| 1276 | —OCH$_2$CH$_2$CH$_2$OCH$_2$CH$_2$CH$_2$C(=O)OH | —OCH$_2$CH$_2$CH$_2$OCH$_2$CH$_2$CH$_2$C(=O)OH |
| 1277 | —OCH$_2$CH$_2$OCH$_2$CH$_2$OCH$_2$CH$_2$(CO)OH | —OCH$_2$CH$_2$OCH$_2$CH$_2$OCH$_2$CH$_2$(CO)OH |

TABLE 1-continued

Compounds of Formulae ((II), (III), (III-A), (III-B), (A-1), (A-2), (A-3), (A-4), (A-5), (B-1), (B-2), (B-3), (B-4), (B-5), (B-6), (B-7), (B-8), (B-9), (B-10), (C-1), (C-2), (C-3), (C-4), (C-5), (C-6), (C-7), (C-8), (C-9), (C-10), (C-11), (C-12), (C-13), (C-14), (C-15), (C-16), (C-17), (C-18), (C-19), (C-20), (C-21), (C-22), (C-23), (C-24), (D-1), (D-2), (D-3), (D-4), (D-5), (D-6), (D-7), (D-8), (D-9), (D-10), (D-11), (D-12), (D-13), (D-14), (D-15), (D-16), (D-17), (D-18), (D-19), (D-20), (D-21), (D-22), (D-23), (D-24), (D-25), (D-26), (D-27), (D-28), (D-29), (D-30), (D-31), (D-32), (D-33), (D-34), (D-35), (D-36), (D-37), (D-38), (D-39), (D-40), (D-41), (D-42), (D-43), (D-44), (D-45), (D-46), (D-47), (D-48), (D-49), (D-50), (D-51), (D-52), (D-53), (D-54), (D-55), (D-56), (D-57), (D-58), (D-59), (D-60), (D-61), (D-62), (D-63), (D-64), (D-65), (D-66), (D-67), (D-68), (D-69), (D-70), (D-71) and (D-72)

| Entry | $R^6$ (in formulae (II), and A-1 to A-5) or $Z^1$ (in formulae (III), (III-A), (III-B), and B-1 to B-10) or $R^6$ in formulae (C-1) to (C-12) or $Z^1$ in formulae (D-1) to (D-26) and (D-53) to (D-72) | $R^7$ (in formulae (II), and A-1 to A5) or $Z^2$ (in formulae (III), (III-A), (III-B), and B-1 to B-10) or $R^7$ in formulae (C-13) to (C-24) or $Z^2$ in formulae (D-27) to (D-52) |
|---|---|---|
| 1278 | —CH$_2$CH$_2$CH$_2$OCH$_2$CH$_2$CH$_2$(C=O)OH | —CH$_2$CH$_2$CH$_2$OCH$_2$CH$_2$CH$_2$(C=O)OH |
| 1279 | —CH$_2$OCH$_2$CH$_2$OCH$_2$CH$_2$CH$_2$(C=O)OH | —CH$_2$OCH$_2$CH$_2$OCH$_2$CH$_2$CH$_2$(C=O)OH |
| 1280 | —OCH$_2$CH$_2$CH$_2$OCH$_2$CH$_2$CH$_2$(C=O)OH | —OCH$_2$CH$_2$CH$_2$OCH$_2$CH$_2$CH$_2$(C=O)OH |
| 1281 | —CH$_2$CH$_2$OCH$_2$CH$_2$CH$_2$CH$_2$(C=O)OH | —CH$_2$CH$_2$OCH$_2$CH$_2$CH$_2$CH$_2$(C=O)OH |
| 1282 | —OCH$_2$CH$_2$OCH$_2$CH$_2$CH$_2$CH$_2$(C=O)OH | —OCH$_2$CH$_2$OCH$_2$CH$_2$CH$_2$CH$_2$(C=O)OH |
| 1283 | —CH$_2$OCH$_2$CH$_2$CH$_2$CH$_2$CH$_2$(C=O)OH | —CH$_2$OCH$_2$CH$_2$CH$_2$CH$_2$CH$_2$(C=O)OH |
| 1284 | —OCH$_2$CH$_2$CH$_2$CH$_2$CH$_2$CH$_2$(C=O)OH | —OCH$_2$CH$_2$CH$_2$CH$_2$CH$_2$CH$_2$(C=O)OH |
| 1285 | —NHCH$_2$CH$_2$(C=O)OH | —NHCH$_2$CH$_2$(C=O)OH |
| 1286 | —NMeCH$_2$CH$_2$(C=O)OH | —NMeCH$_2$CH$_2$(C=O)OH |
| 1287 | —N(CH$_2$CH$_2$(C=O)OH)$_2$ | —N(CH$_2$CH$_2$(C=O)OH)$_2$ |
| 1288 | —NHCH$_2$OCH$_2$(C=O)OH | —NHCH$_2$OCH$_2$(C=O)OH |
| 1289 | —NMeCH$_2$CH$_2$OCH$_2$(C=O)OH | —NMeCH$_2$CH$_2$OCH$_2$(C=O)OH |
| 1290 | —N(CH$_2$CH$_2$OCH$_2$(C=O)OH)$_2$ | —N(CH$_2$CH$_2$OCH$_2$(C=O)OH)$_2$ |
| 1291 | —NHCH$_2$CH$_2$CH$_2$(C=O)OH | —NHCH$_2$CH$_2$CH$_2$(C=O)OH |
| 1292 | —NMeCH$_2$CH$_2$CH$_2$(C=O)OH | —NMeCH$_2$CH$_2$CH$_2$(C=O)OH |
| 1293 | —N(CH$_2$CH$_2$CH$_2$(C=O)OH)$_2$ | —N(CH$_2$CH$_2$CH$_2$(C=O)OH)$_2$ |
| 1294 | —NHCH$_2$CH$_2$OCH$_2$(C=O)OH | —NHCH$_2$CH$_2$OCH$_2$(C=O)OH |
| 1295 | —NMeCH$_2$CH$_2$CH$_2$OCH$_2$(C=O)OH | —NMeCH$_2$CH$_2$CH$_2$OCH$_2$(C=O)OH |
| 1296 | —N(CH$_2$CH$_2$OCH$_2$(C=O)OH)$_2$ | —N(CH$_2$CH$_2$OCH$_2$(C=O)OH)$_2$ |
| 1297 | —NHCH$_2$OCH$_2$CH$_2$(C=O)OH | —NHCH$_2$OCH$_2$CH$_2$(C=O)OH |
| 1298 | —NMeCH$_2$OCH$_2$CH$_2$(C=O)OH | —NMeCH$_2$OCH$_2$CH$_2$(C=O)OH |
| 1299 | —N(CH$_2$CH$_2$OCH$_2$CH$_2$(C=O)OH)$_2$ | —N(CH$_2$CH$_2$OCH$_2$CH$_2$(C=O)OH)$_2$ |
| 1300 | —NHCH$_2$CH$_2$CH$_2$CH$_2$(C=O)OH | —NHCH$_2$CH$_2$CH$_2$CH$_2$(C=O)OH |
| 1301 | —NMeCH$_2$CH$_2$CH$_2$CH$_2$(C=O)OH | —NMeCH$_2$CH$_2$CH$_2$CH$_2$(C=O)OH |
| 1302 | —N(CH$_2$CH$_2$CH$_2$CH$_2$(C=O)OH)$_2$ | —N(CH$_2$CH$_2$CH$_2$CH$_2$(C=O)OH)$_2$ |
| 1303 | —NHCH$_2$CH$_2$CH$_2$OCH$_2$(C=O)OH | —NHCH$_2$CH$_2$CH$_2$OCH$_2$(C=O)OH |
| 1304 | —NMeCH$_2$CH$_2$CH$_2$OCH$_2$(C=O)OH | —NMeCH$_2$CH$_2$CH$_2$OCH$_2$(C=O)OH |
| 1305 | —N(CH$_2$CH$_2$CH$_2$OCH$_2$(C=O)OH)$_2$ | —N(CH$_2$CH$_2$CH$_2$OCH$_2$(C=O)OH)$_2$ |
| 1306 | —NHCH$_2$CH$_2$OCH$_2$CH$_2$(C=O)OH | —NHCH$_2$CH$_2$OCH$_2$CH$_2$(C=O)OH |
| 1307 | —NMeCH$_2$CH$_2$OCH$_2$CH$_2$(C=O)OH | —NMeCH$_2$CH$_2$OCH$_2$CH$_2$(C=O)OH |
| 1308 | —N(CH$_2$CH$_2$CH$_2$OCH$_2$CH$_2$(C=O)OH)$_2$ | —N(CH$_2$CH$_2$CH$_2$OCH$_2$CH$_2$(C=O)OH)$_2$ |
| 1309 | —NHCH$_2$OCH$_2$CH$_2$CH$_2$(C=O)OH | —NHCH$_2$OCH$_2$CH$_2$CH$_2$(C=O)OH |
| 1313 | —NMeCH$_2$OCH$_2$CH$_2$CH$_2$(C=O)OH | —NMeCH$_2$OCH$_2$CH$_2$CH$_2$(C=O)OH |
| 1311 | —N(CH$_2$CH$_2$OCH$_2$CH$_2$CH$_2$(C=O)OH)$_2$ | —N(CH$_2$CH$_2$OCH$_2$CH$_2$CH$_2$(C=O)OH)$_2$ |
| 1312 | —NHCH$_2$CH$_2$OCH$_2$CH$_2$OCH$_2$(C=O)OH | —NHCH$_2$CH$_2$OCH$_2$CH$_2$OCH$_2$(C=O)OH |
| 1313 | —NMeCH$_2$OCH$_2$CH$_2$OCH$_2$(C=O)OH | —NMeCH$_2$OCH$_2$CH$_2$OCH$_2$(C=O)OH |
| 1314 | —N(CH$_2$CH$_2$OCH$_2$CH$_2$OCH$_2$(C=O)OH)$_2$ | —N(CH$_2$CH$_2$OCH$_2$CH$_2$OCH$_2$(C=O)OH)$_2$ |
| 1315 | —NHCH$_2$CH$_2$CH$_2$OCH$_2$CH$_2$OCH$_2$CO$_2$H | —NHCH$_2$CH$_2$CH$_2$OCH$_2$CH$_2$OCH$_2$CO$_2$H |
| 1316 | —NMeCH$_2$CH$_2$CH$_2$OCH$_2$CH$_2$OCH$_2$CO$_2$H | —NMeCH$_2$CH$_2$CH$_2$OCH$_2$CH$_2$OCH$_2$CO$_2$H |
| 1317 | —N(CH$_2$CH$_2$CH$_2$OCH$_2$CH$_2$OCH$_2$CO$_2$H)$_2$ | —N(CH$_2$CH$_2$CH$_2$OCH$_2$CH$_2$OCH$_2$CO$_2$H)$_2$ |
| 1318 | —NHCH$_2$CH$_2$CH$_2$CH$_2$OCH$_2$CH$_2$CO$_2$H | —NHCH$_2$CH$_2$CH$_2$CH$_2$OCH$_2$CH$_2$CO$_2$H |
| 1319 | —NMeCH$_2$CH$_2$CH$_2$CH$_2$OCH$_2$CH$_2$CO$_2$H | —NMeCH$_2$CH$_2$CH$_2$CH$_2$OCH$_2$CH$_2$CO$_2$H |
| 1320 | —N(CH$_2$CH$_2$CH$_2$CH$_2$OCH$_2$CH$_2$CO$_2$H)$_2$ | —N(CH$_2$CH$_2$CH$_2$CH$_2$OCH$_2$CH$_2$CO$_2$H)$_2$ |
| 1321 | —NHCH$_2$CH$_2$OCH$_2$OCH$_2$CH$_2$CO$_2$H | —NHCH$_2$CH$_2$OCH$_2$OCH$_2$CH$_2$CO$_2$H |
| 1322 | —NMeCH$_2$CH$_2$OCH$_2$OCH$_2$CH$_2$CO$_2$H | —NMeCH$_2$CH$_2$OCH$_2$OCH$_2$CH$_2$CO$_2$H |
| 1323 | —N(CH$_2$CH$_2$OCH$_2$OCH$_2$CH$_2$CO$_2$H)$_2$ | —N(CH$_2$CH$_2$OCH$_2$OCH$_2$CH$_2$CO$_2$H)$_2$ |
| 1324 | —NHCH$_2$CH$_2$CH$_2$OCH$_2$CH$_2$CH$_2$CO$_2$H | —NHCH$_2$CH$_2$CH$_2$OCH$_2$CH$_2$CH$_2$CO$_2$H |
| 1325 | —NMeCH$_2$CH$_2$CH$_2$OCH$_2$CH$_2$CH$_2$CO$_2$H | —NMeCH$_2$CH$_2$CH$_2$OCH$_2$CH$_2$CH$_2$CO$_2$H |
| 1326 | —N(CH$_2$CH$_2$CH$_2$OCH$_2$CH$_2$CH$_2$CO$_2$H)$_2$ | —N(CH$_2$CH$_2$CH$_2$OCH$_2$CH$_2$CH$_2$CO$_2$H)$_2$ |
| 1327 | —NHCH$_2$OCH$_2$CH$_2$CH$_2$CH$_2$CO$_2$H | —NHCH$_2$OCH$_2$CH$_2$CH$_2$CH$_2$CO$_2$H |
| 1328 | —NMeCH$_2$OCH$_2$CH$_2$CH$_2$CH$_2$CO$_2$H | —NMeCH$_2$OCH$_2$CH$_2$CH$_2$CH$_2$CO$_2$H |
| 1329 | —N(CH$_2$CH$_2$OCH$_2$CH$_2$CH$_2$CH$_2$CO$_2$H)$_2$ | —N(CH$_2$CH$_2$OCH$_2$CH$_2$CH$_2$CH$_2$CO$_2$H)$_2$ |
| 1330 | —NHCH$_2$CH$_2$CH$_2$CH$_2$CH$_2$CO$_2$H | —NHCH$_2$CH$_2$CH$_2$CH$_2$CH$_2$CO$_2$H |
| 1331 | —NMeCH$_2$CH$_2$CH$_2$CH$_2$CH$_2$CO$_2$H | —NMeCH$_2$CH$_2$CH$_2$CH$_2$CH$_2$CO$_2$H |
| 1332 | —N(CH$_2$CH$_2$CH$_2$CH$_2$CH$_2$CO$_2$H)$_2$ | —N(CH$_2$CH$_2$CH$_2$CH$_2$CH$_2$CO$_2$H)$_2$ |

For each of the compounds depicted above in Table 1 that is a carboxylic acid, the compounds ester derivatives are also provided. The ester can be, e.g., a methyl ester, an ethyl ester, an n-propyl ester, an isopropyl ester, a cyclopropyl ester, an n-butyl ester, a s-butyl ester, an isobutyl ester, or a t-butyl ester, a cyclobutyl ester, a pentyl ester (e.g., an n-pentyl ester), a cyclopentyl ester, or a hexyl ester (e.g., a n-hexyl ester) or a cyclohexyl ester.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated that features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups are described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. The term "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chain or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "heteroalkylene" refers to an alkylene group wherein one or more of the carbon atoms have been replaced by a heteroatom. The term "$C_{n-m}$ heteroalkylene", employed alone or in combination with other terms, refers to a heteroalkylene group containing from n to m carbon atoms. The heteroatoms may be independently selected from the group consisting of O, N and S. A divalent heteroatom (e.g., O or S) replaces a methylene group of the alkylene —CH$_2$—, and a trivalent heteroatom (e.g., N) replaces a methine group. A sulfur atom can be oxidized to a sulfoxide or sulfone group. Examples are divalent straight hydrocarbon groups consisting of methylene groups, —O— atoms and —NH— and NMe-groups, such as, —CH$_2$O—, —CH$_2$CH$_2$O—, —CH$_2$CH$_2$OCH$_2$—. It is understood that in the compounds described herein, the number and position of heteroatoms in a heteroalkylene group is selected to provide a stable compound. Thus, a heteroalkene group typically does not contain two heteroatoms connected to each other within a chain, and typically includes at least two carbon atoms separating each heteroatom. The $C_{n-m}$ heteroalkylene groups include $C_{1-6}$ heteroalkylene and $C_{1-3}$ heteroalkylene.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The terms "halo" or "halogen", used alone or in combination with other terms, refers to fluoro, chloro, bromo and iodo.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms. The term "amino" refers to a group of formula $NH_2$.

The term "carbamyl" refers to a group of formula C(=O)$NH_2$.

The term "carbonyl", employed alone or in combination with other terms, refers to a —C(=O)— group, which also may be written as C(O).

The term "carbonyl", employed alone or in combination with other terms, refers to a —C(=O)— group.

The term "carboxy" refers to a group of formula —C(=O)OH.

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, indenyl and the like. In some embodiments, aryl groups have from 6 to 10 carbon atoms. In some embodiments, the aryl group is phenyl.

The term "heteroaryl" or "heteroaromatic", employed alone or in combination with other terms, refers to a monocyclic or polycyclic aromatic heterocycle having at least one heteroatom ring member selected from sulfur, oxygen and nitrogen. In some embodiments, the heteroaryl is 5- to 10-membered $C_{1-9}$ heteroaryl, which is monocyclic or bicyclic and which has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, imidazo[1,2-b]pyridazine, purine, furopyridine (e.g., furo[3,2-b]pyridine), thienopyridine (e.g. thieno[3,2-b]pyridine) or the like.

A five-membered heteroaryl ring is a heteroaryl group having five ring atoms wherein one or more (e.g., 1, 2, 3 or 4) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl. The term "cycloalkyl", employed alone or in combination with other terms, refers to a non-aromatic, saturated, monocyclic, bicyclic or polycyclic hydrocarbon ring system, including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cyclopentenyl, cyclohexenyl, cyclohexadienyl, norbornyl, norpinyl, bicyclo[2.1.1]hexanyl, bicyclo[1.1.1]pentanyl and the like. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like, for example indanyl or tetrahydronaphthyl. A cycloalkyl group containing a fused aromatic ring can be attached through any ring-forming atom including a ring-forming atom of the fused aromatic ring.

The term "heterocycloalkyl", employed alone or in combination with other terms, refers to non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members or 4-6 ring members. Included in heterocycloalkyl are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Examples of heterocycloalkyl groups include azetidine, pyrrolidine, piperidine, piperazine, morpholine, thiomorpholine, pyran, azepane, tetrahydropyran, tetrahydrofuran, dihydropyran, dihydrofuran and the like. Ring-forming carbon atoms and heteroatoms of a heterocycloalkyl group can be optionally substituted by oxo or sulfido (e.g., C(=O), S(=O), C(S) or S(=O)$_2$, etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 1,2,3,4-tetrahydroquinoline, dihydrobenzofuran, azetidine, azepane, diazepan (e.g., 1,4-diazepan), pyrrolidine, piperidine, piperazine, morpholine, thiomorpholine, pyran, tetrahydrofuran and di- and tetra-hydropyran.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

A "water solubilizing group" is a moiety that has hydrophilic character sufficient to improve or increase the water-solubility of the compound in which it is included, as compared to an analogous compound that does not include the group (i.e., that has hydrogen at the position occupied by the group). The hydrophilic character can be achieved by including suitable functional groups, such as functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups, particularly nitrogen and oxygen atoms. Examples of functional groups that can be included in a water solubilizing group include ether groups (including alkoxy groups, such as $C_{1-6}$ alkoxy groups, alkoxyalkylene groups, such as $C_{1-6}$ alkoxy-$C_{1-4}$ alkylene groups, polyether groups and cyclic ether groups such as tetrahydrofuran, tetrahydropyran and dioxan), hydroxyl groups, primary, secondary, tertiary and cyclic amine groups, quaternary ammonium groups, basic heterocyclic groups, amidine groups, guanidine groups, carboxylic acid groups, carboxamide groups, sulfonic acid groups, mono-, di- and triphosphate groups, etc. Examples of cyclic amine groups include, in particular, 5 to 7-membered non-aromatic heterocyclic groups such as pyrrolidine, pyrrolidone, piperidine, morpholine, piperazine, azepane, 1,4-diazepane, and 1,4-oxazepane rings, carbohydrate groups, etc. In another specific example, in accord with the formula given above for water solubilizing groups, the water solubilizing group is an amino acid tethered from the molecule via a bond to the nitrogen of the amino acid. In a more specific example, a water solubilizing group is an alpha-amino acid or derivative thereof attached to the core molecule. In another example the water-solubilizing group is one of the aforementioned rings tethered to the parent molecule via an alkylene, alkylidene, alkylidyne linker. In a more specific embodiment, the water-solubilizing group is one of the aforementioned rings tethered to the parent molecule via a $C_{1-6}$ alkylene, where one or two of the alkylene carbons is, independently, replaced with one of O, S or NH, but not where any two of the aforementioned heteroatoms are contiguous in the linker. Other water solubilizing groups are well-known and include, by way of example, hydrophilic groups such as alkyl or heterocycloalkyl groups substituted with one or more of an amine, alcohol, a carboxylic acid, a phosphoric acid, a sulfoxide, a carbohydrate, a sugar alcohol, an amino acid, a thiol, a polyol, an ether, a thioether, and a quaternary amine salt.

Examples of water solubilizing groups include groups of the following formulae:

-$L^W$-OR$^{aW}$, -$L^W$-C(O)R$^{bW}$, -$L^W$-C(O)NR$^{cW}$R$^{dW}$, -$L^W$-C(O)OR$^{aW}$, -$L^W$-OC(O)R$^{bW}$, -$L^W$-OC(O)NR$^{cW}$R$^{dW}$-$L^W$-NR$^{cW}$R$^{dW}$-$L^W$-NR$^{cW}$C(O)R$^{bW}$-$L^W$-NR$^{cW}$C(O)NR$^{cW}$R$^{dW}$, -$L^W$-NR$^{cW}$C(O)OR$^{aW}$, -$L^W$-C(=NR$^{eW}$)NR$^{cW}$R$^{dW}$, -$L^W$-NR$^{cW}$C(=NR$^{eW}$)NR$^{cW}$R$^{dW}$, -$L^W$-S(O)$_2$OR$^{aW}$, -$L^W$-NR$^{cW}$S(O)$_2$R$^{bW}$, -$L^W$-S(O)$_2$NR$^{cW}$R$^{dW}$, —P(=O)(OR$^{aW}$)$_2$, —OP(=O)(OR$^{aW}$)$_2$, —OP(=O)(OR$^{aW}$)—OP(=O)(OR$^{aW}$)$_2$, —OP(=O)(OR$^{aW}$)—OP(=O)(OR$^{aW}$)—OP(=O)(OR$^{aW}$)$_2$, and -$L^W$-Cy$^W$;

wherein:

each Cy$^W$ is unsubstituted 5-10 membered heteroaryl or 4-10 membered heterocycloalkyl, or 5-10 membered heteroaryl or 4-10 membered heterocycloalkyl substituted with one or more (e.g., 1, 2, 3, 4 or 5) substituents each independently selected from $C_{1-6}$ alkyl, halogen, $C_{1-6}$ haloalkyl, CN, NO$_2$, OR$^{aW}$, SR$^{aW}$, C(O)R$^{bW}$, C(O)NR$^{cW}$R$^{dW}$, C(O)OR$^{aW}$, OC(O)R$^{bW}$, OC(O)NR$^{cW}$R$^{dW}$, NR$^{cW}$R$^{dW}$, NR$^{cW}$C(O)R$^{bW}$, NR$^{cW}$C(O)NR$^{cW}$R$^{dW}$, NR$^{cW}$C(O)OR$^{aW}$, C(=NR$^{eW}$)NR$^{cW}$R$^{dW}$, NR$^{cW}$C(=NR$^{eW}$)NR$^{cW}$R$^{dW}$, S(O)R$^{bW}$, S(O)$_2$R$^{bW}$, NR$^{cW}$S(O)$_2$R$^{bW}$ and S(O)$_2$NR$^{cW}$R$^{dW}$;

each -$L^W$- is a bond or a linking group selected from groups of the formula -$L^{W1}$-$L^{W2}$-;

the group -$L^{W1}$- is attached to the core molecule and is selected from a bond and groups of the formula —O—, —S—, —S(O)—, —S(O)$_2$—, —C(O)—, —NH—, —NR$^{cW}$, —NR$^{cW}$C(O)—, —C(O)NR$^{cW}$—, —O(CO)—, —C(O)O—, —O(CO)NR$^{cW}$—, —NR$^{cW}$C(O)O—, —O(CO)O—, and —NR$^{cW}$C(O)NR$^{cW}$—;

the group -$L^{W2}$- is selected from a bond, unsubstituted-$C_{1-10}$ alkylene-, unsubstituted-$C_{1-10}$ heteroalkylene, and —$C_{1-10}$ alkylene and —$C_{1-10}$ heteroalkylene substituted with one or more (e.g., 1, 2, 3, 4 or 5 substituents) independently selected from the group consisting of H, halogen, $C_{1-6}$ alkyl, $C_{2-6}$ alkenyl, $C_{2-6}$ alkynyl, CN, NO$_2$, OR$^{aW}$, SR$^{aW}$, C(O)R$^{bW}$, C(O)NR$^{cW}$R$^{dW}$, C(O)OR$^{aW}$, OC(O)R$^{bW}$, OC(O)NR$^{cW}$R$^{dW}$, NR$^{cW}$R$^{dW}$, NR$^{cW}$C(O)R$^{bW}$, NR$^{cW}$C(O)NR$^{cW}$R$^{dW}$, NR$^{cW}$C(O)OR$^{aW}$, C(=NR$^{eW}$)NR$^{cW}$R$^{dW}$, NR$^{cW}$C(=NR$^{eW}$)NR$^{cW}$R$^{dW}$, S(O)R$^{bW}$, S(O)$_2$R$^{bW}$, NR$^{cW}$S(O)$_2$R$^{bW}$, S(O)$_2$NR$^{cW}$R$^{dW}$; —P(=O)(OR$^{aW}$)$_2$, —OP(=O)(OR$^{aW}$)$_2$, —OP(=O)(OR$^{aW}$)—OP(=O)(OR$^{aW}$)$_2$, —OP(=O)(OR$^{aW}$)—OP(=O)(OR$^{aW}$)—OP(=O)(OR$^{aW}$)$_2$, oxo and sulfido;

R$^{aW}$, R$^{bW}$, R$^{cW}$, and R$^{dW}$ are each independently selected from the group consisting of hydrogen, $C_{1-4}$ alkyl, $C_{2-4}$ alkenyl, $C_{2-4}$ alkynyl, $C_{6-10}$ aryl, 5-10 membered heteroaryl, $C_{3-7}$ cycloalkyl, 5-10 membered heterocycloalkyl, $C_{6-10}$ aryl-$C_{1-4}$ alkylene, $C_{3-7}$ cycloalkyl-$C_{1-4}$ alkylene, 5-10 membered heteroaryl-$C_{1-4}$ alkylene, 5-10 membered heterocycloalkyl-$C_{1-4}$ alkylene, and $C_{1-4}$ alkoxy-$C_{1-4}$ alkylene, wherein said $C_{1-4}$ alkyl, $C_{2-4}$ alkenyl, $C_{2-4}$ alkynyl, and $C_{1-4}$ alkoxy-$C_{1-4}$ alkylene forming R$^{aW}$, R$^{bW}$, R$^{cW}$, or R$^{dW}$ are each optionally substituted by 1, 2, 3, 4 or 5 groups independently selected from halo, CN, OR$^{aW*}$, SR$^{aW*}$, C(O)R$^{bW*}$, C(O)NR$^{cW*}$R$^{dW*}$, C(O)OR$^{aW*}$, OC(O)R$^{bW*}$, OC(O)NR$^{cW*}$R$^{dW*}$, NR$^{cW*}$R$^{dW*}$, NR$^{cW*}$C(O)R$^{bW*}$, NR$^{cW*}$C(O)NR$^{cW*}$R$^{dW*}$, NR$^{cW*}$C(O)OR$^{aW*}$, C(=NR$^{eW*}$)

NR$^{cW}$*R$^{dW}$*, NR$^{cW}$*C(=NR$^{eW}$*)NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$* and wherein said C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, and 5-10 membered heterocycloalkyl-C$_{1-4}$ alkylene, forming R$^{aW}$, R$^{bW}$, R$^{cW}$, or R$^{dW}$ are each optionally substituted by 1, 2, 3, 4 or 5 groups independently selected from C$_{1-6}$ alkyl, halo, CN, OR$^{aW}$*, SR$^{aW}$*, C(O)R$^{bW}$*, C(O)NR$^{cW}$*R$^{dW}$*, C(O) OR$^{aW}$*, OC(O)R$^{bW}$*, OC(O)NR$^{cW}$*R$^{dW}$*, NR$^{cW}$*R$^{dW}$*, NR$^{cW}$*C(O)R$^{bW}$*, NR$^{cW}$*C(O)NR$^{cW}$*R$^{dW}$*, NR$^{cW}$*C(O) OR$^{aW}$*, C(=NR$^{eW}$*)NR$^{cW}$*R$^{dW}$*, NR$^{cW}$*C(=NR$^{eW}$*) NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$*;

or R$^{cW}$ and R$^{dW}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from C$_{1-6}$ alkyl, halo, CN, OR$^{aW}$*, SR$^{aW}$*, C(O)R$^{bW}$*, C(O)NR$^{cW}$*R$^{dW}$*, C(O)OR$^{aW}$*, OC(O)R$^{bW}$*, OC(O)NR$^{cW}$*R$^{dW}$*, NR$^{cW}$*R$^{dW}$*, NR$^{cW}$*C(O)R$^{bW}$*, NR$^{cW}$*C(O)NR$^{cW}$*R$^{dW}$*, NR$^{cW}$*C(O)OR$^{aW}$*, C(=NR$^{eW}$*)NR$^{cW}$*R$^{dW}$*, NR$^{cW}$*C (=NR$^{eW}$*)NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$*;

R$^{aW}$*, R$^{bW}$*, R$^{cW}$* and R$^{dW}$* are each independently selected from H, C$_{1-6}$ alkyl, C$_{1-6}$ haloalkyl, C$_{2-6}$ alkenyl, C$_{2-6}$ alkynyl, aryl, C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl, wherein said C$_{1-6}$ alkyl, C$_{1-6}$ haloalkyl, C$_{2-6}$ alkenyl, C$_{2-6}$ alkynyl C$_{6-10}$ aryl-C$_{1-3}$ alkyl, 5-10 membered heteroaryl-C$_{1-3}$ alkyl, C$_{3-7}$ cycloalkyl-C$_{1-3}$ alkyl and 4-10 membered heterocycloalkyl-C$_{1-3}$ alkyl forming R$^{aW}$*, R$^{bW}$*, R$^{cW}$* and R$^{dW}$* are each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$haloalkoxy;

or R$^{cW}$* and R$^{dW}$* attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy;

R$^{eW}$ and R$^{eW}$* are each independently selected from H, C$_{1-4}$ alkyl, OH, and C$_{1-4}$ alkoxy. Water solubilizing groups include H, C$_{1-6}$ alkoxy, C$_{1-6}$ alkoxy-C$_{1-6}$ alkyl, carboxy, carboxy-C$_{1-6}$ alkyl, amino-C$_{1-6}$ alkyl, C$_{1-6}$ alkylamino-C$_{1-6}$ alkyl, di(C$_{1-6}$ alkyl)amino-C$_{1-6}$ alkyl, amino-C$_{1-6}$ alkoxy-C$_{1-6}$ alkyl, C$_{1-6}$ alkylamino-C$_{1-6}$ alkoxy-C$_{1-6}$ alkyl, di(C$_{1-6}$ alkyl)amino-C$_{1-6}$ alkoxy-C$_{1-6}$ alkyl, 4-10 membered heterocycloalkyl-C$_{1-6}$ alkyl, 4-10 membered heterocycloalkyl-C$_{1-4}$ alkoxy-C$_{1-6}$ alkyl, C$_{1-6}$ alkoxy-C$_{1-6}$ alkoxy, amino-C$_{1-6}$ alkoxy, C$_{1-6}$ alkylamino-C$_{1-6}$ alkoxy, di(C$_{1-6}$ alkyl)amino-C$_{1-6}$ alkoxy, amino-C$_{1-6}$ alkoxy-C$_{1-6}$ alkoxy, C$_{1-6}$ alkylamino-C$_{1-6}$ alkoxy-C$_{1-6}$ alkoxy, di(C$_{1-6}$ alkyl)amino-C$_{1-6}$ alkoxy-C$_{1-6}$ alkoxy, 4-10 membered heterocycloalkyl-C$_{1-4}$ alkoxy, or 4-10 membered hetercycloalkyl-C$_{1-6}$ alkoxy, or carboxy-C$_{1-6}$-alkoxy, carboxy-C$_{1-6}$-alkyl-C$_{1-6}$-alkoxy, or carboxy-C$_{1-6}$-alkoxy-C$_{1-6}$-alkoxy.

Examples of water solubilizing groups include methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-amino propoxy, (2-aminoethoxy)methyl, (3-aminopropoxy) methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino) methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino)ethoxy) methyl, (3-(N,N-dimethylamino)propoxy)methyl, 2-(2-(N, N-dimethylamino)ethoxy)ethyl, 2-(2-(N,N-dimethylamino) ethoxy)ethoxy, (N-morpholinyl)methyl, 2-(N-morpholinyl) ethyl, 3-(N-morpholinyl)propyl, 2-(N-morpholinyl)ethoxy, 3-(N-morpholinyl)propoxy, (2-(N-morpholinyl)ethoxy) methyl, (3-(N-morpholinyl)propoxy)methyl, 2-(2-(N-morpholinyl)ethoxy)ethyl, or 2-(2-(N-morpholinyl)ethoxy) ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy) ethoxy, 2-carboxyethoxymethyl, or 2-(2-caroxyethoxy) ethoxy.

Further examples of water solubilizing groups (that can be used for any instance of a water solubilizing group in the compounds described herein) include the groups listed in Table 2.

TABLE 2

| # | Water Solubilizing Group |
|---|---|
| 1 | —OH |
| 2 | —OMe |
| 3 | —OEt |
| 4 | —OPr |
| 5 | —OiPr |
| 6 | —OcPr |
| 7 | —OcBu |
| 8 | —OcPn |
| 9 | —OcHex |
| 10 | —OCH$_2$CH$_2$OH |
| 11 | —OCH$_2$CH$_2$OMe |
| 12 | —OCH$_2$CH$_2$OEt |
| 13 | —OCH$_2$CH$_2$NH$_2$ |
| 14 | —OCH$_2$CH$_2$NHMe |
| 15 | —OCH$_2$CH$_2$NMe$_2$ |
| 16 | (pyrrolidinyl-CH$_2$CH$_2$-O-) |
| 17 | (piperidinyl-CH$_2$CH$_2$-O-) |
| 18 | (HN-piperazinyl-CH$_2$CH$_2$-O-) |
| 19 | (N-methylpiperazinyl-CH$_2$CH$_2$-O-) |

TABLE 2-continued

Water Solubilizing Group

| # | Water Solubilizing Group |
|---|---|
| 20 | morpholine-N-CH₂CH₂-O-⁓ |
| 21 | —OCH₂CH₂CH₂OH |
| 22 | —OCH₂CH₂CH₂OMe |
| 23 | —OCH₂CH₂CH₂OEt |
| 24 | —OCH₂CH₂CH₂NH₂ |
| 25 | —OCH₂CH₂CH₂NHMe |
| 26 | —OCH₂CH₂CH₂NMe₂ |
| 27 | pyrrolidine-N-(CH₂)₃-O-⁓ |
| 28 | piperidine-N-(CH₂)₃-O-⁓ |
| 29 | HN-piperazine-N-(CH₂)₃-O-⁓ |
| 30 | N-methylpiperazine-N-(CH₂)₃-O-⁓ |
| 31 | morpholine-N-(CH₂)₃-O-⁓ |
| 32 | —OCH₂CH₂OCH₂CH₂OH |
| 33 | —OCH₂CH₂OCH₂CH₂OMe |
| 34 | —OCH₂CH₂OCH₂CH₂OEt |
| 35 | —OCH₂CH₂OCH₂CH₂NH₂ |
| 36 | —OCH₂CH₂OCH₂CH₂NHMe |
| 37 | —OCH₂CH₂OCH₂CH₂NMe₂ |
| 38 | pyrrolidine-N-CH₂CH₂-O-CH₂CH₂-O-⁓ |
| 39 | piperidine-N-CH₂CH₂-O-CH₂CH₂-O-⁓ |
| 40 | HN-piperazine-N-CH₂CH₂-O-CH₂CH₂-O-⁓ |
| 41 | N-methylpiperazine-N-CH₂CH₂-O-CH₂CH₂-O-⁓ |
| 42 | morpholine-N-CH₂CH₂-O-CH₂CH₂-O-⁓ |
| 43 | —OCH₂CH₂OCH₂CH₂CH₂OH |
| 44 | —OCH₂CH₂OCH₂CH₂CH₂OMe |
| 45 | —OCH₂CH₂OCH₂CH₂CH₂OEt |
| 46 | —OCH₂CH₂OCH₂CH₂CH₂NH₂ |
| 47 | —OCH₂CH₂OCH₂CH₂CH₂NHMe |
| 48 | —OCH₂CH₂OCH₂CH₂CH₂NMe₂ |
| 49 | pyrrolidine-N-(CH₂)₃-O-CH₂CH₂-O-⁓ |
| 50 | piperidine-N-(CH₂)₃-O-CH₂CH₂-O-⁓ |
| 51 | HN-piperazine-N-(CH₂)₃-O-CH₂CH₂-O-⁓ |
| 52 | N-methylpiperazine-N-(CH₂)₃-O-CH₂CH₂-O-⁓ |
| 53 | morpholine-N-(CH₂)₃-O-CH₂CH₂-O-⁓ |
| 54 | —OCH₂CH₂CH₂OCH₂CH₂OH |
| 55 | —OCH₂CH₂CH₂OCH₂CH₂OMe |
| 56 | —OCH₂CH₂CH₂OCH₂CH₂OEt |
| 57 | —OCH₂CH₂CH₂OCH₂CH₂NH₂ |
| 58 | —OCH₂CH₂CH₂OCH₂CH₂NHMe |
| 59 | —OCH₂CH₂CH₂OCH₂CH₂NMe₂ |
| 60 | pyrrolidine-N-CH₂CH₂-O-(CH₂)₃-O-⁓ |

TABLE 2-continued

Water Solubilizing Group

| # | Water Solubilizing Group |
|---|---|
| 61 | piperidine-N-CH₂CH₂-O-CH₂CH₂CH₂-O-{structure} |
| 62 | piperazine(HN)-N-CH₂CH₂-O-CH₂CH₂CH₂-O-{structure} |
| 63 | N-methylpiperazine-N-CH₂CH₂-O-CH₂CH₂CH₂-O-{structure} |
| 64 | morpholine-N-CH₂CH₂-O-CH₂CH₂CH₂-O-{structure} |
| 65 | —OCH₂CH₂CH₂OCH₂CH₂CH₂OH |
| 66 | —OCH₂CH₂CH₂OCH₂CH₂CH₂OMe |
| 67 | —OCH₂CH₂CH₂OCH₂CH₂CH₂OEt |
| 68 | —OCH₂CH₂CH₂OCH₂CH₂CH₂NH₂ |
| 69 | —OCH₂CH₂CH₂OCH₂CH₂CH₂NHMe |
| 70 | —OCH₂CH₂CH₂OCH₂CH₂CH₂NMe₂ |
| 71 | pyrrolidine-N-CH₂CH₂CH₂-O-CH₂CH₂CH₂-O-{structure} |
| 72 | piperidine-N-CH₂CH₂CH₂-O-CH₂CH₂CH₂-O-{structure} |
| 73 | piperazine(HN)-N-CH₂CH₂CH₂-O-CH₂CH₂CH₂-O-{structure} |
| 74 | N-methylpiperazine-N-CH₂CH₂CH₂-O-CH₂CH₂CH₂-O-{structure} |
| 75 | morpholine-N-CH₂CH₂CH₂-O-CH₂CH₂CH₂-O-{structure} |
| 76 | —OCH₂CH₂NHCH₂CH₂OH |
| 77 | —OCH₂CH₂NHCH₂CH₂OMe |
| 78 | —OCH₂CH₂NHCH₂CH₂OEt |
| 79 | —OCH₂CH₂NHCH₂CH₂NH₂ |
| 80 | —OCH₂CH₂NHCH₂CH₂NHMe |
| 81 | —OCH₂CH₂NHCH₂CH₂NMe₂ |

TABLE 2-continued

Water Solubilizing Group

| # | Water Solubilizing Group |
|---|---|
| 82 | pyrrolidine-N-CH₂CH₂-NH-CH₂CH₂-O-{structure} |
| 83 | piperidine-N-CH₂CH₂-NH-CH₂CH₂-O-{structure} |
| 84 | piperazine(HN)-N-CH₂CH₂-NH-CH₂CH₂-O-{structure} |
| 85 | N-methylpiperazine-N-CH₂CH₂-NH-CH₂CH₂-O-{structure} |
| 86 | morpholine-N-CH₂CH₂-NH-CH₂CH₂-O-{structure} |
| 87 | —OCH₂CH₂NHCH₂CH₂CH₂OH |
| 88 | —OCH₂CH₂NHCH₂CH₂CH₂OMe |
| 89 | —OCH₂CH₂NHCH₂CH₂CH₂OEt |
| 90 | —OCH₂CH₂NHCH₂CH₂CH₂NH₂ |
| 91 | —OCH₂CH₂NHCH₂CH₂CH₂NHMe |
| 92 | —OCH₂CH₂NHCH₂CH₂CH₂NMe₂ |
| 93 | pyrrolidine-N-CH₂CH₂CH₂-NH-CH₂CH₂-O-{structure} |
| 94 | piperidine-N-CH₂CH₂CH₂-NH-CH₂CH₂-O-{structure} |
| 95 | piperazine(HN)-N-CH₂CH₂CH₂-NH-CH₂CH₂-O-{structure} |
| 96 | N-methylpiperazine-N-CH₂CH₂CH₂-NH-CH₂CH₂-O-{structure} |
| 97 | morpholine-N-CH₂CH₂CH₂-NH-CH₂CH₂-O-{structure} |
| 98 | —OCH₂CH₂CH₂NHCH₂CH₂OH |
| 99 | —OCH₂CH₂CH₂NHCH₂CH₂OMe |

TABLE 2-continued

Water Solubilizing Group

| # | Water Solubilizing Group |
|---|---|
| 100 | —OCH$_2$CH$_2$CH$_2$NHCH$_2$CH$_2$OEt |
| 101 | —OCH$_2$CH$_2$CH$_2$NHCH$_2$CH$_2$NH$_2$ |
| 102 | —OCH$_2$CH$_2$CH$_2$NHCH$_2$CH$_2$NHMe |
| 103 | —OCH$_2$CH$_2$CH$_2$NHCH$_2$CH$_2$NMe$_2$ |

104

[pyrrolidinyl-CH$_2$CH$_2$-NH-CH$_2$CH$_2$CH$_2$-O-]

105

[piperidinyl-CH$_2$CH$_2$-NH-CH$_2$CH$_2$CH$_2$-O-]

106

[piperazinyl(HN-)-CH$_2$CH$_2$-NH-CH$_2$CH$_2$CH$_2$-O-]

107

[N-methylpiperazinyl-CH$_2$CH$_2$-NH-CH$_2$CH$_2$CH$_2$-O-]

108

[morpholinyl-CH$_2$CH$_2$-NH-CH$_2$CH$_2$CH$_2$-O-]

| # | Water Solubilizing Group |
|---|---|
| 109 | —OCH$_2$CH$_2$CH$_2$NHCH$_2$CH$_2$CH$_2$OH |
| 110 | —OCH$_2$CH$_2$CH$_2$NHCH$_2$CH$_2$CH$_2$OMe |
| 111 | —OCH$_2$CH$_2$CH$_2$NHCH$_2$CH$_2$CH$_2$OEt |
| 112 | —OCH$_2$CH$_2$CH$_2$NHCH$_2$CH$_2$CH$_2$NH$_2$ |
| 113 | —OCH$_2$CH$_2$CH$_2$NHCH$_2$CH$_2$CH$_2$NHMe |
| 114 | —OCH$_2$CH$_2$CH$_2$NHCH$_2$CH$_2$CH$_2$NMe$_2$ |

115

[pyrrolidinyl-CH$_2$CH$_2$CH$_2$-NH-CH$_2$CH$_2$CH$_2$-O-]

116

[piperidinyl-CH$_2$CH$_2$CH$_2$-NH-CH$_2$CH$_2$CH$_2$-O-]

117

[piperazinyl(HN-)-CH$_2$CH$_2$CH$_2$-NH-CH$_2$CH$_2$CH$_2$-O-]

118

[N-methylpiperazinyl-CH$_2$CH$_2$CH$_2$-NH-CH$_2$CH$_2$CH$_2$-O-]

119

[morpholinyl-CH$_2$CH$_2$CH$_2$-NH-CH$_2$CH$_2$CH$_2$-O-]

| # | Water Solubilizing Group |
|---|---|
| 120 | —OCH$_2$CH$_2$N(CH$_2$CH$_2$OH)$_2$ |
| 121 | —OCH$_2$CH$_2$N(CH$_2$CH$_2$OMe)$_2$ |
| 122 | —OCH$_2$CH$_2$N(CH$_2$CH$_2$OEt)$_2$ |
| 123 | —OCH$_2$CH$_2$N(CH$_2$CH$_2$CH$_2$OH)$_2$ |
| 124 | —OCH$_2$CH$_2$N(CH$_2$CH$_2$CH$_2$OMe)$_2$ |
| 125 | —OCH$_2$CH$_2$N(CH$_2$CH$_2$CH$_2$OEt)$_2$ |
| 126 | —OCH$_2$CH$_2$CH$_2$(HCH$_2$CH$_2$OH)$_2$ |
| 127 | —OCH$_2$CH$_2$CH$_2$N(CH$_2$CH$_2$OMe)$_2$ |
| 128 | —OCH$_2$CH$_2$CH$_2$N(CH$_2$CH$_2$OEt)$_2$ |
| 129 | —OCH$_2$CH$_2$CH$_2$N(CH$_2$CH$_2$CH$_2$OH)$_2$ |
| 130 | —OCH$_2$CH$_2$CH$_2$N(CH$_2$CH$_2$CH$_2$OMe)$_2$ |
| 131 | —OCH$_2$CH$_2$CH$_2$N(CH$_2$CH$_2$CH$_2$OEt)$_2$ |
| 132 | —OCH$_2$CH$_2$NMeCH$_2$CH$_2$OH |
| 133 | —OCH$_2$CH$_2$NMeCH$_2$CH$_2$OMe |
| 134 | —OCH$_2$CH$_2$NMeCH$_2$CH$_2$OEt |
| 135 | —OCH$_2$CH$_2$NMeCH$_2$CH$_2$NH$_2$ |
| 136 | —OCH$_2$CH$_2$NMeCH$_2$CH$_2$NHMe |
| 137 | —OCH$_2$CH$_2$NMeCH$_2$CH$_2$NMe$_2$ |

138

[pyrrolidinyl-CH$_2$CH$_2$-N(Me)-CH$_2$CH$_2$-O-]

139

[piperidinyl-CH$_2$CH$_2$-N(Me)-CH$_2$CH$_2$-O-]

140

[piperazinyl(HN-)-CH$_2$CH$_2$-N(Me)-CH$_2$CH$_2$-O-]

141

[N-methylpiperazinyl-CH$_2$CH$_2$-N(Me)-CH$_2$CH$_2$-O-]

142

[morpholinyl-CH$_2$CH$_2$-N(Me)-CH$_2$CH$_2$-O-]

| # | Water Solubilizing Group |
|---|---|
| 143 | —OCH$_2$CH$_2$NMeCH$_2$CH$_2$CH$_2$OH |
| 144 | —OCH$_2$CH$_2$NMeCH$_2$CH$_2$CH$_2$OMe |
| 145 | —OCH$_2$CH$_2$NMeCH$_2$CH$_2$CH$_2$OEt |
| 146 | —OCH$_2$CH$_2$NMeCH$_2$CH$_2$CH$_2$NH$_2$ |
| 147 | —OCH$_2$CH$_2$NMeCH$_2$CH$_2$CH$_2$NHMe |
| 148 | —OCH$_2$CH$_2$NMeCH$_2$CH$_2$CH$_2$NMe$_2$ |

149

[pyrrolidinyl-CH$_2$CH$_2$CH$_2$-N(Me)-CH$_2$CH$_2$-O-]

TABLE 2-continued

Water Solubilizing Group

| # | Water Solubilizing Group |
|---|---|
| 150 | [piperidine-N-CH₂CH₂CH₂-N(Me)-CH₂CH₂-O~] |
| 151 | [HN-piperazine-N-CH₂CH₂CH₂-N(Me)-CH₂CH₂-O~] |
| 152 | [Me-N-piperazine-N-CH₂CH₂CH₂-N(Me)-CH₂CH₂-O~] |
| 153 | [morpholine-N-CH₂CH₂CH₂-N(Me)-CH₂CH₂-O~] |
| 154 | —OCH₂CH₂CH₂NMeCH₂CH₂OH |
| 155 | —OCH₂CH₂CH₂NMeCH₂CH₂OMe |
| 156 | —OCH₂CH₂CH₂NMeCH₂CH₂OEt |
| 157 | —OCH₂CH₂CH₂NMeCH₂CH₂NH₂ |
| 158 | —OCH₂CH₂CH₂NMeCH₂CH₂NHMe |
| 159 | —OCH₂CH₂CH₂NMeCH₂CH₂NMe₂ |
| 160 | [pyrrolidine-N-CH₂CH₂-N(Me)-CH₂CH₂CH₂-O~] |
| 161 | [piperidine-N-CH₂CH₂-N(Me)-CH₂CH₂CH₂-O~] |
| 162 | [HN-piperazine-N-CH₂CH₂-N(Me)-CH₂CH₂CH₂-O~] |
| 163 | [Me-N-piperazine-N-CH₂CH₂-N(Me)-CH₂CH₂CH₂-O~] |
| 164 | [morpholine-N-CH₂CH₂-N(Me)-CH₂CH₂CH₂-O~] |
| 165 | —OCH₂CH₂CH₂NMeCH₂CH₂CH₂OH |
| 166 | —OCH₂CH₂CH₂NMeCH₂CH₂CH₂OMe |
| 167 | —OCH₂CH₂CH₂NMeCH₂CH₂CH₂OEt |
| 168 | —OCH₂CH₂CH₂NMeCH₂CH₂CH₂NH₂ |
| 169 | —OCH₂CH₂CH₂NMeCH₂CH₂CH₂NHMe |
| 170 | —OCH₂CH₂CH₂NMeCH₂CH₂CH₂NMe₂ |
| 171 | [pyrrolidine-N-CH₂CH₂CH₂-N(Me)-CH₂CH₂CH₂-O~] |
| 172 | [piperidine-N-CH₂CH₂CH₂-N(Me)-CH₂CH₂CH₂-O~] |
| 173 | [HN-piperazine-N-CH₂CH₂CH₂-N(Me)-CH₂CH₂CH₂-O~] |
| 174 | [Me-N-piperazine-N-CH₂CH₂CH₂-N(Me)-CH₂CH₂CH₂-O~] |
| 175 | [morpholine-N-CH₂CH₂CH₂-N(Me)-CH₂CH₂CH₂-O~] |
| 176 | —CH₂OH |
| 177 | —CH₂OMe |
| 178 | —CH₂OEt |
| 179 | —CH₂NH₂ |
| 180 | —CH₂NHMe |
| 181 | —CH₂NMe₂ |
| 182 | [pyrrolidine-N-CH₂-] |
| 183 | [piperidine-N-CH₂-] |
| 184 | [HN-piperazine-N-CH₂-] |
| 185 | [Me-N-piperazine-N-CH₂-] |
| 186 | [morpholine-N-CH₂-] |
| 187 | —CH₂CH₂OH |
| 188 | —CH₂CH₂OMe |

TABLE 2-continued

| # | Water Solubilizing Group |
|---|---|
| 189 | —CH₂CH₂OEt |
| 190 | —CH₂CH₂NH₂ |
| 191 | —CH₂CH₂NHMe |
| 192 | —CH₂CH₂NMe₂ |
| 193 | 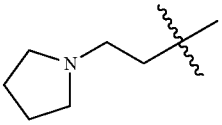 [SMILES: *CCN1CCCC1] |
| 194 | 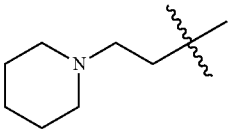 [SMILES: *CCN1CCCCC1] |
| 195 | 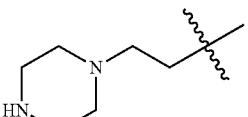 |
| 196 | 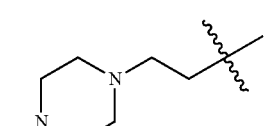 |
| 197 | 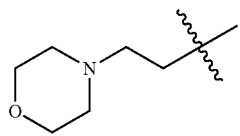 [SMILES: *CCN1CCOCC1] |
| 198 | —CH₂CH₂CH₂OH |
| 199 | —CH₂CH₂CH₂OMe |
| 200 | —CH₂CH₂CH₂OEt |
| 201 | —CH₂CH₂CH₂NH₂ |
| 202 | —CH₂CH₂CH₂NHMe |
| 203 | —CH₂CH₂CH₂NMe₂ |
| 204 | 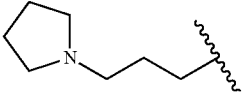 |
| 205 | 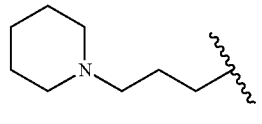 [SMILES: *CCCN1CCCCC1] |
| 206 | 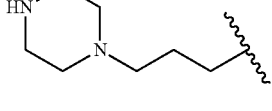 |
| 207 | 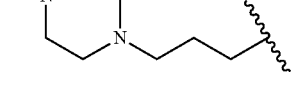 |

TABLE 2-continued

| # | Water Solubilizing Group |
|---|---|
| 208 | 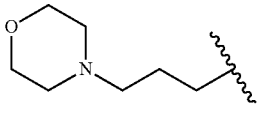 [SMILES: *CCCN1CCOCC1] |
| 209 | —CH₂CH₂CH₂CH₂OH |
| 210 | —CH₂CH₂CH₂CH₂OMe |
| 211 | —CH₂CH₂CH₂CH₂OEt |
| 212 | —CH₂CH₂CH₂CH₂NH₂ |
| 213 | —CH₂CH₂CH₂CH₂NHMe |
| 214 | —CH₂CH₂CH₂CH₂NMe₂ |
| 215 | 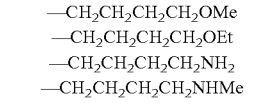 |
| 216 | 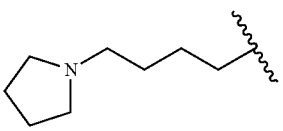 |
| 217 | 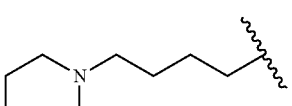 |
| 218 | 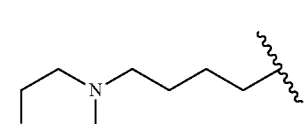 |
| 219 | 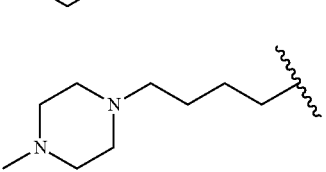 |
| 220 | —CH₂OCH₂CH₂OH |
| 221 | —CH₂OCH₂CH₂OMe |
| 222 | —CH₂OCH₂CH₂OEt |
| 223 | —CH₂OCH₂CH₂NH₂ |
| 224 | —CH₂OCH₂CH₂NHMe |
| 225 | —CH₂OCH₂CH₂NMe₂ |
| 226 |  |
| 227 | 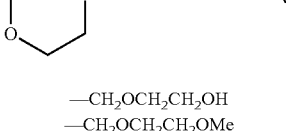 |

TABLE 2-continued

| # | Water Solubilizing Group |
|---|---|
| 228 | 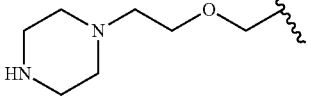 |
| 229 | 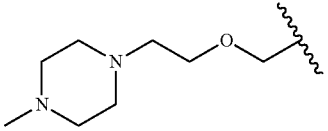 [SMILES: *COCCN1CCN(C)CC1] |
| 230 | 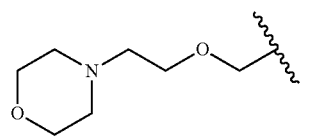 |
| 231 | —CH$_2$NHCH$_2$CH$_2$OH |
| 232 | —CH$_2$NHCH$_2$CH$_2$OMe |
| 233 | —CH$_2$NHCH$_2$CH$_2$OEt |
| 234 | —CH$_2$NHCH$_2$CH$_2$NH$_2$ |
| 235 | —CH$_2$NHCH$_2$CH$_2$NHMe |
| 236 | —CH$_2$NHCH$_2$CH$_2$NMe$_2$ |
| 237 | 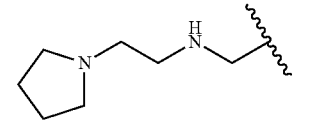 [SMILES: *CNCCN1CCCC1] |
| 238 | 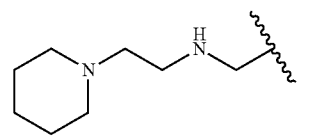 [SMILES: *CNCCN1CCCCC1] |
| 239 | 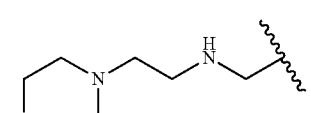 |
| 240 | 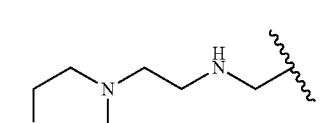 |
| 241 | 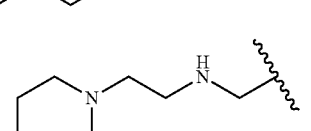 |
| 242 | —CH$_2$N(CH$_2$CH$_2$OH)$_2$ |
| 243 | —CH$_2$N(CH$_2$CH$_2$OMe)$_2$ |
| 244 | —CH$_2$N(CH$_2$CH$_2$OEt)$_2$ |
| 245 | —CH$_2$NMeCH$_2$CH$_2$OH |
| 246 | —CH$_2$NMeCH$_2$CH$_2$OMe |
| 247 | —CH$_2$NMeCH$_2$CH$_2$OEt |
| 248 | —CH$_2$NMeCH$_2$CH$_2$NH$_2$ |
| 249 | —CH$_2$NMeCH$_2$CH$_2$NHMe |
| 250 | —CH$_2$NMeCH$_2$CH$_2$NMe$_2$ |
| 251 | 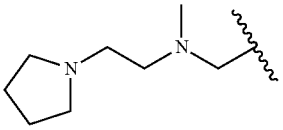 [SMILES: *CN(C)CCN1CCCC1] |
| 252 | 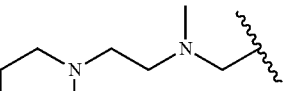 |
| 253 | 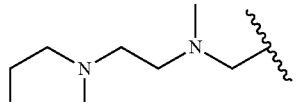 |
| 254 | 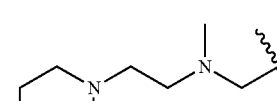 |
| 255 | 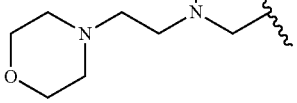 |
| 256 | —CH$_2$CH$_2$OCH$_2$CH$_2$OH |
| 257 | —CH$_2$CH$_2$OCH$_2$CH$_2$OMe |
| 258 | —CH$_2$CH$_2$OCH$_2$CH$_2$OEt |
| 259 | —CH$_2$CH$_2$OCH$_2$CH$_2$NH$_2$ |
| 260 | —CH$_2$CH$_2$OCH$_2$CH$_2$NHMe |
| 261 | —CH$_2$CH$_2$OCH$_2$CH$_2$NMe$_2$ |
| 262 |  |
| 263 | 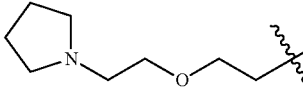 |
| 264 | 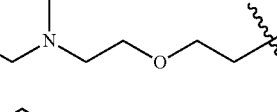 |
| 265 | 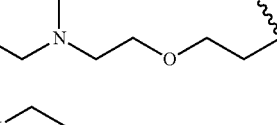 |
| 266 | 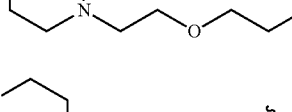 |
| 267 | —CH$_2$CH$_2$NHCH$_2$CH$_2$OH |
| 268 | —CH$_2$CH$_2$NHCH$_2$CH$_2$OMe |

TABLE 2-continued

Water Solubilizing Group

| # | Water Solubilizing Group |
|---|---|
| 269 | —CH₂CH₂NHCH₂CH₂OEt |
| 270 | —CH₂CH₂NHCH₂CH₂NH₂ |
| 271 | —CH₂CH₂NHCH₂CH₂NHMe |
| 272 | —CH₂CH₂NHCH₂CH₂NMe₂ |
| 273 | 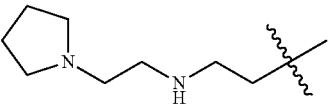 [SMILES: *CCNCCN1CCCC1] |
| 274 | 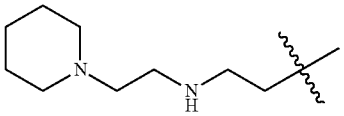 [SMILES: *CCNCCN1CCCCC1] |
| 275 | 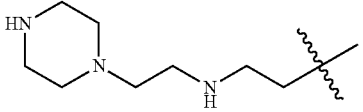 [SMILES: *CCNCCN1CCNCC1] |
| 276 | 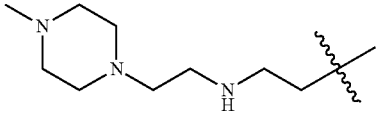 [SMILES: *CCNCCN1CCN(C)CC1] |
| 277 | 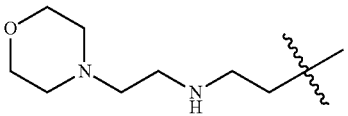 [SMILES: *CCNCCN1CCOCC1] |
| 278 | —CH₂CH₂N(CH₂CH₂OH)₂ |
| 279 | —CH₂CH₂N(CH₂CH₂OMe)₂ |
| 280 | —CH₂CH₂N(CH₂CH₂OE)₂ |
| 281 | —CH₂CH₂NMeCH₂CH₂OH |
| 282 | —CH₂CH₂NMeCH₂CH₂OMe |
| 283 | —CH₂CH₂NMeCH₂CH₂OEt |
| 284 | —CH₂CH₂NMeCH₂CH₂NH₂ |
| 285 | —CH₂CH₂NMeCH₂CH₂NHMe |
| 286 | —CH₂CH₂NMeCH₂CH₂NMe₂ |
| 287 | 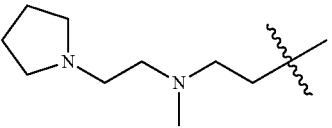 [SMILES: *CCN(C)CCN1CCCC1] |
| 288 | 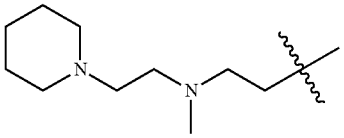 [SMILES: *CCN(C)CCN1CCCCC1] |
| 289 | 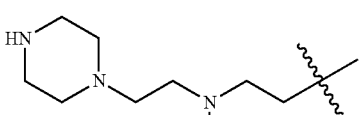 |
| 290 | 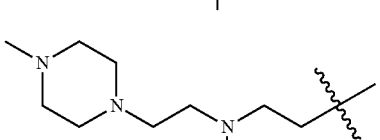 |

TABLE 2-continued

Water Solubilizing Group

| # | Water Solubilizing Group |
|---|---|
| 291 | 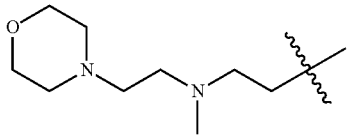 [SMILES: *CCN(C)CCN1CCOCC1] |
| 292 | —NH |
| 293 | —NHMe |
| 294 | —NMe₂ |
| 295 | —NHEt |
| 296 | —NHPr |
| 297 | —NHiPr |
| 298 | —NHcPr |
| 299 | —NHcBu |
| 300 | —NHcPn |
| 301 | —NHcHex |
| 302 | —NHCH₂CH₂OH |
| 303 | —NHCH₂CH₂OMe |
| 304 | —NHCH₂CH₂OEt |
| 305 | —NHCH₂CH₂NH₂ |
| 306 | —NHCH₂CH₂NHMe |
| 307 | —NHCH₂CH₂NMe₂ |
| 308 | 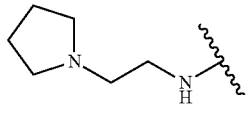 [SMILES: *NCCN1CCCC1] |
| 309 | 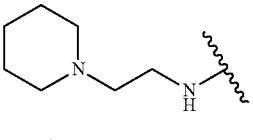 [SMILES: *NCCN1CCCCC1] |
| 310 | 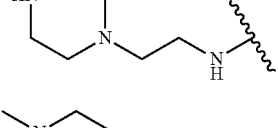 |
| 311 | 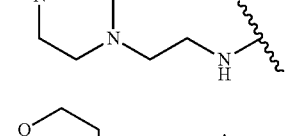 |
| 312 | 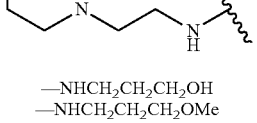 |
| 313 | —NHCH₂CH₂CH₂OH |
| 314 | —NHCH₂CH₂CH₂OMe |
| 315 | —NHCH₂CH₂CH₂OEt |
| 316 | —NHCH₂CH₂CH₂NH₂ |
| 317 | —NHCH₂CH₂CH₂NHMe |
| 318 | —NHCH₂CH₂CH₂NMe₂ |
| 319 | 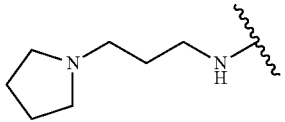 [SMILES: *NCCCN1CCCC1] |
| 320 | 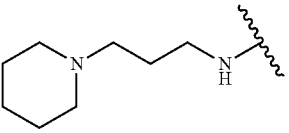 |

TABLE 2-continued

| # | Water Solubilizing Group |
|---|---|
| 321 | (piperazine-CH₂CH₂CH₂-NH-) |
| 322 | (N-methylpiperazine-CH₂CH₂CH₂-NH-) |
| 323 | (morpholine-CH₂CH₂CH₂-NH-) |
| 324 | —NHCH₂CH₂OCH₂CH₂OH |
| 325 | —NHCH₂CH₂OCH₂CH₂OMe |
| 326 | —NHCH₂CH₂OCH₂CH₂OEt |
| 327 | —NHCH₂CH₂OCH₂CH₂NH₂ |
| 328 | —NHCH₂CH₂OCH₂CH₂NHMe |
| 329 | —NHCH₂CH₂OCH₂CH₂NMe₂ |
| 330 | —N(CH₂CH₂OH)₂ |
| 331 | —N(CH₂CH₂OMe)₂ |
| 332 | —N(CH₂CH₂OEt)₂ |
| 333 | —N(CH₂CH₂CH₂OH)₂ |
| 334 | —N(CH₂CH₂CH₂OMe)₂ |
| 335 | —N(CH₂CH₂CH₂OEt)₂ |
| 336 | —N(CH₂CH₂CH₂NH₂)₂ |
| 337 | —N(CH₂CH₂CH₂NHMe)₂ |
| 338 | —N(CH₂CH₂CH₂NMe₂)₂ |
| 339 | (pyrrolidine-CH₂CH₂CH₂-O-) |
| 340 | (bis(piperidine-CH₂CH₂CH₂)-N-) |
| 341 | (bis(piperazine-CH₂CH₂CH₂)-N-) |
| 342 | (bis(N-methylpiperazine-CH₂CH₂CH₂)-N-) |
| 343 | (bis(morpholine-CH₂CH₂CH₂)-N-) |
| 344 | —N(CH₂CH₂OCH₂CH₂OH)₂ |
| 345 | —N(CH₂CH₂OCH₂CH₂OMe)₂ |
| 346 | —N(CH₂CH₂OCH₂CH₂OEt)₂ |
| 347 | —N(CH₂CH₂OCH₂CH₂NH₂)₂ |
| 348 | —N(CH₂CH₂OCH₂CH₂NHMe)₂ |
| 349 | —N(CH₂CH₂OCH₂CH₂NMe₂)₂ |
| 350 | —NMeCH₂CH₂OH |
| 351 | —NMeCH₂CH₂OMe |
| 352 | —NMeCH₂CH₂OEt |
| 353 | —NMeCH₂CH₂NH₂ |
| 354 | —NMeCH₂CH₂NHMe |
| 355 | —NMeCH₂CH₂NMe₂ |
| 356 | (pyrrolidine-CH₂CH₂-NMe-) |
| 357 | (piperidine-CH₂CH₂-NMe-) |
| 358 | (piperazine-CH₂CH₂-NMe-) |
| 359 | (N-methylpiperazine-CH₂CH₂-NMe-) |
| 360 | (morpholine-CH₂CH₂-NMe-) |

TABLE 2-continued

Water Solubilizing Group

| # | Water Solubilizing Group |
|---|---|
| 361 | —NMeCH₂CH₂CH₂OH |
| 362 | —NMeCH₂CH₂CH₂OMe |
| 363 | —NMeCH₂CH₂CH₂OEt |
| 364 | —NMeCH₂CH₂CH₂NH₂ |
| 365 | —NMeCH₂CH₂CH₂NHMe |
| 366 | —NMeCH₂CH₂CH₂NMe₂ |
| 367 | *pyrrolidine-N-CH₂CH₂CH₂-N(Me)-* |
| 368 | *piperidine-N-CH₂CH₂CH₂-N(Me)-* |
| 369 | *piperazine(HN)-N-CH₂CH₂CH₂-N(Me)-* |
| 370 | *N-methylpiperazine-N-CH₂CH₂CH₂-N(Me)-* |
| 371 | *morpholine-N-CH₂CH₂CH₂-N(Me)-* |
| 372 | —NMeCH₂CH₂OCH₂CH₂OH |
| 373 | —NMeCH₂CH₂OCH₂CH₂OMe |
| 374 | —NMeCH₂CH₂OCH₂CH₂OEt |
| 375 | —NMeCH₂CH₂OCH₂CH₂NH₂ |
| 376 | —NMeCH₂CH₂OCH₂CH₂NHMe |
| 377 | —NMeCH₂CH₂OCH₂CH₂NMe₂ |
| 378 | —O(C=O)OMe |
| 379 | —O(C=O)OEt |
| 380 | —O(C=O)OnPr |
| 381 | —O(C=O)OiPr |
| 382 | —O(C=O)OcPr |
| 383 | —O(C=O)OcBu |
| 384 | —O(C=O)OcPn |
| 385 | —O(C=O)OcHex |
| 386 | COOH |
| 387 | —CH₂(C=O)OH |
| 388 | —CH₂(C=O)OMe |
| 389 | —CH₂(C=O)OEt |
| 390 | —CH₂(C=O)OnPr |
| 391 | —CH₂(C=O)OiPr |
| 392 | —CH₂(C=O)OcPr |
| 393 | —CH₂(C=O)OcBu |
| 394 | —CH₂(C=O)OcPn |
| 395 | —CH₂(C=O)OcHex |
| 396 | —OCH₂(C=O)OH |
| 397 | —OCH₂(C=O)OMe |
| 398 | —OCH₂(C=O)OEt |
| 399 | —OCH₂(C=O)OnPr |
| 400 | —OCH₂(C=O)OiPr |
| 401 | —OCH₂(C=O)OcPr |
| 402 | —OCH₂(C=O)OcBu |
| 403 | —OCH₂(C=O)OcPn |
| 404 | —OCH₂(C=O)OcHex |
| 405 | —OCH₂(C=O)OH |
| 406 | —OCH₂(C=O)OMe |
| 407 | —OCH₂(C=O)OEt |
| 408 | —OCH₂(C=O)OnPr |
| 409 | —OCH₂(C=O)OiPr |
| 410 | —OCH₂(C=O)OcPr |
| 411 | —OCH₂(C=O)OcBu |
| 412 | —OCH₂(C=O)OcPn |
| 413 | —OCH₂(C=O)OcHex |
| 414 | —NHCH₂(C=O)OH |
| 415 | —NHCH₂(C=O)OMe |
| 416 | —NHCH₂(C=O)OEt |
| 417 | —NHCH₂(C=O)OnPr |
| 418 | —NHCH₂(C=O)OiPr |
| 419 | —NHCH₂(C=O)OcPr |
| 420 | —NHCH₂(C=O)OcBu |
| 421 | —NHCH₂(C=O)OcPn |
| 422 | —NHCH₂(C=O)OcHex |
| 423 | —NMeCH₂(C=O)OH |
| 424 | —NH(CH₂(C=O)OH)₂ |
| 425 | —CH₂(C=O)OH |
| 426 | —CH₂OCH₂(C=O)OH |
| 427 | —OCH₂CH₂(C=O)OH |
| 428 | —CH₂CH₂CH₂(C=O)OH |
| 429 | —CH₂CH₂OCH₂(C=O)OH |
| 430 | —CH₂OCH₂CH₂(C=O)OH |
| 431 | —OCH₂CH₂CH₂(C=O)OH |
| 432 | —OCH₂CH₂OCH₂(C=O)OH |
| 433 | —CH₂CH₂CH₂CH₂(C=O)OH |
| 434 | —CH₂CH₂CH₂OCH₂(C=O)OH |
| 435 | —CH₂CH₂OCH₂CH₂(C=O)OH |
| 436 | —CH₂OCH₂CH₂CH₂(C=O)OH |
| 437 | —OCH₂CH₂CH₂CH₂(C=O)OH |
| 438 | —CH₂OCH₂CH₂OCH₂(C=O)OH |
| 439 | —OCH₂CH₂CH₂OCH₂(C=O)OH |
| 440 | —OCH₂CH₂OCH₂CH₂(C=O)OH |
| 441 | —CH₂OCH₂CH₂CH₂(C=O)OH |
| 442 | —CH₂CH₂CH₂CH₂CH₂(C=O)OH |
| 443 | —CH₂CH₂CH₂CH₂OCH₂(C=O)OH |
| 444 | —CH₂CH₂CH₂OCH₂CH₂(C=O)OH |
| 445 | —CH₂CH₂OCH₂CH₂CH₂(C=O)OH |
| 446 | —CH₂OCH₂CH₂CH₂CH₂(C=O)OH |
| 447 | —OCH₂CH₂CH₂CH₂CH₂(C=O)OH |
| 448 | —CH₂CH₂OCH₂CH₂OCH₂(C=O)OH |
| 449 | —CH₂OCH₂CH₂CH₂OCH₂(C=O)OH |
| 450 | —OCH₂CH₂CH₂CH₂OCH₂(C=O)OH |
| 451 | —CH₂OCH₂CH₂OCH₂CH₂(C=O)OH |
| 452 | —OCH₂CH₂CH₂OCH₂CH₂(C=O)OH |
| 453 | —OCH₂CH₂OCH₂CH₂CH₂(C=O)OH |
| 454 | —OCH₂CH₂OCH₂CH₂OCH₂(C=O)OH |
| 455 | —CH₂CH₂CH₂CH₂CH₂CH₂(C=O)OH |
| 456 | —CH₂CH₂CH₂CH₂CH₂OCH₂(C=O)OH |
| 457 | —CH₂CH₂CH₂OCH₂CH₂OCH₂(C=O)OH |
| 458 | —CH₂OCH₂CH₂OCH₂CH₂OCH₂(C=O)OH |
| 459 | —OCH₂CH₂OCH₂CH₂OCH₂C(O)OH |
| 460 | —CH₂CH₂CH₂CH₂OCH₂CH₂(C=O)OH |
| 461 | —CH₂CH₂OCH₂CH₂OCH₂CH₂(C=O)OH |
| 462 | —CH₂OCH₂CH₂OCH₂CH₂CH₂(C=O)OH |
| 463 | —OCH₂CH₂CH₂OCH₂CH₂CH₂(C=O)OH |
| 464 | —OCH₂CH₂OCH₂CH₂OCH₂(CO)OH |
| 465 | —CH₂CH₂CH₂OCH₂CH₂CH₂(C=O)OH |
| 466 | —CH₂OCH₂CH₂OCH₂CH₂CH₂(C=O)OH |
| 467 | —OCH₂CH₂CH₂OCH₂CH₂CH₂(C=O)OH |
| 468 | —CH₂CH₂OCH₂CH₂CH₂CH₂(C=O)OH |
| 469 | —OCH₂CH₂OCH₂CH₂CH₂CH₂(C=O)OH |
| 470 | —CH₂OCH₂CH₂CH₂CH₂CH₂(C=O)OH |
| 471 | —OCH₂CH₂CH₂CH₂CH₂CH₂(C=O)OH |
| 472 | —NHCH₂CH₂(C=O)OH |
| 473 | —NMeCH₂CH₂(C=O)OH |
| 474 | —N(CH₂CH₂(C=O)OH)₂ |
| 475 | —NHCH₂CH₂OCH₂(C=O)OH |
| 476 | —NMeCH₂CH₂OCH₂(C=O)OH |
| 477 | —N(CH₂OCH₂(C=O)OH)₂ |
| 478 | —NHCH₂CH₂CH₂CH₂(C=O)OH |
| 479 | —NMeCH₂CH₂CH₂CH₂(C=O)OH |
| 480 | —N(CH₂CH₂CH₂CH₂(C=O)OH)₂ |

TABLE 2-continued

Water Solubilizing Group

| # | Water Solubilizing Group |
|---|---|
| 481 | —NHCH$_2$CH$_2$CH$_2$OCH$_2$(C=O)OH |
| 482 | —NMeCH$_2$CH$_2$CH$_2$OCH$_2$(C=O)OH |
| 483 | —N(CH$_2$CH$_2$CH$_2$OCH$_2$(C=O)OH)$_2$ |
| 484 | —NHCH$_2$CH$_2$OCH$_2$CH$_2$(C=O)OH |
| 485 | —NMeCH$_2$CH$_2$OCH$_2$CH$_2$(C=O)OH |
| 486 | —N(CH$_2$CH$_2$OCH$_2$CH$_2$(C=O)OH)$_2$ |
| 487 | —NHCH$_2$CH$_2$CH$_2$CH$_2$CH$_2$(C=O)OH |
| 488 | —NMeCH$_2$CH$_2$CH$_2$CH$_2$CH$_2$(C=O)OH |
| 489 | —N(CH$_2$CH$_2$CH$_2$CH$_2$CH$_2$(C=O)OH)$_2$ |
| 490 | —NHCH$_2$CH$_2$CH$_2$CH$_2$OCH$_2$(C=O)OH |
| 491 | —NMeCH$_2$CH$_2$CH$_2$CH$_2$OCH$_2$(C=O)OH |
| 492 | —N(CH$_2$CH$_2$CH$_2$CH$_2$OCH$_2$(C=O)OH)$_2$ |
| 493 | —NHCH$_2$CH$_2$CH$_2$OCH$_2$CH$_2$(C=O)OH |
| 494 | —NMeCH$_2$CH$_2$CH$_2$OCH$_2$CH$_2$(C=O)OH |
| 495 | —N(CH$_2$CH$_2$CH$_2$OCH$_2$CH$_2$(C=O)OH)$_2$ |
| 496 | —NHCH$_2$CH$_2$OCH$_2$CH$_2$CH$_2$(C=O)OH |
| 497 | —NMeCH$_2$CH$_2$OCH$_2$CH$_2$CH$_2$(C=O)OH |
| 498 | —N(CH$_2$CH$_2$OCH$_2$CH$_2$CH$_2$(C=O)OH)$_2$ |
| 499 | —NHCH$_2$CH$_2$OCH$_2$CH$_2$OCH$_2$(C=O)OH |
| 500 | —NMeCH$_2$CH$_2$OCH$_2$CH$_2$OCH$_2$(C=O)OH |
| 501 | —N(CH$_2$CH$_2$OCH$_2$CH$_2$OCH$_2$(C=O)OH)$_2$ |
| 502 | —NHCH$_2$CH$_2$CH$_2$OCH$_2$CH$_2$OCH$_2$CO$_2$H |
| 503 | —NMeCH$_2$CH$_2$CH$_2$OCH$_2$CH$_2$OCH$_2$CO$_2$H |
| 504 | —N(CH$_2$CH$_2$CH$_2$OCH$_2$CH$_2$OCH$_2$CO$_2$H)$_2$ |
| 505 | —NHCH$_2$CH$_2$CH$_2$OCH$_2$CH$_2$CO$_2$H |
| 506 | —NMeCH$_2$CH$_2$CH$_2$OCH$_2$CH$_2$CO$_2$H |
| 507 | —N(CH$_2$CH$_2$CH$_2$CH$_2$OCH$_2$CH$_2$CO$_2$H)$_2$ |
| 508 | —NHCH$_2$CH$_2$OCH$_2$CH$_2$OCH$_2$CH$_2$CO$_2$H |
| 509 | —NMeCH$_2$CH$_2$OCH$_2$CH$_2$OCH$_2$CH$_2$CO$_2$H |
| 510 | —N(CH$_2$CH$_2$OCH$_2$CH$_2$OCH$_2$CH$_2$CO$_2$H)$_2$ |
| 511 | —NHCH$_2$CH$_2$CH$_2$OCH$_2$CH$_2$CH$_2$CO$_2$H |
| 512 | —NMeCH$_2$CH$_2$CH$_2$OCH$_2$CH$_2$CH$_2$CO$_2$H |
| 513 | —N(CH$_2$CH$_2$CH$_2$OCH$_2$CH$_2$CH$_2$CO$_2$H)$_2$ |
| 514 | —NHCH$_2$CH$_2$OCH$_2$CH$_2$CH$_2$CH$_2$CO$_2$H |
| 515 | —NMeCH$_2$CH$_2$OCH$_2$CH$_2$CH$_2$CH$_2$CO$_2$H |
| 516 | —N(CH$_2$CH$_2$OCH$_2$CH$_2$CH$_2$CH$_2$CO$_2$H)$_2$ |
| 517 | —NHCH$_2$CH$_2$CH$_2$CH$_2$CH$_2$CH$_2$CO$_2$H |
| 518 | —NMeCH$_2$CH$_2$CH$_2$CH$_2$CH$_2$CH$_2$CO$_2$H |
| 519 | —N(CH$_2$CH$_2$CH$_2$CH$_2$CH$_2$CH$_2$CO$_2$H)$_2$ |

For each of the groups depicted above in Table 2 that is a carboxylic acid, the compounds ester derivatives are also provided. The ester can be, e.g., a methyl ester, an ethyl ester, an n-propyl ester, an isopropyl ester, a cyclopropyl ester, an n-butyl ester, a s-butyl ester, an isobutyl ester, or a t-butyl ester, a cyclobutyl ester, a pentyl ester (e.g., an n-pentyl ester), a cyclopentyl ester, or a hexyl ester (e.g., a n-hexyl ester) or a cyclohexyl ester.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as (3-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences, 17$^{th}$ Ed.*, (Mack Publishing Company, Easton, 1985), p. 1418, Berge et al., *J Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); Al$_2$O$_3$ (aluminium oxide); aq. (aqueous); atm. (atmosphere(s)); Boc (t-butoxycarbonyl); Boc$_2$O (di-tert-butyldicarbonate); BOP ((benzotriazol-1-yloxy)tris(dimethylamino)phosphonium hexafluorophosphate); br (broad); cBu (cyclobutyl); cHex (cyclohexyl); cPn (cyclopentyl); cPr (cyclopropyl); Cbz (carboxybenzyl); calc. (calculated); CeCl$_3$.7H$_2$O (cerium (III) chloride heptahydrate); Cs$_2$CO$_3$ (cesium carbonate); CuI (copper (I) iodide); d (doublet); dd (doublet of doublets); DCM (dichloromethane); DIPEA (N,N-diisopropylethylamine); DMAP (4-dimethylaminopyridine); DMF (N,N-dimethylformamide); DMSO (dimethylsulfoxide); EDTA (ethylenediaminetetraacetic acid); Et (ethyl); EtOAc (ethyl acetate); EtOH (ethanol); Fmoc (9-fluorenylmethylmethoxycarbonyl); g (gram(s)); h (hour(s)); H$_2$ (hydrogen gas); H$_2$O$_2$ (hydrogen peroxide); HATU (N,N,N',N'-tetramethyl-O-(7-azabenzotriazol-1-yl)uronium hexafluorophosphate); HBr (hydrogen bromide); HCl (hydrochloric acid or hydrogen chloride); HPLC (high performance liquid chromatography); HPP (4-hydroxyphenyl pyruvic acid); Hz (hertz); iPr (isopropyl); iPrOH (isopropyl alcohol); J (coupling constant); Ki (inhibition constant); KOAc (potassium acetate); K$_3$PO$_4$ (potassium phosphate); K$_3$PO$_4$.H$_2$O (tripotassium phosphate hydrate); LCMS (liquid chromatography mass spectrometry); LiAlH$_4$ (lithium tetrahydroaluminate); LiBH$_4$ (lithium tetrahydroborate); LiOH (lithium hydroxide); LiOH.H$_2$O (lithium hydroxide monohydrate); m (multiplet); m (molar); mCPBA (m-chloroperbenzoic acid); Me (methyl); MeCN (acetonitrile); MeOH (methanol); MIF (macrophage migration inhibitory factor); rhMIF (recombinant human MIF); mgSO$_4$ (magnesium sulfate); MS (mass spectrometry); mg (milligram(s)); min. (minutes(s)); mL (milliliter(s)); mmol (millimole(s)); N (normal); N$_2$ (nitrogen gas); NaHCO$_3$ (sodium bicarbonate); NaIO$_4$ (sodium metaperiodate); NaN$_3$ (sodium azide); NaOH (sodium hydroxide); Na$_2$SO$_4$ (sodium sulfate); nBu (n-butyl); nBuLi (n-butyllithium); NH$_4$Cl (ammonium chloride); NH$_4$OH (ammonium hydroxide); nM (nanomolar); NMR (nuclear magnetic resonance spectroscopy); nPn (n-pentyl); nPr (n-propyl); Pd (palladium); Pd(dppf)Cl$_2$ ([1,1'-bis(diphenylphosphino)ferrocene]palladium(II) dichloride); Pd(OAc)$_2$ (palladium acetate); Pd(tBu$_3$P)$_2$ (bis(tri-tert-butylphosphine) palladium); pM (picomolar); Pd(PPh$_3$)$_4$ (tetrakis(triphenylphosphine)palladium(O)); PPh$_3$ (triphenylphosphine); psi (pounds per square inch); PPTS (pyridinium p-toluenesulfonate); PTFE (polytetrafluoroethylene); RP-HPLC (reverse phase high performance liquid chromatography); s (singlet); t (triplet or tertiary); tert (tertiary); tt (triplet of triplets); TBAF (tetra-n-butylammoniumfluoride); t-Bu (tert-butyl); TEA (triethylamine); TFA (trifluoroacetic acid); THF (tetrahydrofuran); µg (microgram(s)); µL (microliter(s)); µm (micromolar); wt % (weight percent).

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Scheme 1. For example, compound (i) (wherein X$^1$ is halo, e.g, chloro, bromo, iodo) is reacted with an appropriately substituted alkynylene (e.g., 2-methyl-3-butyn-2-ol or ethynyltrimethylsilane to form the protected alkyne (ii), wherein R is an alkyne protecting group (e.g., i-propyl or trimethylsilyl), which is subsequently deprotected using standard alkyne deprotection conditions (e.g., reaction of compound (iii) in the presence of a base). Lastly, compound (iii) is reacted with an appropriately substituted phenyl group and an alkali metal azide (e.g., sodium azide) in the presence of base (e.g., trans-N,N'-dimethylcyclohexane-1,2-diamine) and a copper catalyst (e.g., copper iodide) to form the 1,3-dipolar cycloaddition compound of Formula (I).

Scheme 1

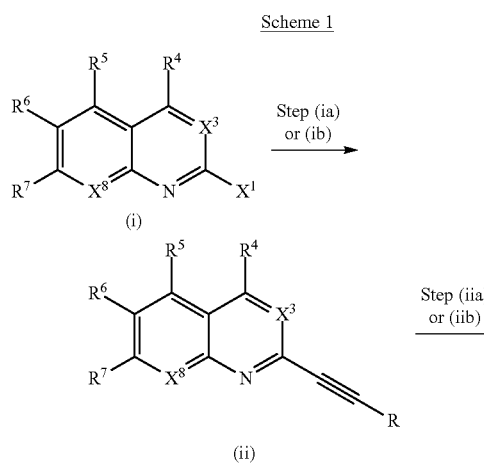

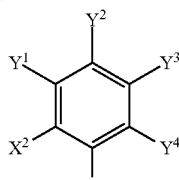

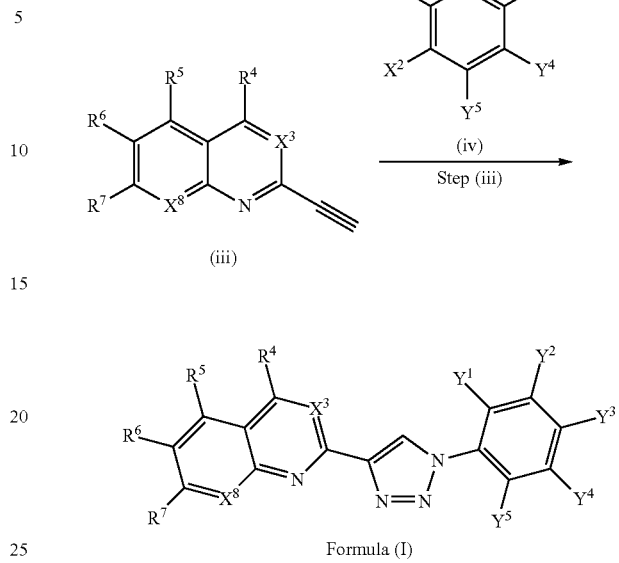

The compounds of Formula (I) can also be prepared as shown in Scheme 2.

Scheme 2

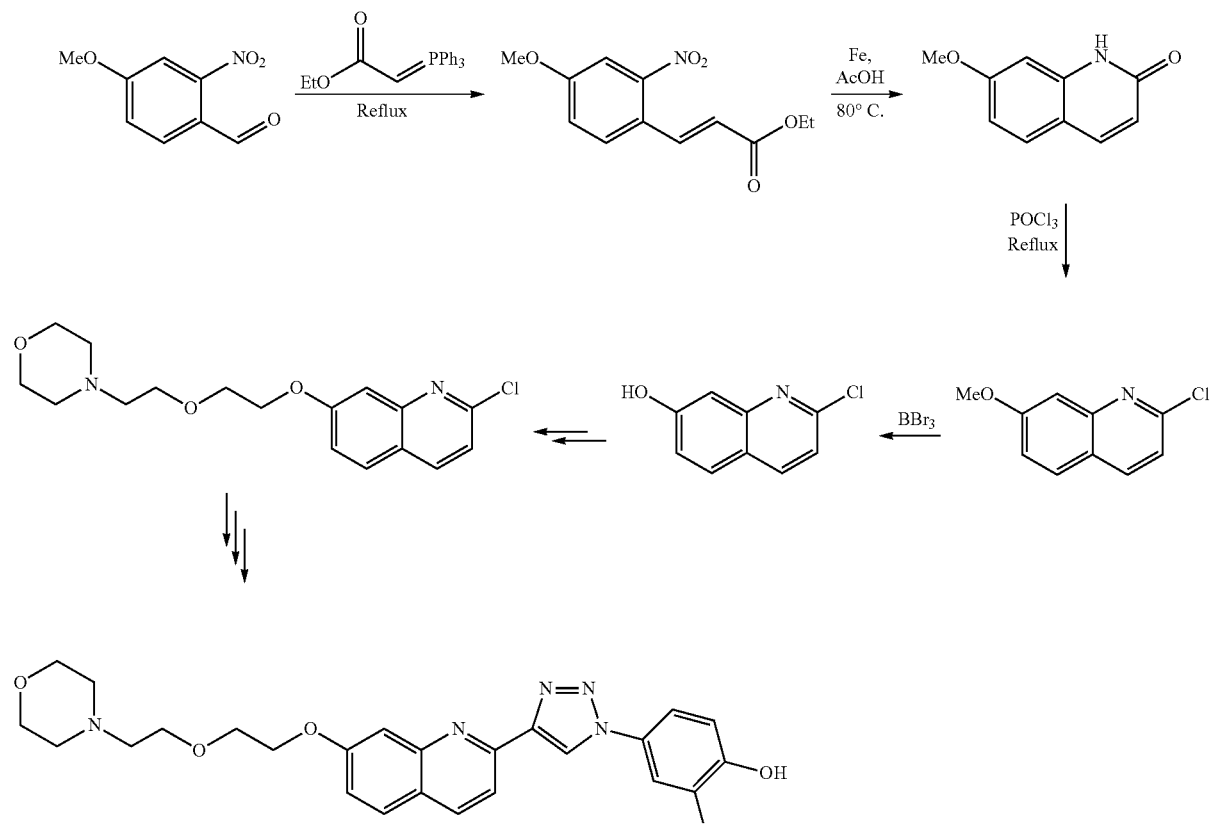

X = H, MIF302
X = F, MIF303

For example, reaction of 4-methoxy-2-nitrobenzaldehyde and ethyl 2-(triphenylphosphoranylidene)acetate under standard Homer-Wadsworth-Emmons conditions forms (E)-ethyl 3-(4-methoxy-2-nitrophenyl)acrylate, which is subsequently cyclized in the presence of acetic acid and an iron catalyst to form 7-methoxyquinolin-2(1H)-one. Reaction of 7-methoxyquinolin-2(1H)-one with phosphorylchloride forms the corresponding 2-chloroquinoline adduct, which is then reacted with boron tribromide to form 2-chloroquinolin-7-ol. After formation of 4-(2-(2-((2-chloroquinolin-7-yl)oxy)ethoxy)ethyl)morpholine (see e.g., Intermediate 10), the compound of Formula (I) may be prepared according to the procedure described in Scheme 1.

The compounds of Formula (I) can also be prepared as shown in Scheme 3.

ol, which is then reacted with 1-bromo-2-methoxyethane in the presence of a base (e.g., $K_2CO_3$) to afford 2-chloro-6-(2-methoxyethoxy)quinazoline. The compound of Formula (I) (e.g., 4-(4-(6-(2-methoxyethoxy)quinazolin-2-yl)-1H-1,2,3-triazol-1-yl)phenol) is then prepared from 2-chloro-6-(2-methoxyethoxy)quinazoline using the procedure described herein in Scheme 1.

For the synthesis of particular compounds, the general schemes described above can be modified. For example, the products or intermediates can be modified to introduce particular functional groups. Alternatively, the substituents can be modified at any step of the overall synthesis by methods know to one skilled in the art, e.g., as described by Larock, *Comprehensive Organic Transformations: A Guide to Functional Group Preparations* (Wiley, 1999); and

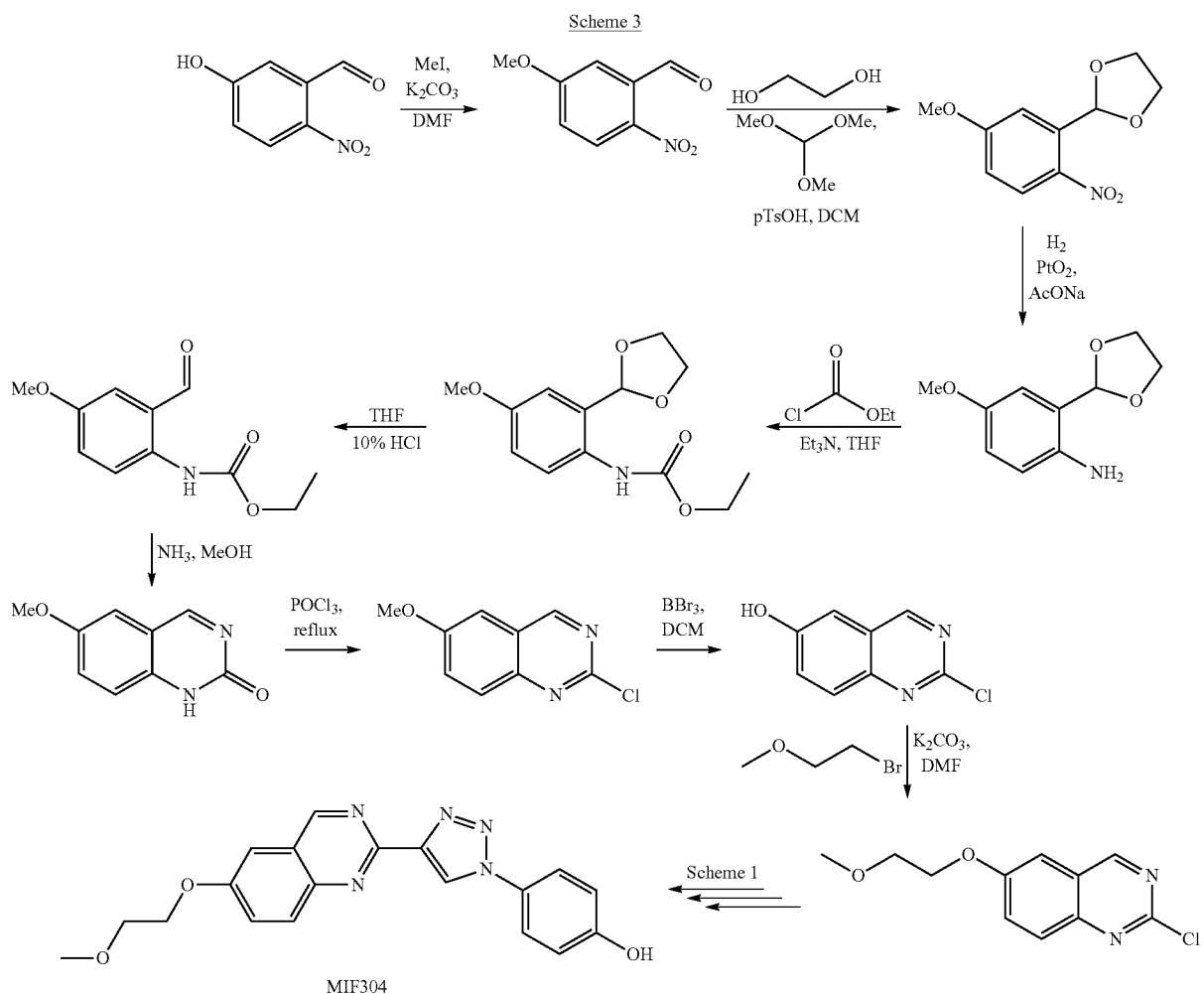

For example, 4-methoxy-2-nitrobenzaldehyde is treated with methyl iodide in the presence of a base (e.g., $K_2CO_3$) to afford 5-methoxy-2-nitrobenzaldehyde. Acetal protection of the aldehyde group and subsequently hydrogenation of the nitro affords 2-(1,3-dioxolan-2-yl)-4-methoxyaniline. Esterification of the amine in the presence of base (e.g., triethylamine) and deprotection of the aldehyde under standard deprotection conditions (e.g., reaction in the presence of a strong acid) affords ethyl (2-formyl-4-methoxyphenyl)carbamate. Cyclization, chlorination, and demethylation as described herein in Scheme 2 affords 2-chloroquinazolin-6-

Katritzky et al. (Ed.), *Comprehensive Organic Functional Group Transformations* (Pergamon Press 1996).

Starting materials, reagents and intermediates whose synthesis is not described herein are either commercially available, known in the literature, or may be prepared by methods known to one skilled in the art.

It will be appreciated by one skilled in the art that the processes described are not the exclusive means by which compounds of the invention may be synthesized and that a broad repertoire of synthetic organic reactions is available to be potentially employed in synthesizing compounds of the invention. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

III. Uses of the Compounds

Compounds of the invention can inhibit the activity of macrophage migration inhibitory factor (MIF) and, thus, are useful in treating diseases and disorders associated with activity of macrophage migration inhibitory factor. For the uses described herein, any of the compounds of the invention, including any of the embodiments thereof, may be used.

The compounds of the invention are useful for inhibiting macrophage migration inhibitory factor (MIF) activity in a subject, e.g. a mammal, such as a human. Methods of using the compounds can comprise administering any of the compounds of the invention to a subject in an amount effective to inhibit MIF activity in the mammal.

The compounds of the invention are useful for treating or for the prophylaxis of inflammation in a subject. The compounds can be administered to a subject that has or is at risk for a condition that comprises an inflammatory cytokine cascade that is at least partially mediated by an MIF. Thus the compounds of the invention are useful for treating diseases involving inflammation, for example, proliferative vascular disease, acute respiratory distress syndrome, cytokine-mediated toxicity, psoriasis, interleukin-2 toxicity, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, inflammatory bowel disease, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, ankylosing spondylitis, Berger's disease, type 1 diabetes, type 2 diabetes, Berger's disease, Retier's syndrome, or Hodgkins disease. A preferred such condition is sepsis, septicemia, and/or endotoxic shock.

MIF has been shown to play an important role in autoimmune disease. The compounds of the invention would therefore be useful in treatment of autoimmune disease. Non-limiting examples of such autoimmune diseases are multiple sclerosis, systemic lupus erythematosus, rheumatoid arthritis, graft versus host disease, autoimmune pulmonary inflammation, autoimmune encephalomyelitis, Guillain-Barre syndrome, autoimmune thyroiditis, insulin dependent diabetes mellitus, Crohn's disease, scleroderma, psoriasis, Sjögren's syndrome and autoimmune inflammatory eye disease.

MIF also is known to promote tumor invasion and metastasis. The compounds of the invention be useful for treatment of a mammal that has a tumor or for the treatment of cancer. Examples of cancers that can be treated include solid tumors, e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head or neck, thyroid cancer, glioblastoma, sarcoma, bladder cancer, etc. Diseases that can be treated with the compounds of the invention also include hematological cancers, e.g., lymphoma, leukemia such as acute lymphoblastic leukemia (ALL), acute myelogenous leukemia (AML), chronic lymphocytic leukemia (CLL), chronic myelogenous leukemia (CML), diffuse large B-cell lymphoma (DLBCL), mantle cell lymphoma, non-Hodgkin lymphoma (including relapsed non-Hodgkin lymphoma, refractory non-Hodgkin lymphoma and recurrent follicular non-Hodgkin lymphoma), Hodgkin lymphoma and multiple myeloma.

Compounds of the invention can be used to treat diseases associated with high MIF expression. Diseases associated with high MIF expression include diseases caused by infection by a protozoan (for example malaria) fungus, bacteria and viruses, including flavivirus, such as West Nile, Dengue, Japanese encephalitis, St Louis encephalitis, or equine encepahalitis viruses; anemia of chronic disease; asthma and autism spectrum disorder (ASD).

Compounds of the invention can be used for treating anemia of chronic disease. In certain embodiment, the subject has or is at risk of developing anemia of chronic disease. In some embodiments, the subject has anemia of chronic disease and the subject is not responsive to erythropoietin (EPO) prior to the administration of the MIF antagonist. In some embodiments, the subject is has a genotype that is associated with high MIF expression. In some embodiments, the subject is Caucasian. Anemia of chronic disease may result from, among other conditions, pathogenic infection (e.g., a malaria infection), cancer, autoimmune diseases or disorders (lupus erythematosis, arthritis, including rheumatoid arthritis, kidney diseases or disorders, organ transplant rejection and aging. The compounds of the invention can treat anemia of chronic disease regardless of its cause.

The compounds of the invention can also be used for treating or for the prophylaxis of malaria. In some embodiments, the subject has malaria or is at risk of developing malaria. In some embodiments, the subject is has a genotype that is associated with high MIF expression. In one embodiment, the subject is Caucasian.

The compounds of the invention can also be used for treating or for the prophylaxis or treatment of sepsis, septicemia, and/or endotoxic shock. The methods comprise administering the above pharmaceutical composition to the mammal in an amount effective to treat the sepsis, septicemia and/or endotoxic shock.

The terms "subject", "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

The term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease. In one embodiment, treating or treatment includes preventing or reducing the risk of developing the disease; e.g., preventing or reducing the risk of developing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatment such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, for the treatment of MIF-associated diseases, disorders or conditions. The one or more additional pharmaceutical agents can be administered to a patient simultaneously or sequentially.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and z For treating autoimmune or inflammatory conditions, the compound of Formula (I) can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holies Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of Formula (I) can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a compound of Formula (I) may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

For the prophylaxis or treatment of anemia of chromic disease comprising, the compounds of the invention can be used in combination with one or more other agents that stimulate erythropoiesis such as erythropoietin ("EPO"), iron, folate, vitamin B12, blood, blood substitute, and plasma or serum that contains a composition with the activity of blood. In a specific embodiment, the invention provides a method of treating anemia of chromic disease, comprising administering to a subject in need thereof a MIF antagonist in combination with EPO. In other embodiments, the MIF antagonist can be administered in combination with a tumor necrosis factor-α (TNFα) antagonist or an interferon (IFN) antagonist (e.g., an IFNγ antagonist) to a subject. Examples of TNFα and IFNγ antagonists include, without limitation, anti-TNF, soluble TNF receptor, anti-IFNγ, soluble IFNγ receptor, p38 MAPK inhibitors, and JAK-STAT inhibitors.

For the treatment or prophylaxis of malaria, the compounds of the invention can be administered in combination with one or more antimalarial agents. Examples of antimalarial agents include amodiaquine; artemesinin; arteether; artemether; artesunate; atovaquone; bulaquine; chloroquine; clindamycin; dihydroartemesinin; doxycycline; halofantrine; mefloquine; mepacrine; primaquine; proguanil; pyrimethamine; sulfadoxine; sulfamethoxypyridazine; quinine; quinimax; and quinidine.

IV. Formulation, Dosage Forms and Administration

When employed as pharmaceuticals, the compounds of the invention can be administered in the form of pharmaceutical compositions. Thus the present disclosure provides a composition comprising a compound Formula (I), or a pharmaceutically acceptable salt thereof, or any of the embodiments thereof, and at least one pharmaceutically acceptable carrier. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the invention can further be useful in investigations of biological processes, in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating macrophage migration inhibitory factor in tissue samples, including human, and for identifying macrophage migration inhibitory factor ligands by inhibition binding of a labeled compound. Accordingly, the present invention includes macrophage migration inhibitory factor assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro macrophage migration inhibitory factor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2 or 3 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a macrophage migration inhibitory factor by monitoring its concentration variation when contacting with the macrophage migration inhibitory factor, through tracking of the labeling. For example, a test compound (labeled) can be evaluated for its ability to reduce binding of another compound which is known to bind to a macrophage migration inhibitory factor (i.e., standard compound). Accordingly, the ability of a test compound to compete with the standard compound for binding to the macrophage migration inhibitory factor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of macrophage migration inhibitory factor associated diseases or disorders, such as those discussed above including cancer and inflammatory diseases, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be macrophage migration inhibitory factor inhibitors according to at least one assay described herein.

EXAMPLES

NMR spectra were recorded on Agilent DD2 600 (600 MHz), DD2 500 (500 MHz) and DD2 400 (400 MHz) instruments. Column chromatography was carried out using CombiFlash over redisep column cartridges employing Merck silica gel (Kieselgel 60, 63-200 μm). Pre-coated silica gel plates F-254 were used for thin-layer analytical chromatography. Mass determinations were performed using electrospray ionization on water Micromass ZQ (LC-MS) and on an Agilent Technologies 6890N (GC-MS). HRMS (ESI-TOF) analyses were performed on Waters Xevo QTOF equipped with Z-spray electrospray ionization source. The purity (≥95%) of all final synthesized compounds was determined by reverse phase HPLC, using a Waters 2487 dual λ absorbance detector with a Waters 1525 binary pump and a Phenomenex Luna 5μ, C18(2) 250×4.6 mm column. Samples were run at 1 mL/min using gradient mixtures of 5-100% of water with 0.1% trifluoroacetic acid (TFA) (A) and 10:1 acetonitrile: water with 0.1% TFA (B) for 22 min followed by 3 min at 100% B.

General Method A

DMSO/H$_2$O (10 mL/4 mL) mixture was degassed by sonication and purging with N$_2$ for 10 minutes. Next, adequate 2-chloroquinoline (compounds 3a-v), 2-bromoquinoline (compounds 3y-z), or 2-chloro-1,8-naphthyridine (compounds 4a-b) (4.22 mmol), corresponding p-iodobenzene derivative (3.52 mmol) followed by trans-N,N-dimethylcyclohexane-1,2-diamine (0.84 mmol), sodium ascorbate (0.42 mmol), copper iodide (0.42 mmol) and sodium azide (4.22 mmol,) were added to the solvent mixture. The reaction was stirred at room temperature for 30 min and then at 70° C. for 24 h. The reaction mixture was then diluted with EtOAc and extracted with H$_2$O (×1) and brine (×1). The aqueous phase was washed with EtOAc, the organic phases were combined and dried with Na$_2$SO$_4$ and solvent evaporated. The crude product was purified by flash chromatography.

General Method B.

4-(4-(6-(2-Methoxyethoxy)pyridin-3-yl)-1H-1,2,3-triazol-1-yl)phenol (1b) and 4-(4-(pyridin-2-yl)-1H-1,2,3-triazol-1-yl)phenol (2a)

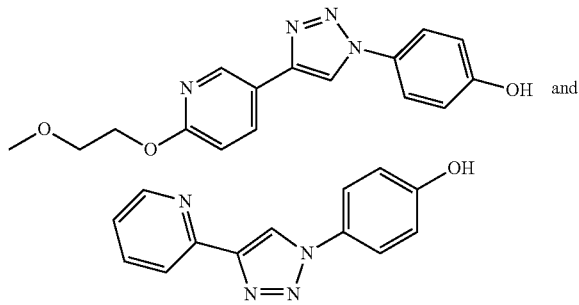

To a suspension in MeOH (15 mL) of THP protected 1b or 2a (0.97 mmol), PPTS (0.1 mmol) was added and the mixture heated to reflux (72° C.) for 48 hours. The reaction mixture was then cooled to room temperature, the solvent was evaporated, and the product was extracted with EtOAc. The organic layer was washed with H$_2$O, NaHCO$_3$, and brine, and dried over Na$_2$SO$_4$. The product was purified by column chromatography to yield the product.

4-(4-(6-(2-Methoxyethoxy)pyridin-3-yl)-1H-1,2,3-triazol-1-yl)phenol (1b)

$^1$H NMR (400 MHz, DMSO-d$_6$) δ 9.99 (s, 1H), 9.09 (s, 1H), 8.68 (d, J=2.5 Hz, 1H), 8.19 (dd, J=8.6, 2.4 Hz, 1H), 7.80-7.60 (m, 2H), 7.06-6.88 (m, 3H), 4.50-4.32 (m, 2H), 3.78-3.61 (m, 2H), 3.31 (s, 3H). $^{13}$C NMR (101 MHz, DMSO-d$_6$) δ 163.31, 158.29, 144.71, 144.07, 136.75, 129.15, 122.39, 120.74, 119.67, 116.53, 111.52, 70.64, 65.26, 58.54. HRMS (ESI): calcd for C$_{16}$H$_{16}$N$_4$O$_3$ [M+H]$^+$ 313.1222, found 313.1974.

4-(4-(Pyridin-2-yl)-1H-1,2,3-triazol-1-yl)phenol (2a)

$^1$H NMR (400 MHz, Acetone-d$_6$) δ 9.00 (s, 1H), 8.84 (s, 1H), 8.64 (d, J=4.0 Hz, 1H), 8.20 (d, J=7.9 Hz, 1H), 7.92 (t, J=7.7 Hz, 1H), 7.84 (d, J=9.0 Hz, 2H), 7.40-7.32 (m, 1H), 7.09 (d, J=9.0 Hz, 2H). $^{13}$C NMR (126 MHz, Acetone-d$_6$) δ 158.83, 151.39, 150.52, 149.44, 137.73, 130.71, 123.78, 123.06, 121.38, 120.53, 117.02. HRMS (ESI): calcd for C$_{13}$H$_{10}$N$_4$O [M+H]$^+$ 239.0855, found 239.0934.

General Method C 4-(6-(2-methoxyethoxy)pyridin-3-yl)-2-methylbut-3-yn-2-ol (6b)

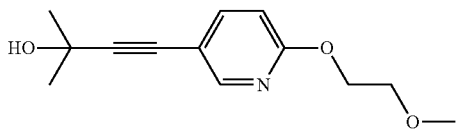 [SMILES: COCCOc1ccc(C#CC(C)(C)O)cn1]

A solution of 5-bromo-2-(2-methoxyethoxy)pyridine (5b) (3.31 mmol), 2-methyl-3-butyn-2-ol (3.64 mmol) and diethylamine (1.64 mL) was stirred under N$_2$ for 30 min. Then, Pd(PPh$_3$)$_2$Cl$_2$ (0.033 mmol) and CuI (0.033) were added and the mixture heated to 40° C. and stirred for 4 h. The reaction was cooled to room temperature and diethylamine evaporated under vacuum. The residue was dissolved in DCM and washed with NH$_4$OH solution. The organic phase was dried over Na$_2$SO$_4$ and the compound purified by flash chromatography. Yield: 80%. $^1$H NMR (400 MHz, CDCl$_3$) δ 8.20 (dd, J=2.3, 0.8 Hz, 1H), 7.57 (dd, J=8.6, 2.4 Hz, 1H), 6.74 (dd, J=8.6, 0.8 Hz, 1H), 4.54-4.39 (m, 2H), 3.80-3.67 (m, 2H), 3.43 (s, 3H), 2.24-2.12 (m, 1H), 1.61 (s, 6H).

General Method D 5-(2-Methoxyethoxy)-2-((trimethylsilyl)ethynyl)pyridine (9b)

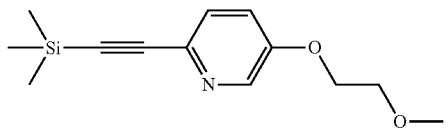

Dry THF (5 mL), 2-chloro-6-(2-methoxyethoxy)pyridine (3.9 mmol), ethynyltrimethylsilane (4.1 mmol), Pd(PPh$_3$)$_2$Cl$_2$ (0.2 mmol,), CuI (0.2 mmol) and dry Et$_3$N (15.6 mmol) were added to a pressure vial. The reaction mixture was stirred at 60° C. for 16 h. The crude reaction mixture was filtered through silica pad and washed with EtOAc. The solvent was evaporated and the product was used in the next step without further purification. Yield: 46%. $^1$H NMR (500 MHz, CDCl$_3$) δ 7.98 (dd, J=13.7, 8.9 Hz, 1H), 7.48 (d, J=8.4 Hz, 1H), 7.41 (dd, J=9.2, 2.7 Hz, 1H), 7.04 (d, J=2.7 Hz, 1H), 4.25-4.20 (m, 1H), 3.84-3.77 (m, 1H), 3.47 (s, 2H), 0.29 (s, 4H).

General Method E

5-Ethynyl-2-(2-methoxyethoxy)pyridine (7b)

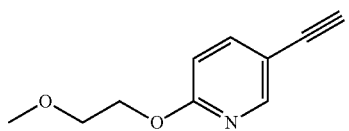

To a solution of 4-(6-(2-methoxyethoxy)pyridin-3-yl)-2-methylbut-3-yn-2-ol (6b) (2.7 mmol) in toluene (4 mL), NaOH (0.6 mmol) was added and heated at reflux for 4 hours. The reaction was cooled to room temperature, diluted with EtOAc and filtered. After solvent evaporation, the compound was purified by flash chromatography. Yield: 57%. $^1$H NMR (400 MHz, CDCl$_3$) δ 8.20 (dd, J=2.3, 0.8 Hz, 1H), 7.57 (dd, J=8.6, 2.4 Hz, 1H), 6.74 (dd, J=8.6, 0.8 Hz, 1H), 4.54-4.39 (m, 2H), 3.80-3.67 (m, 2H), 3.47 (s, 1H), 3.43 (s, 3H).

General Method F

2-Ethynyl-5-(2-methoxyethoxy)pyridine (10b)

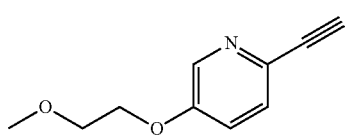

2-((trimethylsilyl)ethynyl)pyridine (3.8 mmol) was dissolved in MeOH (15 mL). Next, K$_2$CO$_3$ (0.38 mmol) was added and the reaction mixture was stirred at room temperature and monitored on TLC. Upon completion the solvent was evaporated and the crude product was purified by flash chromatography (hexanes/EtOAc 1:1) to give pure compound. Yield: 94%. $^1$H NMR (400 MHz, CDCl$_3$) δ 7.98 (d, J=8.8 Hz, 2H), 7.48 (d, J=8.4 Hz, 1H), 7.42 (dd, J=9.3, 2.7 Hz, 1H), 7.04 (d, J=2.8 Hz, 1H), 4.25-4.21 (m, 2H), 3.81 (dd, J=5.4, 3.9 Hz, 2H), 3.47 (s, 3H), 3.20 (s, 1H). HRMS (ESI): calcd for [M+H]$^+$ (C$_{14}$H$_{13}$NO$_2$) 228.1024, found 228.0992.

General Method G

6-Hydroxy2-chloroquinoline (4 mmol) was added to a pressure vial. Next, bromoethylmethyl ether, 2-(2-bromoethoxy)-N-tritylethan-1-amine or 4-(3-bromopropyl)morpholine (4.4 mmol) dissolved in DMF (10 mL), and K$_2$CO$_3$ (6 mmol) were added and the solution was stirred at 80° C. for 16 h. The reaction mixture was cooled to room temperature, diluted with EtOAc and extracted with water (×1) and brine (×3). The aqueous phase was washed with EtOAc (×1) and the organic phase was evaporated. The title compound was purified by flash chromatography.

Intermediate 1.
2-Chloro-6-(2-methoxyethoxy)quinoline (11b)

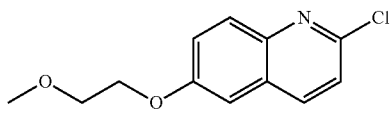 [SMILES: COCCOc1ccc2nc(Cl)ccc2c1]

The title compound was prepared according the general procedure described for the General Method G. Yield: 91%. $^1$H NMR (400 MHz, CDCl$_3$) δ 7.94 (dd, J=24.8, 8.9 Hz, 2H), 7.42 (dd, J=9.3, 2.8 Hz, 1H), 7.32 (d, J=8.6 Hz, 1H), 7.08 (d, J=2.8 Hz, 1H), 4.25-4.20 (m, 2H), 3.85-3.78 (m, 2H), 3.47 (s, 3H).

Intermediate 2. 2-(2-((2-Chloroquinolin-6-yl)oxy)ethoxy)-N-tritylethan-1-amine (11c)

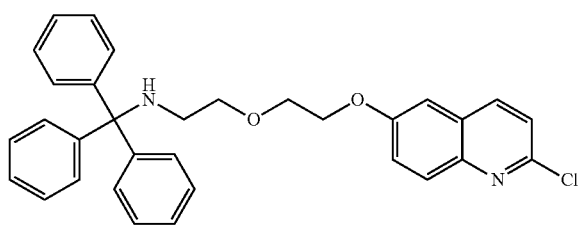 [SMILES: Clc1ccc2cc(OCCOCCNC(c3ccccc3)(c3ccccc3)c3ccccc3)ccc2n1]

The title compound was prepared according the general procedure described for the General Method G. Yield: 50%. $^1$H NMR (400 MHz, CDCl$_3$) δ 7.93 (d, J=8.6 Hz, 1H), 7.87 (d, J=9.2 Hz, 1H), 7.46 (dd, J=7.5, 1.9 Hz, 6H), 7.36-7.15 (m, 11H), 7.05 (d, J=2.8 Hz, 1H), 4.19 (t, J=4.7 Hz, 2H), 3.78 (t, J=4.7 Hz, 2H), 3.69 (t, J=5.3 Hz, 2H), 2.38 (t, J=5.4 Hz, 2H).

Intermediate 3. 4-(3-((2-Chloroquinolin-6-yl)oxy)propyl)morpholine (11t)

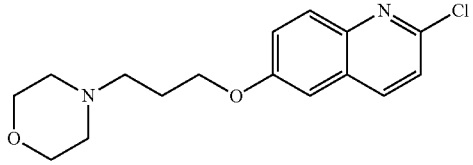 [SMILES: Clc1ccc2cc(OCCCN3CCOCC3)ccc2n1]

The title compound was prepared according the general procedure described for the General Method G. Yield: 50%. ¹H NMR (400 MHz, CDCl₃) δ 7.93 (d, J=8.6 Hz, 1H), 7.87 (d, J=9.2 Hz, 1H), 7.46 (dd, J=7.5, 1.9 Hz, 6H), 7.36-7.15 (m, 11H), 7.05 (d, J=2.8 Hz, 1H), 4.19 (t, J=4.7 Hz, 2H), 3.78 (t, J=4.7 Hz, 2H), 3.69 (t, J=5.3 Hz, 2H), 2.38 (t, J=5.4 Hz, 2H).

Intermediate 4. 2-Chloro-8-methoxyquinoline (11o)

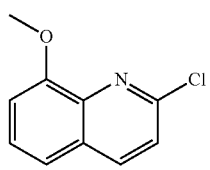

To a solution of 2-chloroquinolin-8-ol (1.11 mmol) and K₂CO₃ (2.0 mmol) in anhydrous acetone (3 mL) was added MeI (1.22 mmol) and the reaction mixture was stirred at 40° C. for 18 h. The solvent was evaporated, the residue dissolved in EtOAc and washed with water and brine. The organic phase was dried with Na₂SO₄ and evaporated to give the title compound. Yield: 85%. ¹H NMR (400 MHz, CDCl₃) δ 8.07 (d, J=6.8 Hz, 1H), 7.48 (t, J=8.0 Hz, 1H), 7.43-7.35 (m, 2H), 7.09 (d, J=7.7 Hz, 1H), 4.07 (s, 3H). HRMS (ESI): calc. for [M+H]⁺ (C₁₀H₈NOCl) 194.0373, found 194.0367.

Intermediate 5. 2-Chloro-8-(2-methoxyethoxy)quinoline (11p)

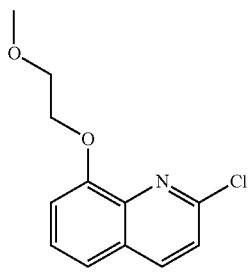 [SMILES: COCCOc1cccc2ccc(Cl)nc12]

To a solution of 2-chloroquinolin-8-ol (1.11 mmol) and K₂CO₃ (2.0 mmol) in anhydrous DMF (3 mL) was added bromoethylmethyl ether (1.22 mmol) and the reaction mixture was stirred at 80° C. for 18 h according to the synthesis of the General Method G. Yield: 98%. ¹H NMR (500 MHz, CDCl₃) δ 8.06 (d, J=8.6 Hz, 1H), 7.46 (d, J=8.0 Hz, 1H), 7.39 (t, J=8.6 Hz, 2H), 7.17 (d, J=7.7 Hz, 1H), 4.40 (t, J=5.3 Hz, 2H), 3.96-3.92 (m, 2H), 3.49 (s, 3H). HRMS (ESI): calc. For [M+H]⁺ (C₁₂H₁₂NO₂Cl) 238.0635, found 238.0627.

Intermediate 6. 2-Chloro-8-(4-methoxyphenyl)quinoline (11q)

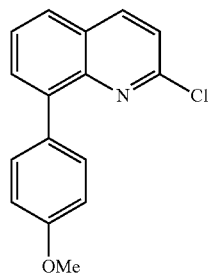 [SMILES: COc1ccc(-c2cccc3ccc(Cl)nc23)cc1]

Step 1. (E)-3-Ethoxy-N'(4'-methoxy-[',1'-biphenyl]-2-yl)acrylamide

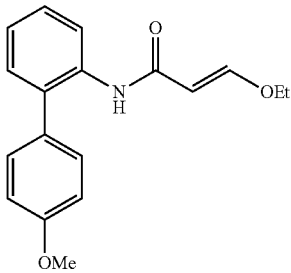 [SMILES: CCO/C=C/C(=O)Nc1ccccc1-c1ccc(OC)cc1]

A mixture of ethyl-(E)-3-ethoxyacrylate (21 mmol) and 2N NaOH (12 mL) was refluxed for 2 h. The solution was then evaporated to dryness. The residue was redissolved in toluene (7 mL), the solution stirred for 3 min and the solvent evaporated. This was repeated 5 times until water was removed from the solid which was used directly in the next step. S€um (E)-3-ethoxyacrylate (3.30 mmol) (20) was added to thionyl chloride (15.2 mmol) and the mixture was refluxed for 90 min. The solution was evaporated and the residue was dissolved in dry THF, 2 mL). 4'-met'oxy-[1,1'-biphenyl]-2-amine (2.19 mmol) and pyridine (5.0 mmol) were added to the solution at 0° C. Resulting mixture was stirred for 18 h at room temperature. Next, water/EtOAc was added to the solution and the aqueous phase was separated and washed with EtOAc. The organic phase was dried with Na₂SO₄, evaporated and the residue was purified on silica chromatography to give the sub-title product. Yield: 43%. ¹H NMR (600 MHz, CDCl₃) δ 8.30 (s, 1H), 7.58 (d, J=12.0 Hz, 1H), 7.34 (t, J=7.7 Hz, 1H), 7.30 (d, J=8.5 Hz, 2H), 7.22 (d, J=7.4 Hz, 1H), 7.14 (t, J=7.3 Hz, 1H), 7.01 (d, J=8.5 Hz, 2H), 5.09 (d, J=12.0 Hz, 1H). 3.91-3.88 (m, 2H), 3.87 (s, 3H), 1.32 (t, J=7.0 Hz, 3H). HRMS (ESI): calc. for [M+H]⁺ (C₁₈H₁₉NO₃) 298.1443, found 298.1439.

Step 2. 8-(4-methoxyphenyl)quinolin-2(1H)-one (23)

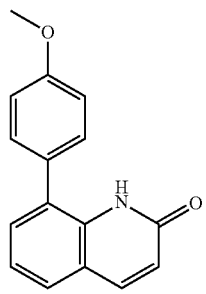 [SMILES: COc1ccc(-c2cccc3ccc(=O)[nH]c23)cc1]

(E)-3-Ethoxy-N-(4'-methoxy-[1,1'-biphenyl]-2-yl)acrylamide (1.29 mmol) was added slowly to 98% $H_2SO_4$ (3 mL) at 0° C. The reaction mixture was stirred for 20 min at 0° C. and was then poured on ice/water. After neutralization with 10N NaOH the aqueous phase was extracted with DCM. The organic phase was dried with $Na_2SO_4$ and evaporated. The residue was purified with silica chromatography to yield the sub-title compound. Yield: 12%. $^1$H NMR (400 MHz, $CDCl_3$) δ 8.87 (s, 1H), 7.82 (d, J=9.5 Hz, 1H), 7.55 (d, J=7.8 Hz, 1H), 7.42 (d, J=7.4 Hz, 1H), 7.34 (d, J=8.5 Hz, 2H), 7.29-7.23 (m, 1H), 7.05 (d, J=8.5 Hz, 2H), 6.66 (d, J=9.5 Hz, 1H), 3.89 (s, 3H). HRMS (ESI): calc. For $[M+H]^+$ ($C_{18}H_{19}NO_3$) 298.1443, found 298.1439.

Step 3. 2-chloro-8-(4-methoxyphenyl)quinolone (11q)

A mixture of 8-(4-methoxyphenyl)quinolin-2(1H)-one (23, 0.16 mmol) in $POCl_3$ (1.60 mmol) was heated at 110° C. for 90 min. The solution was cooled to room temperature, poured into water/DCM mixture and neutralized with $NH_4OH$ solution. The aqueous phase was separated and washed with DCM. The organic phase was dried with $Na_2SO_4$ and evaporated to give the title product. Yield: 46%. $^1$H NMR (400 MHz, $CDCl_3$) δ 8.13 (d, J=8.6 Hz, 1H), 7.79-7.74 (m, 2H), 7.70 (d, J=8.8 Hz, 2H), 7.60 (t, J=7.7 Hz, 1H), 7.39 (d, J=8.6 Hz, 1H), 7.04 (d, J=8.8 Hz, 2H), 3.89 (s, 3H).

Intermediate 7. 2-Chloro-8-phenoxyquinoline (11r)

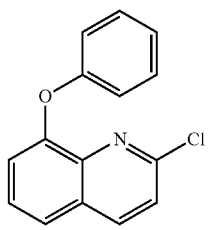 [SMILES: Clc1ccc2cccc(Oc3ccccc3)c2n1]

t-BuOK (0.55 mmol) was suspended in dry THF (3.0 mL) and the mixture was cooled to 0° C. Next, 2-chloroquinolin-8-ol (0.50 mmol) was added to the solution which was stirred for 15 min at 0° C. and diaryliodonium salt (0.60 mmol) was added and the reaction mixture was stirred at 40° C. for 1 h. The reaction was quenched with water/DCM. The aqueous phase was separated and washed with DCM. The organic phase was dried with $Na_2SO_4$ and evaporated. The residue was purified by silica chromatography to give the title product. Yield: 94%. $^1$H NMR (500 MHz, $CDCl_3$) δ 8.13 (d, J=8.5 Hz, 1H), 7.51 (d, J=8.1 Hz, 1H), 7.42 (dt, J=23.4, 7.9 Hz, 4H), 7.17 (dd, J=22.4, 7.5 Hz, 3H), 7.04 (d, J=7.6 Hz, 1H). HRMS (ESI): calc. for $[M+H]^+$ ($C_{15}H_{10}NOCl$) 256.0529, found 256.0516.

Intermediate 8. 2-Chloro-5-phenoxyquinoline (11s)

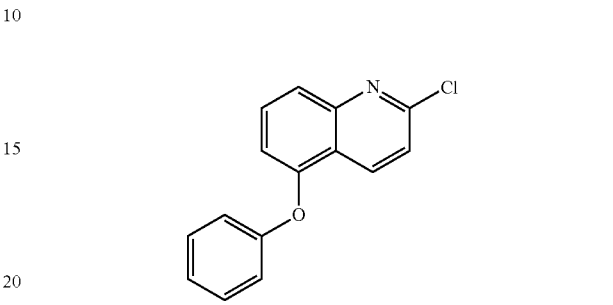

Step 1. 5-phenoxyquinoline (24)

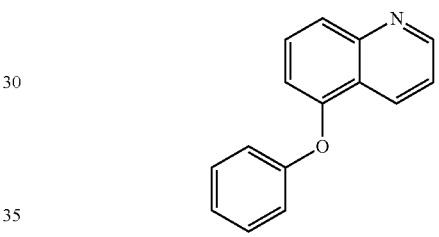

The sub-title product was prepared according to the procedure describe for Intermediate 7 (11r). $^1$H NMR (500 MHz, $CDCl_3$) δ 8.96 (d, J=4.1 Hz, 1H), 8.62 (d, J=8.4 Hz, 1H), 7.91 (d, J=8.5 Hz, 1H), 7.62 (t, J=8.1 Hz, 1H), 7.44 (dd, J=8.4, 4.2 Hz, 1H), 7.39 (t, J=7.1 Hz, 2H), 7.17 (t, J=7.0 Hz, 1H), 7.08 (d, J=7.7 Hz, 2H), 6.96 (d, J=7.7 Hz, 1H). HRMS (ESI): calc. for $[M+H]^+$ ($C_{15}H_{11}NO$) 222.0919, found 222.0926.

Step 2. 1-($\lambda^1$-Oxidanyl)-5-phenoxy-1$\lambda^4$-quinoline (25)

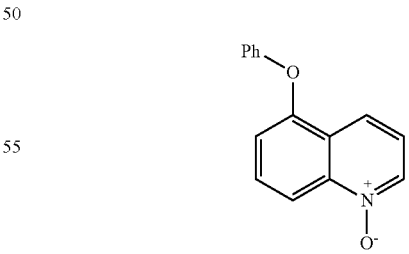

Compound 24 (0.64 mmol) was dissolved in DCM (5 mL) and m-CPBA 77% was added to solution (0.70 mmol). The reaction mixture was stirred at room temperature for 24 h and was next diluted with DCM. The organic phase was washed with sat. $K_2CO_3$, dried with $Na_2SO_4$ and evaporated to give the sub-title compound. Yield: 47%. $^1$H NMR (400 MHz, $CD_2Cl_2$) δ 8.49 (d, J=6.0 Hz, 1H), 8.37 (d, J=8.8 Hz, 1H), 8.12 (d, J=8.7 Hz, 1H), 7.62 (t, J=8.3 Hz, 1H), 7.42 (t, J=7.9 Hz, 2H), 7.33-7.28 (m, 1H), 7.22 (t, J=7.4 Hz, 1H), 7.10 (d, J=8.7 Hz, 2H), 7.00 (d, J=7.8 Hz, 1H). HRMS (ESI): calc. for [M+H]$^+$ (C$_{15}$H$_{11}$NO$_2$) 238.0868, found 238.0867.

Step 3. 2-Chloro-5-phenoxyquinoline (11s)

Compound 25 (0.30 mmol) was dissolved in dry DMF (3 mL). The solution was cooled to 0° C. and thionyl chloride (0.025 mL, 0.30 mmol) was added dropwise. The reaction was stirred at room temperature for 90 min. The reaction was quenched with MeOH, evaporated to dryness and purified on silica chromatography (DCM/MeOH). Yield: 32%. $^1$H NMR (400 MHz, CDCl$_3$) δ 8.55 (d, J=8.8 Hz, 1H), 7.78 (d, J=8.5 Hz, 1H), 7.61 (t, J=8.1 Hz, 1H), 7.40 (t, J=8.0 Hz, 3H), 7.19 (t, J=7.4 Hz, 1H), 7.08 (d, J=8.7 Hz, 2H), 6.92 (d, J=7.8 Hz, 1H). HRMS (ESI): calc. for [M+H]$^+$ (C$_{15}$H$_{10}$NOCl) 256.0529, found 256.0539.

Intermediate 9. 4-(3-((2-Chloro-3-methylquinolin-6-yl)oxy)propyl)morpholine (11u)

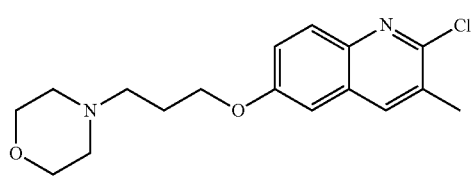 [SMILES: Cc1cc2cc(OCCCN3CCOCC3)ccc2nc1Cl]

Step 1. N-(4-Methoxyphenyl)propionamide (26)

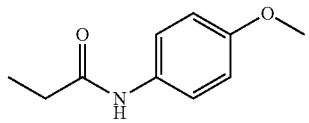

To a solution of p-methoxyaniline in anhydrous DCM (1 mL/mmol) and triethylamine (15 mmol) at 0° C., propionyl chloride (10 mmol) dissolved in anhydrous DCM (0.5 mL/mmol) is added dropwise. The reaction is warmed up to room temperature and stirred for 2 hours. Water (1.5 mL/mmol) is added and extracted with DCM. The organic phase is dried over Na$_2$SO$_4$ and the compound is used for the next step without further purification. Yield: 80%. $^1$H NMR (400 MHz, CDCl$_3$) δ 7.41 (d, J=8.8 Hz, 2H), 7.10 (s, 1H), 6.85 (d, J=8.9 Hz, 2H), 3.78 (s, 3H), 2.37 (q, J=7.5 Hz, 2H), 1.24 (t, J=7.5 Hz, 3H).

Step 2. 2-Chloro-6-methoxy-3-methylquinoline (27)

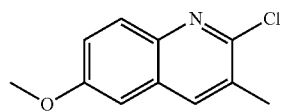

To a solution of POCl$_3$ (7 mmol) at 0 C, DMF (15 mmol) is added dropwise followed by the addition of 26 (10 mmol). The reaction is heated to 75° C. for 4 hours. The solvent is evaporated and poured into ice. The mixture is kept at 4° C. for 1 hour and filtered. The aqueous phase is neutralized with saturated NaHCO$_3$. After filtration, compound 27 is purified by flash chromatography using hexanes/EtOAc (9:1) as eluent. Yield: 52%. $^1$H NMR (400 MHz, CDCl$_3$) δ 7.89-7.85 (m, 1H), 7.40 (d, J=9.0 Hz, 1H), 7.31 (dd, J=9.3, 2.7 Hz, 1H), 7.01 (d, J=2.8 Hz, 1H), 3.92 (s, 3H), 2.52 (s, 3H).

Step 3. 2-Chloro-3-methylquinolin-6-ol (28)

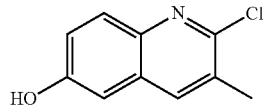

A mixture of 27 and 47% hydrobromic acid (2.5 mL/mmol) is heated at reflux overnight. After solvent evaporation, the mixture is neutralized with a solution of NH$_4$OH and extracted with EtOAc. Compound 28 is purified by flash chromatography using hexanes/EtOAc (6:4) as eluent. Yield: 48%. $^1$H NMR (400 MHz, CD$_3$OD) δ 8.03 (s, 1H), 7.76 (d, J=8.5 Hz, 1H), 7.30 (dt, J=9.3, 3.0 Hz, 1H), 7.11-7.09 (m, 1H), 2.52 (s, 3H).

Step 4. 4-(3-((2-Chloro-3-methylquinolin-6-yl)oxy)propyl)morpholine (11u)

To a solution of 28 (0.8 mmol) and K$_2$CO$_3$ (1.6 mmol) in anhydrous DMF (3 mL/mmol) under N$_2$, 19 is added. The mixture is stirred at 70° C. The reaction is diluted with EtOAc and washed twice with saturated NH$_4$Cl. The organic phase is dried over Na$_2$SO$_4$ and the compound is purified by flash chromatography with DCM/MeOH (8:2) as eluent. Yield: 60%. $^1$H NMR (400 MHz, CDCl$_3$) δ 7.88-7.82 (m, 1H), 7.47-7.43 (m, 1H), 7.28 (dt, J=9.2, 2.9 Hz, 1H), 6.99-6.98 (m, 1H), 4.11 (t, J=6.3 Hz, 2H), 3.72 (t, J=4.6 Hz, 4H), 2.56 (t, J=7.3 Hz, 2H), 2.52-2.37 (m, 7H), 2.03 (p, J=6.7 Hz, 2H).

Intermediate 10. 4-(2-(2-((2-Chloroquinolin-6-yl)oxy)ethoxy)ethyl)morpholine (11v)

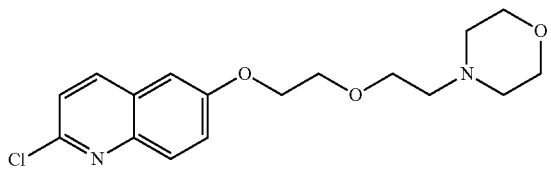 [SMILES: Clc1ccc2cc(OCCOCCN3CCOCC3)ccc2n1]

Step 1. 2-Chloro-6-(2-(2-chloroethoxy)ethoxy)quinoline (29)

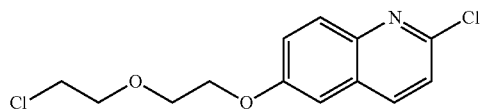 [SMILES: ClCCOCCOc1ccc2nc(Cl)ccc2c1]

To a solution of 2-chloroquinolin-6-ol (0.8 mmol) and K$_2$CO$_3$ (1.6 mmol) in anhydrous DMF (3 mL/mmol) under N₂, bis(2-chloroethyl ether (1.0 mmol) is added dropwise and the mixture is stirred at 70° C. The reaction is diluted with EtOAc and washed twice with saturated NH₄Cl. The organic phase is dried over Na₂SO₄ and the compound is purified by flash chromatography with hexanes/EtOAc (7:3) as eluent. Yield: 50%. ¹H NMR (400 MHz, CDCl₃) δ 7.97 (dd, J=8.6, 0.7 Hz, 1H), 7.90 (d, J=9.2 Hz, 1H), 7.40 (dd, J=9.2, 2.8 Hz, 1H), 7.33 (d, J=8.6 Hz, 1H), 7.09 (d, J=2.7 Hz, 1H), 4.25 (t, J=4.7 Hz, 2H), 3.974 (t, J=4.7 Hz, 2H), 3.85 (t, J=5.8 Hz, 2H), 3.67 (t, J=5.8 Hz, 2H).

Step 2. 4-(2-(2((2-Chloroquinolin-6-yl)oxy)ethoxy)ethyl)morpholine (11v)

A mixture of 29 (1 mmol), morpholine (1 mmol) and K₂CO₃ (1.5 mmol) in anhydrous acetonitrile (3 mL/mmol) is stirred at reflux overnight. After filtration, the solvent is evaporated and the product purified by flash chromatography using DCM/MeOH (9:1). Yield: 61%. ¹H NMR (400 MHz, CDCl₃) δ 7.97 (d, J=8.6 Hz, 1H), 7.90 (d, J=9.2 Hz, 1H), 7.39 (dd, J=9.2, 2.8 Hz, 1H), 7.33 (d, J=8.6 Hz, 1H), 7.07 (d, J=2.8 Hz, 1H), 4.23 (t, J=4.7 Hz, 2H), 3.86 (t, J=4.7 Hz, 2H), 3.80-3.67 (m, 6H), 2.65 (t, J=5.7 Hz, 2H), 2.61-2.46 (m, 4H).

Intermediates 11 & 12. 2-Bromo-5-(4-(2-methoxyethoxy)phenoxy)quinoline (11y) and 2-Bromo-5-(3-(2-methoxyethoxy)phenoxy)quinoline (11z)

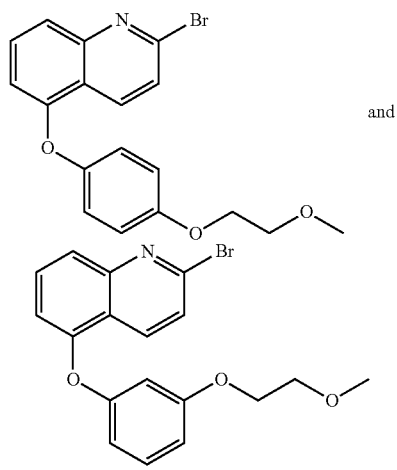

and

Step 1. 5-(4-Methoxyphenoxy)quinoline (30) & 5-(3-methoxyphenoxy)quinoline (31)

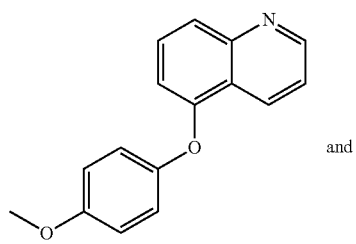

and

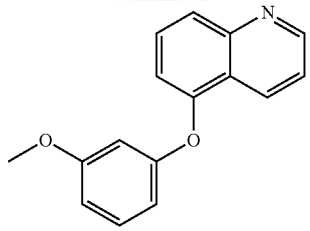

5-hydroxyquinoline (2.76 mmol) and corresponding bromo-methoxybenzene (3.03 mmol) were dissolved in DMSO (5 mL). Next, 2-pyridylacetone (0.54 mmol), CuBr (0.27 mmol) and Cs₂CO₃ (4.14 mmol) were added to the solution which was then stirred at 90° C. for 48 h. The reaction mixture was cooled to room temperature and purified by silica chromatography (Hexanes/EtOAC) to give the sub-title compound.

5-(4-Methoxyphenoxy)quinoline (30). Yield: 32%. ¹H NMR (400 MHz, CDCl₃) δ 8.97 (s, 1H), 8.66 (d, J=8.4 Hz, 1H), 7.80 (d, J=8.4 Hz, 1H), 7.58-7.52 (m, 1H), 7.44 (dd, J=8.4, 3.8 Hz, 1H), 7.05 (d, J=9.0 Hz, 2H), 6.93 (d, J=8.9 Hz, 2H), 6.80 (d, J=7.9 Hz, 1H), 3.83 (s, 3H).

5-(3-Methoxyphenoxy)quinoline (31). Yield: 45%. ¹H NMR (600 MHz, CDCl₃) δ 8.95 (s, 1H), 8.55 (d, J=8.4 Hz, 1H), 7.89 (d, J=8.5 Hz, 1H), 7.61 (t, J=8.1 Hz, 1H), 7.46-7.39 (m, 1H), 7.29-7.23 (m, 1H), 7.01 (d, J=7.6 Hz, 1H), 6.71 (d, J=8.7 Hz, 1H), 6.64 (s, 2H), 3.79 (s, 3H).

Step 2. 4-(Quinolin-5-yloxy)phenol (32) & 3-(quinolin-5-yloxy)phenol (33)

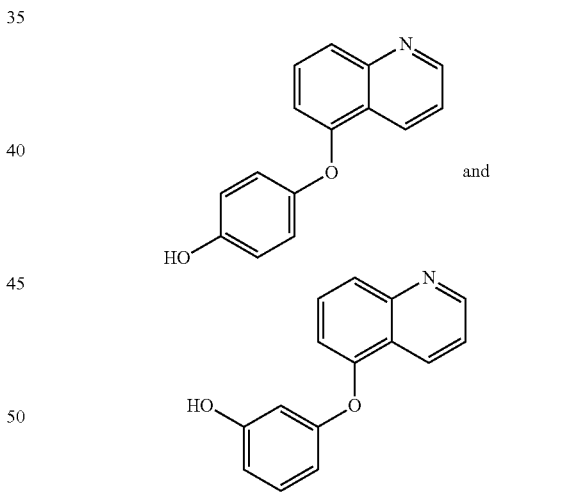

Compound 30 or 31 (0.88 mmol) was dissolved in dry DCM (15 mL) and BBr₃ (1M in DCM, 5.26 mmol) was added dropwise at −78° C. The solution was first stirred at −78° C. for 30 min and was next warmed to room temperature at which it was stirred for 4 h. After the completion the reaction mixture was quenched with MeOH, diluted with DCM (20 mL) and extracted with sat. NaHCO₃ and brine. The organic phase was dried with Na₂SO₄ and evaporated the crude product was purified by silica chromatography (Hexanes/EtOAc) to give the corresponding intermediate 32-33.

4-(Quinolin-5-yloxy)phenol (32). Yield: 96%. ¹H NMR (400 MHz, CD₃OD) δ 8.88 (d, J=4.2 Hz, 1H), 8.77 (d, J=8.4

Hz, 1H), 7.69 (d, J=8.5 Hz, 1H), 7.65-7.54 (m, 2H), 6.99 (d, J=8.9 Hz, 2H), 6.86 (d, J=8.9 Hz, 2H), 6.79 (d, J=7.7 Hz, 1H).

3-(Quinolin-5-yloxy)phenol (33). Yield: 98%. $^1$H NMR (400 MHz, CD$_3$OD) δ 8.89 (d, J=3.2 Hz, 1H), 8.65 (d, J=8.4 Hz, 1H), 7.79 (d, J=8.5 Hz, 1H), 7.69 (t, J=8.1 Hz, 1H), 7.56 (dd, J=8.5, 4.3 Hz, 1H), 7.23-7.16 (m, 1H), 7.02 (d, J=7.7 Hz, 1H), 6.61 (d, J=8.2 Hz, 1H), 6.53 (d, J=8.1 Hz, 1H), 6.49 (s, 1H).

Step 3. 5-(4-(2-Methoxyethoxy)phenoxy)quinoline (34) and 5-(3-(2-methoxyethoxy)phenoxy)quinoline (35)

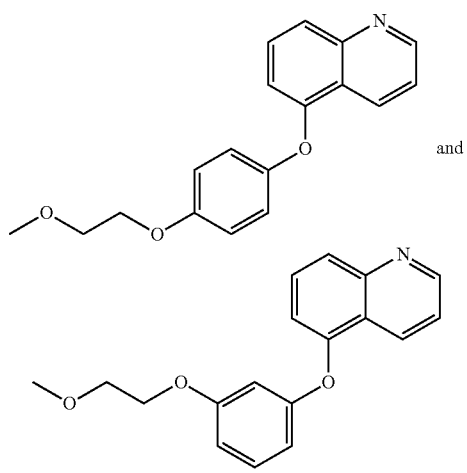

The sub-title compounds were prepared according to the procedure described for the General Method G.

5-(4-(2-Methoxyethoxy)phenoxy)quinoline (34). Yield: 52%. $^1$H NMR (600 MHz, CDCl$_3$) δ 8.97-8.93 (m, 1H), 8.65 (d, J=8.3 Hz, 1H), 7.80 (d, J=8.4 Hz, 1H), 7.55 (t, J=8.1 Hz, 1H), 7.43 (dd, J=8.4, 4.2 Hz, 1H), 7.04 (d, J=8.9 Hz, 2H), 6.96 (d, J=8.9 Hz, 2H), 6.80 (d, J=7.7 Hz, 1H), 4.15-4.10 (m, 2H), 3.79-3.75 (m, 2H), 3.47 (s, 3H).

5-(3-(2-Methoxyethoxy)phenoxy)quinoline (35). Yield: 61%. $^1$H NMR (600 MHz, CDCl$_3$) δ 8.95 (s, 1H), 8.53 (d, J=8.4 Hz, 1H), 7.88 (d, J=8.4 Hz, 1H), 7.61 (t, J=8.0 Hz, 1H), 7.41 (dd, J=7.6, 3.5 Hz, 1H), 7.24 (s, 1H), 7.01 (d, J=7.5 Hz, 1H), 6.72 (d, J=8.1 Hz, 1H), 6.68-6.61 (m, 2H), 4.10-4.07 (m, 2H), 3.72 (t, J=4.4 Hz, 2H), 3.43 (s, 3H).

Step 4. 5-(4-(2-Methoxyethoxy)phenoxy)-1-(λ$^1$-oxidanyl)-1λ$^4$-quinoline (36) and 5-(3-(2-methoxyethoxy)phenoxy)-1-(λ$^1$-oxidanyl)-1λ$^4$-quinoline (37)

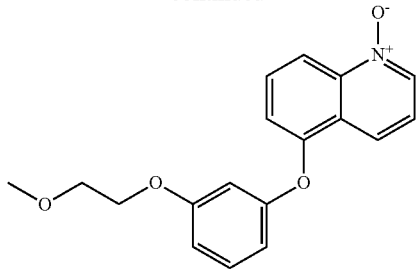

and

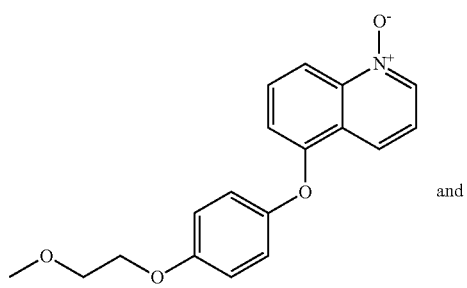

The sub-title compounds were prepared according to the procedure described for Intermediate 9, Step 2 (25).

5-(4-(2-Methoxyethoxy)phenoxy)-1-(2'-oxidanyl)-1λ$^4$-quinoline (36). Yield: 80%. $^1$H NMR (600 MHz, CD$_2$Cl$_2$) δ 8.50 (d, J=5.7 Hz, 1H), 8.31 (d, J=8.8 Hz, 1H), 8.20 (d, J=8.4 Hz, 1H), 7.58 (t, J=8.1 Hz, 1H), 7.34-7.29 (m, 1H), 7.07 (d, J=8.2 Hz, 2H), 6.97 (d, J=8.2 Hz, 2H), 6.86 (d, J=7.6 Hz, 1H), 4.11 (t, J=4.5 Hz, 2H), 3.73 (t, J=4.4 Hz, 2H), 3.42 (s, 3H).

5-(3-(2-Methoxyethoxy)phenoxy)-1-(2'-oxidanyl)-1λ$^4$-quinoline (37). Yield: (84%). $^1$H NMR (600 MHz, CD$_2$Cl$_2$) δ 8.49 (d, J=6.0 Hz, 1H), 8.39 (d, J=8.8 Hz, 1H), 8.08 (d, J=8.5 Hz, 1H), 7.63 (t, J=8.3 Hz, 1H), 7.30 (t, J=7.9 Hz, 2H), 7.06 (d, J=7.7 Hz, 1H), 6.76 (d, J=8.3 Hz, 1H), 6.67 (d, J=8.2 Hz, 1H), 6.65 (s, 1H), 4.09-4.05 (m, 2H), 3.71-3.68 (m, 2H), 3.38 (s, 3H).

Step 5. 2-bromo-5-(4-(2-methoxyethoxy)phenoxy)quinoline (11y) and 2-bromo-5-(3-(2-methoxyethoxy)phenoxy)quinoline (11z)

Compound 36 or 37 (0.35 mmol) was dissolved in dry DCM (35 mL) with molecular sieves 4 Å. Next (Bu)$_4$NBr (0.53 mmol) was added to the solution and after stirring for 10 min. p-toulenesulfonic anhydride (0.53 mmol). The reaction mixture is stirred for 48 h, filtered and purified by silica chromatography (Hexanes/EtOAc) to give the title compound.

2-Ethynyl-5-(4-(2-methoxyethoxy)phenoxy)quinoline (11y). Yield: 67%. $^1$H NMR (600 MHz, CDCl$_3$) δ 8.63 (d, J=8.6 Hz, 1H), 7.79 (d, J=8.5 Hz, 1H), 7.59-7.53 (m, 2H), 7.03 (d, J=8.9 Hz, 2H), 6.97 (s, 2H), 6.79 (d, J=7.7 Hz, 1H), 4.15-4.12 (m, 2H), 3.78-3.76 (m, 2H), 3.47 (s, 3H), 3.27 (s, 1H).

2-Ethynyl-5-(3-(2-methoxyethoxy)phenoxy)quinoline (11z). Yield: 80%. $^1$H NMR (400 MHz, CDCl$_3$) δ 8.55-8.49 (m, 1H), 7.86 (d, J=8.4 Hz, 1H), 7.62 (t, J=8.0 Hz, 1H), 7.55 (d, J=8.6 Hz, 1H), 7.25 (d, J=7.9 Hz, 3H), 7.00 (d, J=7.4 Hz, 1H), 6.74 (d, J=8.2 Hz, 1H), 6.69-6.59 (m, 2H), 4.09 (t, J=4.5 Hz, 2H), 3.73 (t, J=4.5 Hz, 2H), 3.43 (s, 3H), 3.27 (s, 1H).

Intermediate 13. 2-Chloro-1,8-naphthyridine (14)

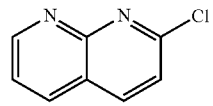 [SMILES: Clc1ccc2cccnc2n1]

Step 1. tert-Butyl 3-hydroxy-3-(2-pivalamidopyridin-3-yl)propanoate (38)

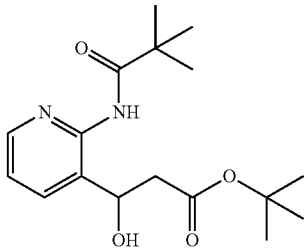 [SMILES: CC(C)(C)OC(=O)CC(O)c1cccnc1NC(=O)C(C)(C)C]

To an oven-dried 250 mL three necked round bottom flask, dry THF (30 mL) and DIPA (21.0 mmol) was added under $N_2$. The solution was cooled to −78° C., n-BuLi (2M in hexane, 21 mmol) was added and the mixture was stirred for 15 min. Next, tert-butyl acetate (21.0 mmol) was added dropwise and the solution was stirred for 20 min. N-(3-formylpyridin-2-yl)pivalamide (10.0 mmol) dissolved in 5 mL dry THF was added to the reaction mixture which was stirred for 40 min. Next, the solution was warmed up to room temperature and quenched with sat. $NH_4Cl$. The aqueous layer was separated and extracted with EtOAc (×3). The combined organic phase was washed with brine dried over $Na_2SO_4$ and evaporated. The residue was purified by silica chromatography to give the sub-title compound. Yield: 90%. $^1$H NMR (500 MHz, CDCl$_3$) δ 8.71 (s, 1H), 8.37 (s, 1H), 7.70 (d, J=7.3 Hz, 1H), 7.18-7.07 (m, 1H), 5.05 (dd, J=8.2, 5.6 Hz, 1H), 4.39 (s, 1H), 2.88-2.79 (m, 1H), 2.67 (d, J=16.1 Hz, 1H), 1.38 (s, 10H), 1.33 (s, 10H). HRMS (ESI): calc. for [M+H]$^+$ (C$_{17}$H$_{26}$N$_2$O$_4$) 323.1971, found 323.1983.

Step 2. 1,8-Naphthyridin-2(1H)-one (39)

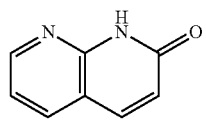 [SMILES: O=c1ccc2cccnc2[nH]1]

A mixture of tert-butyl 3-hydroxy-3-(2-pivalamidopyridin-3-yl)propanoate (30, 7.21 mmol) and 3N HCl was refluxed for 6 h. The solution was then cooled to room temperature, diluted with water/DCM and neutralized with $K_2CO_3$. The aqueous phase was separated and washed with DCM. The organic phase were combined, washed with brine and dried with $Na_2SO_4$ to give 31 (81%) without further purification. $^1$H NMR (400 MHz, CDCl$_3$) δ 11.62 (s, 1H), 8.69 (dd, J=4.8, 1.7 Hz, 1H), 7.91 (dd, J=7.7, 1.7 Hz, 1H), 7.72 (d, J=9.5 Hz, 1H), 7.22 (dd, J=7.7, 4.8 Hz, 1H), 6.75 (d, J=9.5 Hz, 1H).

Step 3. 2-Chloro-1,8-naphthyridine (14)

A mixture of 31 (5.78 mmol) in POCl$_3$ (88 mmol) was heated at 110° C. for 90 min. The solution was cooled to room temperature, poured into water/DCM mixture and neutralized with NH$_4$OH solution. The aqueous phase was separated and washed with DCM. The organic phase was dried with Na$_2$SO$_4$ and evaporated to give the title compound (75%) which was used in the next step without further purification. $^1$H NMR (500 MHz, DMSO-d$_6$) δ 9.16 (s, 1H), 8.64 (d, J=8.1 Hz, 1H), 8.52 (d, J=8.5 Hz, 1H), 7.83-7.77 (m, 1H), 7.71 (d, J=8.5 Hz, 1H). HRMS (ESI): calc. for [M+H]$^+$ (C$_8$H$_5$N$_2$Cl, 165.0220, found 165.0226.

Intermediates 14-29 (12b-z and 15) resulted from the SN in the position 2 of the corresponding quinoline (11b-z) or naphthyridine (14), respectively with trimethylsilyl acetylene according to General Method D, while for 12a General Method E was used. 8-(4-methoxyphenyl)-2-((trimethylsilyl)ethynyl)quinoline (12q) has not been isolated and was directly deptrotected.

Intermediate 14. 2-Methyl-4-(quinolin-2-yl)but-3-yn-2-ol (12a)

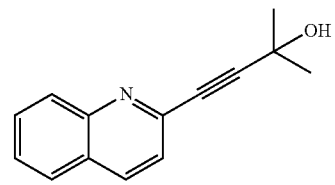 [SMILES: CC(C)(O)C#Cc1ccc2ccccc2n1]

Yield: (60%). 1H NMR (400 MHz, CDCl$_3$) δ 8.07 (dd, J=8.5, 4.4 Hz, 2H), 7.83-7.60 (m, 2H), 7.50 (dq, J=8.5, 4.3 Hz, 2H), 2.30 (s, 1H), 1.80 (s, 6H).

Intermediate 15. 6-(2-Methoxyethoxy)-2-((trimethylsilyl)ethynyl)quinoline (12b)

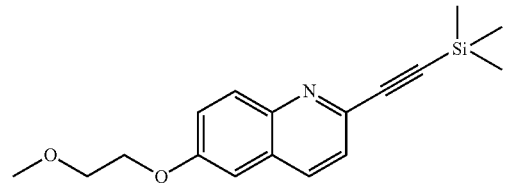

Yield: (70%) 7.98 (dd, J=13.7, 8.9 Hz, 2H), 7.48 (d, J=8.4 Hz, 1H), 7.41 (dd, J=9.2, 2.7 Hz, 1H), 7.04 (d, J=2.7 Hz, 1H), 4.26-4.20 (m, 2H), 3.84-3.79 (m, 2H), 3.47 (s, 3H), 0.29 (s, 9H).

Intermediate 16. 2-(2-((2-(Trimethylsilyl)ethynyl)quinolin-6-yl)oxy)ethoxy)-N-tritylethan-1-amine (12c)

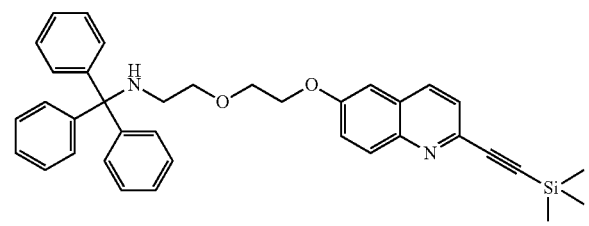 [SMILES: C[Si](C)(C)C#Cc1ccc2cc(OCCOCCNC(c3ccccc3)(c3ccccc3)c3ccccc3)ccc2n1]

Yield: (75%). $^1$H NMR (400 MHz, CDCl$_3$) δ 7.99-7.90 (m, 2H), 7.50-7.41 (m, 6H), 7.32-7.11 (m, 11H), 7.01 (s, 1H), 4.20 (t, J=4.7 Hz, 2H), 3.78 (t, J=4.7 Hz, 2H), 3.69 (t, J=5.1 Hz, 2H), 2.38 (t, J=5.2 Hz, 2H), 0.29 (s, 9H).

Intermediate 17.
3-Methyl-2-((trimethylsilyl)ethynyl)quinoline (12l)

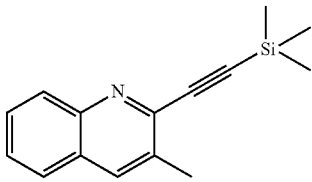 [SMILES: Cc1cc2ccccc2nc1C#C[Si](C)(C)C]

Yield: (63%). ¹H NMR (500 MHz, CDCl₃) δ 8.06 (d, J=8.5 Hz, 1H), 7.92 (s, 1H), 7.69 (d, J=8.1 Hz, 1H), 7.65-7.61 (m, 1H), 7.51-7.46 (m, 1H), 2.58 (s, 3H), 0.31 (d, J=0.7 Hz, 9H).

Intermediate 18.
4-Methyl-2-((trimethylsilyl)ethynyl)quinoline (12m)

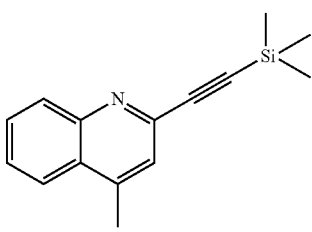 [SMILES: Cc1cc(C#C[Si](C)(C)C)nc2ccccc12]

Yield: (59%). ¹H NMR (500 MHz, CDCl₃) δ 8.09 (d, J=8.3 Hz, 1H), 7.93 (d, J=8.0 Hz, 1H), 7.69 (t, J=7.0 Hz, 1H), 7.54 (t, J=7.5 Hz, 1H), 7.39 (s, 1H), 2.66 (s, 3H), 0.30 (s, 9H).

Intermediate 19.
8-Chloro-2-((trimethylsilyl)ethynyl)quinoline (12n)

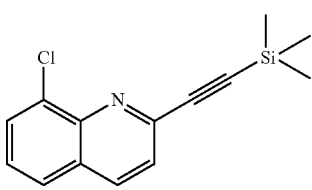 [SMILES: C[Si](C)(C)C#Cc1ccc2cccc(Cl)c2n1]

Yield: (63%). ¹H NMR (600 MHz, CDCl₃) δ 8.12 (d, J=8.4 Hz, 1H), 7.84 (d, J=7.4 Hz, 1H), 7.71 (d, J=8.1 Hz, 1H), 7.59 (d, J=8.4 Hz, 1H), 7.46 (t, J=7.8 Hz, 1H), 0.31 (s, 9H). HRMS (ESI): calc. For [M+H]⁺ (C₁₄H₁₄NsiCl) 260.0662, found 260.0654.

Intermediate 20.
8-Methoxy-2-((trimethylsilyl)ethynyl)quinoline (12o)

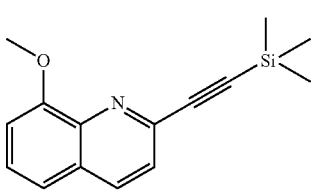 [SMILES: COc1cccc2ccc(C#C[Si](C)(C)C)nc12]

Yield: (64%). ¹H NMR (600 MHz, CDCl₃) δ 8.06 (d, J=8.4 Hz, 1H), 7.55 (d, J=8.4 Hz, 1H), 7.45 (t, J=7.9 Hz, 1H), 7.34 (d, J=8.2 Hz, 1H), 7.04 (d, J=7.7 Hz, 1H), 4.06 (s, 3H), 0.27 (s, 9H). HRMS (ESI): calc. for [M+H]⁺ (C₁₅H₁₇NOSi) 256.1158, found 256.1156.

Intermediate 21. 8-(2-Methoxyethoxy)-2-((trimethylsilyl)ethynyl)quinoline (12p)

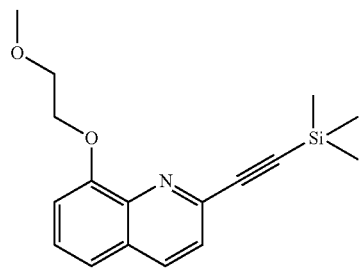 [SMILES: COCCOc1cccc2ccc(C#C[Si](C)(C)C)nc12]

Yield: (68%). ¹H NMR (600 MHz, CDCl₃) δ 8.05 (d, J=8.4 Hz, 1H), 7.53 (d, J=8.4 Hz, 1H), 7.44 (t, J=7.9 Hz, 1H), 7.35 (d, J=8.2 Hz, 1H), 7.13 (d, J=7.7 Hz, 1H), 4.40 (t, J=4.9 Hz, 2H), 3.95 (t, J=4.8 Hz, 2H), 3.48 (s, 3H), 0.28 (s, 9H). HRMS (ESI): calc. For [M+H]⁺ (C₁₇H₂₁NO₂Si) 300.1420, found 300.1421.

Intermediate 22.
8-Phenoxy-2-((trimethylsilyl)ethynyl)quinoline (12r)

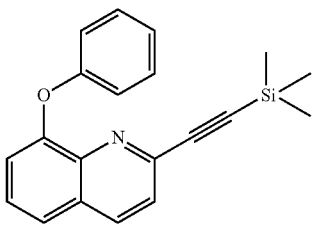 [SMILES: C[Si](C)(C)C#Cc1ccc2cccc(Oc3ccccc3)c2n1]

Yield: (49%). ¹H NMR (400 MHz, CDCl₃) δ 8.18 (d, J=8.5 Hz, 1H), 7.62 (d, J=8.5 Hz, 1H), 7.49 (d, J=8.1 Hz, 1H), 7.39 (t, J=8.0 Hz, 3H), 7.21-7.13 (m, 3H), 6.98 (d, J=7.7 Hz, 1H), 0.25 (s, 9H).

Intermediate 23.
5-Phenoxy-2-((trimethylsilyl)ethynyl)quinoline (12s)

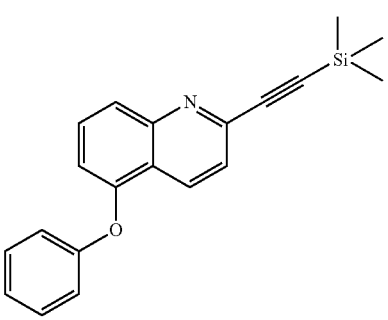 [SMILES: C[Si](C)(C)C#Cc1ccc2c(Oc3ccccc3)cccc2n1]

Yield: (68%). $^1$H NMR (500 MHz, CDCl$_3$) δ 8.76 (s, 1H), 8.15 (s, 1H), 7.66 (dt, J=14.7, 7.2 Hz, 2H), 7.47-7.41 (m, 2H), 7.25-7.19 (m, 1H), 7.10 (d, J=7.9 Hz, 2H), 6.95 (d, J=7.8 Hz, 1H), 0.35 (s, 9H).

Intermediate 24. 4-(3-((2-((Trimethylsilyl)ethynyl)quinolin-6-yl)oxy)propyl)morpholine (12t)

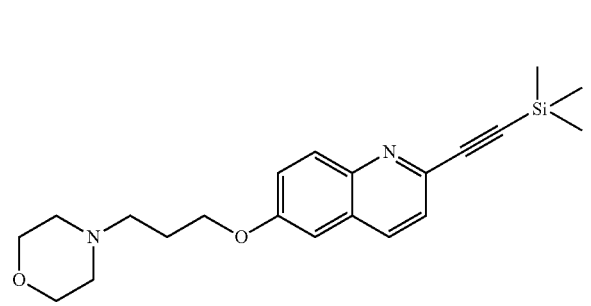 [SMILES: C[Si](C)(C)C#Cc1ccc2cc(OCCCN3CCOCC3)ccc2n1]

Yield: (54%). $^1$H NMR (400 MHz, CDCl$_3$) δ 8.00-7.91 (m, 2H), 7.46 (d, J=8.5 Hz, 1H), 7.33 (dd, J=9.2, 2.8 Hz, 1H), 7.01 (d, J=2.7 Hz, 1H), 4.12 (t, J=6.3 Hz, 2H), 3.77-3.65 (m, 4H), 2.54 (t, J=7.3 Hz, 2H), 2.47 (t, J=4.7 Hz, 4H), 2.09-1.97 (m, 2H), 0.27 (d, J=0.7 Hz, 9H).

Intermediate 25. 4-(3-(3-Methyl-2-((trimethylsilyl)ethynyl)quinolin-6-yl)oxy)propyl)morpholine (12u)

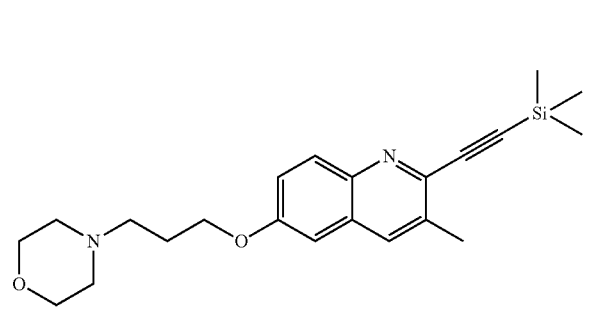 [SMILES: Cc1cc2cc(OCCCN3CCOCC3)ccc2nc1C#C[Si](C)(C)C]

Yield: (61%). $^1$H NMR (400 MHz, CDCl$_3$) δ 7.93 (d, J=9.2 Hz, 1H), 7.79 (s, 1H), 7.29-7.24 (m, 1H), 6.94 (d, J=2.7 Hz, 1H), 4.11 (t, J=6.7 Hz, 2H), 3.72 (t, J=4.5 Hz, 4H), 2.61-2.41 (m, 7H), (p, J=6.8 Hz, 2H), 0.29 (s, 9H).

Intermediate 26. 4-(2-(2-((2-((Trimethylsilyl)ethynyl)quinolin-6-yl)oxy)ethoxy)ethyl)morpholine (12v)

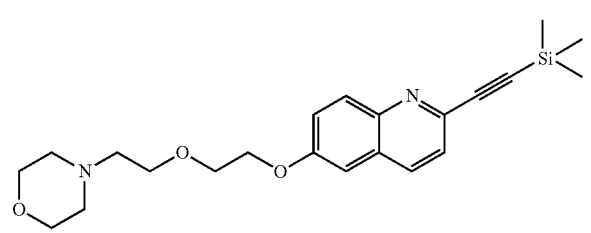 [SMILES: C[Si](C)(C)C#Cc1ccc2cc(OCCOCCN3CCOCC3)ccc2n1]

Yield: (70%). $^1$H NMR (400 MHz, CDCl$_3$) δ 8.02-7.92 (m, 2H), 7.48 (d, J=8.4 Hz, 1H), 7.37 (dd, J=9.1, 2.7 Hz, 1H), 7.03 (d, J=2.8 Hz, 1H), 4.26-4.21 (m, 2H), 3.91-3.85 (m, 2H), 3.69-3.73 (m, 6H), 2.62 (t, J=5.6 Hz, 2H), 2.50-2.52 (m, 4H), 0.29 (s, 9H).

Intermediate 27. 5-(4-(2-Methoxyethoxy)phenoxy)-2-((trimethylsilyl)ethynyl)quinoline (12y)

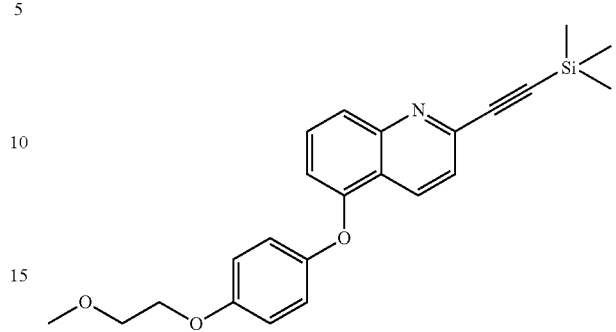

Yield: (46%). $^1$H NMR (600 MHz, CDCl$_3$) δ 8.59 (d, J=8.6 Hz, 1H), 7.78 (d, J=8.5 Hz, 1H), 7.57-7.51 (m, 2H), 7.03 (d, J=8.7 Hz, 2H), 6.96 (d, J=8.7 Hz, 2H), 6.77 (d, J=7.7 Hz, 1H), 4.15-4.12 (m, 2H), 3.79-3.75 (m, 2H), 3.47 (s, 3H), 0.31 (s, 9H).

Intermediate 28. 5-(3-(2-Methoxyethoxy)phenoxy)-2-((trimethylsilyl)ethynyl)quinoline (12z)

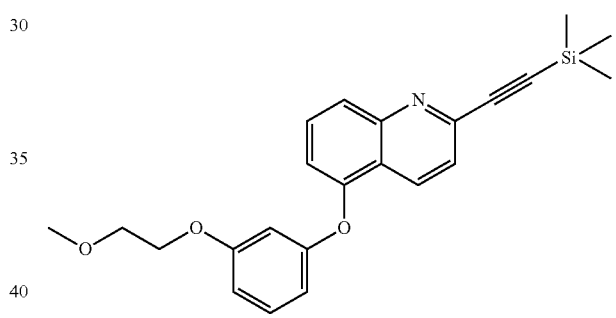

Yield: (82%). $^1$H NMR (400 MHz, CDCl$_3$) δ 8.48 (d, J=8.6 Hz, 1H), 7.86 (d, J=8.5 Hz, 1H), 7.59 (t, J=8.1 Hz, 1H), 7.53 (d, J=8.6 Hz, 1H), 7.25 (d, J=10.2 Hz, 1H), 6.97 (d, J=7.7 Hz, 1H), 6.73 (d, J=7.3 Hz, 1H), 6.64 (d, J=7.7 Hz, 2H), 4.10-4.06 (m, 2H), 3.75-3.71 (m, 2H), 3.43 (s, 3H), 0.31 (s, 9H).

Intermediate 29. 2-((Trimethylsilyl)ethynyl)-1,8-naphthyridine (15)

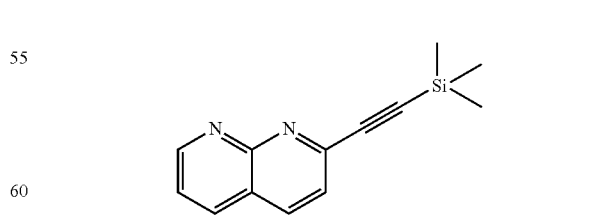

Yield: 47%. $^1$H NMR (500 MHz, CDCl$_3$) δ 9.13 (dd, J=4.1, 1.9 Hz, 1H), 8.18-8.10 (m, 2H), 7.59 (d, J=8.3 Hz, 1H), 7.46 (dd, J=8.1, 4.2 Hz, 1H), 0.30 (s, 9H). HRMS (ESI): calc. For [M+H]$^+$ (C$_{13}$H$_{14}$N$_2$Si) 227.1004, found 227.1000.

Intermediates 30-46 (13b-z and 16) resulted from the deprotection of the TMS group according to General Method F, while 13a has been deprotected according to General Method E.

Intermediate 30. 2-Ethynylquinoline (13a)

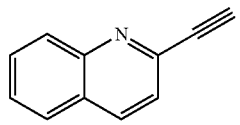

Yield: (74%). $^1$H NMR (400 MHz, CDCl$_3$) δ 8.07 (dd, J=8.5, 4.4 Hz, 2H), 7.83-7.60 (m, 2H), 7.50 (dq, J=8.5, 4.3 Hz, 2H), 3.24 (s, 1H).

Intermediate 31. 2-Ethynyl-6-(2-methoxyethoxy)quinoline (13b)

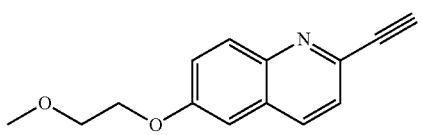 [SMILES: C#Cc1ccc2cc(OCCOC)ccc2n1]

Yield: (94%). $^1$H NMR (400 MHz, CDCl$_3$) δ 7.98 (d, J=8.8 Hz, 2H), 7.48 (d, J=8.4 Hz, 1H), 7.42 (dd, J=9.3, 2.7 Hz, 1H), 7.04 (d, J=2.8 Hz, 1H), 4.25-4.21 (m, 2H), 3.81 (dd, J=5.4, 3.9 Hz, 2H), 3.47 (s, 3H), 3.20 (s, 1H). HRMS (ESI): calcd for [M+H]$^+$ (C$_{14}$H$_{13}$NO$_2$) 228.1024, found 228.0992.

Intermediate 32. 2-(2-((2-Ethynylquinolin-6-yl)oxy)ethoxy)-N-tritylethan-1-amine (13c)

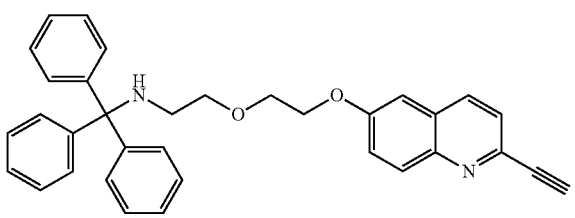 [SMILES: C#Cc1ccc2cc(OCCOCCNC(c3ccccc3)(c3ccccc3)c3ccccc3)ccc2n1]

Yield: (92%). $^1$H NMR (400 MHz, CDCl$_3$) δ 7.95 (d, J=2.2 Hz, 1H), 7.92 (d, J=3.1 Hz, 1H), 7.47-7.42 (m, 6H), 7.28 (dd, J=9.2, 2.8 Hz, 1H), 7.26-7.19 (m, 10H), 7.19-7.11 (m, 3H), 7.01 (d, J=2.8 Hz, 1H), 4.19 (t, J=4.7 Hz, 2H), 3.77 (t, J=4.7 Hz, 2H), 3.68 (t, J=5.3 Hz, 2H), 3.19 (s, 1H), 2.37 (t, J=5.3 Hz, 2H).

Intermediate 33. 2-Ethynyl-3-methylquinoline (13l)

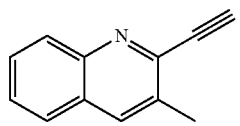

Yield: (89%). $^1$H NMR (500 MHz, CDCl$_3$) δ 8.06 (d, J=8.5 Hz, 1H), 7.95 (s, 1H), 7.71 (d, J=8.1 Hz, 1H), 7.67-7.64 (m, 1H), 7.54-7.49 (m, 1H), 3.42 (s, 1H), 2.60 (s, 3H). HRMS (ESI): calc. For [M+H]$^+$ (C$_{12}$H$_9$N) 168.0813, found 168.765.

Intermediate 34. 2-ethynyl-4-methylquinoline (13m)

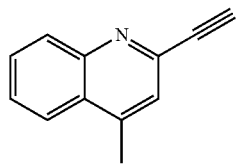

Yield: (87%). $^1$H NMR (500 MHz, CDCl$_3$) δ 8.10 (d, J=8.5 Hz, 1H), 7.99-7.95 (m, 1H), 7.72 (ddd, J=8.4, 6.9, 1.3 Hz, 1H), 7.58 (ddd, J=8.2, 6.9, 1.2 Hz, 1H), 7.40 (s, 1H), 3.21 (s, 1H), 2.69 (s, 3H). HRMS (ESI): calc. for [M+H]$^+$ (C$_{12}$H$_9$N) 168.0813, found 168.0759.

Intermediate 35. 8-chloro-2-ethynylquinoline (13n)

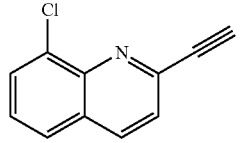

Yield: (94%). $^1$H NMR (400 MHz, CDCl$_3$) δ 8.15 (d, J=8.4 Hz, 1H), 7.85 (d, J=7.5 Hz, 1H), 7.73 (d, J=8.1 Hz, 1H), 7.60 (d, J=8.4 Hz, 1H), 7.47 (t, J=7.8 Hz, 1H), 3.29 (s, 1H). HRMS (ESI): calc. For [M+H]$^+$ (C$_{11}$H$_6$NCl) 188.0267, found 188.0262.

Intermediate 36. 2-Ethynyl-8-methoxyquinoline (13o)

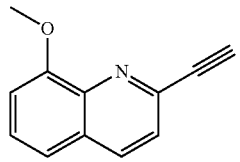

Yield: (86%). $^1$H NMR (600 MHz, CDCl$_3$) δ 8.09 (d, J=7.2 Hz, 1H), 7.56 (d, J=8.4 Hz, 1H), 7.48 (t, J=7.9 Hz, 1H), 7.36 (d, J=8.2 Hz, 1H), 7.06 (d, J=7.7 Hz, 1H), 4.08 (s, 3H), 3.20 (s, 1H). HRMS (ESI): calc. for [M+H]$^+$ (C$_{12}$H$_9$NO) 184.0762, found 184.0759.

Intermediate 37. 2-Ethynyl-8-(2-methoxyethoxy)quinoline (13p)

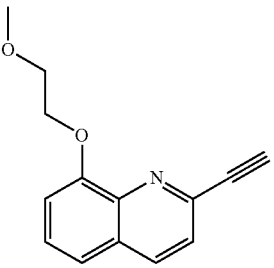 [SMILES: C#Cc1ccc2cccc(OCCOC)c2n1]

Yield: (96%). ¹H NMR (600 MHz, CDCl₃) δ 8.08 (d, J=8.4 Hz, 1H), 7.54 (d, J=8.4 Hz, 1H), 7.46 (t, J=8.0 Hz, 1H), 7.37 (d, J=9.1 Hz, 1H), 7.14 (d, J=8.4 Hz, 1H), 4.43-4.39 (m, 2H), 3.96-3.93 (m, 2H), 3.49 (s, 3H), 3.20 (s, 1H). HRMS (ESI): calc. For [M+H]⁺ ($C_{14}H_{13}NO_2$) 228.1024, found 228.1022.

Intermediate 38.
2-Ethynyl-8-(4-methoxyphenyl)quinoline (13q)

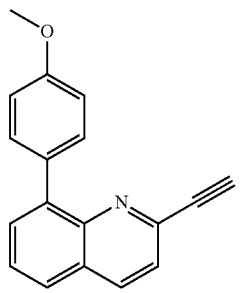 [SMILES: C#Cc1ccc2cccc(-c3ccc(OC)cc3)c2n1]

Yield: (92%). ¹H NMR (400 MHz, CDCl₃) δ 8.18-8.13 (m, 1H), 7.74 (dd, J=13.6, 8.0 Hz, 4H), 7.63-7.53 (m, 2H), 7.04 (d, J=7.3 Hz, 2H), 3.89 (s, 3H), 3.16 (s, 1H). HRMS (ESI): calc. for [M+H]⁺ ($C_{18}H_{13}NO$) 260.1064, found 260.1075.

Intermediate 39. 2-Ethynyl-8-phenoxyquinoline (13r)

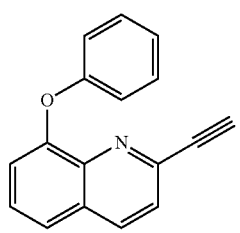 [SMILES: C#Cc1ccc2cccc(Oc3ccccc3)c2n1]

Yield: (94%). ¹H NMR (500 MHz, CDCl₃) δ 8.16 (d, J=8.5 Hz, 1H), 7.61 (d, J=8.5 Hz, 1H), 7.49 (d, J=8.1 Hz, 1H), 7.40 (t, J=8.7 Hz, 3H), 7.21-7.15 (m, 3H), 6.99 (dd, J=7.8, 1.5 Hz, 1H), 3.22 (s, 1H). HRMS (ESI): calc. for [M+H]⁺ ($C_{17}H_{11}NO$) 246.0919, found 246.0911.

Intermediate 40. 2-Ethynyl-5-phenoxyquinoline (13s)

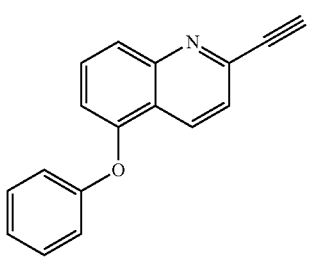 [SMILES: C#Cc1ccc2c(Oc3ccccc3)cccc2n1]

Yield: (90%). ¹H NMR (400 MHz, CDCl₃) δ 8.59 (d, J=8.5 Hz, 1H), 7.89 (d, J=8.5 Hz, 1H), 7.65-7.54 (m, 2H), 7.39 (t, J=7.2 Hz, 2H), 7.18 (t, J=7.4 Hz, 1H), 7.07 (d, J=8.0 Hz, 2H), 6.95 (d, J=7.7 Hz, 1H), 3.32 (s, 1H). HRMS (ESI): calc. for [M+H]⁺ ($C_{17}H_{11}NO$) 246.0919, found 246.0910.

Intermediate 41. 4-(3-((2-Ethynylquinolin-6-yl)oxy)propyl)morpholine (13t)

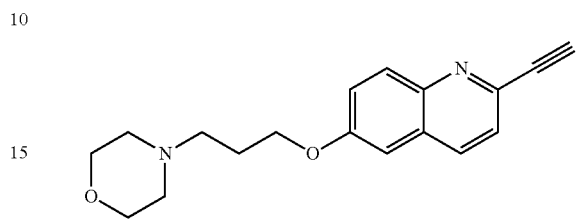

Yield: (91%). ¹H NMR (400 MHz, CDCl₃) δ 8.00-7.96 (m, 2H), 7.49 (d, J=8.5 Hz, 1H), 7.36 (dd, J=9.3, 2.9 Hz, 1H), 7.05 (t, J=3.2 Hz, 1H), 4.14 (t, J=6.1 Hz, 2H), 3.73 (t, J=4.8 Hz, 4H), 3.20 (s, 1H), 2.57 (t, J=6.9 Hz, 2H), 2.49 (s, 4H), 2.12-1.98 (m, 2H).

Intermediate 42. 4-(3-((2-Ethynyl-3-methylquinolin-6-yl)oxy)propyl)morpholine (13u)

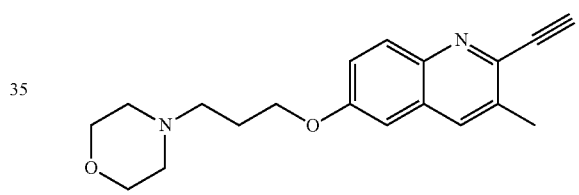

Yield: (88%). ¹H NMR (400 MHz, CDCl₃) δ 7.92 (d, J=9.2 Hz, 1H), 7.80 (s, 1H), 7.27 (dd, J=9.2, 2.8 Hz, 1H), 6.96 (d, J=2.7 Hz, 1H), 4.12 (t, J=6.4 Hz, 2H), 3.72 (t, J=4.6 Hz, 4H), 3.36 (s, 1H), 2.60-2.42 (m, 7H), 2.02 (p, J=6.7 Hz, 2H).

Intermediate 43. 4-(2-(2-((2-Ethynylquinolin-6-yl)oxy)ethoxy)ethyl)morpholine (13v)

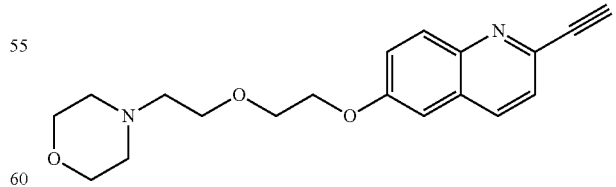

Yield: (94%). ¹H NMR (400 MHz, CDCl₃) δ 8.00 (d, J=2.4 Hz, 1H), 7.98 (d, J=3.2 Hz, 1H), 7.49 (d, J=8.5 Hz, 1H), 7.39 (dd, J=9.3, 2.8 Hz, 1H), 7.05 (d, J=2.7 Hz, 1H), 4.24 (t, J=4.7 Hz, 2H), 3.89 (t, J=4.7 Hz, 2H), 3.74-3.69 (m, 6H), 3.20 (s, 1H), 2.62 (t, J=5.7 Hz, 2H), 2.52-2.50 (m, 4H).

Intermediate 44. 2-Ethynyl-5-(4-(2-methoxyethoxy)phenoxy)quinoline (13y)

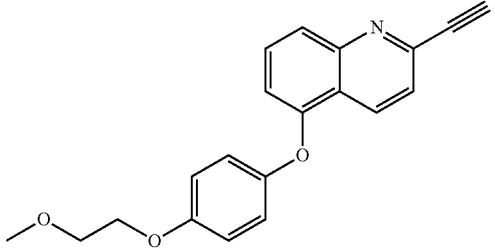 [SMILES: C#Cc1ccc2c(Oc3ccc(OCCOC)cc3)cccc2n1]

Yield: (67%). ¹H NMR (600 MHz, CDCl₃) δ 8.63 (d, J=8.6 Hz, 1H), 7.79 (d, J=8.5 Hz, 1H), 7.59-7.53 (m, 2H), 7.03 (d, J=8.9 Hz, 2H), 6.97 (s, 2H), 6.79 (d, J=7.7 Hz, 1H), 4.15-4.12 (m, 2H), 3.78-3.76 (m, 2H), 3.47 (s, 3H), 3.27 (s, 1H).

Intermediate 45. 2-Ethynyl-5-(3-(2-methoxyethoxy)phenoxy)quinoline (13z)

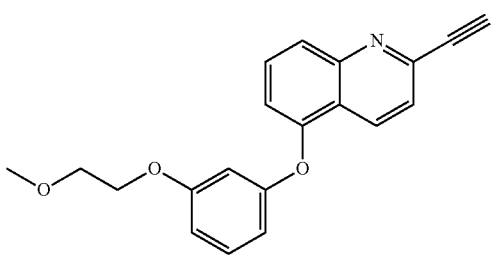 [SMILES: C#Cc1ccc2c(Oc3cccc(OCCOC)c3)cccc2n1]

Yield: (80%). ¹H NMR (400 MHz, CDCl₃) δ 8.55-8.49 (m, 1H), 7.86 (d, J=8.4 Hz, 1H), 7.62 (t, J=8.0 Hz, 1H), 7.55 (d, J=8.6 Hz, 1H), 7.25 (d, J=7.9 Hz, 3H), 7.00 (d, J=7.4 Hz, 1H), 6.74 (d, J=8.2 Hz, 1H), 6.69-6.59 (m, 2H), 4.09 (t, J=4.5 Hz, 2H), 3.73 (t, J=4.5 Hz, 2H), 3.43 (s, 3H), 3.27 (s, 1H).

Intermediate 46. 2-Ethynyl-1,8-naphthyridine (16)

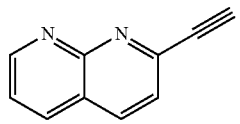

Yield: (93%). ¹H NMR (500 MHz, CD₃OD) δ 9.09 (dd, J=4.3, 1.9 Hz, 1H), 8.45 (dd, J=8.3, 2.6 Hz, 2H), 7.75 (d, J=8.3 Hz, 1H), 7.65 (dd, J=8.2, 4.3 Hz, 1H), 4.02 (s, 1H). HRMS (ESI): calc. For [M+H]⁺ (C₁₀H₆N₂) 155.0609, found 155.0620.

Intermediate 47. 2-(2-Bromoethoxy)-N-tritylethan-1-amine (18)

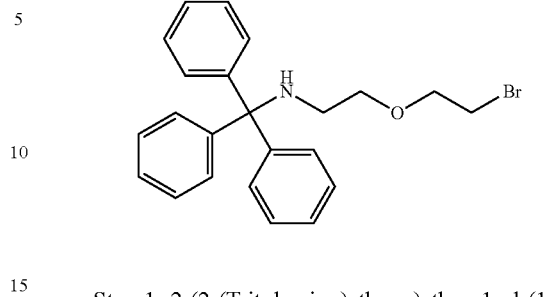

Step 1. 2-(2-(Tritylamino)ethoxy)ethan-1-ol (17)

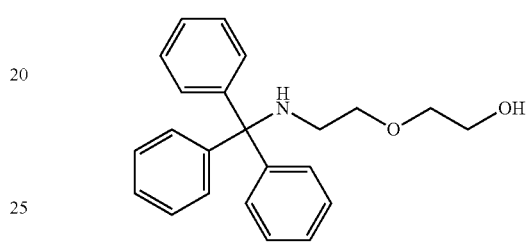

To a solution of 2-(2-aminoethoxy)ethanol (10 mmol) in anhydrous DCM (5 mL/mmol) under N₂, Et₃N (10 mmol) at 0° C. is added dropwise. After 20 min, a solution of trityl chloride (10 mmol) in anhydrous DCM (2 mL/mmol) is added during 15 min. The mixture is stirred at room temperature and monitoring by TLC. The reaction is washed with water and extracted with DCM. The organic phase is dried over Na₂SO₄ and 2-(2-(tritylamino)ethoxy)ethan-1-ol (17) is purified by flash chromatography with hexanes/EtOAc (9:1) as eluent. Yield: 90%. ¹H NMR (400 MHz, CDCl₃) δ 7.51-7.44 (m, 6H), 7.31-7.23 (m, 6H), 7.22-7.15 (m, 3H), 3.70 (t, J=4.6 Hz, 2H), 3.62 (t, J=5.3 Hz, 2H), 3.49 (t, J=4.6 Hz, 2H), 2.36 (t, J=5.3 Hz, 2H).

Step 2. 2-(2-Bromoethoxy)-N-tritylethan-1-amine

To a solution of 17 (9 mmol) in anhydrous DCM (5 mL/mmol) at −18 C, carbon tetrabromide (9 mmol) is added portionwise. The mixture is stirred for 15 min at −18° C. and then, PPh₃ (9 mmol eq) is added portionwise and the mixture stirred for 1 h. The reaction is washed with water and extracted with DCM. Organic layers are dried over Na₂SO₄ and the compound 18 was purified by flash chromatography with hexanes/DCM (9:1). Yield: 61%. ¹H NMR (400 MHz, CDCl₃) δ 7.51-7.43 (m, 6H), 7.31-7.25 (m, 6H), 7.21-7.13 (m, 3H), 3.67 (t, J=6.1 Hz, 2H), 3.61 (t, J=5.2 Hz, 2H), 3.42 (t, J=6.1 Hz, 2H), 2.35 (t, J=5.3 Hz, 2H).

Intermediate 48. 4-(3-Bromopropyl)morpholine (19)

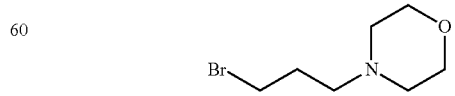

The title compound was synthesized according to the procedure described for Intermediate 47 (18). Yield: 50%. ¹H NMR (400 MHz, CDCl₃) δ 3.75-3.62 (m, 4H), 3.45 (t, J=6.6 Hz, 2H), 2.51-2.34 (m, 6H), 2.00 (p, J=6.8 Hz, 2H).

Intermediates 49 and 50. Methyl 4-((2-((trimethylsilyl)ethynyl)quinolin-5-yl)oxy)benzoate (12aa') and Methyl 3-((2-((trimethylsilyl)ethynyl)quinolin-5-yl)oxy)benzoate (12bb')

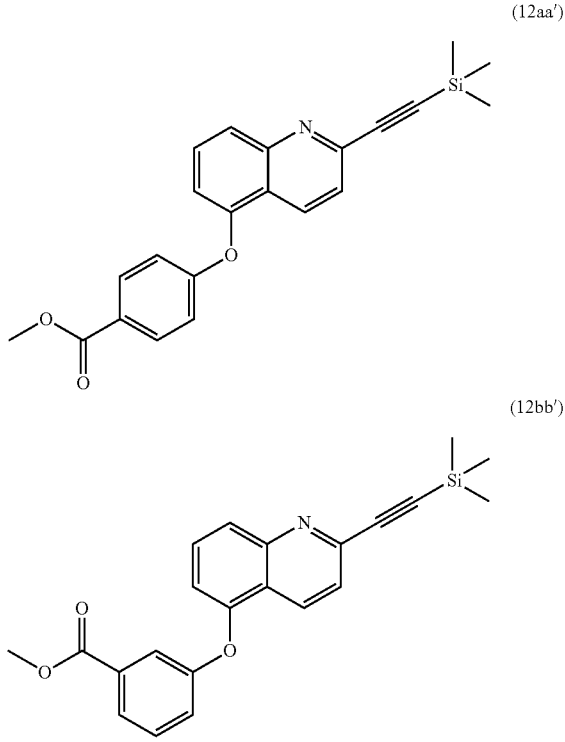

Intermediates 12aa' and 12bb' were prepared according to the procedure described for General Method D.

Methyl 4-((2-((trimethylsilyl)ethynyl)quinolin-5-yl)oxy)benzoate (12aa') (Yield: 84%) $^1$H NMR (600 MHz, CDCl$_3$) δ 8.37 (d, J=8.6 Hz, 1H), 8.04 (d, J=8.3 Hz, 2H), 7.95 (d, J=8.5 Hz, 1H), 7.66 (t, J=8.0 Hz, 1H), 7.53 (d, J=8.6 Hz, 1H), 7.09 (d, J=7.6 Hz, 1H), 7.04 (d, J=8.3 Hz, 2H), 3.91 (s, 3H), 0.31 (s, 9H).

Methyl 3-((2-((trimethylsilyl)ethynyl)quinolin-5-yl)oxy)benzoate (12bb'). (Yield: 85%) $^1$H NMR (600 MHz, CDCl$_3$) δ 8.48 (d, J=8.5 Hz, 1H), 7.89 (d, J=8.5 Hz, 1H), 7.85 (d, J=7.6 Hz, 1H), 7.72 (s, 1H), 7.61 (t, J=8.1 Hz, 1H), 7.55 (d, J=8.6 Hz, 1H), 7.46 (t, J=7.9 Hz, 1H), 7.27 (s, 1H), 6.94 (d, J=7.6 Hz, 1H), 3.90 (s, 3H), 0.31 (s, 9H).

Intermediates 51 and 52. Methyl 4-((2-ethynylquinolin-5-yl)oxy)benzoate (13aa') and Methyl 3-((2-ethynylquinolin-5-yl)oxy)benzoate. (13bb')

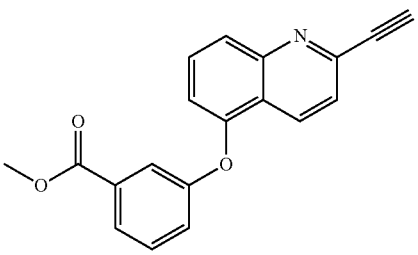

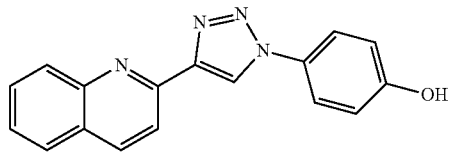 [SMILES: Oc1ccc(-n2cc(-c3ccc4ccccc4n3)nn2)cc1]

Intermediates 12aa' and 12bb' were prepared according to the procedure described for General Method F.

Methyl 4-((2-ethynylquinolin-5-yl)oxy)benzoate (13aa') (Yield: 95%) $^1$H NMR (600 MHz, CDCl$_3$) δ 8.41 (d, J=8.6 Hz, 1H), 8.04 (d, J=8.7 Hz, 2H), 7.95 (d, J=8.6 Hz, 1H), 7.68 (t, J=8.1 Hz, 1H), 7.55 (d, J=8.6 Hz, 1H), 7.11 (d, J=7.6 Hz, 1H), 7.04 (d, J=8.7 Hz, 2H), 3.91 (s, 4H), 3.29 (s, 1H).

Methyl 3-((2-ethynylquinolin-5-yl)oxy)benzoate (13bb') (Yield: 98%) $^1$H NMR (600 MHz, CDCl$_3$) δ 8.52 (d, J=8.5 Hz, 1H), 7.89 (d, J=8.5 Hz, 1H), 7.85 (d, J=7.6 Hz, 1H), 7.72 (s, 1H), 7.63 (t, J=8.1 Hz, 1H), 7.57 (d, J=8.6 Hz, 1H), 7.46 (t, J=7.9 Hz, 1H), 7.28 (s, 1H), 6.96 (d, J=7.6 Hz, 1H), 3.90 (s, 3H), 3.29 (s, 1H).

Example 1. 4-(4-(Quinolin-2-yl)-1H-1,2,3-triazol-1-yl)phenol (3a)

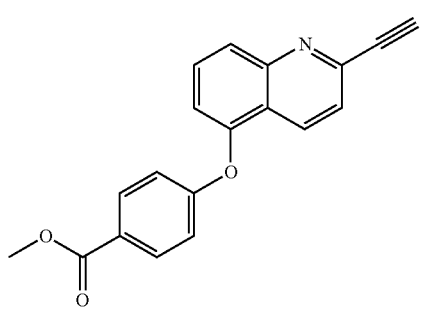

The title compound was prepared through the reaction between Intermediate 30 (13a) according to General Method A and further deprotection of THP following General Method B. Yield: (35%). $^1$H NMR (400 MHz, DMSO-d$_6$) δ 10.01 (s, 1H), 9.32 (s, 1H), 8.53 (d, J=8.5 Hz, 1H), 8.31 (d, J=8.6 Hz, 1H), 8.05 (t, J=8.5 Hz, 2H), 7.88-7.78 (m, 3H), 7.63 (ddd, J=8.0, 6.9, 1.2 Hz, 1H), 7.02-6.94 (m, 2H). $^{13}$C NMR (126 MHz, DMSO-d$_6$) δ 157.93, 149.92, 147.81, 137.28, 130.15, 128.59, 128.37, 127.39, 126.49, 122.06, 121.71, 116.05. HRMS (ESI) calc. For [M+H]$^+$ C$_{17}$H$_{12}$N$_4$O, 289.1011, found 289.1079.

Examples 2-27 (3b, 3d-z and 4a-b) were prepared following the procedure described for General Method A. Examples 2-10 (3b,d-k) were synthesized starting from 2-ethynyl-6-(2-methoxyethoxy)quinoline (Intermediate 31, 13b) and the corresponding substituted p-iodobenzene, while Examples 11-25 (31-z) were obtained from the appropriate ethynylquinoline of Intermediates 33-45 (131-z). Examples 26-27 (4a,b) have been synthesized from 2-ethynyl-1,8-naphthyridine (Intermediate 46 (16)) and the corresponding substituted p-iodobenzene.

Example 2. 4-(4-(6-(2-Methoxyethoxy)quinolin-2-yl)-1H-1,2,3-triazol-1-yl)phenol (3b)

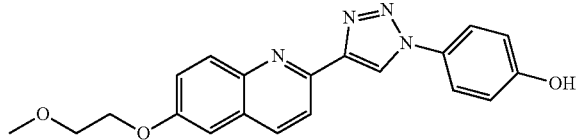 [SMILES: COCCOc1ccc2nc(-c3cn(-c4ccc(O)cc4)nn3)ccc2c1]

Yield: (39%). $^1$H NMR (500 MHz, DMSO-d$_6$) δ 9.96 (s, 1H), 9.21 (s, 1H), 8.37 (d, J=8.6 Hz, 1H), 8.23 (d, J=8.5 Hz, 1H), 7.97-7.93 (m, 1H), 7.85-7.81 (m, 2H), 7.47-7.43 (m, 2H), 6.98-6.95 (m, 2H), 4.29-4.25 (m, 2H), 3.77-3.74 (m, 2H), 3.35 (s, 3H). $^{13}$C NMR (126 MHz, DMSO-d$_6$) δ 157.88, 156.46, 148.06, 147.63, 143.42, 135.93, 129.98, 128.68, 128.46, 122.64, 122.04, 121.14, 118.62, 116.00, 106.72, 70.22, 67.32, 58.18. HRMS (ESI): calcd for [M+H]$^+$ (C$_{20}$H$_{18}$N$_4$O$_3$) 363.1457, found 363.1414.

Example 3. 2-(1-(4-Fluorophenyl)-1H-1,2,3-triazol-4-yl)-6-(2-methoxyethoxy)quinoline (3d)

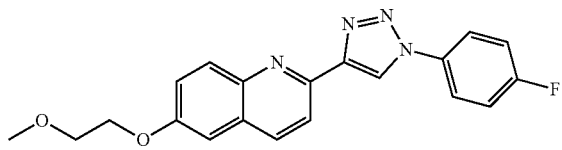 [SMILES: COCCOc1ccc2nc(-c3cn(-c4ccc(F)cc4)nn3)ccc2c1]

Yield: (78%). $^1$H NMR (500 MHz, CD$_2$Cl$_2$) δ 8.72 (s, 1H), 8.31 (d, J=8.5 Hz, 1H), 8.18 (d, J=8.5 Hz, 1H), 7.95 (d, J=9.2 Hz, 1H), 7.89-7.82 (m, 2H), 7.41 (dd, J=9.2, 2.8 Hz, 1H), 7.33-7.25 (m, 2H), 7.16 (d, J=2.8 Hz, 1H), 4.25 (dd, J=5.4, 3.9 Hz, 2H), 3.83-3.79 (m, 2H), 3.45 (s, 3H). $^{13}$C NMR (126 MHz, CD$_2$Cl$_2$) δ 164.10, 162.12, 157.66, 150.05, 148.46, 144.77, 136.18, 134.05, 131.06, 129.49, 123.28, 123.17, 123.10, 121.04, 119.35, 117.37, 117.18, 106.82, 71.46, 68.33, 59.47. HRMS (ESI): calc. For [M+H]$^+$ (C$_{20}$H$_{17}$N$_4$O$_2$F) 365.1414, found 365.1420.

Example 4. 2-(1-(4-Chlorophenyl)-1H-1,2,3-triazol-4-yl)-5-(2-methoxyethoxy)pyridine (3e)

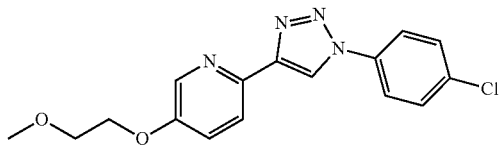 [SMILES: COCCOc1ccc(-c2cn(-c3ccc(Cl)cc3)nn2)nc1]

Yield: (80%). $^1$H NMR (500 MHz, DMSO-d$_6$) δ 9.24 (s, 1H), 8.37 (d, J=2.7 Hz, 1H), 8.04 (t, J=8.0 Hz, 3H), 7.68 (d, J=8.8 Hz, 2H), 7.56 (dd, J=8.7, 2.9 Hz, 1H), 4.26-4.21 (m, 2H), 3.73-3.67 (m, 2H), 3.33 (s, 3H). $^{13}$C NMR (126 MHz, DMSO-d$_6$) δ 154.46, 148.17, 141.94, 137.77, 135.39, 132.97, 129.80, 121.92, 121.77, 120.46, 120.28, 70.24, 67.50, 58.18. HRMS (ESI): calc. for [M+H]$^+$ (C$_{16}$H$_{15}$ClN$_4$O$_2$) 178.0868, found 178.0867.

Example 5. 4-(4-(6-(2-Methoxyethoxy)quinolin-2-yl)-1H-1,2,3-triazol-1-yl)aniline (3f)

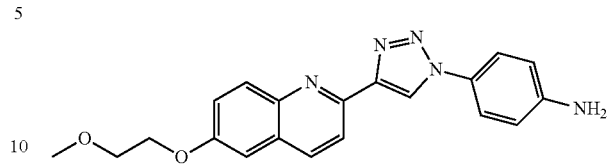

Yield: (11%). $^1$H NMR (600 MHz, CD$_2$Cl$_2$) δ 8.61 (s, 1H), 8.30 (d, J=8.5 Hz, 1H), 8.17 (d, J=8.5 Hz, 1H), 7.95 (d, J=9.2 Hz, 1H), 7.59 (d, J=8.7 Hz, 2H), 7.40 (dd, J=9.2, 2.8 Hz, 1H), 7.16 (d, J=2.7 Hz, 1H), 6.82 (d, J=8.7 Hz, 2H), 4.26-4.23 (m, 2H), 3.99 (s, 2H), 3.82-3.79 (m, 2H), 3.45 (s, 3H). $^{13}$C NMR (151 MHz, CD$_2$Cl$_2$) δ 157.40, 149.36, 148.75, 148.08, 144.63, 136.02, 130.93, 129.96, 129.27, 128.87, 123.09, 122.61, 120.73, 119.28, 115.57, 106.60, 71.35, 68.16. HRMS (ESI): calc. For [M+H]$^+$ (C$_{20}$H$_{19}$N$_5$O$_2$) 362.1617, found 377.1637.

Example 6. 6-(2-Methoxyethoxy)-2-(1-(4-methoxyphenyl)-1H-1,2,3-triazol-4-yl)quinoline (3g)

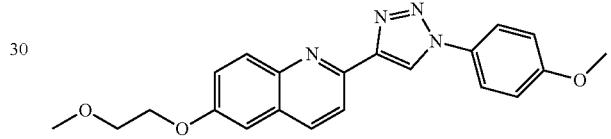

Yield: (40%). $^1$H NMR (500 MHz, CD$_2$Cl$_2$) δ 8.67 (s, 1H), 8.31 (d, J=8.5 Hz, 1H), 8.18 (d, J=8.5 Hz, 1H), 7.95 (d, J=9.1 Hz, 1H), 7.79-7.74 (m, 2H), 7.40 (dd, J=9.2, 2.8 Hz, 1H), 7.16 (d, J=2.7 Hz, 1H), 7.11-7.06 (m, 2H), 4.27-4.23 (m, 2H), 3.88 (s, 3H), 3.82-3.79 (m, 2H), 3.45 (s, 3H). $^{13}$C NMR (126 MHz, CD$_2$Cl$_2$) δ 160.56, 157.55, 149.68, 148.69, 144.72, 136.11, 131.07, 131.01, 129.39, 123.18, 122.65, 120.95, 119.35, 115.35, 106.76, 71.43, 68.28, 59.45, 56.22. HRMS (ESI): calc. for [M+H]$^+$ (C$_{21}$H$_{20}$N$_4$O$_3$) 377.1614, found 377.1600.

Example 7. 4-(4-(6-(2-Methoxyethoxy)quinolin-2-yl)-1H-1,2,3-triazol-1-yl)benzonitrile (3h)

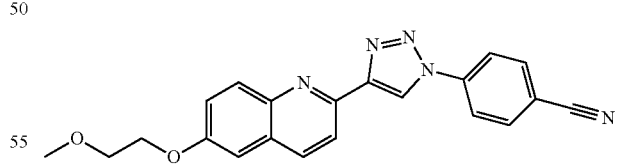

Yield: (71%). $^1$H NMR (500 MHz, CD$_2$Cl$_2$) δ 8.84 (s, 1H), 8.31 (d, J=8.5 Hz, 1H), 8.20 (d, J=8.5 Hz, 1H), 8.06-8.03 (m, 2H), 7.96 (d, J=9.2 Hz, 1H), 7.92-7.88 (m, 2H), 7.42 (dd, J=9.2, 2.8 Hz, 1H), 7.17 (d, J=2.8 Hz, 1H), 4.25 (dd, J=5.3, 3.9 Hz, 2H), 3.83-3.79 (m, 2H), 3.45 (s, 3H). $^{13}$C NMR (126 MHz, CD$_2$Cl$_2$) δ 157.78, 150.57, 147.97, 144.78, 140.43, 136.26, 134.60, 131.07, 129.61, 123.44, 121.17, 120.56, 119.35, 118.36, 113.06, 106.78, 71.44, 68.35. HRMS (ESI): calc. For [M+H]$^+$ (C$_{21}$H$_{17}$N$_5$O$_2$) 372.1461, found 372.1457.

Example 8. 4-(4-(6-(2-Methoxyethoxy)quinolin-2-yl)-1H-1,2,3-triazol-1-yl)benzamide (3i)

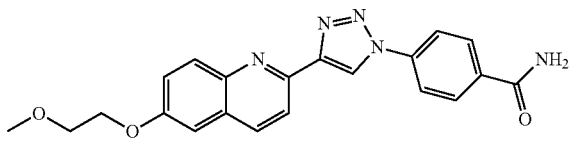 [SMILES: COCCOc1ccc2nc(-c3cn(-c4ccc(C(N)=O)cc4)nn3)ccc2c1]

Yield: (48%). $^1$H NMR (500 MHz, DMSO-d$_6$) δ 9.51 (s, 1H), 8.39 (d, J=8.6 Hz, 1H), 8.25 (d, J=8.5 Hz, 1H), 8.20 (d, J=8.7 Hz, 2H), 8.17-8.10 (m, 3H), 7.96 (d, J=8.9 Hz, 1H), 7.53 (s, 1H), 7.49-7.44 (m, 2H), 4.27 (dd, J=5.3, 3.7 Hz, 2H), 3.77-3.73 (m, 2H), 3.35 (s, 3H). $^{13}$C NMR (126 MHz, DMSO-d$_6$) δ 166.70, 156.58, 148.55, 147.30, 143.46, 138.36, 136.08, 134.23, 130.02, 129.20, 128.60, 122.81, 121.50, 119.74, 118.70, 106.72, 70.23, 67.35, 58.20. HRMS (ESI): calc. for [M+H]$^+$ (C$_{21}$H$_{20}$N$_5$O$_3$) 390.1566, found 390.1550.

Example 9. 4-(4-(6-(2-Methoxyethoxy)quinolin-2-yl)-1H-1,2,3-triazol-1-yl)-2-methylphenol (3j)

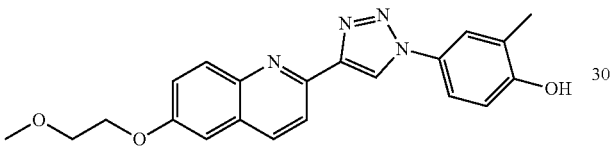

Yield: (40%). $^1$H NMR (500 MHz, DMSO-d$_6$) δ 9.87 (s, 1H), 9.19 (s, 1H), 8.37 (d, J=8.5 Hz, 1H), 8.22 (d, J=8.6 Hz, 1H), 7.94 (d, J=8.8 Hz, 1H), 7.78 (d, J=2.5 Hz, 1H), 7.66 (dd, J=8.6, 2.7 Hz, 1H), 7.49-7.40 (m, 2H), 6.96 (d, J=8.6 Hz, 1H), 4.26 (dd, J=5.4, 3.7 Hz, 2H), 3.78-3.72 (m, 2H), 3.35 (s, 3H), 2.23 (s, 3H). $^{13}$C NMR (126 MHz, DMSO-d$_6$) δ 156.46, 155.95, 148.03, 147.67, 143.44, 135.95, 129.99, 128.47, 128.43, 125.38, 122.84, 122.67, 121.03, 119.02, 118.62, 115.01, 106.71, 70.24, 67.33, 58.20, 15.97. HRMS (ESI): calc. For [M+H]$^+$ (C$_{21}$H$_{20}$N$_4$O$_3$) 377.1614, found 377.1614.

Example 10. 2-Methoxy-4-(4-(6-(2-methoxyethoxy)quinolin-2-yl)-1H-1,2,3-triazol-1-yl)phenol (3k)

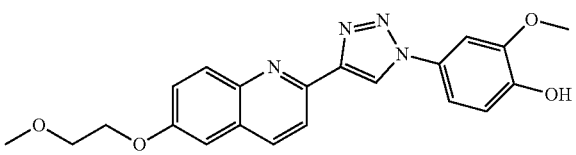

Yield: (30%). $^1$H NMR (500 MHz, CD$_2$Cl$_2$) δ 8.68 (s, 1H), 8.31 (d, J=8.6 Hz, 1H), 8.18 (d, J=8.6 Hz, 1H), 7.95 (d, J=9.2 Hz, 1H), 7.44 (d, J=2.3 Hz, 1H), 7.40 (dd, J=9.2, 2.8 Hz, 1H), 7.29 (dd, J=8.5, 2.4 Hz, 1H), 7.16 (d, J=2.7 Hz, 1H), 7.06 (d, J=8.5 Hz, 1H), 5.95 (s, 1H), 4.27-4.23 (m, 2H), 4.00 (s, 3H), 3.83-3.79 (m, 2H), 3.45 (s, 3H). $^{13}$C NMR (126 MHz, CD$_2$Cl$_2$) δ 157.59, 149.67, 148.68, 147.88, 146.90, 144.74, 136.15, 130.99, 130.71, 129.43, 123.23, 121.07, 119.37, 115.23, 114.05, 106.82, 105.10, 71.45, 68.31, 59.47. HRMS (ESI): calc. for [M+H]$^+$ (C$_{21}$H$_{20}$N$_4$O$_4$) 393.1563, found 393.1580.

Example 11. 4-(4-(3-Methylquinolin-2-yl)-1H-1,2,3-triazol-1-yl)phenol (3l)

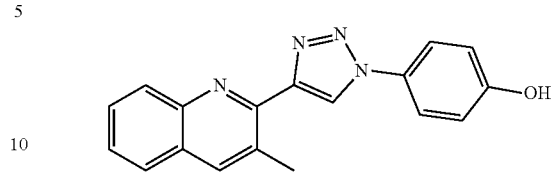

Yield: (62%). $^1$H NMR (600 MHz, DMSO-d$_6$) δ 9.99 (s, 1H), 9.18 (s, 1H), 8.31 (s, 1H), 8.01 (d, J=8.4 Hz, 1H), 7.94 (d, J=8.1 Hz, 1H), 7.84 (d, J=8.8 Hz, 2H), 7.77-7.71 (m, 1H), 7.60 (t, J=7.5 Hz, 1H), 6.97 (d, J=8.1 Hz, 2H), 2.83 (s, 3H). $^{13}$C NMR (151 MHz, DMSO-d$_6$) δ 157.92, 149.69, 148.72, 145.85, 137.47, 129.54, 129.16, 128.62, 128.36, 127.23, 127.09, 126.75, 123.35, 122.16, 116.05, 20.79. HRMS (ESI): calc. For [M+H]$^+$ (C$_{18}$H$_{14}$N$_4$O) 303.1246, found 303.1242.

Example 12. 4-(4-(4-Methylquinolin-2-yl)-1H-1,2,3-triazol-1-yl)phenol (3m)

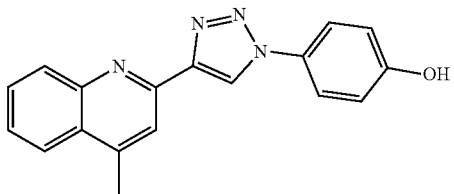 [SMILES: Cc1cc(-c2cn(-c3ccc(O)cc3)nn2)nc2ccccc12]

Yield: (17%). $^1$H NMR (600 MHz, DMSO-d$_6$) δ 10.02 (s, 1H), 9.29 (s, 1H), 8.18 (s, 1H), 8.13 (d, J=8.3 Hz, 1H), 8.04 (d, J=8.0 Hz, 1H), 7.85 (d, J=8.8 Hz, 2H), 7.80 (t, J=7.6 Hz, 1H), 7.66-7.61 (m, 1H), 6.96 (d, J=8.8 Hz, 2H), 2.79 (s, 3H). $^{13}$C NMR (151 MHz, DMSO-d$_6$) δ 158.37, 150.05, 148.44, 147.87, 145.85, 130.28, 129.50, 129.11, 127.77, 126.80, 124.83, 122.53, 122.11, 119.21, 116.47, 18.89. HRMS (ESI): calc. for [M+H]$^+$ (C$_{18}$H$_{14}$N$_4$O) 303.1246, found 303.1246.

Example 13. 4-(4-(8-Chloroquinolin-2-yl)-1H-1,2,3-triazol-1-yl)phenol (3n)

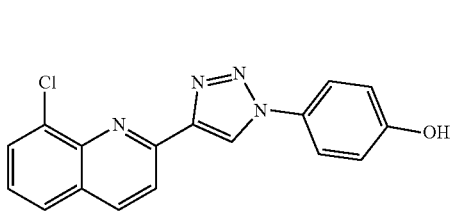 [SMILES: Oc1ccc(-n2cc(-c3ccc4cccc(Cl)c4n3)nn2)cc1]

Yield: (39%). $^1$H NMR (400 MHz, DMSO-d$_6$) δ 10.01 (s, 1H), 9.24 (s, 1H), 8.60 (d, J=8.6 Hz, 1H), 8.37 (d, J=8.6 Hz, 1H), 8.01 (dd, J=13.6, 7.9 Hz, 2H), 7.87 (d, J=7.5 Hz, 2H), 7.60 (t, J=7.8 Hz, 1H), 6.98 (d, J=7.5 Hz, 2H). $^{13}$C NMR (151 MHz, DMSO-d$_6$) δ 158.04, 150.62, 147.63, 143.44, 138.05, 131.94, 130.24, 128.79, 128.58, 127.57, 126.77, 122.35, 122.17, 119.34, 116.02. HRMS (ESI): calc. For [M+H]$^+$ (C$_{17}$H$_{11}$N$_4$OCl) 323.0700, found 323.0700.

Example 14. 2-(1-(4-Fluorophenyl)-1H-1,2,3-triazol-4-yl)-8-methoxyquinoline (3o)

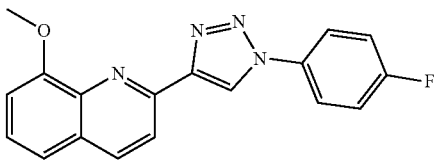 [SMILES: COc1cccc2ccc(-c3cn(-c4ccc(F)cc4)nn3)nc12]

Yield: (40%). ¹H NMR (400 MHz, CDCl₃) δ 8.89 (s, 1H), 8.47 (d, J=8.6 Hz, 1H), 8.29 (d, J=8.6 Hz, 1H), 7.85 (dd, J=8.9, 4.5 Hz, 2H), 7.51-7.42 (m, 2H), 7.28 (d, J=8.5 Hz, 2H), 7.12-7.08 (d, J=8.6 Hz, 1H). ¹³C NMR (151 MHz, CDCl₃) δ 163.51, 161.85, 155.02, 149.28, 149.21, 139.83, 137.40, 133.46, 133.44, 129.23, 126.98, 122.64, 122.59, 121.45, 119.95, 119.54, 117.07, 116.91, 108.42, 56.29. HRMS (ESI): calc. for [M+H]⁺ (C₁₈H₁₃N₄OF) 321.1152, found 321.1138.

Example 15. 2-(1-(4-Fluorophenyl)-1H-1,2,3-triazol-4-yl)-8-(3-methoxyethoxy)quinoline (3p)

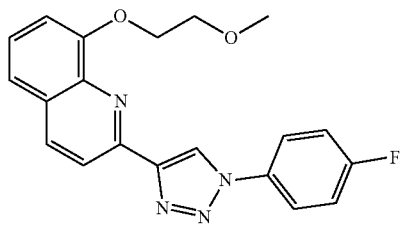 [SMILES: COCCOc1cccc2ccc(-c3cn(-c4ccc(F)cc4)nn3)nc12]

Yield: (61%). ¹H NMR (400 MHz, CDCl₃) δ 8.87 (s, 1H), 8.45 (d, J=8.6 Hz, 1H), 8.27 (d, J=8.5 Hz, 1H), 7.83 (dd, J=8.5, 4.6 Hz, 2H), 7.46 (d, J=4.3 Hz, 2H), 7.27 (d, J=10.7 Hz, 2H), 7.16 (t, J=4.3 Hz, 1H), 4.44 (t, J=4.9 Hz, 2H), 4.00 (t, J=4.9 Hz, 2H), 3.54 (s, 3H). ¹³C NMR (151 MHz, CDCl₃) δ 163.53, 161.88, 154.34, 149.18, 149.02, 139.83, 137.58, 133.48, 133.46, 129.34, 126.99, 122.83, 122.78, 121.79, 120.53, 119.41, 117.04, 116.89, 111.00, 71.12, 69.00, 59.49. HRMS (ESI): calc. For [M+H]⁺ (C₂₀H₁₇N₄O₂F) 365.1414, found 365.1416.

Example 16. 4-(4-(8-(4-Methoxyphenyl)quinolin-2-yl)-1H-1,2,3-triazol-1-yl)phenol (3q)

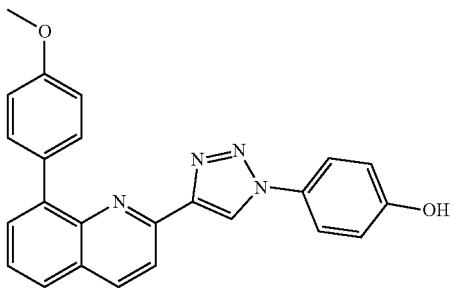 [SMILES: COc1ccc(-c2cccc3ccc(-c4cn(-c5ccc(O)cc5)nn4)nc23)cc1]

Yield: (30%). ¹H NMR (500 MHz, DMSO-d₆) δ 10.00 (s, 1H), 8.75 (s, 1H), 8.54 (d, J=8.5 Hz, 1H), 8.27 (d, J=8.5 Hz, 1H), 7.97 (d, J=8.0 Hz, 1H), 7.80 (d, J=7.8 Hz, 3H), 7.74 (d, J=8.4 Hz, 2H), 7.66 (t, J=7.5 Hz, 1H), 7.10 (d, J=8.2 Hz, 2H), 6.96 (d, J=8.4 Hz, 2H), 3.83 (s, 3H). ¹³C NMR (126 MHz, DMSO-d₆) δ 158.66, 158.08, 149.28, 148.14, 144.75, 138.74, 137.75, 131.93, 131.08, 130.19, 128.59, 127.92, 127.19, 126.59, 122.65, 121.70, 118.21, 116.04, 113.37, 55.12. HRMS (ESI): calc. for [M+H]⁺ (C₂₄H₁₈N₄O₂) 395.1508, found 395.1503.

Example 17. 4-(4-(8-Phenoxyquinolin-2-yl)-1H-1,2,3-triazol-1-yl)phenol (3r)

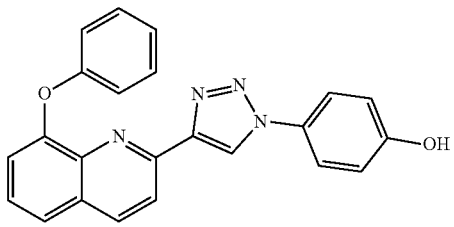 [SMILES: Oc1ccc(-n2cc(-c3ccc4cccc(Oc5ccccc5)c4n3)nn2)cc1]

Yield (75%). ¹H NMR (400 MHz, DMSO-d₆) δ 10.01 (s, 1H), 8.80 (s, 1H), 8.58-8.50 (m, 1H), 8.30 (d, J=8.6 Hz, 1H), 7.78 (t, J=9.1 Hz, 3H), 7.56 (t, J=7.9 Hz, 1H), 7.41 (t, J=7.7 Hz, 2H), 7.26 (d, J=7.6 Hz, 1H), 7.19-7.09 (m, 3H), 6.96 (d, J=8.7 Hz, 2H). ¹³C NMR (151 MHz, DMSO-d₆) δ 158.02, 157.75, 152.51, 149.21, 147.93, 140.12, 137.46, 129.91, 129.08, 128.54, 126.77, 123.31, 123.23, 122.22, 121.60, 118.95, 118.88, 117.80, 116.06. HRMS (ESI): calc. For [M+H]⁺ (C₂₃H₁₆N₄O₂) 381.1352, found 381.1338.

Example 18. 4-(4-(5-Phenoxyquinolin-2-yl)-1H-1,2,3-triazol-1-yl)phenol (3s)

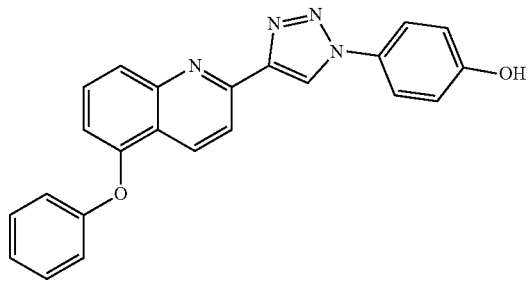 [SMILES: Oc1ccc(-n2cc(-c3ccc4c(Oc5ccccc5)cccc4n3)nn2)cc1]

Yield: (56%). ¹H NMR (600 MHz, DMSO-d₆) δ 10.01 (s, 1H), 9.34 (s, 1H), 8.66 (d, J=8.7 Hz, 1H), 8.33 (d, J=8.7 Hz, 1H), 7.88-7.81 (m, 3H), 7.74 (t, J=8.1 Hz, 1H), 7.46 (t, J=8.0 Hz, 2H), 7.22 (t, J=7.4 Hz, 1H), 7.15 (d, J=7.9 Hz, 2H), 6.98 (dd, J=14.3, 8.2 Hz, 3H). ¹³C NMR (151 MHz, DMSO-d₆) δ 158.00, 156.61, 152.55, 150.66, 148.70, 147.72, 131.48, 130.29, 130.27, 128.62, 124.09, 123.74, 122.15, 121.96, 120.49, 118.88, 118.47, 116.05, 113.03. HRMS (ESI): calc. for [M+H]⁺ (C₂₃H₁₆N₄O₂) 381.1352, found 381.1354.

Example 19. 4-(4-(6-(3-Morpholinopropoxy)quinolin-2-yl)-1H-1,2,3-triazol-1-yl)phenol (3t)

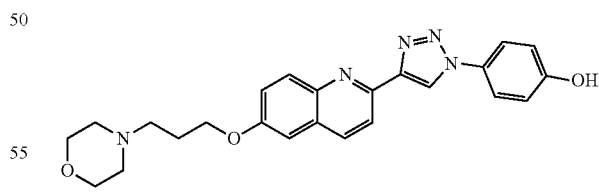

Yield: (40%). ¹H NMR (400 MHz, DMSO-d₆) δ 9.99 (s, 1H), 9.22 (s, 1H), 8.38 (d, J=8.6 Hz, 1H), 8.22 (d, J=8.6 Hz, 1H), 7.93 (d, J=9.7 Hz, 1H), 7.84 (d, J=8.8 Hz, 2H), 7.45-7.40 (m, 2H), 6.97 (d, J=8.8 Hz, 2H), 4.17 (t, J=6.4 Hz, 2H), 3.59 (t, J=4.8 Hz, 4H), 2.47 (t, J=7.1 Hz, 2H), 2.43-2.34 (m, 4H), 2.04-1.89 (m, 2H). ¹³C NMR (101 MHz, DMSO-d₆) δ 158.34, 157.08, 148.53, 148.00, 143.82, 136.40, 130.39, 129.13, 128.99, 123.18, 122.49, 121.59, 119.05, 116.46, 107.07, 66.70, 66.65, 55.29, 53.84, 26.23. HRMS (ESI): calc. For [M+H]⁺ (C₂₄H₂₅N₅O₃) 432.1957, found 432.2154.

Example 20. 4-(4-(3-Methyl-6-(3-morpholino-propoxy)quinolin-2-yl)-1H-1,2,3-triazol-1-yl)phenol (3u)

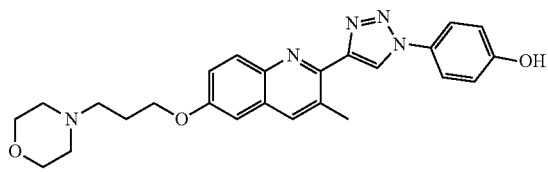 [SMILES: Cc1cc2cc(OCCCN3CCOCC3)ccc2nc1-c1cn(-c2ccc(O)cc2)nn1]

Yield: (42%). ¹H NMR (400 MHz, CDCl₃) δ 8.36 (s, 1H), 7.98 (d, J=9.2 Hz, 1H), 7.90 (s, 1H), 7.49 (d, J=8.3 Hz, 2H), 7.30 (d, J=9.8 Hz, 1H), 6.99 (s, 1H), 6.85 (d, J=8.4 Hz, 2H), 4.17 (t, J=6.3 Hz, 2H), 3.77 (t, J=4.8 Hz, 4H), 2.86 (s, 3H), 2.69-2.60 (m, 3H), 2.60-2.49 (m, 4H), 2.09 (p, J=6.8 Hz, 3H). ¹³C NMR (101 MHz, CDCl₃) δ 162.07, 157.42, 156.93, 147.48, 142.33, 136.82, 130.87, 129.98, 129.96, 129.04, 122.36, 122.18, 116.69, 110.15, 105.11, 66.89, 66.25, 55.64, 53.90, 26.24, 21.27. HRMS (ESI): calc. for [M+H]⁺ ($C_{25}H_{27}N_5O_3$) 446.2114, found 446.2354.

Example 21. 4-(4-(6-(2-(2-Morpholinoethoxy)ethoxy)quinolin-2-yl)-1H-1,2,3-triazol-1-yl)phenol (3v)

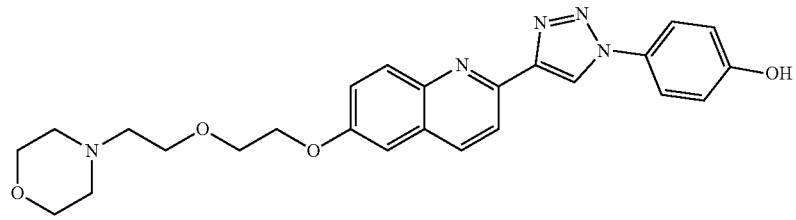 [SMILES: Oc1ccc(-n2cc(-c3ccc4cc(OCCOCCN5CCOCC5)ccc4n3)nn2)cc1]

Yield: (34%). ¹H NMR (400 MHz, CDCl₃) δ 8.20 (d, J=8.6 Hz, 1H), 8.02 (s, 1H), 7.94 (d, J=8.7 Hz, 1H), 7.89 (d, J=9.2 Hz, 1H), 7.42 (d, J=8.7 Hz, 2H), 7.31 (dd, J=9.2, 2.8 Hz, 1H), 6.91 (d, J=8.8 Hz, 2H), 6.78 (d, J=2.8 Hz, 1H), 4.07-4.04 (m, 2H), 3.90-3.88 (m, 2H), 3.78-3.75 (m, 6H), 2.74 (t, J=5.3 Hz, 2H), 2.66-2.57 (m, 4H). ¹³C NMR (101 MHz, CDCl₃) δ 157.15, 156.73, 147.01, 143.80, 135.43, 130.29, 129.45, 128.61, 128.08, 122.63, 121.53, 119.29, 119.16, 116.56, 105.88, 69.87, 67.57, 67.53, 67.45, 66.26, 53.98. HRMS (ESI) calc. For [M+H]⁺ ($C_{25}H_{27}N_5O_4$) 462.2063, found 462.1948.

Example 22. 2-Fluoro-4-(4-(6-(2-(2-morpholinoethoxy)ethoxy)quinolin-2-yl)-1H-1,2,3-triazol-1-yl)phenol (3w)

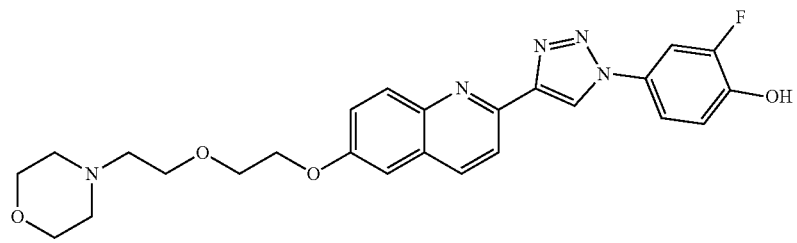 [SMILES: Oc1ccc(-n2cc(-c3ccc4cc(OCCOCCN5CCOCC5)ccc4n3)nn2)cc1F]

Yield: (41%). ¹H NMR (400 MHz, CDCl₃) δ 8.13 (d, J=8.5 Hz, 1H), 7.89 (d, J=8.5 Hz, 1H), 7.79 (d, J=8.8 Hz, 2H), 7.31 (dd, J=11.4, 2.5 Hz, 1H), 7.23 (d, J=2.7 Hz, 1H), 7.13-7.07 (m, 1H), 6.97 (t, J=8.8 Hz, 1H), 6.69 (d, J=2.7 Hz, 1H), 3.92-3.85 (m, 2H), 3.84-3.77 (m, 6H), 3.76-3.71 (m, 2H), 3.48 (s, 1H), 2.76 (t, J=5.0 Hz, 2H), 2.65 (s, 4H). ¹³C NMR (101 MHz, DMSO-d₆) δ 164.39, 156.53, 147.48, 143.44, 136.02, 129.99, 129.36, 128.54, 125.62, 122.75, 121.37, 118.64, 116.89, 111.74, 109.48, 109.24, 106.81, 68.68, 68.27, 67.51, 66.14, 57.59, 53.68. HRMS (ESI) calc. for [M+H]⁺ ($C_{25}H_{26}FN_5O_4$) 480.1969, found 480.1978.

Example 23. 4-(2-(2-((2-(1-(4-Fluorophenyl)-1H-1,2,3-triazol-4-yl)quinolin-6-yl)oxy)ethoxy)ethyl)morpholine (3x)

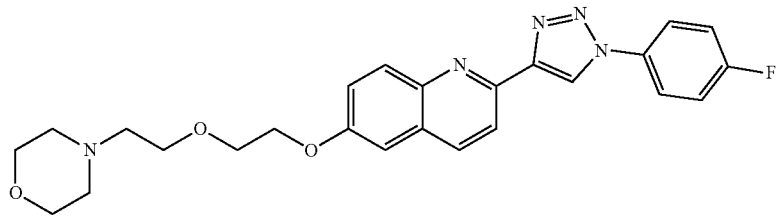 [SMILES: Fc1ccc(-n2cc(-c3ccc4cc(OCCOCCN5CCOCC5)ccc4n3)nn2)cc1]

Yield: (37%). ¹H NMR (400 MHz, CDCl₃) δ 8.70 (s, 1H), 8.34 (d, J=8.5 Hz, 1H), 8.15 (d, J=8.6 Hz, 1H), 7.97 (d, J=9.2 Hz, 1H), 7.91-7.76 (m, 2H), 7.40 (dd, J=9.2, 2.7 Hz, 1H), 7.30-7.22 (m, 2H), 7.11 (d, J=2.7 Hz, 1H), 4.27 (dd, J=5.7, 3.8 Hz, 2H), 3.91 (dd, J=5.7, 3.7 Hz, 2H), 3.73 (dt, J=9.4, 5.1 Hz, 5H), 2.64 (t, J=5.7 Hz, 2H), 2.53 (d, J=5.7 Hz, 3H). ¹³C NMR (101 MHz, CDCl₃) δ 163.92, 157.12, 149.66, 148.02, 144.32, 135.85, 130.69, 122.97, 122.71, 122.63, 120.53, 119.21, 117.08, 116.85, 106.40, 69.63, 67.85, 66.77, 66.72, 58.31, 54.13. HRMS (ESI) calc. For [M+H]⁺ ($C_{25}H_{26}FN_5O_3$) 464.2020, found 464.2085.

Example 24. 4-(4-(5-(4-(2-Methoxyethoxy)phenoxy)quinolin-2-yl)-1H-1,2,3-triazol-1-yl)phenol (3y)

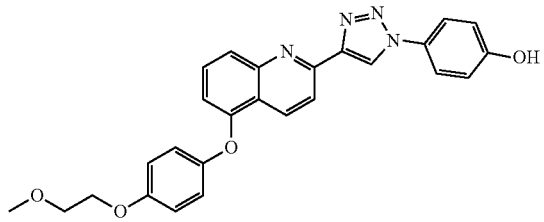 [SMILES: COCCOc1ccc(Oc2cccc3nc(-c4cn(-c5ccc(O)cc5)nn4)ccc23)cc1]

Yield: (21%). ¹H NMR (600 MHz, DMSO-d₆) δ 10.02 (s, 1H), 9.33 (s, 1H), 8.75 (d, J=8.5 Hz, 1H), 8.33 (d, J=8.2 Hz, 1H), 7.85 (d, J=7.0 Hz, 2H), 7.76 (d, J=8.2 Hz, 1H), 7.68 (t, J=7.1 Hz, 1H), 7.15 (d, J=7.1 Hz, 2H), 7.04 (d, J=7.0 Hz, 2H), 6.97 (d, J=7.2 Hz, 2H), 6.81 (d, J=6.8 Hz, 1H), 4.11 (s, 3H), 3.67 (s, 2H). ¹³C NMR (151 MHz, DMSO-d₆) δ 158.04, 155.31, 153.99, 150.60, 149.22, 148.61, 147.76, 131.50, 130.19, 128.60, 122.72, 122.15, 121.92, 121.04, 119.95, 118.23, 116.06, 115.85, 110.81, 70.40, 67.32, 58.19. HRMS (ESI): calc. for [M+H]⁺ ($C_{26}H_{22}N_4O_4$) 455.1719, found 455.1716.

Example 25. 2-Fluoro-4-(4-(5-(3-(2-methoxyethoxy)phenoxy)quinolin-2-yl)-1H-1,2,3-triazol-1-yl)phenol (3z)

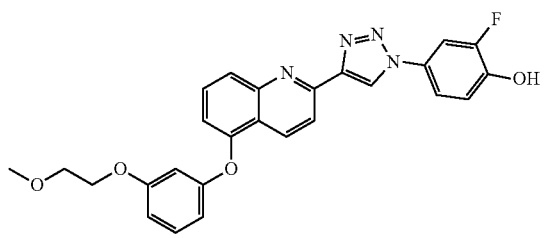 [SMILES: COCCOc1cccc(Oc2cccc3nc(-c4cn(-c5ccc(O)c(F)c5)nn4)ccc23)c1]

Yield: (5%). ¹H NMR (600 MHz, CD₂Cl₂) δ 8.76 (s, 1H), 8.65 (d, J=8.7 Hz, 1H), 8.37 (d, J=8.7 Hz, 1H), 7.84 (d, J=8.5 Hz, 1H), 7.72 (d, J=10.8 Hz, 1H), 7.65 (t, J=8.1 Hz, 1H), 7.55 (d, J=9.3 Hz, 1H), 7.29 (t, J=8.2 Hz, 1H), 7.21 (t, J=8.9 Hz, 1H), 7.02 (d, J=7.6 Hz, 1H), 6.73 (d, J=8.3 Hz, 1H), 6.69 (d, J=8.1 Hz, 1H), 6.66 (s, 1H), 5.61 (s, 1H), 4.09-4.07 (m, 2H), 3.71-3.69 (m, 2H), 3.39 (s, 3H). ¹³C NMR (151 MHz, CD₂Cl₂) δ 160.92, 159.02, 153.35, 152.29, 151.20, 150.70, 149.80, 149.65, 144.83, 144.73, 132.12, 130.96, 130.77, 130.72, 130.21, 124.76, 122.04, 121.53, 118.84, 118.66, 118.64, 117.73, 117.71, 114.12, 111.64, 110.30, 109.88, 109.72, 106.01, 71.42, 68.06, 59.37. HRMS (ESI): calc. For [M+H]⁺ ($C_{26}H_{21}N_4O_4$) 473.1625, found 473.1629.

Example 26. 4-(4-(1,8-Naphthyridin-2-yl)-1H-1,2,3-triazol-1-yl)phenol (4a)

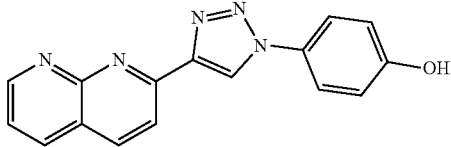 [SMILES: Oc1ccc(-n2cc(-c3ccc4cccnc4n3)nn2)cc1]

Yield: (12%). ¹H NMR (500 MHz, DMSO-d₆) δ 10.01 (s, 1H), 9.41 (s, 1H), 9.11 (dd, J=4.2, 2.0 Hz, 1H), 8.61 (d, J=8.5 Hz, 1H), 8.51 (dd, J=8.1, 2.0 Hz, 1H), 8.40 (d, J=8.4 Hz, 1H), 7.89-7.83 (m, 2H), 7.64 (dd, J=8.1, 4.2 Hz, 1H), 7.01-6.95 (m, 2H). ¹³C NMR (126 MHz, DMSO-d₆) δ 158.02, 155.56, 154.10, 152.84, 147.67, 138.95, 137.52, 128.59, 122.42, 122.21, 122.16, 122.13, 119.16, 116.05. HRMS (ESI): calc. for [M+H]⁺ ($C_{16}H_{11}N_5$) 290.1042, found 290.1022.

Example 27. 2-(1-(4-Chlorophenyl)-1H-1,2,3-triazol-4-yl)-1,8-naphthyridine (4b)

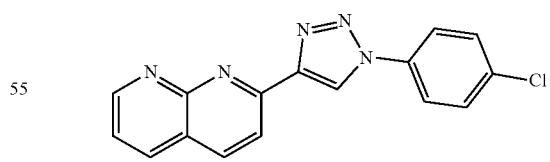

Yield: (41%). ¹H NMR (500 MHz, DMSO-d₆) δ 9.65 (s, 1H), 9.12 (dd, J=4.2, 2.0 Hz, 1H), 8.63 (d, J=8.4 Hz, 1H), 8.52 (dd, J=8.1, 2.0 Hz, 1H), 8.42 (d, J=8.4 Hz, 1H), 8.17-8.12 (m, 2H), 7.75-7.70 (m, 2H), 7.65 (dd, J=8.1, 4.2 Hz, 1H). ¹³C NMR (126 MHz, DMSO-d₆) δ 155.52, 154.18, 152.50, 148.08, 139.07, 137.52, 135.29, 133.31, 129.86, 122.89, 122.84, 122.20, 122.10, 119.16, 40.02. HRMS (ESI): calc. for [M+H]⁺ ($C_{16}H_{10}N_5Cl$) 308.0703, found 308.0702.

Example 28. 4-(4-(6-(2-(2-Aminoethoxy)ethoxy)quinolin-2-yl)-1H-1,2,3-triazol-1-yl)phenol (3c)

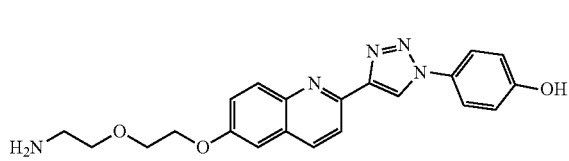 [SMILES: NCCOCCOc1ccc2nc(-c3cn(-c4ccc(O)cc4)nn3)ccc2c1]

Step 1. 4-(4-(6-(2-(2-(Tritylamino)ethoxy)ethoxy)quinolin-2-yl)-1H-1,2,3-triazol-1-yl)phenol (3c')

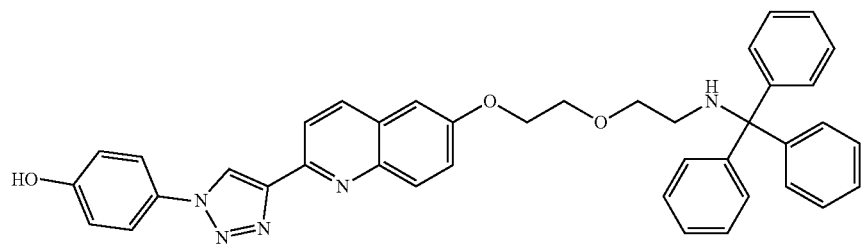 [SMILES: Oc1ccc(-n2cc(-c3ccc4cc(OCCOCCNC(c5ccccc5)(c5ccccc5)c5ccccc5)ccc4n3)nn2)cc1]

The sub-title compound was prepared according to General Method A. Yield: (40%). $^1$H NMR (400 MHz, CDCl$_3$) δ 8.70 (s, 1H), 8.35 (d, J=8.6 Hz, 1H), 8.13 (d, J=8.6 Hz, 1H), 7.99 (d, J=9.4 Hz, 1H), 7.64 (d, J=8.5 Hz, 2H), 7.51-7.43 (m, 6H), 7.34-7.13 (m, 10H), 7.09 (d, J=2.8 Hz, 1H), 7.00 (d, J=8.5 Hz, 2H), 4.23 (t, J=4.7 Hz, 2H), 3.82 (s, 2H), 3.72 (s, 2H), 2.40 (s, 2H).

Step 2. 4-(4-(6-(2-(2-Aminoethoxy)ethoxy)quinolin-2-yl)-1H-1,2,3-triazol-1-yl)phenol (3c)

Compound 3c' is dissolved in anhydrous DCM (3 mL/mmol) and cooled to 0° C. Trifluoroacetic acid (2 mL/mmol) is added dropwise, the reaction is warmed to room temperature and stirred for 1 h. Saturated NaHCO$_3$ is added to neutralize the reaction and extracted with DCM. Combined organic layers are dried over Na$_2$SO$_4$ and the final compound purified by flash chromatography in DCM/MeOH (7:3). Yield: (65%). $^1$H NMR (400 MHz, DMSO-d$_6$) δ 10.02 (s, 1H), 9.22 (s, 1H), 8.38 (d, J=8.6 Hz, 1H), 8.24 (d, J=8.6 Hz, 1H), 7.96 (d, J=10.0 Hz, 1H), 7.86-7.77 (m, 3H), 7.47-7.43 (m, 2H), 6.97 (d, J=8.7 Hz, 2H), 4.31 (t, J=4.3 Hz, 2H), 3.90 (t, J=4.4 Hz, 2H), 3.71 (t, J=5.2 Hz, 2H), 3.06-3.02 (m, 2H). $^{13}$C NMR (101 MHz, DMSO-d$_6$) δ 157.99, 156.42, 147.72, 143.48, 136.06, 130.08, 129.57, 128.69, 128.52, 122.71, 122.10, 121.23, 118.76, 116.08, 106.76, 68.87, 67.45, 66.87, 47.08. HRMS (ESI) calc. for [M+H]$^+$ (C$_{21}$H$_{21}$N$_5$O$_3$) 392.1644, found 392.0754.

Example 29. 4-(4-(7-(2-(2-Morpholinoethoxy)ethoxy)quinolin-2-yl)-1H-1,2,3-triazol-1-yl)phenol

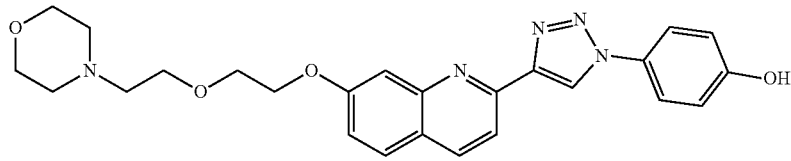 [SMILES: Oc1ccc(-n2cc(-c3ccc4ccc(OCCOCCN5CCOCC5)cc4n3)nn2)cc1]

Step 1. (E)-Ethyl 3-(4-methoxy-2-nitrophenyl)acrylate

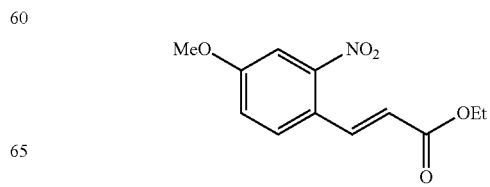

To a solution of 4-methoxy-2-nitrobenzaldehyde (500 mg, 2.8 mmol) in anhydrous toluene (36 mL) under $N_2$ atmosphere, ethyl 2-(triphenyl-2P-phosphanylidene)acetate (1.2 g, 3.6 mmol) was added and stirred at reflux for 2 hours. After solvent evaporation, compound (E)-ethyl 3-(4-methoxy-2-nitrophenyl)acrylate was purified by flash chromatography using hexanes:ethyl acetate as solvent. Yield 90%. $^1$H NMR (400 MHz, $CDCl_3$) δ 8.02 (d, J=15.8 Hz, 1H), 7.58 (d, J=8.7 Hz, 1H), 7.49 (d, J=2.6 Hz, 1H), 7.15 (dd, J=8.7, 2.6 Hz, 1H), 6.29 (d, J=15.8 Hz, 1H), 4.27 (q, J=7.1 Hz, 2H), 3.90 (s, 3H), 1.33 (t, J=7.1 Hz, 3H).

Step 2. 7-Methoxyquinolin-2(1H)-one

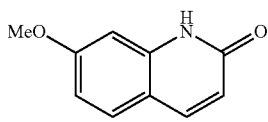 [SMILES: COc1ccc2ccc(=O)[nH]c2c1]

(E)-Ethyl 3-(4-methoxy-2-nitrophenyl)acrylate (438 mg, 2.5 mmol) was dissolved in 10 mL acetic acid glacial. Iron powder (837 mg, 15 mmol) was then added and heated at 80° C. for 2 h. The mixture was filtered over diatomaceous earth and purified by flash chromatography using dichloromethane: methanol as solvent. Yield 70%. $^1$H NMR (400 MHz, $CDCl_3$) δ 11.46 (s, 1H), 7.71 (d, J=9.4 Hz, 1H), 7.44 (d, J=8.7 Hz, 1H), 6.81 (dd, J=8.7, 2.4 Hz, 1H), 6.76 (d, J=2.3 Hz, 1H), 6.53 (d, J=9.4 Hz, 1H), 3.90 (s, 3H).

Step 3. 2-Chloro-7-methoxyquinoline

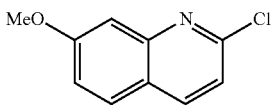 [SMILES: COc1ccc2ccc(Cl)nc2c1]

300 mg (1.9 mmol) of 7-methoxyquinolin-2(1H)-one was dissolved in 1.1 mL of $POCl_3$ (12 mmol) and heated at reflux for 3 h. The mixture was poured into iced water, neutralized with sat $NaHCO_3$ and extracted with ethyl acetate. Yield 98%. $^1$H NMR (400 MHz, $CDCl_3$) δ 8.01 (d, J=8.5 Hz, 1H), 7.68 (d, J=8.9 Hz, 1H), 7.35 (d, J=2.4 Hz, 1H), 7.25 (d, J=8.3 Hz, 1H), 7.20 (dd, J=8.9, 2.5 Hz, 1H), 3.93 (s, 3H).

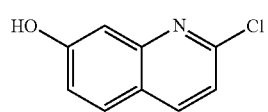 [SMILES: Oc1ccc2ccc(Cl)nc2c1]

Step 4. 2-Chloroquinolin-7-ol

A solution of 2-chloro-7-methoxyquinoline (330 mg, 1.7 mmol) in anhydrous dichloromethane (15 mL) under $N_2$ atmosphere was cooled to −78° C. 10.4 mL of 1 M $BBr_3$ in dichloromethane was added dropwise and stirred at −78° C. for 30 min. The mixture was then heated to 50° C. and stirred overnight. The reaction was quenched with 10 mL MeOH and solvent evaporated. The crude was redissolved in dichloromethane and extracted with sat $NaHCO_3$ and brine. The sub-title product was purified by flash chromatography using hexanes: ethyl acetate. Yield 88% $^1$H NMR (400 MHz, Methanol-$d_4$) δ 8.19 (d, J=8.5 Hz, 1H), 7.80 (d, J=9.5 Hz, 1H), 7.27 (d, J=8.5 Hz, 1H), 7.22-7.15 (m, 2H).

Step 5. 2-Chloro-7-(2-(2-chloroethoxy)ethoxy)quinolone

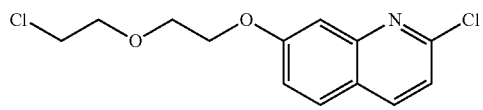 [SMILES: ClCCOCCOc1ccc2ccc(Cl)nc2c1]

In a pressure vial, under $N_2$, 2-chloroquinolin-7-ol (269 mg, 1.5 mmol) and 415 mg of $K_2CO_3$ (3 mmol) were dissolved in 4 mL anhydrous DMF. 1-chloro-2-(2-chloroethoxy)ethane (0.26 mL, 2.25 mmol) was added and the reaction stirred at 70° C. overnight. The reaction was dissolved in ethyl acetate and washed with with $H_2O$ and sat $NH_4Cl$. The sub-title product was obtained via flash chromatography using hexanes: ethyl acetate. Yield 60%. $^1$H NMR (400 MHz, $CDCl_3$) δ 8.00 (d, J=8.5 Hz, 1H), 7.69 (d, J=8.9 Hz, 1H), 7.33 (d, J=2.5 Hz, 1H), 7.27-7.21 (m, 2H), 4.30-4.22 (m, 2H), 3.99-3.92 (m, 2H), 3.85 (t, J=5.9 Hz, 2H), 3.67 (t, J=5.9 Hz, 2H).

Step 6. 4-(2-(2((2-Chloroquinolin-7-yl)oxy)ethoxy) ethyl)morpholine

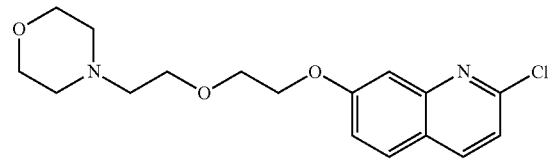 [SMILES: Clc1ccc2ccc(OCCOCCN3CCOCC3)cc2n1]

In a pressure vial under $N_2$, 2-chloro-7-(2-(2-chloroethoxy)ethoxy)quinolone (250 mg, 0.85 mmol), morpholine (0.075 mL, 0.85 mL) and $K_2CO_3$ (360 mg, 2.6 mmol) were dissolved in 3 mL anhydrous DMF and the reaction stirred at 100° C. overnight following the procedure of Example 29, Step 5. The sub-title compound was purified by chromatography using dichloromethane: methanol as solvent. Yield 40%. $^1$H NMR (400 MHz, $CDCl_3$) δ 8.00 (d, J=8.5 Hz, 1H), 7.68 (d, J=9.0 Hz, 1H), 7.33 (d, J=2.5 Hz, 1H), 7.25-7.20 (m, 2H), 4.30-4.20 (m, 2H), 3.93-3.85 (m, 2H), 3.71 (q, J=5.2, 4.7 Hz, 6H), 2.62 (t, J=5.7 Hz, 2H), 2.51 (dd, J=6.8, 2.9 Hz, 4H).

Step 7. 4-(2-(24(24(Trimethylsilyl)ethynyl)quinolin-7-yl)oxy)ethoxy)ethyl)morpholine

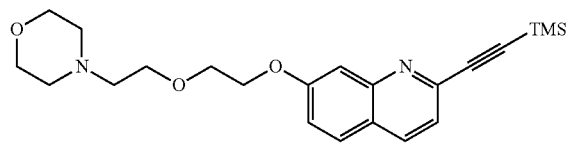 [SMILES: C[Si](C)(C)C#Cc1ccc2ccc(OCCOCCN3CCOCC3)cc2n1]

In a pressure vial under $N_2$ atmosphere, 4-(2-(2-((2-chloroquinolin-7-yl)oxy)ethoxy)ethyl)morpholine (125 mg, 0.37 mmol), trimethylsylyl acetylene (35 mg, 0.75 mmol), CuI (2.6 mg, 0.018 mmol), $Pd(PPh_3)_2Cl_2$ (13 mg, 0.018 mmol) and $Et_3N$ (0.14 mL, 1.88 mmol) were dissolved in 2 mL anhydrous acetonitrile. The reaction was stirred at 70° C. overnight. The mixture was filtered over diatomaceous earth and the sub-title product purified by flash chromatography using ethyl acetate: methanol as solvent. Yield 95%. $^1$H NMR (400 MHz, $CDCl_3$) δ 8.01 (d, J=8.3 Hz, 1H), 7.65 (d, J=8.9 Hz, 1H), 7.42-7.37 (m, 2H), 7.20 (dd, J=9.0, 2.5 Hz, 1H), 4.24 (dd, J=5.7, 3.7 Hz, 2H), 3.88 (dd, J=5.6, 3.8 Hz, 2H), 3.76-3.65 (m, 6H), 2.62 (t, J=5.7 Hz, 2H), 2.51 (t, J=4.7 Hz, 4H), 0.29 (s, 9H).

Step 8. 4-(2-(2-((2-Ethynylquinolin-7-yl)oxy)ethoxy)ethyl)morpholine

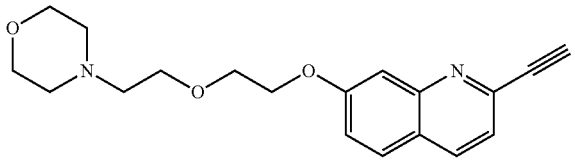 [SMILES: C#Cc1ccc2ccc(OCCOCCN3CCOCC3)cc2n1]

4-(2-(2-((2-((Trimethylsilyl)ethynyl)quinolin-7-yl)oxy)ethoxy)ethyl)morpholine (150 mg, 0.035 mmol) was dissolved in anhydrous methanol (4.5 mL). Next, K$_2$CO$_3$ (56 mg, 0.035 mmol) was added and the reaction stirred at room temperature for 1 h. The solution was filtered, solvent evaporated, and the product was used in the next step without further purification. Yield 95%. $^1$H NMR (400 MHz, CDCl$_3$) δ 8.04 (d, J=8.3 Hz, 1H), 7.68 (d, J=9.0 Hz, 1H), 7.42 (d, J=8.3 Hz, 1H), 7.39 (d, J=2.5 Hz, 1H), 7.23 (dd, J=8.9, 2.4 Hz, 1H), 4.28-4.24 (m, 2H), 3.90-3.87 (m, 2H), 3.74-3.66 (m, 7H), 2.62 (t, J=5.7 Hz, 2H), 2.54-2.48 (m, 4H).

Step 9. 4-(4-(7-(2-(2-Morpholinoethoxy)ethoxy)quinolin-2-yl)-1H-1,2,3-triazol-1-yl)phenol DMSO/H$_2$O (1:1) mixture was degassed and purged with N$_2$ for 10 min. Next, 4-(2-(2-((2-((trimethylsilyl)ethynyl)quinolin-7-yl)oxy)ethoxy)ethyl)morpholine was added followed by 4-iodophenol, trans-N,N'-dimethylcyclohexane-1,2-diamine, sodium ascorbate, cooper iodide and sodium azide. The reaction was stirred at room temperature for 30 min and then at 70° C. overnight. The reaction mixture was then diluted with ethyl acetate and extracted with H$_2$O and brine. The aqueous phase was extracted with ethyl acetate and the combined organic phases were combined and dried over Na$_2$SO$_4$. The product was purified by flash chromatography using dichloromethane:methanol as solvent. Yield 37%. $^1$H NMR (400 MHz, CDCl$_3$) δ 8.52 (s, 1H), 8.16 (s, 2H), 7.69 (d, J=8.9 Hz, 1H), 7.56-7.49 (m, 2H), 7.26 (s, 1H), 7.17 (dd, J=8.9, 2.5 Hz, 1H), 6.99-6.91 (m, 2H), 4.17-4.15 (m, 2H), 3.92-3.85 (m, 2H), 3.77-3.69 (m, 6H), 2.68 (t, J=5.5 Hz, 2H), 2.60-2.53 (m, 4H). $^{13}$C NMR (101 MHz, CDCl$_3$) δ 160.03, 157.25, 149.33, 147.16, 136.79, 136.74, 129.45, 128.84, 123.10, 121.82, 120.20, 119.70, 116.73, 116.56, 107.33, 69.54, 68.19, 67.34, 66.46, 58.46, 53.93. HRMS (ESI): calc for [M+H]$^+$ (C$_{25}$H$_{27}$N$_5$O$_4$) 462.2063, found 462.2113.

Example 30. 2-Fluoro-4-(4-(7-(2-(2-morpholinoethoxy)ethoxy)quinolin-2-yl)-1H-1,2,3-triazol-1-yl)phenol

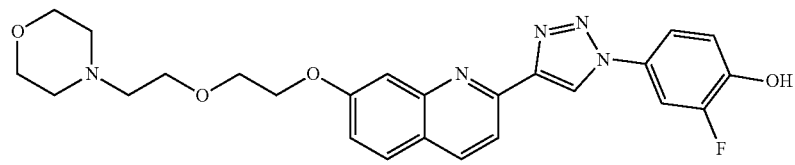 [SMILES: Oc1ccc(-n2cc(-c3ccc4ccc(OCCOCCN5CCOCC5)cc4n3)nn2)cc1F]

The title compound was prepared according to the procedure described for Example 29, substituting 2-fluoro-4-iodophenol for 4-iodophenol in Step 9. Yield 31%. $^1$H NMR (400 MHz, CDCl$_3$) δ 8.59 (s, 1H), 8.21-8.14 (m, 2H), 7.70 (d, J=8.9 Hz, 1H), 7.56 (d, J=10.6 Hz, 1H), 7.40 (d, J=9.1 Hz, 1H), 7.32 (s, 1H), 7.19 (dd, J=8.9, 2.4 Hz, 1H), 7.12 (t, J=8.8 Hz, 1H), 4.26-4.20 (m, 2H), 3.92-3.86 (m, 2H), 3.77-3.67 (m, 6H), 2.65 (t, J=5.6 Hz, 2H), 2.54 (d, J=4.8 Hz, 4H). $^{13}$C NMR (101 MHz, CDCl$_3$) δ 160.03, 159.08, 157.25, 149.33, 147.16, 136.79, 136.74, 129.45, 128.84, 124.28, 123.10, 121.82, 120.20, 119.70, 116.73, 116.56, 107.33, 69.54, 68.19, 67.34, 66.46, 58.46, 53.93. HRMS (ESI): calc for [M+H]$^+$ C$_{25}$H$_{26}$FN$_5$O$_4$ 480.1969, found 480.2029.

Example 31. 4-(4-(6-(2-Methoxyethoxy)quinazolin-2-yl)-1H-1,2,3-triazol-1-yl)phenol

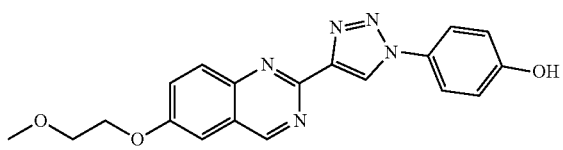 [SMILES: COCCOc1ccc2nc(-c3cn(-c4ccc(O)cc4)nn3)ncc2c1]

Step 1. 5-Methoxy-2-nitrobenzaldehyde

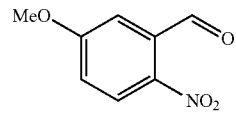

To a solution of 5-hydroxy-2-nitrobenzaldehyde (3 g, 18 mmol), K$_2$CO$_3$ (12.3 g, 74 mmol) in anhydrous DMF (60 mL) and MeI in ether (2.0 M, 18 mL) were added and stirred overnight at room temperature. After the conversion, the mixture was filtered, diluted with ethyl acetate, and washed with H$_2$O and sat NH$_4$Cl. The organic phase was dried over Na$_2$SO$_4$ to yield the sub-title compound which was used for the next step without further purification. Yield 99%. $^1$H NMR (400 MHz, CDCl$_3$) δ 10.48 (s, 1H), 8.16 (d, J=9.1 Hz, 1H), 7.32 (d, J=2.9 Hz, 1H), 7.15 (dd, J=9.1, 2.9 Hz, 1H), 3.95 (s, 3H).

Step 2. 2-(5-Methoxy-2-nitrophenyl)-1,3-dioxolane

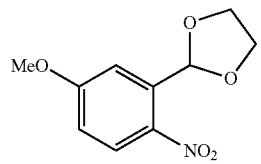

A solution of 5-methoxy-2-nitrobenzaldehyde (3.3 g, 18 mmol), ethylene glycol (2 mL), trimethyl orthoformate (2.3 mL) and p-TsOH (3.46 mg, 0.018 mmol) in anhydrous dichloromethane (75 mL) was stirred at room temperature for 24 h. The mixture was then washed with sat NaHCO₃ and brine, and the product purified by flash chromatography using hexanes: ethyl acetate as solvent. Yield 66%. ¹H NMR (400 MHz, CDCl₃) δ 8.02 (d, J=9.0 Hz, 1H), 7.29 (d, J=2.8 Hz, 1H), 6.91 (dd, J=9.0, 2.9 Hz, 1H), 6.56 (s, 1H), 4.09-3.99 (m, 4H), 3.89 (s, 3H).

Step 3. 2-(1,3-Dioxolan-2-yl)-4-methoxyaniline

To a solution of 2-(5-methoxy-2-nitrophenyl)-1,3-dioxolane (2.7 g, 11.9 mmol) in ethyl acetate (15 mL), PtO₂ (166 mg) and of AcONa (79 mg) were added under N₂. The suspension was stirred under H₂ atmosphere overnight. The resulting solution was filtered through diatomaceous earth and the product purified by flash chromatography using hexanes: ethyl acetate as solvent. Yield 81%. ¹H NMR (400 MHz, CDCl₃) δ 6.94 (d, J=2.9 Hz, 1H), 6.75 (dd, J=8.6, 3.0 Hz, 1H), 6.63 (d, J=8.6 Hz, 1H), 5.82 (s, 1H), 4.12-4.02 (m, 4H), 3.74 (s, 3H).

Step 4. Ethyl (2-(1,3-Dioxolan-2-yl)-4-methoxyphenyl)carbamate

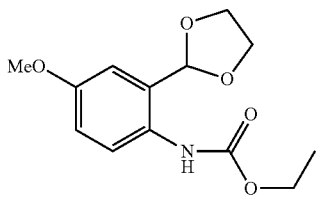 [SMILES: CCOC(=O)Nc1ccc(OC)cc1C1OCCO1]

To a solution of 2-(1,3-dioxolan-2-yl)-4-methoxyaniline (1.89 g, 9.7 mmol) in anhydrous THF (30 mL), Et₃N (1.1 mL) was added dropwise at 0° C. followed by the addition of ethyl chloroformate (1.12 mL). The reaction mixture was stirred at 0° C. for 15 min. After evaporation of the solvent, the crude residue was redissolved in dichloromethane and washed with H₂O. The sub-title product was purified by flash chromatography using hexanes: ethyl acetate as solvent. Yield 80%. ¹H NMR (400 MHz, CDCl₃) δ 7.81 (s, 1H), 7.49 (s, 1H), 7.00 (d, J=3.0 Hz, 1H), 6.88 (dd, J=8.9, 3.0 Hz, 1H), 5.85 (s, 1H), 4.20 (q, J=7.1 Hz, 2H), 4.14-4.02 (m, 4H), 3.78 (s, 3H), 1.30 (t, J=7.1 Hz, 3H).

Step 5. ethyl (2-Formyl-4-methoxyphenyl)carbamate

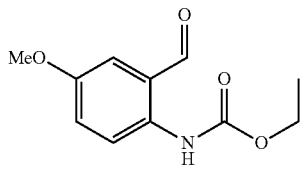 [SMILES: CCOC(=O)Nc1ccc(OC)cc1C=O]

To a solution of ethyl (2-(1,3-dioxolan-2-yl)-4-methoxyphenyl)carbamate (2.1 g, 8.0 mmol) in THF (23 mL), 20% HCl (3 mL) was added dropwise and the reaction was stirred at room temperature for 30 min. After neutralization with sat NaHCO₃ and extraction with ethyl acetate, the product was used in the next step without further purification. Yield 99%. ¹H NMR (400 MHz, CDCl₃) δ 10.27 (s, 1H), 8.39 (d, J=9.1 Hz, 1H), 7.17 (dd, J=9.1, 3.0 Hz, 1H), 7.12 (d, J=3.0 Hz, 1H), 4.21 (q, J=7.1 Hz, 2H), 3.84 (s, 3H), 1.31 (t, J=7.1 Hz, 3H).

Step 6. 6-Methoxyquinazolin-2(1H)-one

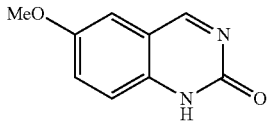

NH₃ in MeOH (2.0 M, 30 mL) was stirred at −78° C. for 1 h under N₂ atmosphere. Ethyl (2-formyl-4-methoxyphenyl)carbamate (1.8 g, 8.0 mmol) dissolved in dry MeOH (2 mL) was then added. Under high pressure conditions, the reaction was heated to 140° C. and stirred for 2 h. After cooling the reaction mixture to room temperature, and solvent evaporation, the crude residue was redissolved in cold MeOH and filtered. The brown powder obtained was used in the next step without further purification. Yield 64%. ¹H NMR (400 MHz, DMSO-d₆) δ 9.44 (d, J=2.2 Hz, 1H), 8.05-7.93 (m, 1H), 6.87 (d, J=8.0 Hz, 2H), 6.84-6.75 (m, 1H), 3.70 (s, 3H).

Step 7. 2-Chloro-6-methoxyquinazoline

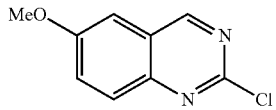 [SMILES: COc1ccc2nc(Cl)ncc2c1]

The sub-title compound was prepared according to the procedure described for Example 29, Step 3. Purification by flash chromatography using dichloromethane: methanol as solvent. Yield 82%. ¹H NMR (400 MHz, CDCl₃) δ 9.19 (s, 1H), 7.90 (d, J=9.2 Hz, 1H), 7.59 (dd, J=9.2, 2.8 Hz, 1H), 7.16 (d, J=2.7 Hz, 1H), 3.96 (s, 3H).

Step 8. 2-Chloroquinazolin-6-ol

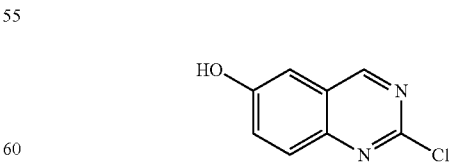

The sub-title compound was prepared according to the procedure described for Example 29, Step 4. Yield 70%. ¹H NMR (400 MHz, Methanol-d₄) δ 9.16 (s, 1H), 7.82 (d, J=9.2 Hz, 1H), 7.60 (dd, J=9.1, 2.7 Hz, 1H), 7.28 (d, J=2.7 Hz, 1H).

Step 9. 2-Chloro-6-(2-methoxyethoxy)quinazoline

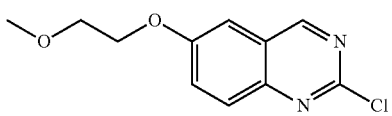 [SMILES: COCCOc1ccc2nc(Cl)ncc2c1]

In a pressure vial under N₂, 2-chloroquinazolin-6-ol (280 mg, 1.5 mmol), 1-bromo-2-methoxyethane (0.36 mL, 3.9 mmol) and K₂CO₃ (538 mg, 3.9 mmol) were stirred at 70° C. overnight. After dilution with ethyl acetate and washing with H₂O and sat NH₄Cl, the product was purified by flash chromatography using hexanes: ethyl acetate as solvent. Yield 30%. ¹H NMR (400 MHz, CDCl₃) δ 9.10 (s, 1H), 7.89 (d, J=8.7 Hz, 1H), 7.63 (dd, J=9.2, 2.7 Hz, 1H), 7.14 (d, J=2.7 Hz, 1H), 4.25 (t, J=4.5 Hz, 2H), 3.83 (t, J=4.6 Hz, 2H), 3.47 (s, 3H).

Step 10. 6-(2-Methoxyethoxy)-2-((trimethylsilyl)ethynyl)quinazoline

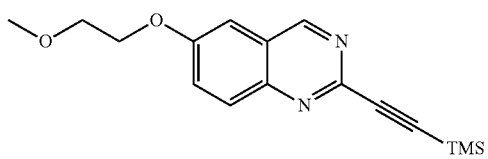 [SMILES: COCCOc1ccc2nc(C#C[Si](C)(C)C)ncc2c1]

The sub-title compound was prepared according to the procedure described for Example 29, Step 7. Yield 76%. ¹H NMR (400 MHz, CDCl₃) δ 9.23 (s, 1H), 7.95 (d, J=9.3 Hz, 1H), 7.61 (dd, J=9.3, 2.8 Hz, 1H), 7.14 (d, J=2.7 Hz, 1H), 4.29-4.22 (m, 2H), 3.86-3.80 (m, 2H), 3.48 (s, 3H), 0.31 (s, 9H).

Step 11. 2-Ethynyl-6-(2-methoxyethoxy)quinazoline

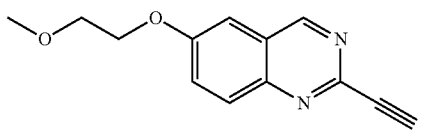 [SMILES: C#Cc1ncc2cc(OCCOC)ccc2n1]

The sub-title compound was prepared according to the procedure described for Example 29, Step 8. Yield 99%. ¹H NMR (400 MHz, CDCl₃) δ 9.25 (s, 1H), 7.95 (d, J=9.2 Hz, 1H), 7.63 (dd, J=9.2, 2.7 Hz, 1H), 7.15 (d, J=2.7 Hz, 1H), 4.30-4.23 (m, 2H), 3.86-3.81 (m, 2H), 3.48 (s, 3H), 3.14 (s, 1H).

Step 12. 4-(4-(6-(2-Methoxyethoxy)quinazolin-2-yl)-1H-1,2,3-triazol-1-yl)phenol The title compound was prepared according to the procedure described for Example 29, Step 9. Yield 41%. ¹H NMR (400 MHz, CDCl₃) δ 9.36 (s, 1H), 8.67 (s, 1H), 8.06 (d, J=9.2 Hz, 1H), 7.69-7.66 (m, 2H), 7.63 (dd, J=9.2, 2.8 Hz, 1H), 7.19 (d, J=2.8 Hz, 1H), 7.04-6.99 (m, 2H), 4.31-4.26 (m, 2H), 3.87-3.82 (m, 2H), 3.49 (s, 3H). ¹³C NMR (101 MHz, CDCl₃) δ 159.24, 157.75, 156.91, 156.13, 153.45, 146.79, 130.03, 130.01, 127.94, 122.80, 122.78, 122.47, 116.55, 104.90, 70.74, 67.85, 59.32. HRMS (ESI): calc for [M+H]⁺ C₁₉H₁₇N₅O₃ 364.1331, found 364.1390.

Example 32. 3-((2-(1-(3-Fluoro-4-hydroxyphenyl)-1H-1,2,3-triazol-4-yl)quinolin-5-yl)oxy)benzoic acid (3bb)

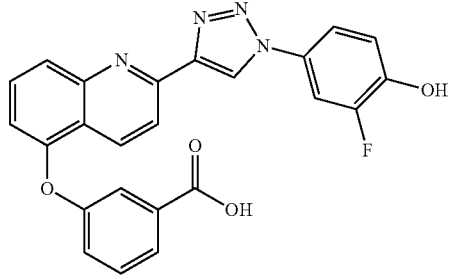 [SMILES: O=C(O)c1cccc(Oc2cccc3nc(-c4cn(-c5ccc(O)c(F)c5)nn4)ccc23)c1]

Step 1. Methyl 3-((2-(1-(3-fluoro-4-hydroxyphenyl)-1H-1,2,3-triazol-4-yl)quinolin-5-yl)oxy)benzoate (3bb)

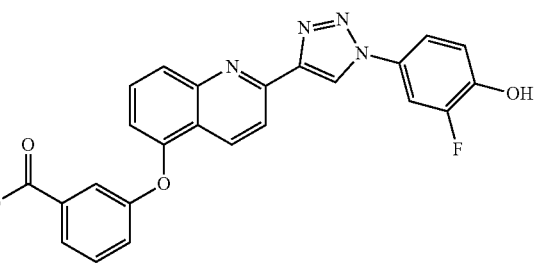

2-Fluoro-4-iodophenol (1.0 mmol) followed by trans-N,N-dimethylcyclohexane-1,2-diamine (0.2 mmol), sodium ascorbate (0.4 mmol), copper iodide (0.2 mmol) and sodium azide (1.0 mmol,) were added to DMSO (2.5 mL). The mixture was stirred at 70° C. for 2 h and then Intermediate 52 (13bb') (0.5 mmol) followed by H₂O (0.5 mL) were added to the reaction which was stirred overnight. The solution was then diluted with EtOAc and extracted with H₂O (×1) and brine (×1). The aqueous phase was washed with EtOAc, the organic phases were combined and dried with Na₂SO₄ and solvent evaporated. The crude product was purified by flash chromatography (DCM/MeOH) to give the sub-title product 3bb' (Yield: 75%). ¹H NMR (600 MHz, DMSO-d₆) δ 10.49 (s, 1H), 9.43 (s, 1H), 8.64 (d, J=8.6 Hz, 1H), 8.33 (d, J=8.4 Hz, 1H), 7.97 (d, J=11.5 Hz, 1H), 7.90 (d, J=8.2 Hz, 1H), 7.79 (t, J=7.1 Hz, 2H), 7.74 (d, J=8.3 Hz, 1H), 7.61 (t, J=7.5 Hz, 1H), 7.57 (s, 1H), 7.47 (d, J=7.7 Hz, 1H), 7.16 (t, J=8.6 Hz, 1H), 7.13 (d, J=7.3 Hz, 1H), 3.83 (s, 3H).

Step 2. 3-((2-(1-(3-Fluoro-4-hydroxyphenyl)-1H-1,2,3-triazol-4-yl)quinolin-5-yl)oxy)benzoic acid (3bb)

Compound 3bb' from Step 1 (0.04 mmol) was dissolved in dioxane (3 mL) and 2N NaOH (0.5 mL) was added to the solution which was then stirred at room temperature overnight. Upon completion the reaction mixture was concentrated to around 1 mL dioxane, diluted with EtOAc (10 mL) and the pH was adjusted to about 3. The aqueous phase was washed with EtOAc (3×10 mL), dried with $Na_2SO_4$ and evaporated. The residue was purified by silica gel chromatography (DCM/MeOH) to give the title product (Yield: 75%). $^1$H NMR (600 MHz, DMSO-$d_6$) δ 10.70 (s, 1H), 9.43 (s, 1H), 8.65 (d, J=8.7 Hz, 1H), 8.33 (d, J=8.7 Hz, 1H), 7.96 (d, J=11.6 Hz, 1H), 7.88 (d, J=8.4 Hz, 1H), 7.81-7.72 (m, 3H), 7.52 (s, 2H), 7.37 (d, J=7.5 Hz, 1H), 7.18 (t, J=9.0 Hz, 1H), 7.10 (d, J=7.6 Hz, 1H). $^{13}$C NMR (151 MHz, DMSO-$d_6$) δ 167.30, 157.30, 152.45, 151.97, 151.00, 150.36, 149.15, 148.23, 146.22, 146.14, 131.95, 130.79, 130.68, 128.63, 128.57, 125.09, 124.69, 122.63, 121.11, 119.04, 118.92, 118.68, 118.66, 117.40, 117.38, 114.46, 109.93, 109.78. HRMS (ESI): calc. for [M+H]$^+$ ($C_{24}H_{15}FN_4O_4$) 443.1156, found 443.1154.

Example 33. 2,6-Difluoro-4-(4-(6-(2-(2-morpholinoethoxy)ethoxy)quinolin-2-yl)-1H-1,2,3-triazol-1-yl)phenol

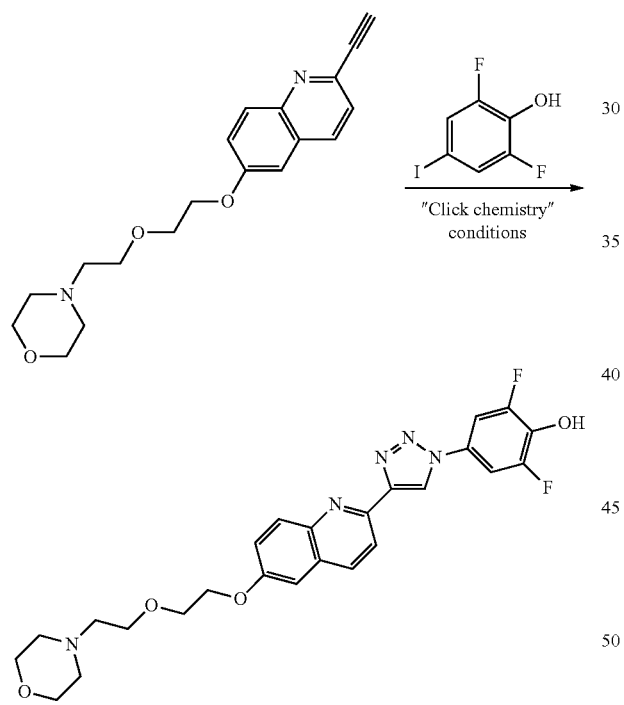

The title compound was prepared according to standard "click chemistry" conditions (e.g., reaction in the presence of sodium azide, copper iodide, sodium ascorbate, and (1R,2R)—N$^1$,N$^2$-dimethylcyclohexane-1,2-diamine) as described herein. $^1$H NMR (400 MHz, DMSO-$d_6$) δ 9.36 (s, 1H), 8.36 (d, J=8.6 Hz, 1H), 8.20 (d, J=8.6 Hz, 1H), 7.92 (d, J=10.0 Hz, 1H), 7.89-7.84 (m, 2H), 7.45-7.41 (m, 2H), 4.28-4.19 (m, 2H), 3.80-3.78 (m, 2H), 3.60 (t, J=5.8 Hz, 2H), 3.55-3.47 (m, 4H), 2.49-2.46 (m, 2H), 2.38 (t, J=4.6 Hz, 4H). $^{13}$C NMR (151 MHz, DMSO-$d_6$) δ 156.57, 153.09, 153.03, 151.48, 151.42, 148.40, 147.31, 143.44, 136.09, 134.36, 129.99, 128.59, 127.16, 122.82, 121.55, 118.63, 105.04, 104.86, 68.68, 68.23, 67.52, 66.11, 57.58, 53.66. HRMS (ESI): calc for [M+H]$^+$ ($C_{25}H_{25}F_2N_5O_4$) 498.1875, found 498.1940.

Example 34. 4-(4-(6-(2-(2-Aminoethoxy)ethoxy)quinolin-2-yl)-1H-1,2,3-triazol-1-yl)-2-fluorophenol

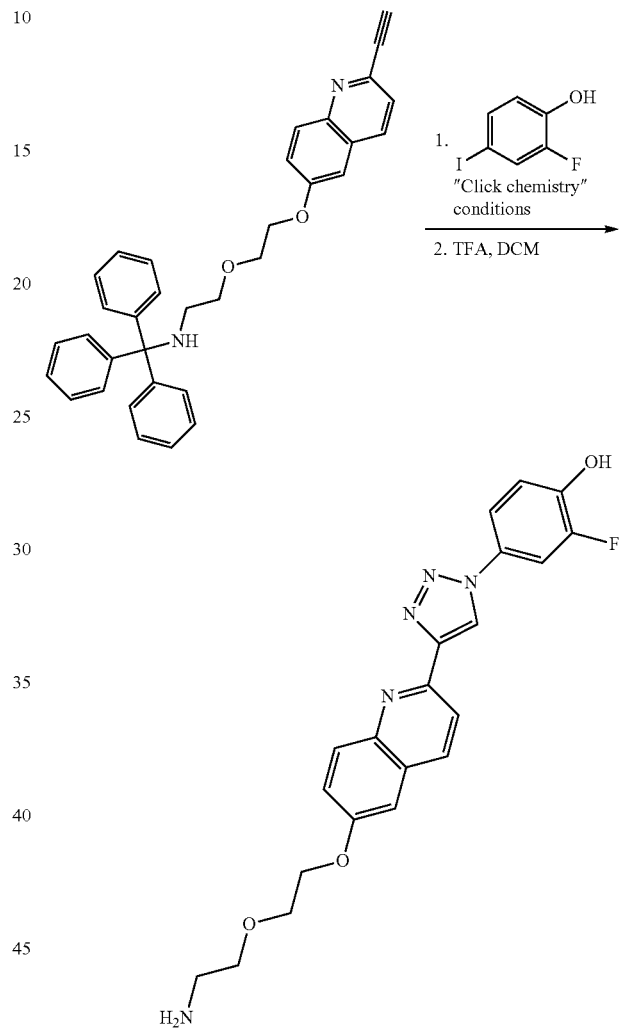

The title compound was prepared according to standard "Click chemistry" conditions (e.g., reaction in the presence of sodium azide, copper iodide, sodium ascorbate, and (1R,2R)—N$^1$,N$^2$-dimethylcyclohexane-1,2-diamine) as described herein and subsequent amine deprotection in the presence of trifluoroacetic acid. $^1$H NMR (400 MHz, DMSO-$d_6$) δ 10.51 (s, 1H), 9.30 (s, 1H), 8.39 (d, J=8.6 Hz, 1H), 8.24 (d, J=8.6 Hz, 1H), 7.99-7.91 (m, 2H), 7.84 (s, 2H), 7.76-7.69 (m, 1H), 7.48-7.42 (m, 2H), 7.16 (t, J=9.0 Hz, 1H), 4.35-4.27 (m, 2H), 3.90 (t, J=4.3 Hz, 2H), 3.71 (t, J=5.2 Hz, 2H), 3.08-3.00 (m, 2H). $^{13}$C NMR (151 MHz, DMSO-$d_6$) δ 156.4, 150.7 (d, J=242.8 Hz), 148.2, 147.5, 145.6 (d, J=11.9 Hz), 143.5, 136.1, 130.0, 128.5, 128.3 (d, J=8.8 Hz), 122.7, 121.4, 118.7, 118.2 (d, J=3.5 Hz), 116.9 (d, J=3.1 Hz), 109.3 (d, J=23.2 Hz), 106.7, 68.83, 67.4, 66.8, 38.6. HRMS (ESI): calc for [M+H]$^+$ ($C_{21}H_{20}FN_5O_3$) 410.1550, found 410.1625.

Example 35. 4-((2-(1-(3-Fluoro-4-hydroxyphenyl)-1H-1,2,3-triazol-4-yl)quinolin-5-yl)oxy)benzoic acid (3aa)

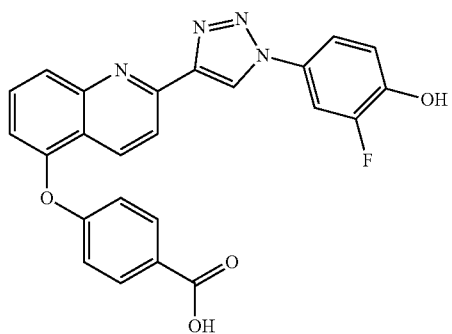 [SMILES: O=C(O)c1ccc(Oc2cccc3nc(-c4cn(-c5ccc(O)c(F)c5)nn4)ccc23)cc1]

The title product was prepared according to the procedure described for Example 32, substituting Intermediate 51 (13aa') for Intermediate 52 (13bb') (Yield: 61%). $^1$H NMR (600 MHz, DMSO-$d_6$) δ 12.89 (s, 1H), 10.57 (s, 1H), 9.43 (s, 1H), 8.56 (d, J=8.7 Hz, 1H), 8.38-8.29 (m, 1H), 7.97 (t, J=7.6 Hz, 3H), 7.93 (d, J=8.4 Hz, 1H), 7.82 (t, J=8.0 Hz, 1H), 7.74 (d, J=8.5 Hz, 1H), 7.24 (d, J=7.4 Hz, 1H), 7.16 (dd, J=20.8, 8.6 Hz, 3H). $^{13}$C NMR (151 MHz, DMSO-$d_6$) δ 167.53, 159.36, 151.60, 150.56, 149.99, 148.74, 147.78, 146.09, 146.01, 131.49, 130.38, 128.00, 127.94, 124.52, 122.18, 120.76, 118.65, 118.31, 118.28, 117.34, 116.96, 116.93, 114.60, 109.47, 109.31. HRMS (ESI): calc. for [M+H]$^+$ (C$_{24}$H$_{15}$FN$_4$O$_4$) 443.1156, found 443.1153.

The following additional examples were prepared by methods analogous to those described herein.

Example 36. 3-((2-(1-(3,4-Difluorophenyl)-1H-1,2,3-triazol-4-yl)quinolin-5-yl)oxy)benzoic acid

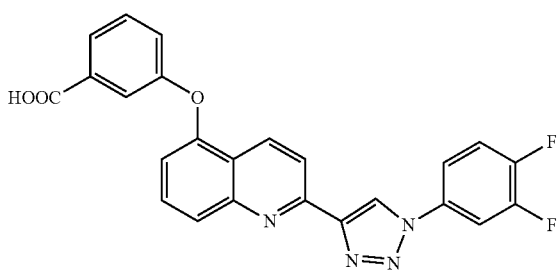 [SMILES: O=C(O)c1cccc(Oc2cccc3nc(-c4cn(-c5ccc(F)c(F)c5)nn4)ccc23)c1]

The title product was prepared according to the procedure described for Example 32 replacing 2-fluoro-4-iodophenol by 1,2-difluoro-4-iodobenzene in the "click chemistry" step. $^1$H NMR (600 MHz, DMSO-$d_6$) δ 9.57 (s, 1H), 8.67 (d, J=8.7 Hz, 1H), 8.31 (d, J=8.9 Hz, 2H), 8.00 (d, J=8.9 Hz, 1H), 7.82 (d, J=8.6 Hz, 1H), 7.77-7.70 (m, 2H), 7.65 (d, J=7.6 Hz, 1H), 7.44 (s, 1H), 7.34 (t, J=7.9 Hz, 1H), 7.13 (d, J=7.7 Hz, 1H), 6.99 (d, J=7.6 Hz, 1H). $^{13}$C NMR (151 MHz, dmso) δ 167.4, 156.2, 152.7, 150.2, 149.6 (dd, J=247.6, 13.7 Hz), 149.4 (dd, J=247.3, 12.1 Hz), 148.7, 148.2, 133.2 (dd, J=8.8, 2.7 Hz), 131.7, 130.4, 129.0, 124.7, 123.6, 122.7, 120.7, 118.8 (d, J=18.6 Hz), 118.7, 118.4, 117.4 (dd, J=6.7, 3.3 Hz), 113.5, 110.6 (d, J=22.1 Hz). HRMS (ESI): calc for [M+H]$^+$ C$_{24}$H$_{14}$F$_2$N$_4$O$_3$ 445.1107 found 445.1112.

Example 37. 4-(4-(5-(3-(Aminomethyl)phenoxy)quinolin-2-yl)-1H-1,2,3-triazol-1-yl)-2-fluorophenol

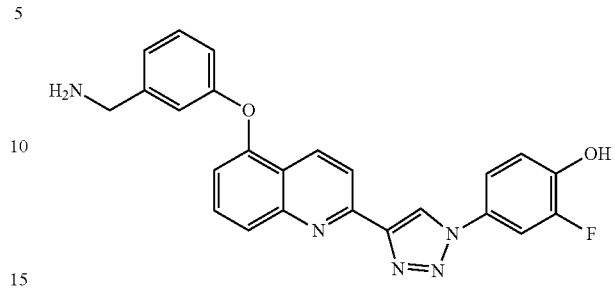

The title product was prepared according to the procedure described for Example 32 replacing methyl bromobenzoate by (3-bromophenyl)methanamine protected with Boc in the reaction with 5-hydroxyquinoline to give the intermediate analog to 13bb' with phenyl methanamine. Final deprotection of Boc group yielded the title compound. $^1$H NMR (600 MHz, DMSO-$d_6$) δ 9.43 (s, 1H), 8.63 (d, J=8.1 Hz, 1H), 8.34 (d, J=8.2 Hz, 1H), 8.22 (s, 2H), 7.97 (d, J=11.3 Hz, 1H), 7.87 (d, J=7.7 Hz, 1H), 7.81-7.72 (m, 2H), 7.52-7.46 (m, 1H), 7.30 (d, J=8.0 Hz, 2H), 7.23-7.14 (m, 2H), 7.06 (d, J=6.3 Hz, 1H), 4.04 (s, 2H). NMR (151 MHz, dmso) δ 156.8, 152.1, 150.73 (d, J=242.7 Hz), 150.6, 148.7, 147.8, 145.7 (d, J=11.8 Hz), 136.5, 131.4, 130.5, 128.2 (d, J=8.7 Hz), 124.4, 122.2, 120.6, 119.0, 118.7, 118.6, 118.4, 118.2 (d, J=3.4 Hz), 116.9 (d, J=3.3 Hz), 116.4, 113.6, 109.4 (d, J=23.2 Hz), 41.9. HRMS (ESI): calc for [M+H]$^+$ C$_{24}$H$_{18}$FN$_5$O$_2$ 428.1517 found 428.1515.

Example 38. 2-Fluoro-4-(4-(5-(3-(2-(2-morpholinoethoxy)ethoxy)phenoxy)quinolin-2-yl)-1H-1,2,3-triazol-1-yl)phenol

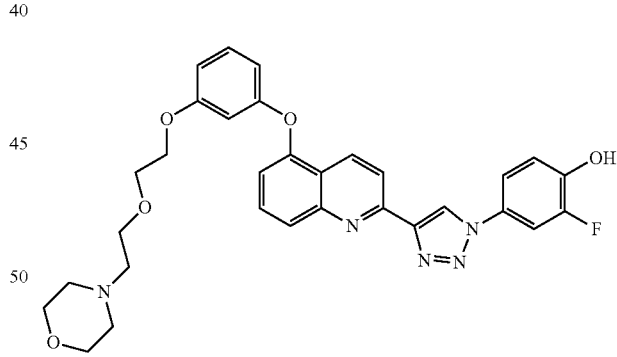

The title product was prepared according to the procedure described for Example 32 replacing methyl bromobenzoate by 4-(2-(2-(3-bromophenoxy)ethoxy)ethyl)morpholine, which is obtained following the synthesis of 4-(2-(2-((2-Chloroquinolin-7-yl)oxy)ethoxy)ethyl)morpholine. $^1$H NMR (600 MHz, DMSO-$d_6$) δ 10.46 (s, 1H), 9.40 (s, 1H), 8.61 (d, J=8.5 Hz, 1H), 8.30 (d, J=8.5 Hz, 1H), 7.99-7.92 (m, 1H), 7.82 (d, J=8.5 Hz, 1H), 7.73 (t, J=8.5 Hz, 2H), 7.30 (t, J=8.2 Hz, 1H), 7.14 (t, J=9.0 Hz, 1H), 7.03 (d, J=7.7 Hz, 1H), 6.77 (d, J=8.4 Hz, 1H), 6.71 (d, J=2.9 Hz, 1H), 6.65 (d, J=8.2 Hz, 1H), 4.09-4.03 (m, 2H), 3.67 (t, J=4.2 Hz, 2H), 3.53 (t, J=5.9 Hz, 2H), 3.49 (t, J=4.7 Hz, 4H), 2.41 (d, J=6.1 Hz, 2H), 2.34 (s, 4H). $^{13}$C NMR (151 MHz, dmso) δ 160.1, 157.8, 151.5, 150.7 (d, J=242.6 Hz), 149.9, 148.7, 147.8, 145.6 (d, J=11.8 Hz), 131.5, 130.8, 130.3, 128.3 (d, J=8.6 Hz), 123.9, 122.2, 120.6, 118.5, 118.2 (d, J=3.8 Hz), 117.0 (d, J=3.5 Hz), 113.5, 110.7, 110.3, 109.5 (d, J=23.3 Hz), 105.3, 68.7, 68.2, 67.3, 66.2, 57.6, 53.7. HRMS (ESI): calc for [M+H]+ C31H30FN5O5 572.2304 found 572.2309.

Example 39. 4-((2-(1-(3-Fluoro-4-hydroxyphenyl)-1H-1,2,3-triazol-4-yl)quinolin-8-yl)oxy)benzoic acid

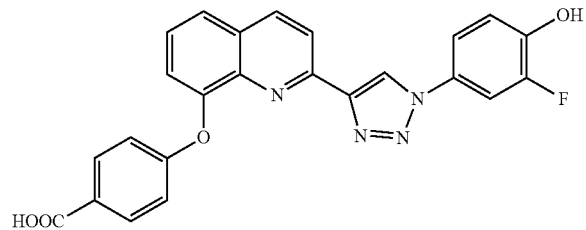 [SMILES: O=C(O)c1ccc(Oc2cccc3ccc(-c4cn(-c5ccc(O)c(F)c5)nn4)nc23)cc1]

The title product was prepared according to the procedure described for Example 32 starting from 2-chloroquinolin-8-ol and methyl 4-iodobenzoate instead of 5-hydroxyquinoline and methyl 4-bromobenzoate to yield the corresponding intermediates. $^1$H NMR (600 MHz, DMSO-d$_6$) δ 8.75 (s, 1H), 8.58 (d, J=8.6 Hz, 1H), 8.30 (d, J=8.5 Hz, 1H), 7.93 (d, J=8.2 Hz, 1H), 7.88 (d, J=8.2 Hz, 1H), 7.84 (d, J=11.6 Hz, 1H), 7.62 (t, J=7.9 Hz, 1H), 7.57 (d, J=8.8 Hz, 1H), 7.46 (d, J=7.6 Hz, 1H), 7.17 (t, J=9.0 Hz, 1H), 7.09 (d, J=8.2 Hz, 2H). $^{13}$C NMR (151 MHz, dmso) δ 167.6, 161.8, 151.7, 151.2 (d, J=242.9 Hz), 149.7, 148.4, 146.4 (d, J=11.7 Hz), 140.7, 138.1, 131.7, 129.6, 128.3 (d, J=8.8 Hz), 127.3, 124.7, 122.2, 120.0, 119.4, 118.7 (d, J=3.1 Hz), 117.9, 117.5 (d, J=2.5 Hz), 109.9 (d, J=23.1 Hz). HRMS (ESI): calc for [M+H]+ C24H15FN4O4 443.1150 found 443.1074.

Example 40. 3-((2-(1-(3-Fluoro-4-hydroxyphenyl)-1H-1,2,3-triazol-4-yl)quinolin-8-yl)oxy)benzoic acid

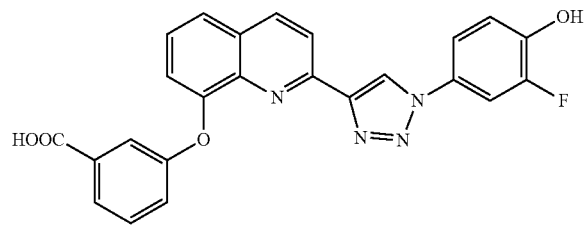 [SMILES: O=C(O)c1cccc(Oc2cccc3ccc(-c4cn(-c5ccc(O)c(F)c5)nn4)nc23)c1]

The title product was prepared according to the procedure described for Example 39 replacing 4-methyl iodobenzoate by 3-methyl iodobenzoate in the initial step. $^1$H NMR (600 MHz, DMSO-d$_6$) δ 8.73 (s, 1H), 8.56 (d, J=8.5 Hz, 1H), 8.28 (d, J=8.5 Hz, 1H), 7.91 (d, J=8.3 Hz, 2H), 7.86 (d, J=8.2 Hz, 1H), 7.82 (d, J=11.6 Hz, 1H), 7.60 (t, J=7.8 Hz, 1H), 7.56 (d, J=8.9 Hz, 1H), 7.44 (d, J=7.5 Hz, 1H), 7.15 (t, J=9.0 Hz, 1H), 7.07 (d, J=8.2 Hz, 2H). $^{13}$C NMR (151 MHz, dmso) δ 166.8, 158.4, 151.7, 150.7 (d, J=242.9 Hz), 149.3, 147.9, 145.7 (d, J=11.9 Hz), 140.3, 137.6, 132.5, 130.2, 129.2, 128.3 (d, J=8.8 Hz), 126.9, 124.2, 123.9, 123.1, 121.8, 119.2, 119.1, 118.4, 118.2 (d, J=3.6 Hz), 117.1 (d, J=3.2 Hz), 109.6 (d, J=23.2 Hz). HRMS (ESI): calc for [M+H]+ C24H15FN4O4 443.1150 found 1157.

Examples 41-45 were obtained from 2-chloroquinolin-7-ol or 2-chloroquinolin-6-ol and the corresponding bromo ethyl ester following General Method G to give the appropriate intermediates. 2-Fluoro-4-iodophenol or 4-iodophenol were used in the "click chemistry" step to give the corresponding ethyl esters. Final hydrolysis in the presence of 2N NaOH yielded the desired final compounds.

Example 41. 2-((2-(1-(3-Fluoro-4-hydroxyphenyl)-1H-1,2,3-triazol-4-yl)quinolin-7-yl)oxy)acetic acid

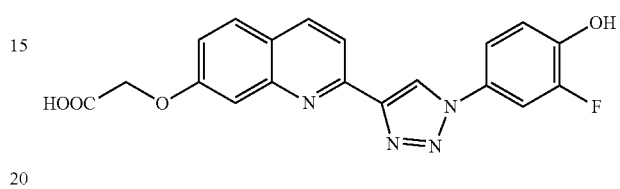

$^1$H NMR (400 MHz, DMSO-d$_6$) δ 9.40 (s, 1H), 8.38 (d, J=8.9 Hz, 1H), 8.10 (t, J=7.5 Hz, 1H), 7.97-7.86 (m, 2H), 7.75 (dd, J=19.4, 8.5 Hz, 1H), 7.26 (d, J=13.7 Hz, 2H), 7.16 (d, J=12.9 Hz, 1H), 4.45 (s, 2H). $^{13}$C NMR (126 MHz, dmso) δ 162.0, 151.5 (d, J=245.4 Hz), 149.4, 148.8, 146.7, 145.0 (d, J=10.6 Hz), 141.2, 139.2, 129.8, 128.6 (d, J=8.7 Hz), 128.2, 122.2, 120.7, 118.2 (d, J=3.7 Hz), 116.7 (d, J=2.5 Hz), 111.7, 109.2 (d, J=2.7 Hz), 106.5, 64.7. HRMS (ESI): calc for [M+H]$^1$ C19H13FN4O4 381.0994 found 381.0104.

Example 42. 4-((2-(1-(3-Fluoro-4-hydroxyphenyl)-1H-1,2,3-triazol-4-yl)quinolin-7-yl)oxy)butanoic acid

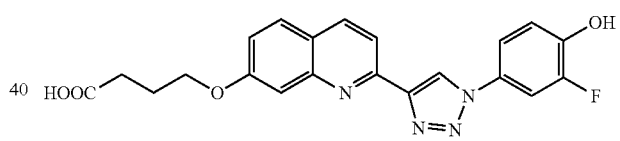

$^1$H NMR (400 MHz, DMSO-d$_6$) δ 9.30 (s, 1H), 8.40 (d, J=8.5 Hz, 1H), 8.11 (dd, J=8.5, 2.4 Hz, 1H), 7.95-7.83 (m, 2H), 7.67 (d, J=8.8 Hz, 1H), 7.36 (s, 1H), 7.25 (d, J=8.9 Hz, 1H), 7.18 (t, J=9.2 Hz, 1H), 4.18 (t, J=6.3 Hz, 2H), 2.38 (t, J=7.3 Hz, 2H), 2.03 (quint, J=6.8 Hz, 2H). $^{13}$C NMR (101 MHz, DMSO-d$_6$) δ 177.8, 161.5, 154.7, 151.0 (d, J=238.7 Hz), 149.9, 148.2, 146.6, 145.7 (d, J=19.3 Hz), 136.9, 129.2 (d, J=8.1 Hz), 127.7, 122.5, 121.7, 118.4 (d, J=3.9 Hz), 116.8 (d, J=2.1 Hz), 116.0, 109.2, (d, J=21.0 Hz), 107.4, 67.2, 31.0, 24.5. HRMS (ESI): calc for [M+H]+ C21H17FN4O4 409.1307 found 409.1466.

Example 43. 4-((2-(1-(3-Fluoro-4-hydroxyphenyl)-1H-1,2,3-triazol-4-yl)quinolin-6-yl)oxy)butanoic acid

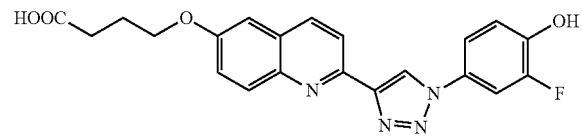 [SMILES: O=C(O)CCCOc1ccc2nc(-c3cn(-c4ccc(O)c(F)c4)nn3)ccc2c1]

$^1$H NMR (400 MHz, DMSO-d$_6$) δ 9.27 (s, 1H), 8.36 (d, J=8.6 Hz, 1H), 8.21 (d, J=8.6 Hz, 1H), 8.00-7.85 (m, 2H), 7.69 (ddd, J=9.1, 2.6, 1.3 Hz, 1H), 7.44-7.42 (m, 2H), 7.17 (t, J=9.0 Hz, 1H), 4.15 (t, J=6.5 Hz, 2H), 2.41 (t, J=7.3 Hz, 2H), 2.03 (p, J=6.9 Hz, 2H). $^{13}$C NMR (101 MHz, DMSO-d$_6$) δ 174.4, 156.6, 151.8 (d, J=262.5 Hz), 148.2, 147.4, 146.5 (d, J=14.0 Hz), 143.4, 136.0, 130.0, 128.6, 128.3 (d, J=8.5 Hz), 122.8, 121.3, 118.6, 118.3 (d, J=3.9 Hz), 116.8 (d, J=2.4 Hz), 109.3 (d, J=20.0 Hz), 106.7, 67.3, 30.7, 24.4. HRMS (ESI): calc for [M+H]$^1$ 409.1307. found 409.1466.

Example 44. 2-(2-((2-(1-(3-Fluoro-4-hydroxyphenyl)-1H-1,2,3-triazol-4-yl)quinolin-6-yl)oxy)ethoxy)acetic acid

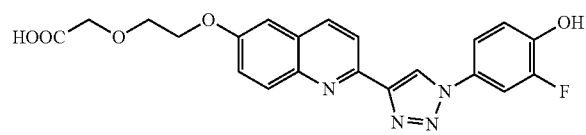 [SMILES: O=C(O)COCCOc1ccc2nc(-c3cn(-c4ccc(O)c(F)c4)nn3)ccc2c1]

$^1$H NMR (400 MHz, DMSO-d$_6$) δ 12.66 (s, 1H), 10.46 (s, 1H), 9.32 (s, 1H), 8.38 (d, J=8.6 Hz, 1H), 8.23 (d, J=8.6 Hz, 1H), 7.97-7.93 (m, 2H), 7.76-7.69 (m, 1H), 7.47-7.44 (m, 2H), 7.16 (t, J=9.0 Hz, 1H), 4.32-4.25 (m, 2H), 4.14 (s, 2H), 3.92-3.90 (m, 2H). $^{13}$C NMR (101 MHz, DMSO-d$_6$) δ 171.6, 156.5, 150.2 (d, J=242.5 Hz), 148.1, 147.4, 145.6 (d, J=10.5 Hz), 143.3, 136.2, 129.9, 128.5, 128.3 (d, J=8.8 Hz), 122.8, 121.5, 118.7, 118.2 (d, J=3.2 Hz), 116.9 (d, J=2.8 Hz), 109.3 (d, J=23.5 Hz), 106.8, 68.9, 67.7, 67.6. HRMS (ESI): calc for [M+H]$^+$ C$_{21}$H$_{17}$FN$_4$O$_5$ 425.1256 found 425.1455.

Example 45. 3-(2-(1-(4-hydroxyphenyl)-1H-1,2,3-triazol-4-yl)quinolin-6-yl)propanoic acid

$^1$H NMR (400 MHz, DMSO-d$_6$) δ 13.09 (s, 1H), 9.96 (s, 1H), 9.21 (s, 1H), 8.36 (d, J=8.5 Hz, 1H), 8.20 (d, J=8.6 Hz, 1H), 7.94 (d, J=9.2 Hz, 1H), 7.81 (d, J=8.4 Hz, 2H), 7.46 (d, J=8.3 Hz, 1H), 7.37 (s, 1H), 6.94 (d, J=8.3 Hz, 2H), 4.83 (s, 2H). $^{13}$C NMR (101 MHz, dmso) δ 169.86, 157.91, 155.72, 148.00, 147.86, 143.54, 136.10, 130.03, 128.69, 128.30, 122.43, 122.08, 121.27, 118.70, 116.03, 107.13, 64.76, 39.52, 39.31, 39.10, 38.89. HRMS (ESI): calc for [M+H]$^+$ C$_{19}$H$_{14}$N$_4$O$_4$ 363.1088 found 363.1093.

Example A. Protein Expression and Purification

Recombinant human MIF (rhMIF) was expressed as previously reported (Bernhagen et al., *Proc. Natl. Acad. Sci. USA*, 2005, 102, 6665-6670). *E. coli* cells were pelleted by centrifugation and stored at −80° C. The purification followed published protocols (see Bernhagen et al., *Proc. Natl. Acad. Sci. USA*, 2005, 102, 6665-6670; Sun et al., *Proc. Natl. Acad. Sci.* 1996, 93, 5191-5196) using modified conditions. Cell pellets were re-suspended in a lysis buffer containing 20 mM Tris-HCl pH 7.5, 20 mM sodium chloride, 10% glycerol, 2 mM magnesium chloride, and 0.2× cOmplete™ EDTA-free protease inhibitor cocktail (Roche), lysed by sonication and centrifuged at 27,000×g for 30 min. The supernatant was filtered through a 0.22 µm syringe filter and applied to Hi-Trap SP HP and Hi-Trap Q SP columns (GE Healthcare) in tandem. As rhMIF bound to neither ion-exchange resin, the flow-through was collected, being sufficiently pure (~90%) for crystallography. Higher purity was achieved by size-exclusion chromatography on a Superdex 200 16/60 column (GE Healthcare). The resulting rhMIF was assessed by SDS gel electrophoresis to be of sufficiently high purity (>95%) for tautomerase assays. Pure protein was concentrated to 30.6 mg/mL in 20% glycerol and stored at −80° C.

Example B. Inhibition of Tautomerase Activity of Human MIF

Inhibition of the tautomerase activity of MIF was measured using 4-hydroxyphenyl pyruvic acid (HPP) as substrate, largely following previously reported protocols (Taylor et al., *Biochemistry*, 1999, 38, 7444-7452). HPP was dissolved in 0.5 M acetate buffer, pH 6.0 to a final concentration of 10 mM and incubated overnight at room temperature to allow equilibration of the keto and enol forms. MIF (6 µL) was premixed in 500 mM boric acid, pH 6.2 (142 µL) and transferred to a transparent U bottom 96-well plate to a final concentration of 50 nM MIF. At this concentration high signal-to-noise and linearity were observed after analysis of progress curves for enol production at different protein concentrations. Inhibitors were dissolved in DMSO to 10 mM and an initial screen was performed. For compounds that showed ca. 25% or greater inhibition at 10 µM, an inhibition constant, was measured.

Compounds were placed into wells (2 µL) at 6 different concentrations and incubated for 30 minutes until the assay was started by addition of HPP (504) at two concentrations (1.0 and 2.5 mM). The negative control was MIF incubated with DMSO vehicle, which in all assays was 1% and did not influence tautomerase activity. MIF activity was monitored at 305 nm for formation of the borate-enol complex using an Infinite F500 plate reader (TECAN, Morrisville, N.C.) for 175 seconds. Calculation of initial velocities and the non-linear regression analyses for the enzyme kinetics were repeated three times with the program Prism6 (GraphPad, La Jolla, Calif.).

Data obtained for the Example compounds, obtained using the methods described in Example B, are provided in Table 3. Results are also included for a reference compound ISO-1 (Chang, K. F.; Al-Abed, Y. *Bioorg. Med. Chem. Lett.* 2006, 16, 3376-3379; Balachandran, S. et al. *Bioorg. Med. Chem. Lett.* 2009, 19, 4773-4776). X-ray crystal structures were obtained for complexes of 3a, 3b, and 3v (Examples 1, 2, and 21) with human MIF as described below in Example C, which confirm the binding of these inhibitors in the tautomerase active site.

TABLE 3

| Assay Data | |
|---|---|
| Example No. | K$_i$ (µM) |
| 1 | 0.59 |
| 2 | 0.57 |
| 3 | 8.9 |
| 4 | ND (3%)$^a$ |
| 5 | ND (13%)$^a$ |

TABLE 3-continued

Assay Data

| Example No. | $K_i$ (μM) |
| --- | --- |
| 6 | ND (0%)[a] |
| 7 | ND (8%)[a] |
| 8 | ND (0%)[a] |
| 9 | ND (15%)[a] |
| 10 | ND (8%)[a] |
| 11 | 7.3 |
| 12 | 2.3 |
| 13 | ND (16%)[a] |
| 14 | 56 |
| 15 | 64 |
| 16 | ND (21%)[a] |
| 17 | 2.95 |
| 18 | 0.37 |
| 19 | 1.95 |
| 20 | 3.12 |
| 21 | 0.41 |
| 22 | 0.15 |
| 23 | 29.6 |
| 24 | 0.36 |
| 25 | 0.082 |
| 26 | 1.48 |
| 27 | ND (9%)[a] |
| 28 | 0.77 |
| 29 | 0.85 |
| 30 | 0.29 |
| 31 | 2.35 |
| 32 | 0.023 |
| 33 | 3.746 |
| 34 | 0.33 |
| 35 | 0.11 |
| 36 | 4.931 |
| 37 | 0.568 |
| 38 | 0.128 |
| 39 | 0.296 |
| 40 | 0.112 |
| 41 | 2.235 |
| 42 | 0.043 |
| 43 | 0.034 |
| 44 | 0.045 |
| ISO-1 | 21 |

[a] % inhibition at 10 μM
ND = Ki not determined

Example C. X-Ray Crystallography

To obtain co-crystals of MIF in complex with 4-(4-(quinolin-2-yl)-1H-1,2,3-triazol-1-yl)phenol (Example 1, 3a), 100 μM 3a in DMSO was added to rhMIF (24 μg/mL) to achieve a 3:1 molar ratio and incubated for 1 hour at 5° C. The solution was centrifuged at 13,000×g to remove precipitated compound and used to set up hanging-drop crystallization experiments. A reservoir of 2.0 M ammonium sulfate, 0.1 M Tris pH 7, and 3% isopropanol was added to the protein solution in a 1:1 ratio and stored at 20° C. Diffraction-quality crystals with a rod morphology grew within two weeks. The crystals were cryo-protected in 25% glycerol, 2.0M ammonium sulfate, 0.1 M Tris pH 7, and 3% isopropanol. Data was collected at the Advanced Photon Source remotely on the NE-CAT 24-ID-E beam line.

Co-crystals of MIF in complex with 4-(4-(6-(2-methoxyethoxy)quinolin-2-yl)-1H-1,2,3-triazol-1-yl)phenol (Example 2, 3b) were obtained by soaking crystals of apo MIF. Crystals were obtained by the hanging-drop method at 20° C. A reservoir of 2.2 M ammonium sulfate, 0.1 M Tris pH 7, and 3% isopropanol mixed in a 1:1 ratio with rhMIF (16 mg/mL) was used to produce 2 μL drops. Once crystals formed, 0.5 μL of a suspension of 10 mM 3b in 10% DMSO, 2.0 M ammonium sulfate, 90 mM Tris pH 7, and 2.7% isopropanol was added to the drop and allowed to incubate for 14 days. Crystals were cryo-protected with 25% glycerol, 2.2 M ammonium sulfate, 0.1 M Tris pH 7, and 3% isopropanol.

Crystals of 4-(4-(6-(2-methoxyethoxy)quinolin-2-yl)-1H-1,2,3-triazol-1-yl)phenol (Example 2, 3b) were diffracted on a Rigaku 007 HF+ source equipped with a Saturn 944+ CCD detector. HKL2000 was used to index, integrate, and scale the MIF-3a data set in the P4212 space group and the MIF-3b in the P212121 space group. Phases were obtained by molecular replacement with PDB file 3U18 using the CCP4 and PHASER programs. Model building was performed in COOT with iterative restrained refinement with REFMAC. A rendering of 3b bound to human MIF from a 1.81-Å crystal structure is shown in FIG. 1.

Example D. Aqueous Solubility

Table 4 shows the aqueous solubility (μg compound/mL solvent) of representative compounds of the invention.

TABLE 4

Aqueous Solubility

| Example No. | Solubility (μg/mL) |
| --- | --- |
| 1 | 2.2 |
| 2 | 3.6 |
| 21 | 48.5 |
| 22 | 27.2 |
| 28 | 13.9 |
| 32 | 47.2 |
| 34 | 9.1 |
| 43 | 19.2 |
| 44 | 867.4 |
| 45 | 364.5 |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:
1. A compound of Formula (I):

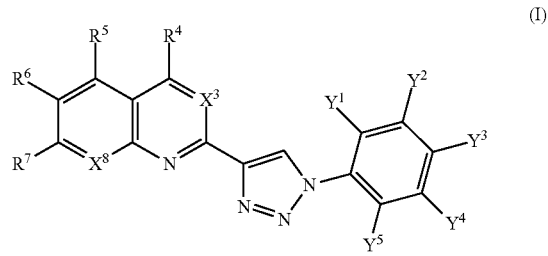

or a pharmaceutically acceptable salt thereof, wherein:
$X^3$ is $CR^3$ or N;
$X^8$ is $CR^8$ or N;
$R^3$ is selected from the group consisting of H, halogen, $C_{1-6}$ alkyl, and $C_{1-6}$ haloalkyl;
$R^4$ is selected from the group consisting of H, halogen, $C_{1-6}$ alkyl, and $C_{1-6}$ haloalkyl;
$R^5$, $R^6$, $R^7$ and $R^8$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)_2R^{b1}$, $NR^{c1}S(O)_2R^{b1}$ and $S(O)_2NR^{c1}R^{d1}$;

wherein each of said $C_{1-6}$ alkyl, $C_{2-6}$ alkenyl, and $C_{2-6}$ alkynyl forming $R^5$, $R^6$, $R^7$ or $R^8$ is independently unsubstituted or substituted with 1, 2, 3, 4 or 5 substituents independently selected from the group consisting of halogen, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, and $S(O)_2NR^{c2}R^{d2}$ and wherein each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $R^5$, $R^6$, $R^7$ or $R^8$ is independently unsubstituted or substituted with 1, 2, 3, 4 or 5 substituents independently selected from the group consisting of $C_{1-6}$ alkyl, halogen, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, and $S(O)_2NR^{c2}R^{d2}$;

or any one of $R^5$, $R^6$, $R^7$, and $R^8$ may represent a group of formula $Ar^S$;

or $R^6$ and $R^7$ in combination with the atoms to which they are attached may form a 5-7 membered carbocyclic or heterocyclic ring that is unsubstituted or substituted by 1, 2 or 3 substituents each independently selected from $R^9$;

or at least one of $R^5$, $R^6$, $R^7$, or $R^8$ may be each independently a water solubilizing group;

each $R^9$ is independently selected from the group consisting of halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)_2R^{b1}$, $NR^{c1}S(O)_2R^{b1}$, and $S(O)_2NR^{c1}R^{d1}$;

wherein each of said $C_{1-6}$ alkyl, $C_{2-6}$ alkenyl, and $C_{2-6}$ alkynyl forming $R^9$ is independently unsubstituted or substituted with 1, 2, 3, 4 or 5 substituents independently selected from the group consisting of halogen, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, and $S(O)_2NR^{c2}R^{d2}$; and wherein each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $R^9$ is independently unsubstituted or substituted with 1, 2, 3, 4 or 5 substituents independently selected from the group consisting of $C_{1-6}$ alkyl, halogen, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, $S(O)_2NR^{c2}R^{d2}$, and water solubilizing groups;

$Y^1$, $Y^2$, $Y^3$, $Y^4$, and $Y^5$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)_2R^{b3}$, $NR^{c3}S(O)_2R^{b3}$, and $S(O)_2NR^{c2}R^{d2}$;

wherein each of said $C_{1-6}$ alkyl, $C_{2-6}$ alkenyl, and $C_{2-6}$ alkynyl forming $Y^1$, $Y^2$, $Y^3$, $Y^4$ or $Y^5$ is independently unsubstituted or substituted with 1, 2, 3, 4 or 5 substituents independently selected from the group consisting of halogen, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)_2R^{b4}$, $NR^{c4}S(O)_2R^{b4}$, and $S(O)_2NR^{c4}R^{d4}$; and wherein each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $Y^1$, $Y^2$, $Y^3$, $Y^4$ or $Y^5$ is independently unsubstituted or substituted with 1, 2, 3, 4 or 5 substituents independently selected from the group consisting of $C_{1-6}$ alkyl, halogen, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)_2R^{b4}$, $NR^{c4}S(O)_2R^{b4}$ and $S(O)_2NR^{c4}R^{d4}$;

or $Y^3$ is NH, and $Y^2$ and $Y^3$ or $Y^3$ and $Y^4$, in combination with the carbon atoms to which they are attached, form a 5-membered fused heteroaromatic ring that is unsubstituted or substituted by 1 or 2 substituents independently selected from $Y^6$;

each $Y^6$ is independently selected from the group consisting of halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $(=NR^{e3})NR^{c3}R^{d3}$, $NR^{c3}C$ (=NR$^{e3}$)NR$^{c3}$R$^{d3}$, S(O)R$^{b3}$, S(O)$_2$R$^{b3}$, NR$^{c3}$S(O)$_2$R$^{b3}$, and S(O)$_2$NR$^{c1}$R$^{d1}$;

wherein each of said C$_{1-6}$ alkyl, C$_{2-6}$ alkenyl, and C$_{2-6}$ alkynyl forming Y$^6$ is independently unsubstituted or substituted with 1, 2, 3, 4 or 5 substituents independently selected from the group consisting of halogen, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)$_2$R$^{b4}$, NR$^{c4}$S(O)$_2$R$^{b4}$, and S(O)$_2$NR$^{c4}$R$^{d4}$; and wherein each of said C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkylene, C$_{6-10}$ aryl-C$_{1-4}$ alkylene, 5-10 membered heteroaryl-C$_{1-4}$ alkylene and 4-10 membered heterocycloalkyl-C$_{1-4}$ alkylene forming Y$^6$ is independently unsubstituted or substituted with 1, 2, 3, 4 or 5 substituents independently selected from the group consisting of C$_{1-6}$ alkyl, halogen, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)$_2$R$^{b4}$, NR$^{c4}$S(O)$_2$R$^{b4}$, and S(O)$_2$NR$^{c4}$R$^{d4}$;

each Ar$^S$ is:

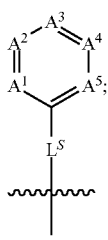

A$^1$ is N or CZ$^1$;
A$^2$ is N or CZ$^2$;
A$^3$ is N or CZ$^3$;
A$^4$ is N or CZ$^4$;
A$^5$ is N or CZ$^5$;
provided that 0, 1 or 2 of Z$^1$, Z$^2$, Z$^3$, Z$^4$, and Z$^5$ are nitrogen;

Z$^1$, Z$^2$, Z$^3$, Z$^4$, and Z$^5$ are each independently selected from the group consisting of H, halogen, C$_{1-6}$ alkyl, C$_{2-6}$ alkenyl, C$_{2-6}$ alkynyl, C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkylene, C$_{6-10}$ aryl-C$_{1-4}$ alkylene, 5-10 membered heteroaryl-C$_{1-4}$ alkylene, 4-10 membered heterocycloalkyl-C$_{1-4}$ alkylene, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)$_2$R$^{b5}$, NR$^{c5}$S(O)$_2$R$^{b5}$, and S(O)$_2$NR$^{c5}$R$^{d5}$;

wherein each of said C$_{1-6}$ alkyl, C$_{2-6}$ alkenyl, and C$_{2-6}$ alkynyl forming Z$^1$, Z$^2$, Z$^3$, Z$^4$, or Z$^5$ is independently unsubstituted or substituted with 1, 2, 3, 4 or 5 substituents independently selected from the group consisting of halogen, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)$_2$R$^{b6}$, NR$^{c6}$S(O)$_2$R$^{b6}$, and S(O)$_2$NR$^{c6}$R$^{d6}$; and wherein each of said C$_{3-7}$ cycloalkyl, C$_{6-10}$ aryl, 5-10 membered heteroaryl, 4-10 membered heterocycloalkyl, C$_{3-7}$ cycloalkyl-C$_{1-4}$ alkylene, C$_{6-10}$ aryl-C$_{1-4}$ alkylene, 5-10 membered heteroaryl-C$_{1-4}$ alkylene and 4-10 membered heterocycloalkyl-C$_{1-4}$ alkylene forming Z$^1$, Z$^2$, Z$^3$, Z$^4$, or Z$^5$ is independently unsubstituted or substituted with 1, 2, 3, 4 or 5 substituents independently selected from the group consisting of C$_{1-6}$ alkyl, halogen, C$_{1-6}$ haloalkyl, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)$_2$R$^{b6}$, NR$^{c6}$S(O)$_2$R$^{b6}$, and S(O)$_2$NR$^{c6}$R$^{d6}$;

or wherein any one or two of Z$^1$, Z$^2$, Z$^3$, Z$^4$, and Z$^5$ is independently selected from water solubilizing groups;

provided that at least one of R$^5$, R$^6$, R$^7$, R$^8$, Z$^1$, and Z$^2$ is a water solubilizing group;

L$^S$ is a bond, O, NR$^{c6}$, C$_{1-4}$ alkylene, C(O), NR$^{c6}$C(O), or C(O)NR$^{c6}$;

R$^{a1}$, R$^{b1}$, R$^{a2}$, R$^{b2}$, R$^{a3}$, R$^{b3}$, R$^{a4}$, R$^{b4}$, R$^{a5}$, R$^{b5}$, R$^{a6}$ and R$^{b6}$ are each independently selected from the group consisting of hydrogen, C$_{1-4}$ alkyl, C$_{2-4}$ alkenyl, C$_{2-4}$ alkynyl, C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, 5-10 membered heterocycloalkyl-C$_{1-4}$ alkylene, and C$_{1-4}$ alkoxy-C$_{1-4}$ alkylene, wherein each of said C$_{1-4}$ alkyl, C$_{2-4}$ alkenyl, C$_{2-4}$ alkynyl, and C$_{1-4}$ alkoxy-C$_{1-4}$ alkylene forming R$^{a1}$, R$^{b1}$, R$^{a2}$, R$^{b2}$, R$^{a3}$, R$^{b3}$, R$^{a4}$, R$^{b4}$, R$^{a5}$, R$^{b5}$, R$^{a6}$ or R$^{b6}$ is independently unsubstituted or substituted by 1, 2, 3, 4 or 5 groups independently selected from the group consisting of halogen, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$ and wherein said C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, and 5-10 membered heterocycloalkyl-C$_{1-4}$ alkylene, forming R$^{a1}$, R$^{b1}$, R$^{a2}$, R$^{b2}$, R$^{a3}$, R$^{b3}$, R$^{a4}$ or R$^{b4}$ is independently unsubstituted or substituted by 1, 2, 3, 4 or 5 groups independently selected from the group consisting of C$_{1-6}$ alkyl, halogen, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$;

R$^{c1}$, R$^{d1}$, R$^{c2}$, R$^{d2}$, R$_{c3}$, R$^{d3}$, R$^{c4}$, R$^{d4}$, R$^{c5}$, R$^{d5}$, R$^{c6}$, and R$^{d6}$ are each independently selected from the group consisting of hydrogen, C$_{1-4}$ alkyl, C$_{2-4}$ alkenyl, C$_{2-4}$ alkynyl, C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, 5-10 membered heterocycloalkyl-C$_{1-4}$ alkylene, and C$_{1-4}$ alkoxy-C$_{1-4}$ alkylene, wherein each of said $C_{1-4}$ alkyl, $C_{2-4}$ alkenyl, $C_{2-4}$ alkynyl, and $C_{1-4}$ alkoxy-$C_{1-4}$ alkylene forming $R^{c1}$, $R^{d1}$, $R^{c2}$, $R^{d2}$, $R^{c3}$, $R^{d3}$, $R^{c4}$, $R^{d4}$, $R^{c5}$, $R^{d5}$, $R^{c6}$, or $R^{d6}$ is independently unsubstituted or substituted by 1, 2, 3, 4 or 5 groups independently selected from the group consisting of halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, and $S(O)_2NR^{c7}R^{d7}$ and wherein each of said $C_{6-10}$ aryl, 5-10 membered heteroaryl, $C_{3-7}$ cycloalkyl, 5-10 membered heterocycloalkyl, $C_{6-10}$ alkylene, $C_{3-7}$ cycloalkyl-$C_{1-4}$ alkylene, 5-10 membered heteroaryl-$C_{1-4}$ alkylene, and 5-10 membered heterocycloalkyl-$C_{1-4}$ alkylene, forming $R^{c1}$, $R^{d1}$, $R^{c2}$, $R^{d2}$, $R^{c3}$, $R^{d3}$, $R^{c4}$, $R^{d4}$, $R^{c5}$, $R^{d5}$, $R^{c6}$, or $R^{d6}$ is independently unsubstituted or substituted by 1, 2, 3, 4 or 5 groups independently selected from the group consisting of $C_{1-6}$ alkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, and $S(O)_2NR^{c7}R^{d7}$;

or $R^{c1}$ and $R^{d1}$, $R^{c2}$ and $R^{d2}$, $R^{c3}$ and $R^{d3}$, $R^{c4}$ and $R^{d4}$, $R^{c5}$ and $R^{d5}$, or $R^{c6}$ and $R^{d6}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from the group consisting of $C_{1-6}$ alkyl, halo, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c7}R^{d7}$, $S(O)R^{b7}$, $S(O)NR^{c7}R^{d7}$, $S(O)_2R^{b7}$, $NR^{c7}S(O)_2R^{b7}$, and $S(O)_2NR^{c7}R^{d7}$;

$R^{a7}$, $R^{b7}$, $R^{c7}$ and $R^{d7}$ are each independently selected from the group consisting of H, $C_{1-6}$ alkyl, $C_{1-6}$ haloalkyl, $C_{2-6}$ alkenyl, $C_{2-6}$ alkynyl, $C_{6-10}$ aryl, 5-10 membered heteroaryl, $C_{3-7}$ cycloalkyl, 4-10 membered heterocycloalkyl, $C_{6-10}$ aryl-$C_{1-4}$ alkylene, 5-10 membered heteroaryl-$C_{1-4}$ alkylene, $C_{3-7}$ cycloalkyl-$C_{1-4}$ alkylene, and 4-10 membered heterocycloalkyl-$C_{1-3}$ alkylene, wherein said $C_{1-6}$ alkyl, $C_{1-6}$ haloalkyl, $C_{2-6}$ alkenyl, $C_{2-6}$ alkynyl, $C_{6-10}$ aryl, 5-10 membered heteroaryl, $C_{3-7}$ cycloalkyl, 4-10 membered heterocycloalkyl, $C_{6-10}$ aryl-$C_{1-4}$ alkylene, 5-10 membered heteroaryl-$C_{1-4}$ alkylene, $C_{3-7}$ cycloalkyl-$C_{1-4}$ alkylene, and 4-10 membered heterocycloalkyl-$C_{1-3}$ alkylene forming $R^{a7}$, $R^{b7}$, $R^{c7}$ and $R^{d7}$ are each optionally substituted with 1, 2 or 3 substituents independently selected from the group consisting of OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl, and $C_{1-6}$ haloalkoxy;

or $R^{c7}$ and $R^{d7}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from the group consisting of OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy; and $R^{e1}$, $R^{e2}$, $R^{e3}$, $R^{e4}$, $R^{e5}$, $R^{e6}$ and $R^{e7}$ are each independently selected from the group consisting of H, $C_{1-4}$ alkyl, OH, and $C_{1-4}$ alkoxy;

each water solubilizing group is independently selected from the group consisting of -$L^W$-$OR^{aW}$, -$L^W$-C(O)$R^{bW}$, -$L^W$-C(O)NR$^{cW}R^{dW}$, -$L^W$-C(O)$OR^{aW}$, -$L^W$-OC(O)$R^{bW}$, -$L^W$-OC(O)NR$^{cW}R^{dW}$, -$L^W$-NR$^{cW}R^{dW}$, -$L^W$-NR$^{cW}$C(O)$R^{bW}$, -$L^W$-NR$^{cW}$C(O)NR$^{cW}R^{dW}$, -$L^W$-NR$^{cW}$C(O)$OR^{aW}$, -$L^W$-C(=NR$^{eW}$)NR$^{cW}R^{dW}$, -$L^W$-NR$^{cW}$C(=NR$^{eW}$)NR$^{cW}R^{dW}$, -$L^W$-S(O)$_2$$OR^{aW}$, -$L^W$-NR$^{cW}$S(O)$_2R^{bW}$, S(O)$_2$NR$^{cW}R^{dW}$, —P(=O)($OR^{aW}$)$_2$, -OP(=O)($OR^{aW}$)$_2$, —OP(=O)($OR^{aW}$)—OP(=O)($OR^{aW}$)$_2$, —OP(=O)($OR^{aW}$)—OP(=O)($OR^{aW}$)—OP(=O)($OR^{aW}$)$_2$, and -$L^W$-$Cy^W$; Wherein:

each $Cy^W$ is unsubstituted 5-10 membered heteroaryl or 4-10 membered heterocycloalkyl, or 5-10 membered heteroaryl or 4-10 membered heterocycloalkyl substituted with one or more (e.g., 1, 2, 3, 4 or 5) substituents each independently selected from $C_{1-6}$ alkyl, halogen, $C_{1-6}$ haloalkyl, CN, NO$_2$, $OR^{aW}$, $SR^{aW}$, C(O)$R^{bW}$, C(O)NR$^{cW}R^{dW}$, C(O)$OR^{aW}$, OC(O)$R^{bW}$, OC(O)NR$^{cW}R^{dW}$, NR$^{cW}R^{dW}$, NR$^{cW}$C(O)$R^{bW}$, NR$^{cW}$C(O)NR$^{cW}R^{dW}$, NR$^{cW}$C(O)$OR^{aW}$, C(=NR$^{eW}$)NR$^{cW}R^{dW}$, NR$^{cW}$C(=NR$^{eW}$)NR$^{cW}R^{dW}$, S(O)$R^{bW}$, S(O)$_2R^{bW}$, NR$^{cW}$S(O)$_2R^{bW}$ and S(O)$_2$Nle$^WR^{dW}$;

each -$L^W$- is a bond or a linking group selected from groups of the formula -$L^{W1}$-$L^{W2}$-;

the group -$L^{wi}$- is attached to the core molecule and is selected from a bond and groups of the formula —O—, —S—, —S(O)—, —S(O)$_2$—, —C(O)—, —NH—, —NR$^{cW}$—, —NR$^{cW}$C(O)—, —C(O)NR$^{cW}$—, —O(CO)—, —C(O)O—, —O(CO)NR$^{cW}$—, —NR$^{cW}$C(O)O—, —O(CO)O—, and —NR$^{cW}$C(O)NR$^{cW}$—;

the group -$L^{W2}$- is selected from a bond, unsubstituted-$C_{1-10}$ alkylene-, unsubstituted-$C_{1-10}$ heteroalkylene, and —$C_{1-10}$ alkylene and —$C_{1-10}$ heteroalkylene substituted with one or more (e.g., 1, 2, 3, 4 or 5 substituents) independently selected from the group consisting of H, halogen, $C_{1-6}$ alkyl, $C_{2-6}$ alkenyl, $C_{2-6}$ alkynyl, CN, NO$_2$, $OR^{aW}$, $SR^{aW}$, C(O)$R^{bW}$, C(O)NR$^{cW}R^{dW}$, C(O)$OR^{aW}$, OC(O)$R^{bW}$, OC(O)N-R$^{cW}R^{dW}$, NR$^{cW}R^{dW}$, NR$^{cW}$C(O)$R^{bW}$, NR$^{cW}$C(O)N-R$^{cW}R^{dW}$, NR$^{cW}$C(O)$OR^{aW}$, C(=NR$^{eW}$)NR$^{cW}R^{dW}$, NR$^{cW}$C(=NR$^{eW}$)NR$^{cW}R^{dW}$, S(O)$R^{bW}$, S(O)$_2R^{bW}$, NR$^{cW}$S(O)$_2R^{bW}$, S(O)$_2$NR$^{cW}R^{dW}$, —P(=O)($OR^{aW}$)$_2$, —OP(=O)($OR^{aW}$)$_2$, —OP(=O)($OR^{aW}$)—OP(=O)($OR^{aW}$)$_2$, —OP(=O)($OR^{aW}$)—OP(=O)($OR^{aW}$)—OP(=O)($OR^{aW}$)$_2$, oxo and sulfido;

$R^{aW}$, $R^{bW}$, $R^{cW}$, and $R^{dW}$ are each independently selected from the group consisting of hydrogen, $C_{1-4}$ alkyl, $C_{2-4}$ alkenyl, $C_{2-4}$ alkenyl, $C_{6-10}$ aryl, 5-10 membered heteroaryl, $C_{3-7}$ cycloalkyl, 5-10 membered heterocycloalkyl, $C_{6-10}$ aryl-$C_{14}$ alkylene, $C_{3-7}$ cycloalkyl-$C_{1-4}$ alkylene, 5-10 membered heteroaryl-$C_{14}$ alkylene, 5-10 membered heterocycloalkyl-$C_{1-4}$ alkylene, and $C_{1-4}$ alkoxy-$C_{1-4}$ alkylene, wherein said $C_{1-4}$ alkyl, $C_{2-4}$ alkenyl, $C_{2-4}$ alkynyl, and $C_{1-4}$ alkoxy-$C_{1-4}$ alkylene forming $R^{aW}$, $R^{bW}$, $R^{aW}$, or $R^{dW}$ are each optionally substituted by 1, 2, 3, 4 or 5 groups independently selected from halo, CN, $OR^{aW*}$, $SR^{aW*}$, $C(O)R^{bW*}$, C(O)

NR$^{cW}$*R$^{dW}$*, C(O)OR$^{aW}$*, OC(O)R$^{bW}$*, OC(O)NR$^{cW}$*R$^{dW}$*, NR$^{cW}$*R$^{dW}$*, NR$^{cW}$*C(O)R$^{bW}$*, NR$^{cW}$*C(O)NR$^{cW}$*R$^{dW}$*, NR$^{cW}$*C(O)OR$^{aW}$*, C(=NR$^{eW}$*)NR$^{cW}$*R$^{dW}$*, NR$^{cW}$*C(=NR$^{eW}$*)NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$* and Wherein said $C_{6-10}$ aryl, 5-10 membered heteroaryl, $C_{3-7}$ cycloalkyl, 5-10 membered heterocycloalkyl, $C_{6-10}$ aryl-$C_{14}$ alkylene, $C_{3-7}$ cycloalkyl-$C_{1-4}$ alkylene, 5-10 membered heteroaryl-$C_{1-4}$ alkylene, and 5-10 membered heterocycloalkyl-$C_{1-4}$ alkylene, forming R$^{aW}$, R$^{bW}$, R$^{aW}$, or R$^{dW}$ are each optionally substituted by 1, 2, 3, 4 or 5 groups independently selected from $C_{1-6}$ alkyl, halo, CN, OR$^{aW}$*, SR$^{aW}$*, C(O)R$^{bW}$*, C(O)NR$^{cW}$*R$^{dW}$*, C(O)OR$^{aW}$*, OC(O)R$^{bW}$*, OC(O)NR$^{cW}$*R$^{dW}$*, NR$^{cW}$*R$^{dW}$*, NR$^{cW}$*C(O)R$^{bW}$*, NR$^{cW}$*C(O)NR$^{cW}$*R$^{dW}$*, NR$^{cW}$*C(O)OR$^{aW}$*, C(=NR$^{eW}$*)NR$^{cW}$*R$^{dW}$*, NR$^{cW}$*C(=NR$^{eW}$*)NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$*;

or R$^{cW}$ and R$^{dW}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from $C_{1-6}$ alkyl, halo, CN, OR$^{aW}$*, SR$^{aW}$*, C(O)R$^{bW}$*, C(O)NR$^{cW}$*R$^{dW}$*, C(O) OR$^{a}$*, OC(O)R$^{b}$*, OC(O)NR$^{cW}$*R$^{dW}$*, NR$^{cW}$*R$^{dW}$*, NR$^{cW}$*C(O)R$^{bW}$*, NR$^{cW}$*C(O)NR$^{cW}$*R$^{dW}$*, NR$^{cW}$*C(O)OR$^{aW}$*, C(=NR$^{eW}$*)NR$^{cW}$*R$^{dW}$*, NR$^{cW}$*C(=NR$^{eW}$*)NR$^{cW}$*R$^{dW}$*, S(O)R$^{bW}$*, S(O)NR$^{cW}$*R$^{dW}$*, S(O)$_2$R$^{bW}$*, NR$^{cW}$*S(O)$_2$R$^{bW}$* and S(O)$_2$NR$^{cW}$*R$^{dW}$*;

R$^{aW}$*, R$^{bW}$*, R$^{cW}$* and R$^{dW}$* are each independently selected from H, $C_{1-6}$ alkyl, $C_{1-6}$ haloalkyl, $C_{2-6}$ alkenyl, $C_{2-6}$ alkynyl, aryl, $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl, wherein said $C_{1-6}$ alkyl, $C_{1-6}$ haloalkyl, $C_{2-6}$ alkenyl, $C_{2-6}$ alkynyl $C_{6-10}$ aryl-$C_{1-3}$ alkyl, 5-10 membered heteroaryl-$C_{1-3}$ alkyl, $C_{3-7}$ cycloalkyl-$C_{1-3}$ alkyl and 4-10 membered heterocycloalkyl-$C_{1-3}$ alkyl forming R$^{aW}$* R$^{bW}$*, R$^{eW}$* and R$^{dW}$* are each optionally substituted with 1, 2 or 3 substituents independently selected from OH, CN, amino, NH($C_{1-6}$ alkyl), N($C_{1-6}$ alkyl)$_2$, halo, $C_{1-6}$ alkyl, $C_{1-6}$ alkoxy, $C_{1-6}$ haloalkyl and $C_{1-6}$ haloalkoxy, or R$^{cW}$* and R$^{dW}$* attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from OH, CN, amino, NH($C_{1-6}$ alkyl), N($C_{1-6}$ alkyl)$_2$ halo $C_{1-6}$ alkyl, $C_{1-6}$ alkoxy, $C_{1-6}$ haloalkyl and $C_{1-6}$ haloalkoxy;

R$^{eW}$ and R$^{eW}$* are each independently selected from H, $C_{1-4}$ alkyl, OH, and $C_{1-4}$ alkoxy;

with the proviso that when $Y^1$, $Y^2$, $Y^4$, $Y^5$, and $R^4$ are each H, $Y^3$ is F, and $X^3$ is H or $C_{1-6}$ alkyl, then at least one of $R^5$, $R^6$, and $R^7$ is not H.

2. The compound of claim 1, wherein $R^5$ and $R^8$ are independently selected from the group consisting of H, $C_{6-10}$ aryl, and OR$^{a1}$, wherein the $C_{6-10}$ aryl is unsubstituted or substituted with 1, 2, or 3 substituents independently selected from the group consisting of $C_{1-6}$ alkyl, halogen, and OR$^{a2}$.

3. The compound of claim 1, wherein $R^5$ is H, unsubstituted phenyl, phenyl substituted with 1 substituent selected from the group consisting of $C_{1-6}$ alkyl, halogen, $C_{1-6}$ alkoxy, and OR$^{a2}$, wherein $R^1$ is unsubstituted phenyl or phenyl substituted with 1 group independently selected from the group consisting of OR$^{a5}$ and C(O)OR$^{a5}$.

4. The compound of claim 1, wherein $R^5$ is H, 4-methoxyphenyl, 4-(2-methoxy(ethoxy))phenyl, 4-carboxyphenyl, or phenoxy.

5. The compound of claim 1, wherein at least one water solubilizing group in (I) is selected from the group consisting of:

—OH

—OMe

—OEt

—OPr

—OiPr

—CH$_2$CH$_2$OCH$_2$CH$_2$NMe$_2$

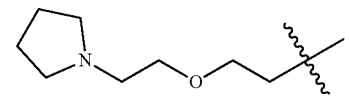 [SMILES: *CCOCCN1CCCC1]

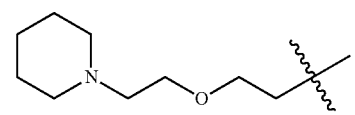 [SMILES: *CCOCCN1CCCCC1]

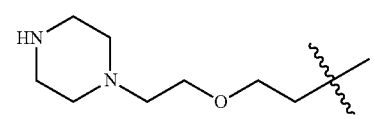 [SMILES: *CCOCCN1CCNCC1]

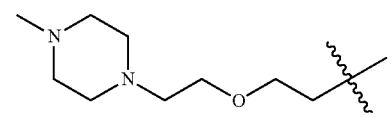 [SMILES: *CCOCCN1CCN(C)CC1]

-continued

—OcPr

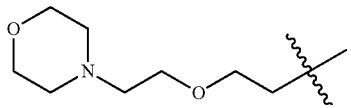 [SMILES: *CCOCCN1CCOCC1]

—OcBu   —CH₂CH₂NHCH₂CH₂OH

—OcPn   —CH₂CH₂NHCH₂CH₂OMe

—OcHex   —CH₂CH₂NHCH₂CH₂OEt

—OCH₂CH₂OH   —CH₂CH₂NHCH₂CH₂NH₂

—OCH₂CH₂OMe   —CH₂CH₂NHCH₂CH₂NHMe

—OCH₂CH₂OEt   —CH₂CH₂NHCH₂CH₂NMe₂

—OCH₂CH₂NH₂

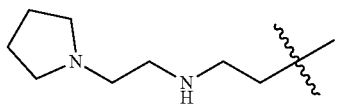 [SMILES: *CCNCCN1CCCC1]

—OCH₂CH₂NHMe

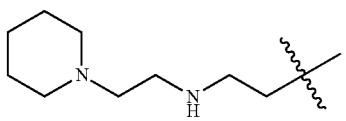 [SMILES: *CCNCCN1CCCCC1]

—OCH₂CH₂NMe₂

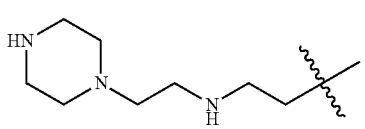 [SMILES: *CCNCCN1CCNCC1]

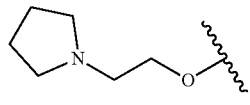 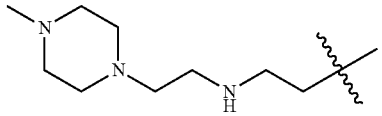 [SMILES: *CCNCCN1CCN(C)CC1]

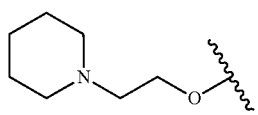 [SMILES: *OCCN1CCCCC1] 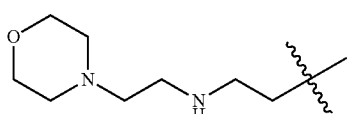

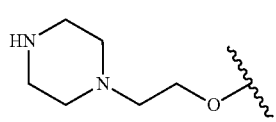   —CH₂CH₂N(CH₂CH₂OH)₂

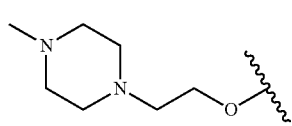 [SMILES: *OCCN1CCN(C)CC1]   —CH₂CH₂N(CH₂CH₂OMe)₂

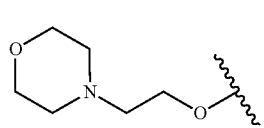   —CH₂CH₂N(CH₂CH₂OEt)₂

—OCH₂CH₂CH₂OH   —CH₂CH₂NMeCH₂CH₂OH

—OCH₂CH₂CH₂OMe   —CH₂CH₂NMeCH₂CH₂OMe

—OCH₂CH₂CH₂OEt   —CH₂CH₂NMeCH₂CH₂OEt

—OCH₂CH₂CH₂NH₂   —CH₂CH₂NMeCH₂CH₂NH₂

—OCH₂CH₂CH₂NHMe   —CH₂CH₂NMeCH₂CH₂NHMe

—OCH₂CH₂CH₂NMe₂   —CH₂CH₂NMeCH₂CH₂NMe₂

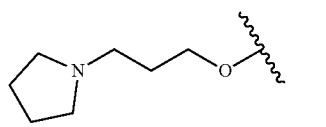 [SMILES: *OCCCN1CCCC1] 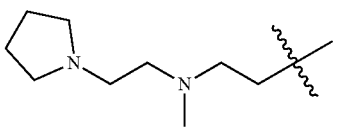 [SMILES: *CCN(C)CCN1CCCC1]
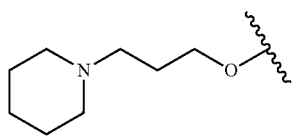 [SMILES: *OCCCN1CCCCC1] 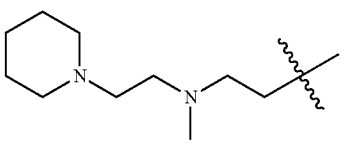 [SMILES: *CCN(C)CCN1CCCCC1]
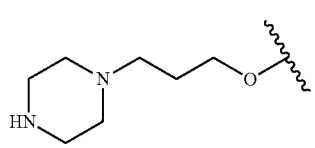 [SMILES: *OCCCN1CCNCC1] 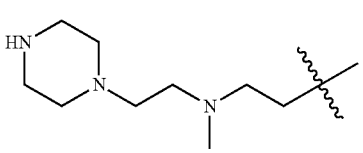 [SMILES: *CCN(C)CCN1CCNCC1]
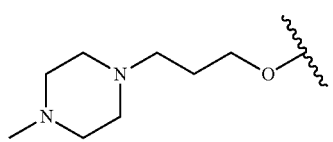 [SMILES: *OCCCN1CCN(C)CC1] 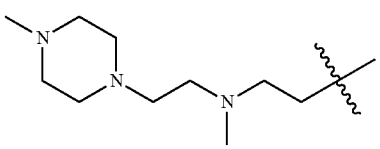 [SMILES: *CCN(C)CCN1CCN(C)CC1]
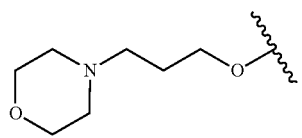 [SMILES: *OCCCN1CCOCC1] 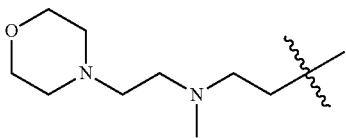 [SMILES: *CCN(C)CCN1CCOCC1]
—OCH₂CH₂OCH₂CH₂OH —NH
—OCH₂CH₂OCH₂CH₂OMe —NHMe
—OCH₂CH₂OCH₂CH₂OEt —NMe₂
—OCH₂CH₂OCH₂CH₂NH₂ —NHEt
—OCH₂CH₂OCH₂CH₂NHMe —NHPr
—OCH₂CH₂OCH₂CH₂NMe₂ —NHiPr
—NHcPr
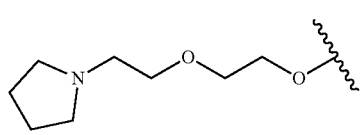 [SMILES: *OCCOCCN1CCCC1]
—NHcBu
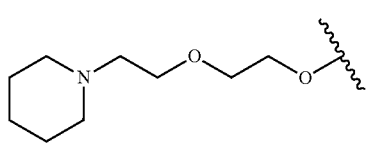 [SMILES: *OCCOCCN1CCCCC1]
—NHcPn
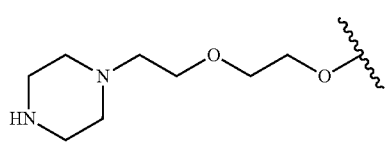 [SMILES: *OCCOCCN1CCNCC1]
—NHcHex
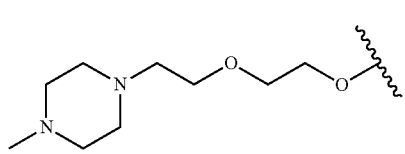 [SMILES: *OCCOCCN1CCN(C)CC1]

—NHCH₂CH₂OH

—OCH₂CH₂OCH₂CH₂CH₂OH
—OCH₂CH₂OCH₂CH₂CH₂OMe
—OCH₂CH₂OCH₂CH₂CH₂OEt
—OCH₂CH₂OCH₂CH₂CH₂NH₂
—OCH₂CH₂OCH₂CH₂CH₂NHMe
—OCH₂CH₂OCH₂CH₂CH₂NMe₂

—NHCH₂CH₂OMe
—NHCH₂CH₂OEt
—NHCH₂CH₂NH₂
—NHCH₂CH₂NHMe
—NHCH₂CH₂NMe₂

—NHCH₂CH₂OH

—OCH₂CH₂CH₂OCH₂CH₂OH
—OCH₂CH₂CH₂OCH₂CH₂OMe
—OCH₂CH₂CH₂OCH₂CH₂OEt
—OCH₂CH₂CH₂OCH₂CH₂NH₂
—OCH₂CH₂CH₂OCH₂CH₂NHMe
—OCH₂CH₂CH₂OCH₂CH₂NMe₂

—NHCH₂CH₂CH₂OMe
—NHCH₂CH₂CH₂OEt
—NHCH₂CH₂CH₂NH₂
—NHCH₂CH₂CH₂NHMe
—NHCH₂CH₂CH₂NMe₂

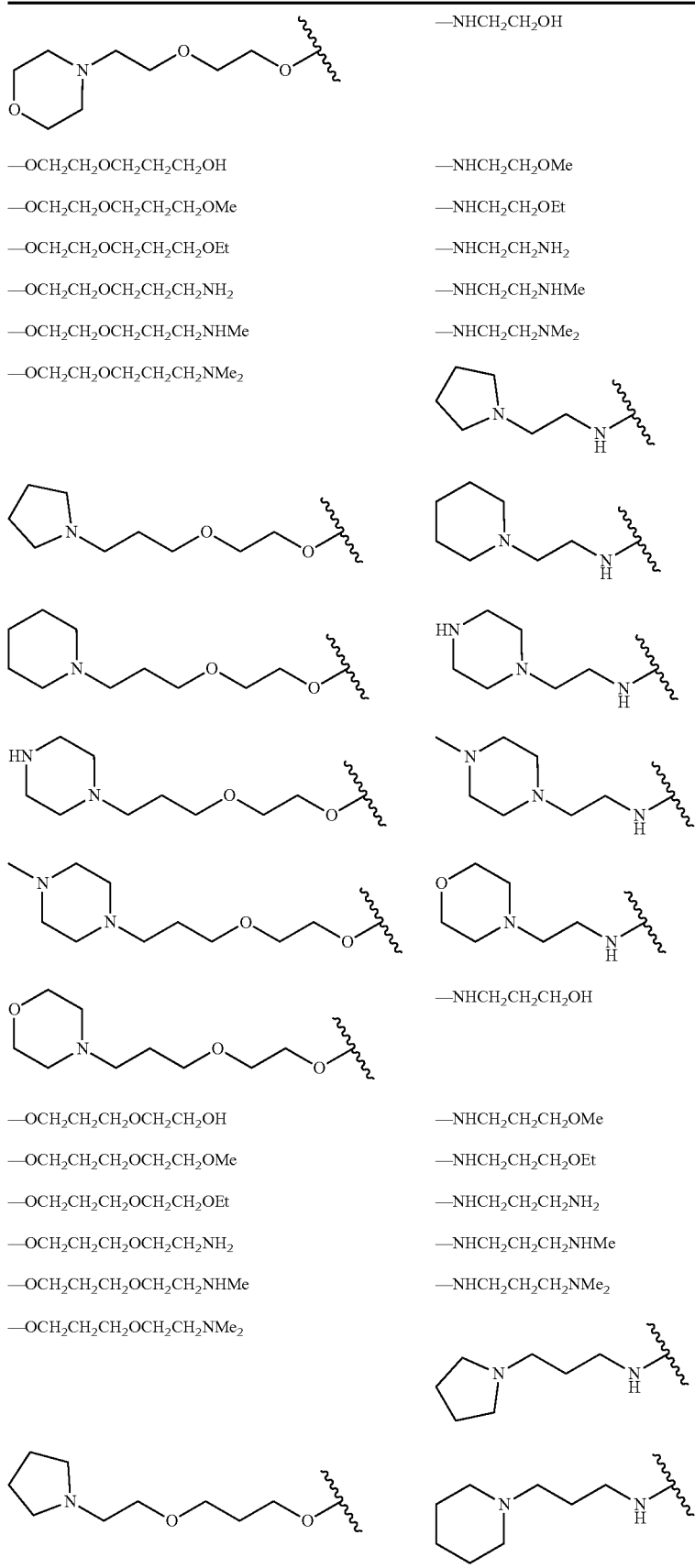

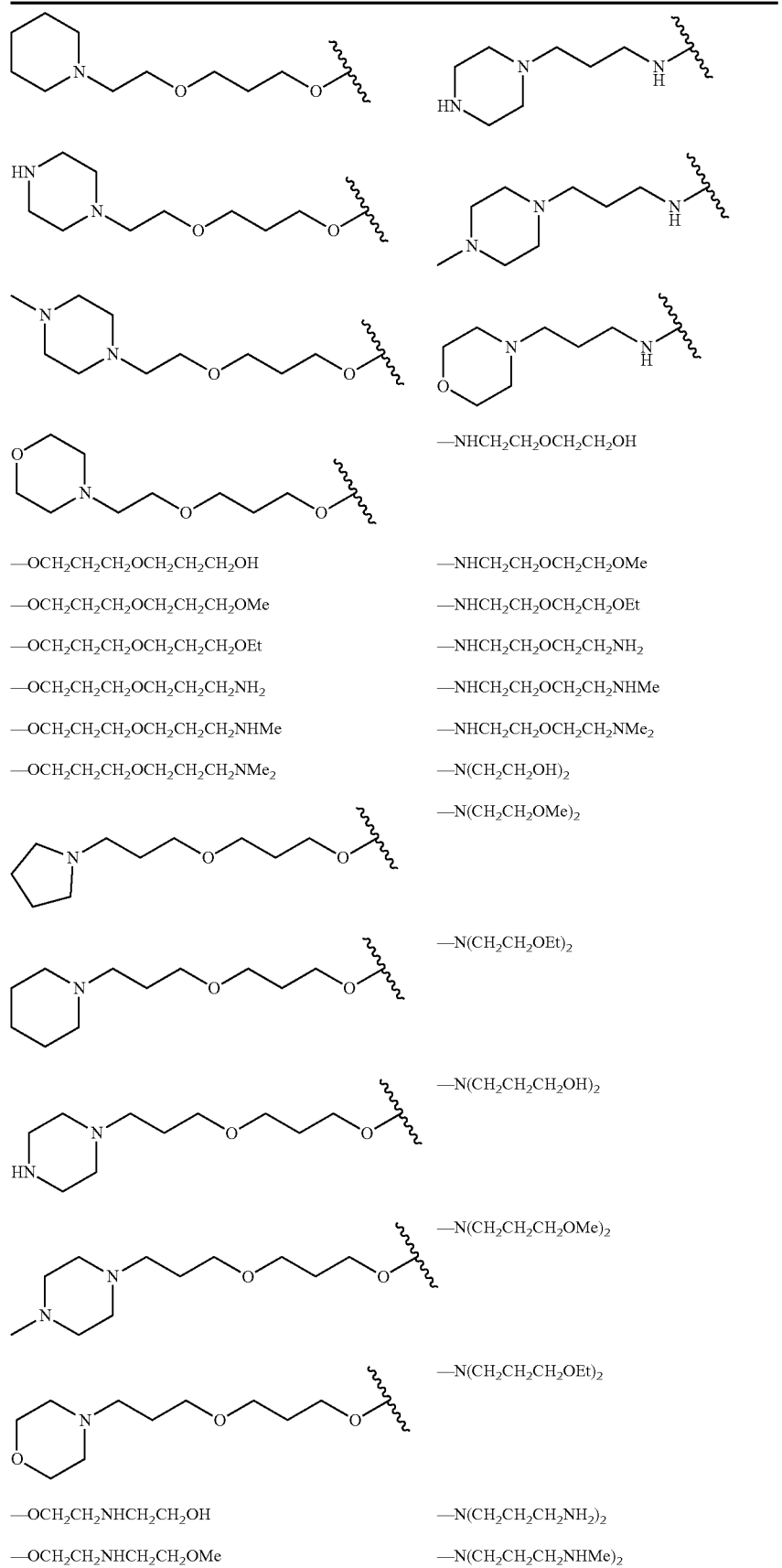

—OCH₂CH₂CH₂OCH₂CH₂CH₂OH
—OCH₂CH₂CH₂OCH₂CH₂CH₂OMe
—OCH₂CH₂CH₂OCH₂CH₂CH₂OEt
—OCH₂CH₂CH₂OCH₂CH₂CH₂NH₂
—OCH₂CH₂CH₂OCH₂CH₂CH₂NHMe
—OCH₂CH₂CH₂OCH₂CH₂CH₂NMe₂

—OCH₂CH₂NHCH₂CH₂OH
—OCH₂CH₂NHCH₂CH₂OMe

—NHCH₂CH₂OCH₂CH₂OH
—NHCH₂CH₂OCH₂CH₂OMe
—NHCH₂CH₂OCH₂CH₂OEt
—NHCH₂CH₂OCH₂CH₂NH₂
—NHCH₂CH₂OCH₂CH₂NHMe
—NHCH₂CH₂OCH₂CH₂NMe₂
—N(CH₂CH₂OH)₂
—N(CH₂CH₂OMe)₂
—N(CH₂CH₂OEt)₂
—N(CH₂CH₂CH₂OH)₂
—N(CH₂CH₂CH₂OMe)₂
—N(CH₂CH₂CH₂OEt)₂
—N(CH₂CH₂CH₂NH₂)₂
—N(CH₂CH₂CH₂NHMe)₂

-continued
—OCH₂CH₂NHCH₂CH₂OEt
—OCH₂CH₂NHCH₂CH₂NH₂
—N(CH₂CH₂CH₂NMe₂)₂
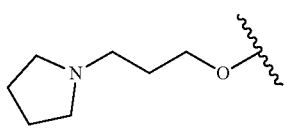 [SMILES: *OCCCN1CCCC1]
—OCH₂CH₂NHCH₂CH₂NHMe
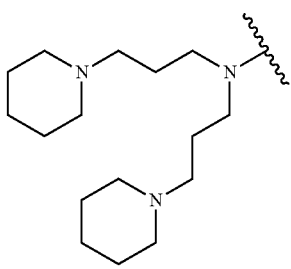 [SMILES: *N(CCCN1CCCCC1)CCCN1CCCCC1]
—OCH₂CH₂NHCH₂CH₂NMe₂
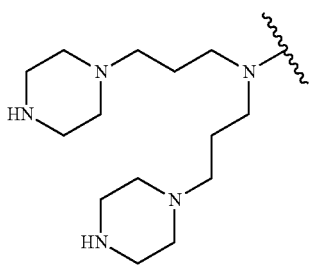 [SMILES: *N(CCCN1CCNCC1)CCCN1CCNCC1]
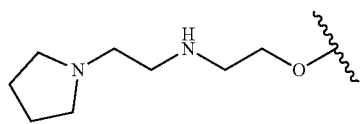 [SMILES: *OCCNCCN1CCCC1]
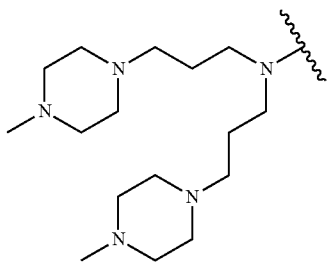 [SMILES: *N(CCCN1CCN(C)CC1)CCCN1CCN(C)CC1]
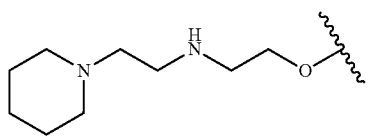
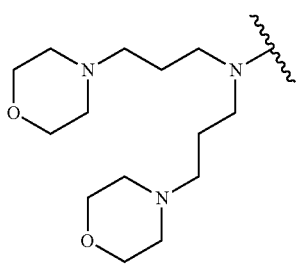 [SMILES: *N(CCCN1CCOCC1)CCCN1CCOCC1]
—N(CH₂CH₂OCH₂CH₂OH)₂
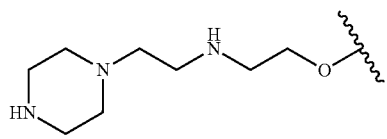 [SMILES: *OCCNCCN1CCNCC1]
—N(CH₂CH₂OCH₂CH₂OMe)₂
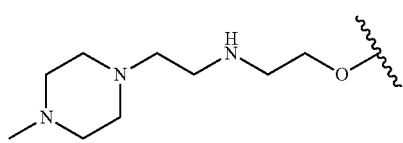 [SMILES: *OCCNCCN1CCN(C)CC1]

-continued

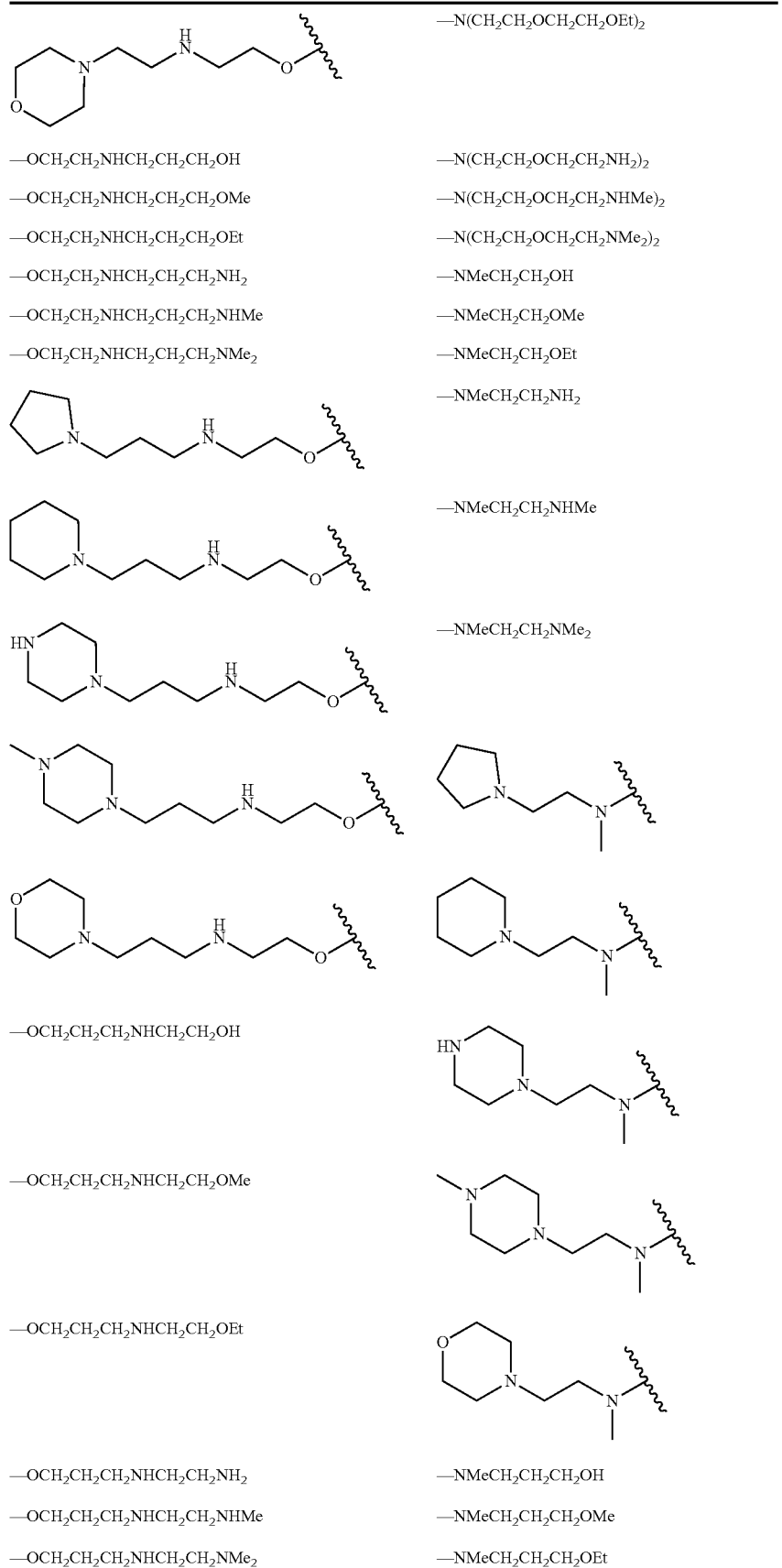

—OCH₂CH₂NHCH₂CH₂CH₂OH
—OCH₂CH₂NHCH₂CH₂CH₂OMe
—OCH₂CH₂NHCH₂CH₂CH₂OEt
—OCH₂CH₂NHCH₂CH₂CH₂NH₂
—OCH₂CH₂NHCH₂CH₂CH₂NHMe
—OCH₂CH₂NHCH₂CH₂CH₂NMe₂

—OCH₂CH₂CH₂NHCH₂CH₂OH

—OCH₂CH₂CH₂NHCH₂CH₂OMe

—OCH₂CH₂CH₂NHCH₂CH₂OEt

—OCH₂CH₂CH₂NHCH₂CH₂NH₂
—OCH₂CH₂CH₂NHCH₂CH₂NHMe
—OCH₂CH₂CH₂NHCH₂CH₂NMe₂

—N(CH₂CH₂OCH₂CH₂OEt)₂

—N(CH₂CH₂OCH₂CH₂NH₂)₂
—N(CH₂CH₂OCH₂CH₂NHMe)₂
—N(CH₂CH₂OCH₂CH₂NMe₂)₂
—NMeCH₂CH₂OH
—NMeCH₂CH₂OMe
—NMeCH₂CH₂OEt
—NMeCH₂CH₂NH₂

—NMeCH₂CH₂NHMe

—NMeCH₂CH₂NMe₂

—NMeCH₂CH₂CH₂OH
—NMeCH₂CH₂CH₂OMe
—NMeCH₂CH₂CH₂OEt

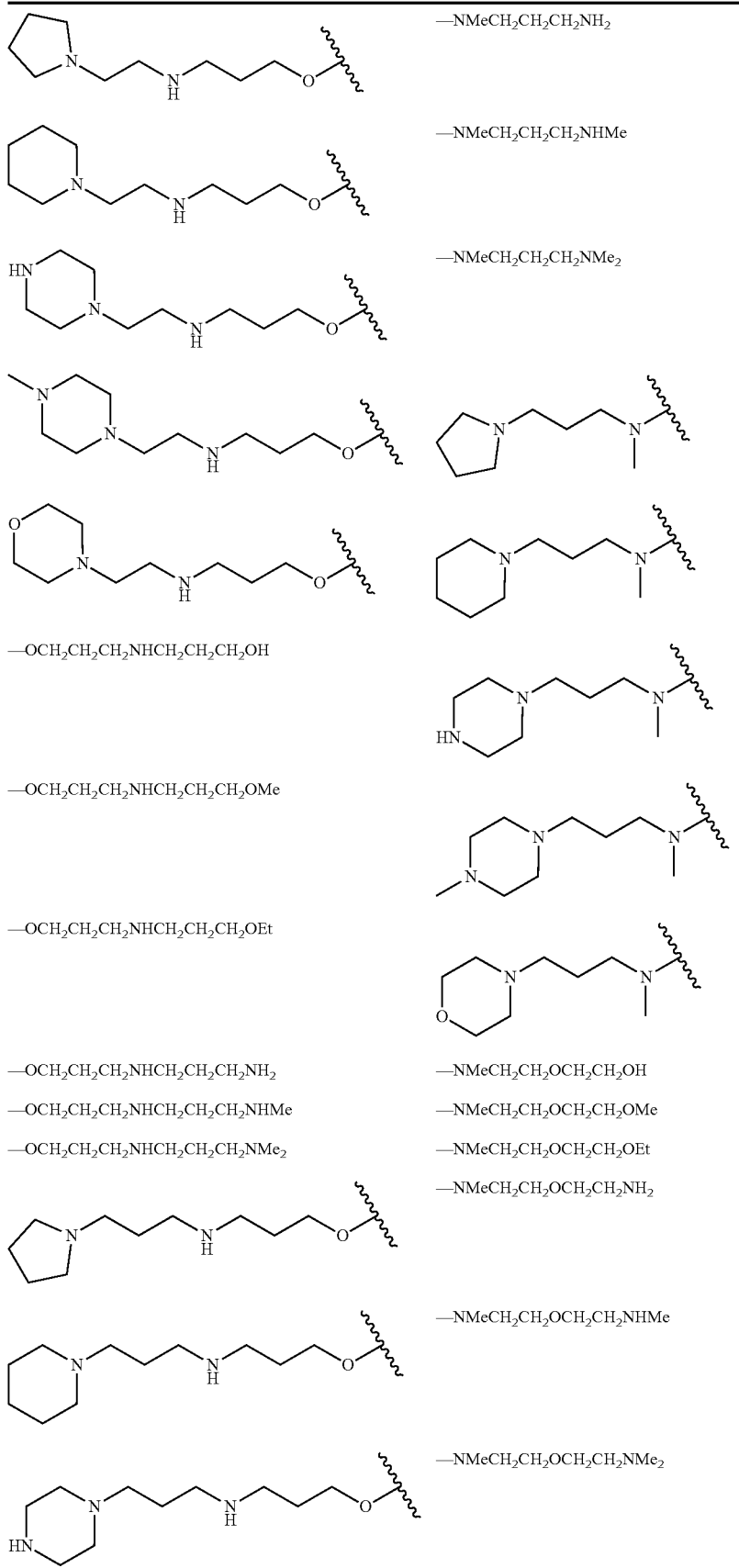

—NMeCH₂CH₂CH₂NH₂

—NMeCH₂CH₂CH₂NHMe

—NMeCH₂CH₂CH₂NMe₂

—OCH₂CH₂CH₂NHCH₂CH₂CH₂OH

—OCH₂CH₂CH₂NHCH₂CH₂CH₂OMe

—OCH₂CH₂CH₂NHCH₂CH₂CH₂OEt

—OCH₂CH₂CH₂NHCH₂CH₂CH₂NH₂
—OCH₂CH₂CH₂NHCH₂CH₂CH₂NHMe
—OCH₂CH₂CH₂NHCH₂CH₂CH₂NMe₂

—NMeCH₂CH₂OCH₂CH₂OH
—NMeCH₂CH₂OCH₂CH₂OMe
—NMeCH₂CH₂OCH₂CH₂OEt
—NMeCH₂CH₂OCH₂CH₂NH₂

—NMeCH₂CH₂OCH₂CH₂NHMe

—NMeCH₂CH₂OCH₂CH₂NMe₂

-continued

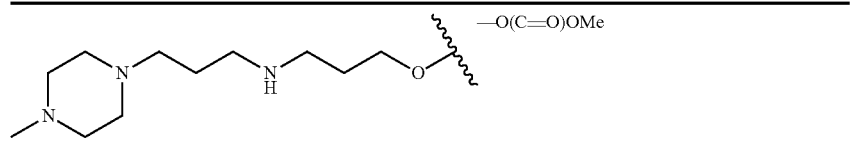   —O(C=O)OMe

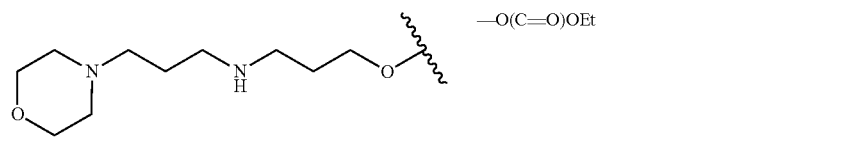   —O(C=O)OEt

—OCH₂CH₂N(CH₂CH₂OH)₂           —O(C=O)OnPr
—OCH₂CH₂N(CH₂CH₂OMe)₂          —O(C=O)OiPr
—OCH₂CH₂N(CH₂CH₂OEt)₂          —O(C=O)OcPr
—OCH₂CH₂N(CH₂CH₂CH₂OH)₂        —O(C=O)OcBu
—OCH₂CH₂N(CH₂CH₂CH₂OMe)₂       —O(C=O)OcPn
—OCH₂CH₂N(CH₂CH₂CH₂OEt)₂       —O(C=O)OcHex
—OCH₂CH₂CH₂(CH₂CH₂OH)₂         —COOH
—OCH₂CH₂CH₂N(CH₂CH₂OMe)₂       —CH₂(C=O)OH
—OCH₂CH₂CH₂N(CH₂CH₂OEt)₂       —CH₂(C=O)OMe
—OCH₂CH₂CH₂N(CH₂CH₂CH₂OH)₂     —CH₂(C=O)OEt
—OCH₂CH₂CH₂N(CH₂CH₂CH₂OMe)₂    —CH₂(C=O)OnPr
—OCH₂CH₂CH₂N(CH₂CH₂CH₂OEt)₂    —CH₂(C=O)OiPr
—OCH₂CH₂NMeCH₂CH₂OH            —CH₂(C=O)OcPr
—OCH₂CH₂NMeCH₂CH₂OMe           —CH₂(C=O)OcBu
—OCH₂CH₂NMeCH₂CH₂OEt           —CH₂(C=O)OcPn
—OCH₂CH₂NMeCH₂CH₂NH₂           —CH₂(C=O)OcHex
—OCH₂CH₂NMeCH₂CH₂NHMe          —OCH₂(C=O)OH
—OCH₂CH₂NMeCH₂CH₂NMe₂          —OCH₂(C=O)OMe

—OCH₂(C=O)OEt

—OCH₂(C=O)OnPr

—OCH₂(C=O)OiPr

—OCH₂(C=O)OcPr

-continued

| | |
|---|---|
|  | —OCH$_2$(C=O)OcBu |
| —OCH$_2$CH$_2$NMeCH$_2$CH$_2$CH$_2$OH | —OCH$_2$(C=O)OcPn |
| —OCH$_2$CH$_2$NMeCH$_2$CH$_2$CH$_2$OMe | —OCH$_2$(C=O)OcHex |
| —OCH$_2$CH$_2$NMeCH$_2$CH$_2$CH$_2$OEt | —OCH$_2$(C=O)OH |
| —OCH$_2$CH$_2$NMeCH$_2$CH$_2$CH$_2$NH$_2$ | —OCH$_2$(C=O)OMe |
| —OCH$_2$CH$_2$NMeCH$_2$CH$_2$CH$_2$NHMe | —OCH$_2$(C=O)OEt |
| —OCH$_2$CH$_2$NMeCH$_2$CH$_2$CH$_2$NMe$_2$ | —OCH$_2$(C=O)OnPr |
| 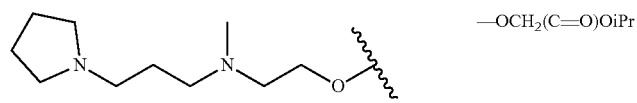 | —OCH$_2$(C=O)OiPr |
| 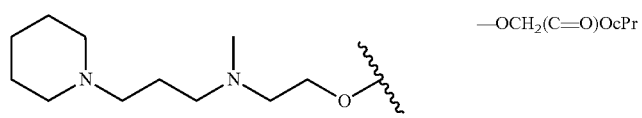 | —OCH$_2$(C=O)OcPr |
| 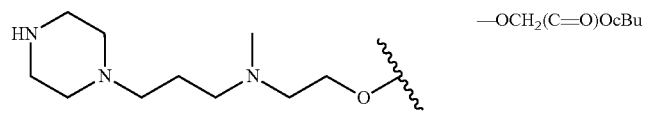 | —OCH$_2$(C=O)OcBu |
| 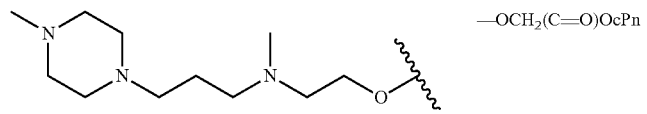 | —OCH$_2$(C=O)OcPn |
| 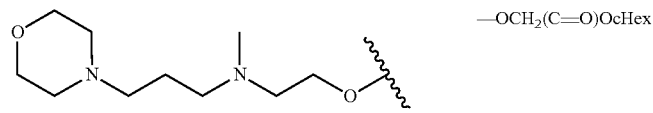 | —OCH$_2$(C=O)OcHex |
| —OCH$_2$CH$_2$CH$_2$NMeCH$_2$CH$_2$OH | —NHCH$_2$(C=O)OH |
| —OCH$_2$CH$_2$CH$_2$NMeCH$_2$CH$_2$OMe | —NHCH$_2$(C=O)OMe |
| —OCH$_2$CH$_2$CH$_2$NMeCH$_2$CH$_2$OEt | —NHCH$_2$(C=O)OEt |
| —OCH$_2$CH$_2$CH$_2$NMeCH$_2$CH$_2$NH$_2$ | —NHCH$_2$(C=O)OnPr |
| —OCH$_2$CH$_2$CH$_2$NMeCH$_2$CH$_2$NHMe | —NHCH$_2$(C=O)OiPr |
| —OCH$_2$CH$_2$CH$_2$NMeCH$_2$CH$_2$NMe$_2$ | —NHCH$_2$(C=O)OcPr |
| 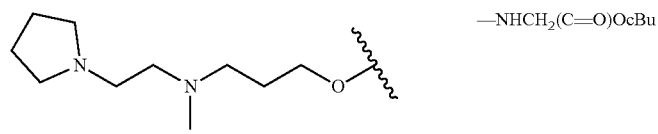 | —NHCH$_2$(C=O)OcBu |
| 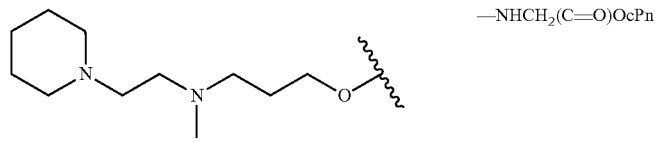 | —NHCH$_2$(C=O)OcPn |

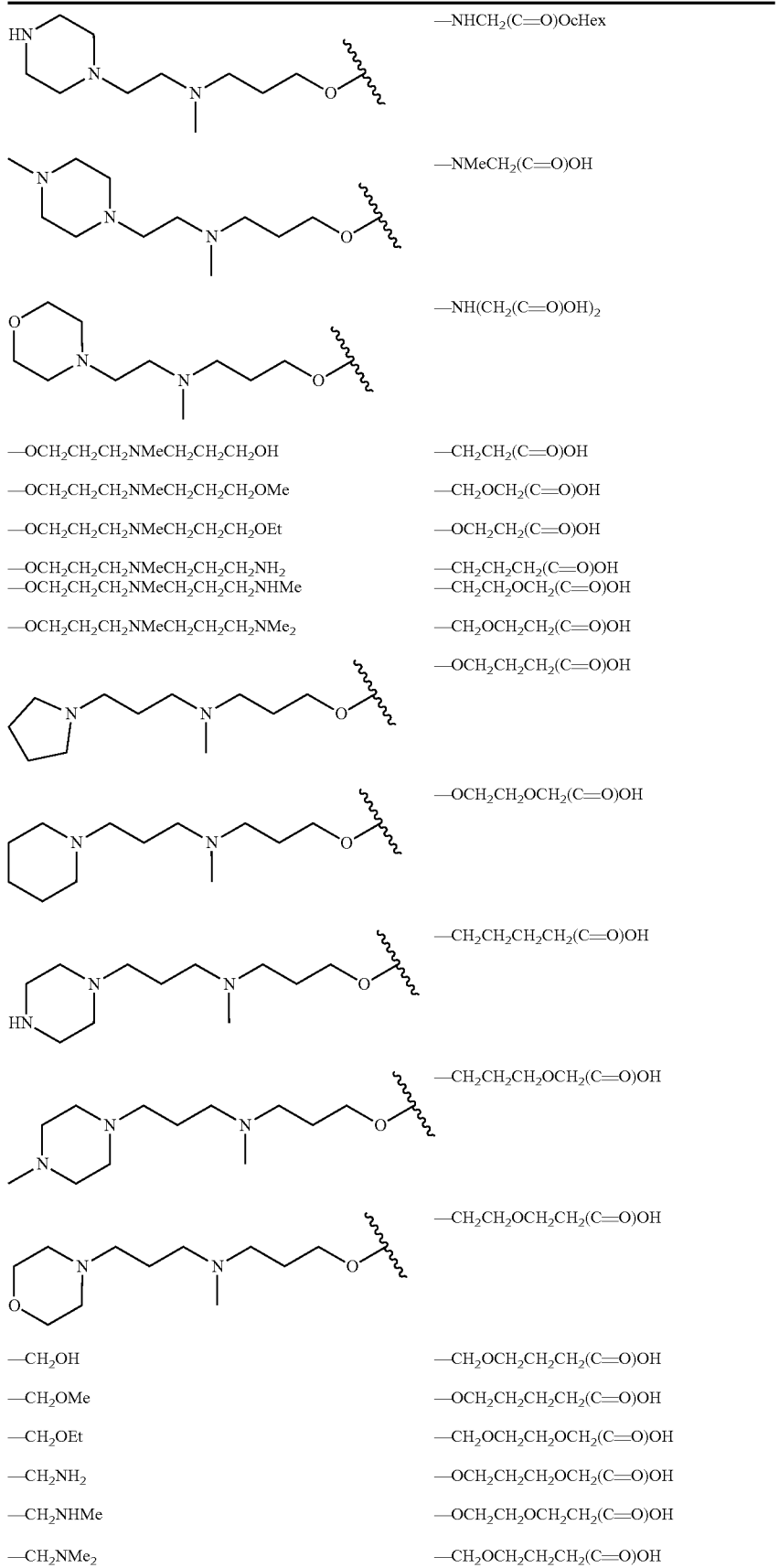

—NHCH₂(C═O)OcHex

—NMeCH₂(C═O)OH

—NH(CH₂(C═O)OH)₂

—OCH₂CH₂CH₂NMeCH₂CH₂CH₂OH     —CH₂CH₂(C═O)OH
—OCH₂CH₂CH₂NMeCH₂CH₂CH₂OMe     —CH₂OCH₂(C═O)OH
—OCH₂CH₂CH₂NMeCH₂CH₂CH₂OEt     —OCH₂CH₂(C═O)OH
—OCH₂CH₂CH₂NMeCH₂CH₂CH₂NH₂     —CH₂CH₂CH₂(C═O)OH
—OCH₂CH₂CH₂NMeCH₂CH₂CH₂NHMe     —CH₂CH₂OCH₂(C═O)OH
—OCH₂CH₂CH₂NMeCH₂CH₂CH₂NMe₂     —CH₂OCH₂CH₂(C═O)OH

—OCH₂CH₂CH₂(C═O)OH

—OCH₂CH₂OCH₂(C═O)OH

—CH₂CH₂CH₂CH₂(C═O)OH

—CH₂CH₂CH₂OCH₂(C═O)OH

—CH₂CH₂OCH₂CH₂(C═O)OH

—CH₂OH     —CH₂OCH₂CH₂CH₂(C═O)OH
—CH₂OMe     —OCH₂CH₂CH₂CH₂(C═O)OH
—CH₂OEt     —CH₂OCH₂CH₂OCH₂(C═O)OH
—CH₂NH₂     —OCH₂CH₂CH₂OCH₂(C═O)OH
—CH₂NHMe     —OCH₂CH₂OCH₂CH₂(C═O)OH
—CH₂NMe₂     —CH₂OCH₂CH₂CH₂(C═O)OH

-continued

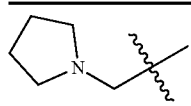 

—CH₂CH₂CH₂CH₂CH₂(C=O)OH

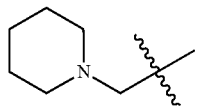 [SMILES: *CN1CCCCC1] 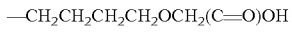

—CH₂CH₂CH₂CH₂OCH₂(C=O)OH

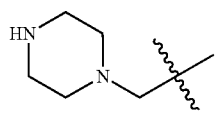 

—CH₂CH₂CH₂OCH₂CH₂(C=O)OH

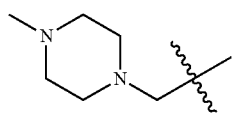 [SMILES: *CN1CCN(C)CC1] 

—CH₂CH₂OCH₂CH₂CH₂(C=O)OH

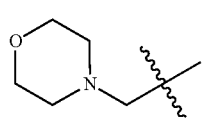 

—CH₂OCH₂CH₂CH₂CH₂(C=O)OH

—CH₂CH₂OH   —OCH₂CH₂CH₂CH₂CH₂(C=O)OH
—CH₂CH₂OMe  —CH₂CH₂OCH₂CH₂OCH₂(C=O)OH
—CH₂CH₂OEt  —CH₂OCH₂CH₂CH₂OCH₂(C=O)OH
—CH₂CH₂NH₂  —OCH₂CH₂CH₂CH₂OCH₂(C=O)OH
—CH₂CH₂NHMe —CH₂OCH₂CH₂OCH₂CH₂(C=O)OH
—CH₂CH₂NMe₂ —OCH₂CH₂CH₂OCH₂CH₂(C=O)OH

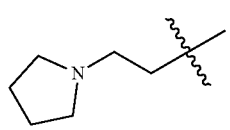 [SMILES: *CCN1CCCC1] —OCH₂CH₂OCH₂CH₂CH₂(C=O)OH

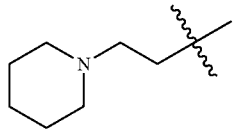 [SMILES: *CCN1CCCCC1] —OCH₂CH₂OCH₂CH₂OCH₂(C=O)OH

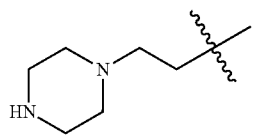 [SMILES: *CCN1CCNCC1] —CH₂CH₂CH₂CH₂CH₂CH₂(C=O)OH

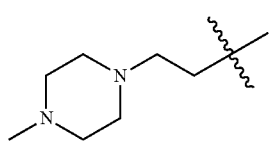 [SMILES: *CCN1CCN(C)CC1] —CH₂CH₂CH₂CH₂CH₂OCH₂(C=O)OH

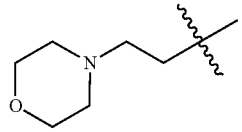 [SMILES: *CCN1CCOCC1] —CH₂CH₂CH₂OCH₂CH₂OCH₂(C=O)OH

—CH₂CH₂CH₂OH   —CH₂OCH₂CH₂OCH₂CH₂OCH₂(C=O)OH

| | |
|---|---|
| —CH₂CH₂CH₂OMe | —OCH₂CH₂CH₂OCH₂CH₂OCH₂(C=O)OH |
| —CH₂CH₂CH₂OEt | —CH₂CH₂CH₂CH₂OCH₂(C=O)OH |
| —CH₂CH₂CH₂NH₂ | —CH₂CH₂OCH₂CH₂OCH₂CH₂(C=O)OH |
| —CH₂CH₂CH₂NHMe | —CH₂OCH₂CH₂CH₂OCH₂CH₂(C=O)OH |
| —CH₂CH₂CH₂NMe₂ | —OCH₂CH₂CH₂CH₂OCH₂CH₂(C=O)OH |
| 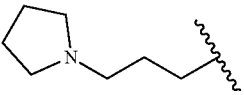 [SMILES: *CCCN1CCCC1] | —OCH₂CH₂OCH₂CH₂OCH₂CH₂(C=O)OH |
| 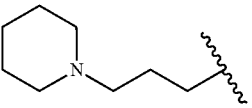 [SMILES: *CCCN1CCCCC1] | —CH₂CH₂CH₂OCH₂CH₂CH₂(C=O)OH |
| 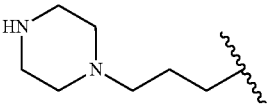 | —CH₂OCH₂CH₂OCH₂CH₂CH₂(C=O)OH |
| 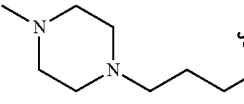 | —OCH₂CH₂CH₂OCH₂CH₂CH₂(C=O)OH |
| 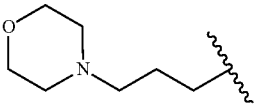 | —CH₂CH₂OCH₂CH₂CH₂CH₂(C=O)OH |
| —CH₂CH₂CH₂CH₂OH | —OCH₂CH₂OCH₂CH₂CH₂CH₂(C=O)OH |
| —CH₂CH₂CH₂CH₂OMe | —CH₂OCH₂CH₂CH₂CH₂CH₂(C=O)OH |
| —CH₂CH₂CH₂CH₂OEt | —OCH₂CH₂CH₂CH₂CH₂CH₂(C=O)OH |
| —CH₂CH₂CH₂CH₂NH₂ | —NHCH₂CH₂(C=O)OH |
| —CH₂CH₂CH₂CH₂NHMe | —NMeCH₂CH₂(C=O)OH |
| —CH₂CH₂CH₂CH₂NMe₂ | —N(CH₂CH₂(C=O)OH)₂ |
| 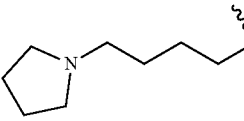 | —NHCH₂CH₂OCH₂(C=O)OH |
| 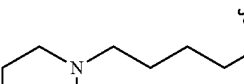 | —NMeCH₂CH₂OCH₂(C=O)OH |
| 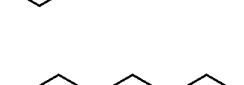 | —N(CH₂CH₂OCH₂(C=O)OH)₂ |
| 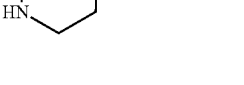 | —NHCH₂CH₂CH₂(C=O)OH |

-continued

| | |
|---|---|
| 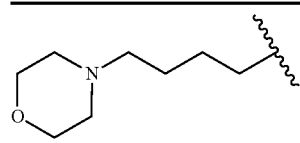 | —NMeCH$_2$CH$_2$CH$_2$(C═O)OH |
| —CH$_2$OCH$_2$CH$_2$OH | —N(CH$_2$CH$_2$CH$_2$(C═O)OH)$_2$ |
| —CH$_2$OCH$_2$CH$_2$OMe | —NHCH$_2$CH$_2$CH$_2$OCH$_2$(C═O)OH |
| —CH$_2$OCH$_2$CH$_2$OEt | —NMeCH$_2$CH$_2$CH$_2$OCH$_2$(C═O)OH |
| —CH$_2$OCH$_2$CH$_2$NH$_2$ | —N(CH$_2$CH$_2$CH$_2$OCH$_2$(C═O)OH)$_2$ |
| —CH$_2$OCH$_2$CH$_2$NHMe | —NHCH$_2$CH$_2$CH$_2$OCH$_2$CH$_2$(C═O)OH |
| —CH$_2$OCH$_2$CH$_2$NMe$_2$ | —NMeCH$_2$CH$_2$CH$_2$OCH$_2$CH$_2$(C═O)OH |
| 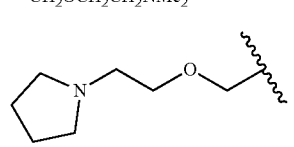 | —N(CH$_2$CH$_2$OCH$_2$CH$_2$(C═O)OH)$_2$ |
| 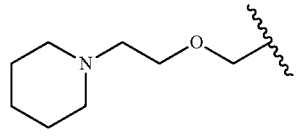 | —NHCH$_2$CH$_2$CH$_2$CH$_2$CH$_2$(C═O)OH |
| 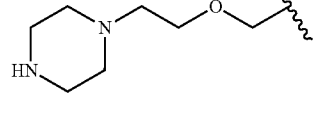 | —NMeCH$_2$CH$_2$CH$_2$CH$_2$CH$_2$(C═O)OH |
| 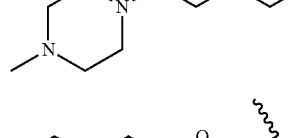 | —N(CH$_2$CH$_2$CH$_2$CH$_2$CH$_2$(C═O)OH)$_2$ |
| 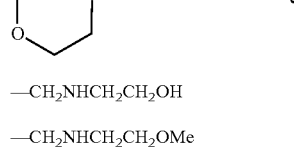 | —NHCH$_2$CH$_2$CH$_2$CH$_2$OCH$_2$(C═O)OH |
| —CH$_2$NHCH$_2$CH$_2$OH | —NMeCH$_2$CH$_2$CH$_2$CH$_2$OCH$_2$(C═O)OH |
| —CH$_2$NHCH$_2$CH$_2$OMe | —N(CH$_2$CH$_2$CH$_2$CH$_2$OCH$_2$(C═O)OH)$_2$ |
| —CH$_2$NHCH$_2$CH$_2$OEt | —NHCH$_2$CH$_2$CH$_2$OCH$_2$CH$_2$(C═O)OH |
| —CH$_2$NHCH$_2$CH$_2$NH$_2$ | —NMeCH$_2$CH$_2$CH$_2$OCH$_2$CH$_2$(C═O)OH |
| —CH$_2$NHCH$_2$CH$_2$NHMe | —N(CH$_2$CH$_2$CH$_2$OCH$_2$CH$_2$(C═O)OH)$_2$ |
| —CH$_2$NHCH$_2$CH$_2$NMe$_2$ | —NHCH$_2$CH$_2$OCH$_2$CH$_2$CH$_2$(C═O)OH |
| 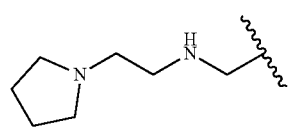 [SMILES: *CNCCN1CCCC1] | —NMeCH$_2$CH$_2$OCH$_2$CH$_2$CH$_2$(C═O)OH |
| 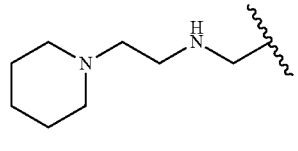 [SMILES: *CNCCN1CCCCC1] | —N(CH$_2$CH$_2$OCH$_2$CH$_2$CH$_2$(C═O)OH)$_2$ |

-continued

| | |
|---|---|
| [piperazine-CH2CH2-NH-CH2~] | —NHCH2CH2OCH2CH2OCH2(C=O)OH |
| [N-methylpiperazine-CH2CH2-NH-CH2~] | —NMeCH2CH2OCH2CH2OCH2(C=O)OH |
| [morpholine-CH2CH2-NH-CH2~] | —N(CH2CH2OCH2CH2OCH2(C=O)OH)2 |
| —CH2N(CH2CH2OH)2 | —NHCH2CH2CH2OCH2CH2OCH2CO2H |
| —CH2N(CH2CH2OMe)2 | —NMeCH2CH2CH2OCH2CH2OCH2CO2H |
| —CH2N(CH2CH2OEt)2 | —N(CH2CH2CH2OCH2CH2OCH2CO2H)2 |
| —CH2NMeCH2CH2OH | —NHCH2CH2OCH2CH2OCH2CO2H |
| —CH2NMeCH2CH2OMe | —NMeCH2CH2OCH2CH2OCH2CO2H |
| —CH2NMeCH2CH2OEt | —N(CH2CH2OCH2CH2OCH2CO2H)2 |
| —CH2NMeCH2CH2NH2 | —NHCH2CH2OCH2CH2OCH2CO2H |
| —CH2NMeCH2CH2NHMe | —NMeCH2CH2OCH2CH2OCH2CO2H |
| —CH2NMeCH2CH2NMe2 | —N(CH2CH2OCH2CH2OCH2CO2H)2 |
| [pyrrolidine-CH2CH2-NMe-CH2~] | —NHCH2CH2OCH2CH2CH2CO2H |
| [piperidine-CH2CH2-NMe-CH2~] | —NMeCH2CH2OCH2CH2CH2CO2H |
| [piperazine-CH2CH2-NMe-CH2~] | —N(CH2CH2CH2OCH2CH2CH2CO2H)2 |
| [N-methylpiperazine-CH2CH2-NMe-CH2~] | —NHCH2CH2OCH2CH2CH2CO2H |
| [morpholine-CH2CH2-NMe-CH2~] | —NMeCH2CH2OCH2CH2CH2CO2H |
| —CH2CH2OCH2CH2OH | —N(CH2CH2OCH2CH2CH2CO2H)2 |
| —CH2CH2OCH2CH2OMe | —NHCH2CH2CH2CH2CH2CO2H |

| | |
|---|---|
| —CH$_2$CH$_2$OCH$_2$CH$_2$OEt | —NMeCH$_2$CH$_2$CH$_2$CH$_2$CH$_2$CH$_2$CO$_2$H |
| —CH$_2$CH$_2$OCH$_2$CH$_2$NH$_2$ | —N(CH$_2$CH$_2$CH$_2$CH$_2$CH$_2$CH$_2$CO$_2$H)$_2$ |
| —CH$_2$CH$_2$OCH$_2$CH$_2$NHMe. | |

6. The compound of claim 1, wherein at least one of $R^5$, $R^6$, $R^7$, and $R^8$ is $Ar^S$.

7. The compound of claim 1, wherein $Z^1$, $Z^2$, $R^6$, $R^7$, and $R^8$ are independently selected from the group consisting of H, $C_{1-6}$ alkoxy, $C_{1-6}$ alkoxy-$C_{1-6}$ alkyl, carboxy, carboxy-$C_{1-6}$ alkyl, amino-$C_{1-6}$ alkyl, $C_{1-6}$ alkylamino-$C_{1-6}$ alkyl, di($C_{1-6}$ alkyl)amino-$C_{1-6}$ alkyl, amino-$C_{1-6}$ alkoxy-$C_{1-6}$ alkyl, $C_{1-6}$ alkylamino-$C_{1-6}$ alkoxy-$C_{1-6}$ alkyl, di($C_{1-6}$ alkyl) amino-$C_{1-6}$ alkoxy-$C_{1-6}$ alkyl, 4-10 membered hetercycloalkyl-$C_{1-6}$ alkyl, 4-10 membered hetercycloalkyl-$C_{1-4}$ alkoxy-$C_{1-6}$ alkyl, $C_{1-6}$ alkoxy-$C_{1-6}$ alkoxy, amino-C alkoxy, $C_{1-6}$ alkylamino-$C_{1-6}$ alkoxy, di($C_{1-6}$ alkyl)amino-$C_{1-6}$ alkoxy, amino-$C_{1-6}$ alkoxy-$C_{1-6}$ alkoxy, $C_{1-6}$ alkylamino-$C_{1-6}$ alkoxy-$C_{1-6}$ alkoxy, di($C_{1-6}$ alkyl)amino-$C_{1-6}$ alkoxy-$C_{1-6}$ alkoxy, 4-10 membered hetercycloalkyl-$C_{1-4}$ alkoxy, or 4-10 membered hetercycloalkyl-$C_{1-6}$ alkoxy, carboxy-$C_{1-6}$-alkoxy, carboxy-$C_{1-6}$-alkyl-$C_{1-6}$-alkoxy, and carboxy-$C_{1-6}$-alkoxy-$C_{1-6}$-alkoxy.

8. The compound of claim 1, wherein at least one of $Z^1$, $Z^2$, $R^6$, $R^7$, and $R^8$ is selected from the group consisting of H, methoxy, ethoxy, methoxymethyl, ethoxymethyl, 2-methoxyethyl, 2-ethoxyethyl, 2-(methoxy)ethoxy, 2-(ethoxy)ethoxy, carboxy, carboxymethyl, 2-carboxyethyl, aminomethyl, 2-aminoethyl, 3-aminopropyl, 2-aminoethoxy, 3-aminopropoxy, (2-aminoethoxy)methyl, (3-aminopropoxy)methyl, 2-(2-aminoethoxy)ethyl, 2-(2-aminoethoxy)ethoxy, N-methylaminomethyl, 2-N-methylaminoethyl, 3-N-methylaminopropyl, 2-N-methylaminoethoxy, 3-N-methylaminopropoxy, (2-N-methylaminoethoxy)methyl, (3-N-methylaminopropoxy)methyl, 2-(2-N-methylaminoethoxy)ethyl, 2-(2-N-methylaminoethoxy)ethoxy, (N,N-dimethylamino)methyl, 2-(N,N-dimethylamino)ethyl, 3-(N,N-dimethylamino)propyl, 2-(N,N-dimethylamino)ethoxy, 3-(N,N-dimethylamino)propoxy, (2-(N,N-dimethylamino) ethoxy)methyl, (3-(N,N-dimethylamino)propoxy)methyl, 2-(2-(N,N-dimethylamino)ethoxy)ethyl, 2-(2-(N,N-dimethylamino)ethoxy)ethoxy, (N-morpholinyl)methyl, 2-(N-morpholinyl)ethyl, 3-(N-morpholinyl)propyl, 2-(N-morpholinyl)ethoxy, 3-(N-morpholinyl)propoxy, (2-(N-morpholinyl)ethoxy)methyl, (3-(N-morpholinyl)propoxy)methyl, 2-(2-(N-morpholinyl)ethoxy)ethyl, or 2-(2-(N-morpholinyl) ethoxy)ethoxy, 3-carboxypropyl, carboxymethoxy, 2-carboxyethoxy, 3-carboxypropoxy, carboxymethoxymethyl, 2-(carboxymethoxy)ethyl, 2-(carboxymethoxy) ethoxy, 2-carboxyethoxymethyl, and 2-(2-carboxyethoxy) ethoxy.

9. The compound of claim 1, wherein $L^S$ is O or NH.

10. The compound of claim 1, wherein at least one of $R^6$, $R^7$, and $R^8$ is H, $OR^{a1}$, or $C_{1-6}$ alkyl substituted with one or more substituents selected from the group consisting of $OR^{a2}$, $C(O)OR^{a2}$, and $NR^{c2}R^{d2}$.

11. The compound of claim 1, wherein $R^8$ is H, chloro, methoxy, 2-(methoxy)ethoxy, 4-methoxyphenyl, or phenoxy.

12. The compound of claim 1, wherein $Y^1$ is H or halogen; $Y^2$ is H, halogen, $C_{1-6}$ alkyl, or $OR^{a3}$; $Y^3$ is OH, CN, $OR^{a3}$, $NR^{c3}R^{d3}$ or $C(O)NR^{c3}R^{d3}$; $Y^4$ is H or halo; and $Y^5$ is H or F.

13. The compound of claim 1, wherein one or two of $A^1$, $A^2$, $A^3$, $A^4$ and $A^5$ in $Ar^S$ is/are N.

14. The compound of claim 1, wherein $Ar^S$ is a group of any of the following formulae:

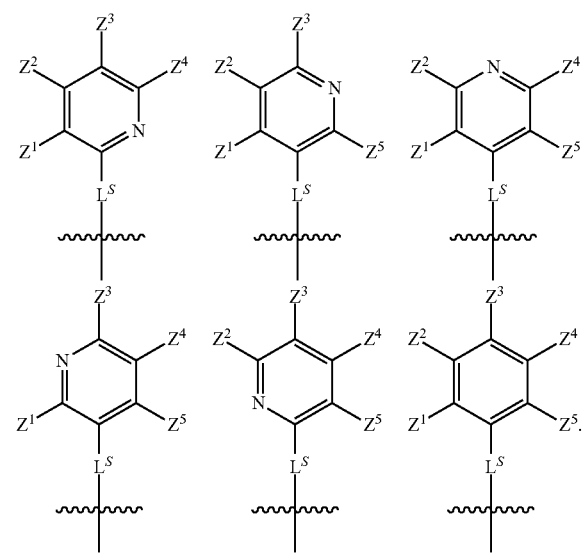

15. The compound of claim 14, wherein $Z^1$, $Z^2$, $Z^3$, $Z^4$, and $Z^5$ are each independently selected from the group consisting of H, $C_{1-6}$ alkyl, halogen, and $C_{1-6}$ alkoxy, or wherein any one or two of $Z^1$, $Z^2$, $Z^3$, $Z^4$, and $Z^5$ is independently selected from water solubilizing groups.

16. The compound of claim 1, wherein $Ar^S$ is a group of the following formula:

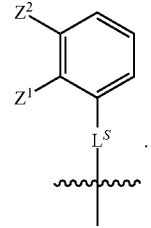

17. The compound of claim 1, wherein:
$X^3$ is $CR^3$ or N;
$X^8$ is $CR^8$ or N;
$R^3$ is selected from the group consisting of H, halogen, $C_{1-6}$ alkyl, and $C_{1-6}$haloalkyl;
$R^4$ is selected from the group consisting of H, halogen $C_{1-6}$ alkyl, and $C_{1-6}$haloalkyl;
$R^5$, $R^6$, $R^7$ and $R^8$ are each independently selected from the group consisting of H, water solubilizing groups, halogen, $C_{1-6}$ alkyl, $C_{2-6}$ alkenyl, $C_{2-6}$ alkynyl, $C_{6-10}$ aryl, and $OR^{a1}$, wherein each $C_{6-10}$ aryl forming $R^5$, $R^6$, R[7] or R[8] is independently unsubstituted or substituted with 1, 2, 3, 4 or 5 substituents independently selected from the group consisting of $C_{1-6}$ alkyl, halogen, and $OR^{a2}$;

$Y^1$, $Y^2$, $Y^3$, $Y^4$ and $Y^5$ are each independently selected from the group consisting of H, halogen, $C_{1-6}$ alkyl, $C_{2-6}$ alkenyl, $C_{2-6}$ alkynyl, CN, $OR^{a3}$, $NR^{c3}R^{d3}$ and $C(O)NR^{c3}R^{d3}$;

$R^{a1}$, $R^{a2}$, and $R^{a3}$ are each independently selected from the group consisting of hydrogen, $C_{1-4}$ alkyl, and $C_{6-10}$ aryl, wherein each said $C_{1-4}$ alkyl forming $R^{a1}$, $R^{a2}$, or $R^{a3}$ is independently unsubstituted or substituted by 1, 2, or 3 groups independently selected from the group consisting of halo and $OR^{a5}$ and wherein each said $C_{6-10}$ aryl forming $R^{a1}$, $R^{a2}$, and $R^{a3}$ is independently unsubstituted or substituted by 1, 2, or 3, groups independently selected from the group consisting of $C_{1-6}$ alkyl, halo, $OR^{a5}$, and $C(O)OR^{a5}$;

$R^{c3}$ and $R^{d3}$ are each independently selected from the group consisting of hydrogen and $C_{1-4}$ alkyl;

each $R^{a5}$ is independently selected from the group consisting of H and $C_{1-6}$ alkyl, wherein said $C_{1-6}$ alkyl, forming $R^{a5}$ is optionally substituted with 1, 2 or 3 substituents independently selected from the group consisting of OH, amino, $NH(C_{1-6}$ alkyl), $N(C_{1-6}$ alkyl)$_2$, $C_{1-6}$ alkoxy and 4-10 membered heterocycloalkyl-$C_{1-3}$ alkylene; and $R^{c5}$ and $R^{d5}$ are each independently selected from the group consisting of H and $C_{1-6}$ alkyl.

18. The compound of claim 1, wherein:
$X^3$ is $CR^8$;
$X^8$ is $CR^8$ or N;
$R^3$ is H or $C_{1-6}$ alkyl;
$R^4$ is H or $C_{1-6}$ alkyl;
$R^5$ is H, a water solubilizing group, $C_{6-10}$ aryl, or $OR^{a1}$, wherein each $C_{6-10}$ aryl forming $R^5$ is independently unsubstituted or substituted with 1, 2, or 3 substituents independently selected from the group consisting of $C_{1-6}$ alkyl, halogen, and $OR^{a2}$;
$R^6$ is H, a water solubilizing group, or $OR^{a1}$,
$R^7$ is H;
$R^8$ is H, a water solubilizing group, halogen, $C_{6-10}$ aryl, or $OR^{a1}$, wherein each $C_{6-10}$ aryl forming $R^8$ is independently unsubstituted or substituted with 1, 2, or 3 substituents independently selected from the group consisting of $C_{1-6}$ alkyl, halogen, and $OR^{a2}$;
$Y^1$ is H;
$Y^2$ is H, halogen, $C_{1-6}$ alkyl, or $OR^{a3}$;
$Y^3$ is OH, halogen, CN, $OR^{a3}$, $NR^{c3}R^{d3}$ or $C(O)NR^{c3}R^{d3}$;
$Y^4$ is H;
$Y^5$ is H;
$R^{a1}$, $R^{a2}$, and $R^{a3}$ are each independently selected from the group consisting of hydrogen, $C_{1-4}$ alkyl, and $C_{6-10}$ aryl, wherein each said $C_{1-4}$ alkyl forming $R^{a1}$, $R^{a2}$, or $R^{a3}$ is independently unsubstituted or substituted by 1, 2, or 3 groups independently selected from the group consisting of halo and $OR^{a5}$ and wherein each said $C_{6-10}$ aryl forming $R^{a1}$, $R^{a2}$, and $R^{a3}$ is independently unsubstituted or substituted by 1, 2, or 3, groups independently selected from the group consisting of $C_{1-6}$ alkyl, halo, $OR^{a5}$, and $C(O)OR^{a5}$;

$R^{c3}$ and $R^{d3}$ are each independently selected from the group consisting of hydrogen and $C_{1-4}$ alkyl;

each $R^{a5}$ is independently selected from H and $C_{1-6}$ alkyl, wherein said $C_{1-6}$ alkyl, forming $R^{a5}$ is optionally substituted with 1, 2 or 3 substituents independently selected from the group consisting of OH, amino, $NH(C_{1-6}$ alkyl), $N(C_{1-6}$ alkyl)$_2$, $C_{1-6}$ alkoxy and 4-10 membered heterocycloalkyl-$C_{1-4}$ alkyl; and $R^{c5}$ and $R^{d5}$ are each independently selected from the group consisting of H and $C_{1-6}$ alkyl.

19. The compound of claim 1, wherein:
$X^3$ is $CR^3$ or N;
$X^8$ is $CR^8$ or N;
$R^3$ is selected from the group consisting of H, F, methyl and ethyl;
$R^4$ is selected from the group consisting of H, F, methyl and ethyl;
$R^5$ is selected from the group consisting of H, $Ar^S$; and water solubilizing groups;
$R^6$ is selected from the group consisting of H, $Ar^S$; and water solubilizing groups;
$R^7$ is selected from the group consisting of H, $Ar^S$; and water solubilizing groups;
$R^8$ is selected from the group consisting of H, $Ar^S$; and water solubilizing groups;
$Y^1$, $Y^2$, $Y^4$ and $Y^5$ are each independently selected from the group consisting of H and F; and
$Y^3$ is selected from the group consisting of H, F, Cl and OH.

20. The compound of claim 1, which is a compound of Formula (II) or Formula (III):

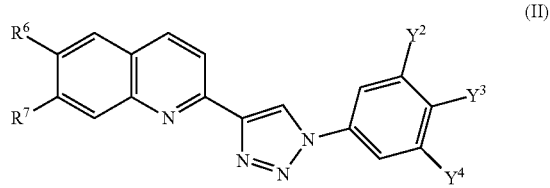

(II)

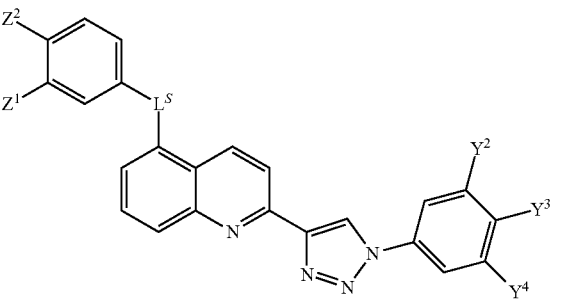

(III)

or a pharmaceutically acceptable salt thereof.

21. A compound selected from the group consisting of:
4-(4-(6-(2-methoxyethoxy)quinolin-2-yl)-1H-1,2,3-triazol-1-yl)phenol;
4-(4-(6-(2-(2-aminoethoxy)ethoxy)quinolin-2-yl)-1H-1,2,3-triazol-1-yl)phenol;
2-(1-(4-fluorophenyl)-1H-1,2,3-triazol-4-yl)-6-(2-methoxyethoxy)quinoline;
2-(1-(4-chlorophenyl)-1H-1,2,3-triazol-4-yl)-6-(2-methoxyethoxy)quinoline;
4-(4-(6-(2-methoxyethoxy)quinolin-2-yl)-1H-1,2,3-triazol-1-yl)aniline;
2-(1-(4-methoxyphenyl)-1H-1,2,3-triazol-4-yl)-6-(2-methoxyethoxy)quinoline;
4-(4-(6-(2-methoxyethoxy)quinolin-2-yl)-1H-1,2,3-triazol-1-yl)benzonitrile;
4-(4-(6-(2-methoxyethoxy)quinolin-2-yl)-1H-1,2,3-triazol-1-yl)benzamide;

4-(4-(6-(2-methoxyethoxy)quinolin-2-yl)-1H-1,2,3-triazol-1-yl)-2-methylphenol;
2-methoxy-4-(4-(6-(2-methoxyethoxy)quinolin-2-yl)-1H-1,2,3-triazol-1-yl)phenol;
2-(1-(4-fluorophenyl)-1H-1,2,3-triazol-4-yl)-8-methoxyquinoline;
8-(2-ethoxyethoxy)-2-(1-(4-fluorophenyl)-1H-1,2,3-triazol-4-yl)quinoline;
2-(1-(4-fluorophenyl)-1H-1,2,3-triazol-4-yl)-8-(2-methoxyethoxy)quinoline;
4-(4-(8-(4-methoxyphenoxy)quinolin-2-yl)-1H-1,2,3-triazol-1-yl)phenol;
2-(1-(4-fluorophenyl)-1H-1,2,3-triazol-4-yl)-8-phenoxyquinoline;
2-(1-(4-fluorophenyl)-1H-1,2,3-triazol-4-yl)-5-phenoxyquinoline;
4-(4-(6-(3-morpholinopropoxy)quinolin-2-yl)-1H-1,2,3-triazol-1-yl)phenol;
4-(4-(3-methyl-6-(3-morpholinopropoxy)quinolin-2-yl)-1H-1,2,3-triazol-1-yl)phenol;
4-(4-(6-(2-(2-morpholinoethoxy)ethoxy)quinolin-2-yl)-1H-1,2,3-triazol-1-yl)phenol;
2-fluoro-4-(4-(6-(2-(2-morpholinoethoxy)ethoxy)quinolin-2-yl)-1H-1,2,3-triazol-1-yl)phenol;
4-(2-(2-((2-(1-(4-fluorophenyl)-1H-1,2,3-triazol-4-yl)quinolin-6-yl)oxy)ethoxy)ethyl) morpholine;
4-(2-(2-((2-(1-(4-fluorophenyl)-1H-1,2,3-triazol-4-yl)quinolin-6-yl)oxy)ethoxy)ethyl) morpholine;
2-fluoro-4-(4-(5-(3-(2-methoxyethoxy)phenoxy)quinolin-2-yl)-1H-1,2,3-triazol-1-yl)phenol;
4-((2-(1-(3-fluoro-4-hydroxyphenyl)-1H-1,2,3-triazol-4-yl)quinolin-5-yl)oxy)benzoic acid;
4-(4-(7-(2-(2-morpholinoethoxy)ethoxy)quinolin-2-yl)-1H-1,2,3-triazol-1-yl)phenol;
4-(4-(6-(2-methoxyethoxy)quinazolin-2-yl)-1H-1,2,3-triazol-1-yl)phenol;
3-((2-(1-(3-fluoro-4-hydroxyphenyl)-1H-1,2,3-triazol-4-yl)quinolin-5-yl)oxy)benzoic acid;
3-((2-(1-(4-hydroxyphenyl)-1H-1,2,3-triazol-4-yl)quinolin-5-yl)oxy)benzoic acid;
4-((2-(1-(4-hydroxyphenyl)-1H-1,2,3-triazol-4-yl)quinolin-5-yl)oxy)benzoic acid;
4-(4-(5-(3-(aminomethyl)phenoxy)quinolin-2-yl)-1H-1,2,3-triazol-1-yl)phenol;
4-(4-(5-(4-(aminomethyl)phenoxy)quinolin-2-yl)-1H-1,2,3-triazol-1-yl)phenol;
4-(4-(5-(4-(2-methoxyethoxy)phenoxy)quinolin-2-yl)-1H-1,2,3-triazol-1-yl)phenol;
4-(4-(5-(3-(2-methoxyethoxy)phenoxy)quinolin-2-yl)-1H-1,2,3-triazol-1-yl)phenol;
4-(4-(5-(3-(2-(2-morpholinoethoxy)ethoxy)phenoxy)quinolin-2-yl)-1H-1,2,3-triazol-1-yl)phenol;
4-(4-(5-(4-(2-(2-morpholinoethoxy)ethoxy)phenoxy)quinolin-2-yl)-1H-1,2,3-triazol-1-yl)phenol;
2-(1-(4-hydroxyphenyl)-1H-1,2,3-triazol-4-yl)-7-methyl-1,7-naphthyridin-8(7H)-one;
4-(4-(6-(2-(2-aminoethoxy)ethoxy)quinolin-2-yl)-1H-1,2,3-triazol-1-yl)-2-fluorophenol;
4-(4-(6-(2-(2-aminoethoxy)ethoxy)quinolin-2-yl)-1H-1,2,3-triazol-1-yl)-2,6-difluorophenol;
2-fluoro-4-(4-(5-(2-(2-morpholinoethoxy)ethoxy)quinolin-2-yl)-1H-1,2,3-triazol-1-yl)phenol;
2-fluoro-4-(4-(7-(2-(2-morpholinoethoxy)ethoxy)quinolin-2-yl)-1H-1,2,3-triazol-1-yl)phenol;
2-fluoro-4-(4-(6-(2-(2-(pyridin-2-yl)ethoxy)ethoxy)quinolin-2-yl)-1H-1,2,3-triazol-1-yl)phenol;
2-fluoro-4-(4-(6-(2-(2-(piperidin-1-yl)ethoxy)ethoxy)quinolin-2-yl)-1H-1,2,3-triazol-1-yl)phenol;
4-(4-(6-(2-(2-(1H-imidazol-1-yl)ethoxy)ethoxy)quinolin-2-yl)-1H-1,2,3-triazol-1-yl)-2-fluorophenol;
2-fluoro-4-(4-(6-(2-(2-(4-methylpiperazin-1-yl)ethoxy)ethoxy)quinolin-2-yl)-1H-1,2,3-triazol-1-yl)phenol;
2-((2-(1-(3-fluoro-4-hydroxyphenyl)-1H-1,2,3-triazol-4-yl)quinolin-6-yl)oxy)acetic acid;
N-(2-(diethylamino)ethyl)-2-(1-(3-fluoro-4-hydroxyphenyl)-1H-1,2,3-triazol-4-yl)quinoline-6-carboxamide;
4-((2-(1-(3-fluoro-4-hydroxyphenyl)-1H-1,2,3-triazol-4-yl)quinolin-6-yl)oxy)benzoic acid;
2-(2-(1-(3-fluoro-4-hydroxyphenyl)-1H-1,2,3-triazol-4-yl)quinolin-6-yl)acetic acid;
2,6-difluoro-4-(4-(6-(2-(2-morpholinoethoxy)ethoxy)quinolin-2-yl)-1H-1,2,3-triazol-1-yl)phenol;
2-fluoro-5-((2-(1-(3-fluoro-4-hydroxyphenyl)-1H-1,2,3-triazol-4-yl)quinolin-5-yl)oxy)benzoic acid; and
3-fluoro-5-((2-(1-(3-fluoro-4-hydroxyphenyl)-1H-1,2,3-triazol-4-yl)quinolin-5-yl)oxy)benzoic acid,
2-fluoro-4-(4-(5-(3-(2-(2-morpholinoethoxy)ethoxy)phenoxy)quinolin-2-yl)-1H-1,2,3-triazol-1-yl)phenol;
4-((2-(1-(3-fluoro-4-hydroxyphenyl)-1H-1,2,3-triazol-4-yl)quinolin-7-yl)oxy)butanoic acid;
2-(2-((2-(1-(3-fluoro-4-hydroxyphenyl)-1H-1,2,3-triazol-4-yl)quinolin-6-yl)oxy)ethoxy)acetic acid,
or a pharmaceutically acceptable salt thereof.

22. A compound selected from the group consisting of:
3-((2-(1-(3,4-difluorophenyl)-1H-1,2,3-triazol-4-yl)quinolin-5-yl)oxy)benzoic acid;
4-(4-(5-(3-(aminomethyl)phenoxy)quinolin-2-yl)-1H-1,2,3-triazol-1-yl)-2-fluorophenol;
2-fluoro-4-(4-(5-(3-(2-(2-morpholinoethoxy)ethoxy)phenoxy)quinolin-2-yl)-1H-1,2,3-triazol-1-yl)phenol;
4-((2-(1-(3-fluoro-4-hydroxyphenyl)-1H-1,2,3-triazol-4-yl)quinolin-8-yl)oxy)benzoic acid;
3-((2-(1-(3-fluoro-4-hydroxyphenyl)-1H-1,2,3-triazol-4-yl)quinolin-8-yl)oxy)benzoic acid;
2-((2-(1-(3-fluoro-4-hydroxyphenyl)-1H-1,2,3-triazol-4-yl)quinolin-7-yl)oxy)acetic acid;
4-((2-(1-(3-fluoro-4-hydroxyphenyl)-1H-1,2,3-triazol-4-yl)quinolin-7-yl)oxy)butanoic acid;
4-((2-(1-(3-fluoro-4-hydroxyphenyl)-1H-1,2,3-triazol-4-yl)quinolin-6-yl)oxy)butanoic acid; and
2-(2-((2-(1-(3-fluoro-4-hydroxyphenyl)-1H-1,2,3-triazol-4-yl)quinolin-6-yl)oxy)ethoxy)acetic acid,
or a pharmaceutically acceptable salt thereof.

23. A composition comprising the compound of claim 1, or a pharmaceutically acceptable salt thereof, and a pharmaceutically acceptable carrier.

24. A compound of Formula (I):

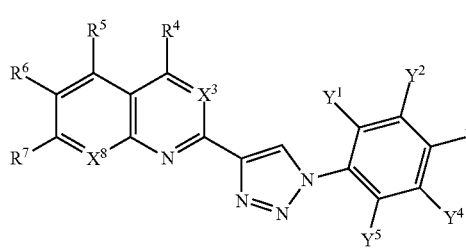

or a pharmaceutically acceptable salt thereof, wherein:
$X^3$ is CH;
$X^8$ is CH;

$R^4$ is H;

$R^5$, $R^6$, and $R^7$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^{e1})NR^{c1}R^{d1}$, $NR^{c1}C(=NR^{e1})NR^{c1}R^{d1}$, $S(O)R^{b1}$, $S(O)_2R^{b1}$, $NR^{c1}S(O)_2R^{b1}$, and $S(O)_2NR^{c1}R^{d1}$;

wherein each of said $C_{1-6}$ alkyl, $C_{2-6}$ alkenyl, and $C_{2-6}$ alkynyl; forming $R^5$, $R^6$, and $R^7$ is independently unsubstituted or substituted with 1, 2, 3, 4 or 5 substituents independently selected from the group consisting of halogen, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, and $S(O)_2NR^{c2}R^{d2}$;

wherein each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $R^5$, $R^6$, and $R^7$ is independently unsubstituted or substituted with 1, 2, 3, 4 or 5 substituents independently selected from the group consisting of $C_{1-6}$ alkyl, halogen, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^{e2})NR^{c2}R^{d2}$, $NR^{c2}C(=NR^{e2})NR^{c2}R^{d2}$, $S(O)R^{b2}$, $S(O)_2R^{b2}$, $NR^{c2}S(O)_2R^{b2}$, and $S(O)_2NR^{c2}R^{d2}$;

or $R^5$ may represent a group of formula $Ar^S$;

or at least one of $R^5$, $R^6$, and $R^7$ may be each independently a water solubilizing group;

$Y^1$, $Y^2$ and $Y^5$ are H;

$Y^3$ is $OR^{a3}$ or $OC(O)R^{b3}$;

$Y^5$ is F;

$Ar^S$ is:

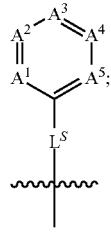

$A^1$ is N or $CZ^1$;

$A^2$ is N or $CZ^2$;

$A^3$ is N or $CZ^3$;

$A^4$ is N or $CZ^4$;

$A^5$ is N or $CZ^5$;

provided that 0, 1 or 2 of $Z^1$, $Z^2$, $Z^3$, $Z^4$, and $Z^5$ are nitrogen;

$Z^1$, $Z^2$, $Z^3$, $Z^4$, and $Z^5$ are each independently selected from the group consisting of H, halogen, $C_{1-6}$ alkyl, $C_{2-6}$ alkenyl, $C_{2-6}$ alkynyl, $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene, 4-10 membered heterocycloalkyl-$C_{1-4}$ alkylene, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)_2R^{b5}$, $NR^{c5}S(O)_2R^{b5}$, and $S(O)_2NR^{c5}R^{d5}$;

wherein each of said $C_{1-6}$ alkyl, $C_{2-6}$ alkenyl, and $C_{2-6}$ alkynyl forming $Z^1$, $Z^2$, $Z^3$, $Z^4$, or $Z^5$ is independently unsubstituted or substituted with 1, 2, 3, 4 or 5 substituents independently selected from the group consisting of halogen, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)_2R^{b6}$, $NR^{c6}S(O)_2R^{b6}$, and $S(O)_2NR^{c6}R^{d6}$; and wherein each of said $C_{3-7}$ cycloalkyl, $C_{6-10}$ aryl, 5-10 membered heteroaryl, 4-10 membered heterocycloalkyl, $C_{3-7}$ cycloalkyl-$C_{1-4}$ alkylene, $C_{6-10}$ aryl-$C_{1-4}$ alkylene, 5-10 membered heteroaryl-$C_{1-4}$ alkylene and 4-10 membered heterocycloalkyl-$C_{1-4}$ alkylene forming $Z^1$, $Z^2$, $Z^3$, $Z^4$, or $Z^5$ is independently unsubstituted or substituted with 1, 2, 3, 4 or 5 substituents independently selected from the group consisting of $C_{1-6}$ alkyl, halogen, $C_{1-6}$ haloalkyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)_2R^{b6}$, $NR^{c6}S(O)_2R^{b6}$, and $S(O)_2NR^{c6}R^{d6}$;

or wherein any one or two of $Z^1$, $Z^2$, $Z^3$, $Z^4$, and $Z^5$ is independently selected from water solubilizing groups;

provided that at least one of $R^5$, $R^6$, $R^7$, $R^8$, $Z^1$, and $Z^2$ is a water solubilizing group, each occurrence of which is independently selected from the group consisting of:

—OH

—OMe

—$CH_2CH_2OCH_2CH_2NMe_2$

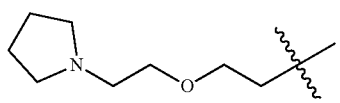 [SMILES: *CCOCCN1CCCC1]

—OEt 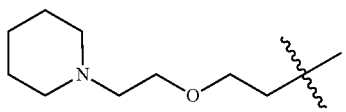 [SMILES: *CCOCCN1CCCCC1]
—OPr 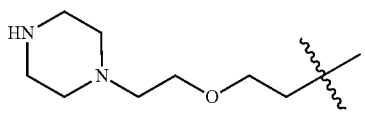 [SMILES: *CCOCCN1CCNCC1]
—OiPr 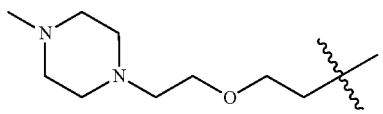 [SMILES: *CCOCCN1CCN(C)CC1]
—OcPr 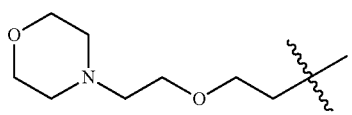 [SMILES: *CCOCCN1CCOCC1]
—OcBu
—OcPn
—OcHex
—OCH₂CH₂OH
—OCH₂CH₂OMe
—OCH₂CH₂OEt
—CH₂CH₂NHCH₂CH₂OH
—CH₂CH₂NHCH₂CH₂OMe
—CH₂CH₂NHCH₂CH₂OEt
—CH₂CH₂NHCH₂CH₂NH₂
—CH₂CH₂NHCH₂CH₂NHMe
—CH₂CH₂NHCH₂CH₂NMe₂
—OCH₂CH₂NH₂ 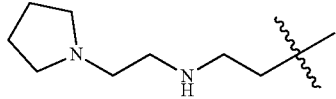 [SMILES: *CCNCCN1CCCC1]
—OCH₂CH₂NHMe 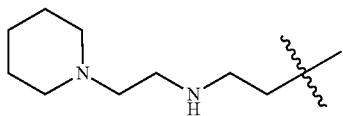 [SMILES: *CCNCCN1CCCCC1]
—OCH₂CH₂NMe₂ 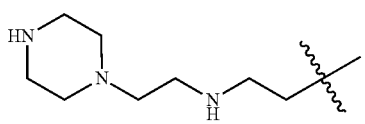 [SMILES: *CCNCCN1CCNCC1]
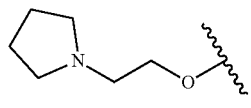 [SMILES: *OCCN1CCCC1] 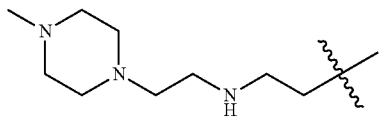 [SMILES: *CCNCCN1CCN(C)CC1]
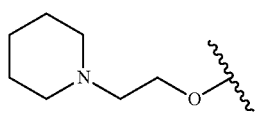 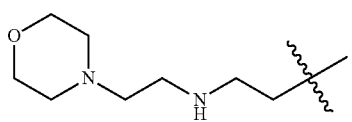 [SMILES: *CCNCCN1CCOCC1]
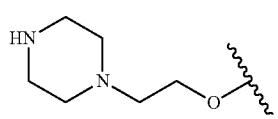
—CH₂CH₂N(CH₂CH₂OH)₂
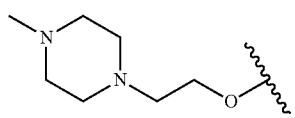
—CH₂CH₂N(CH₂CH₂OMe)₂

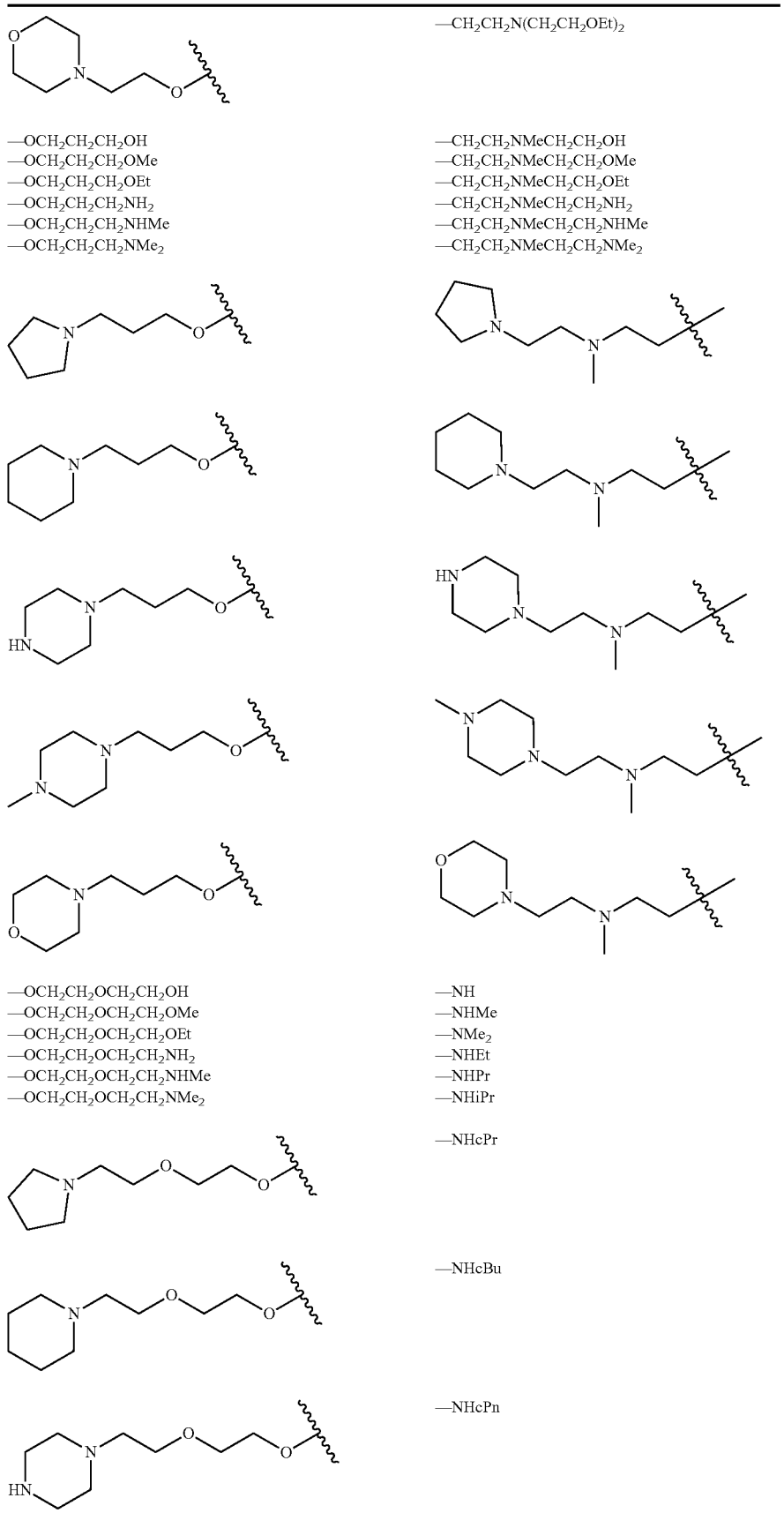

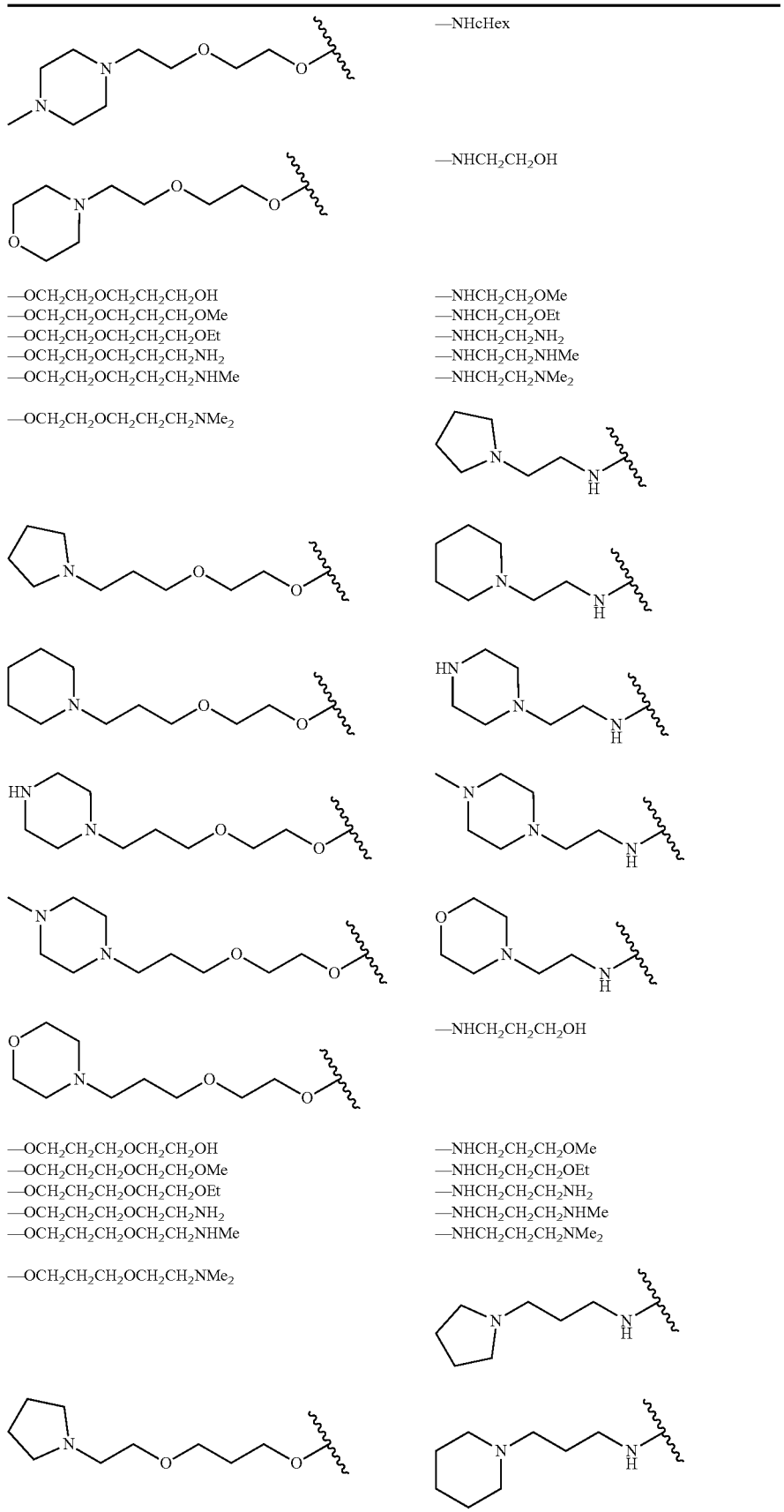

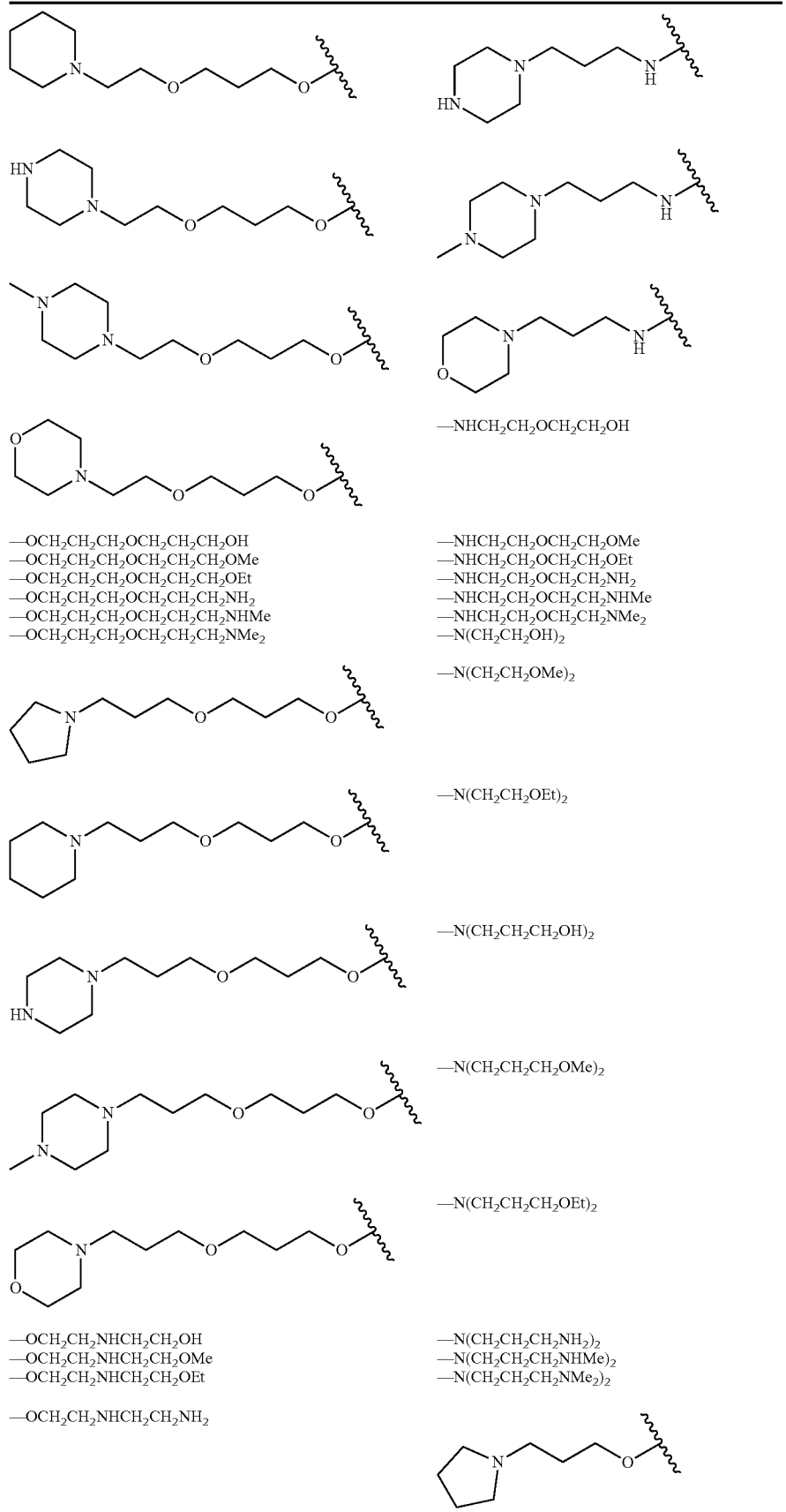

—OCH₂CH₂NHCH₂CH₂NHMe
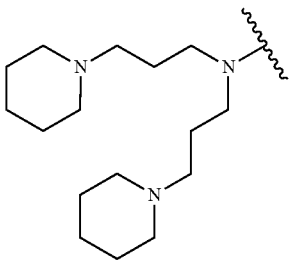 [SMILES: *N(CCCN1CCCCC1)CCCN1CCCCC1]
—OCH₂CH₂NHCH₂CH₂NMe₂
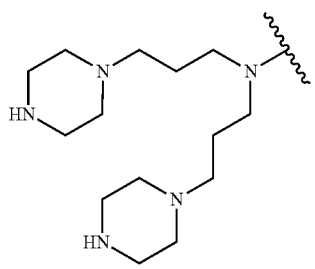 [SMILES: *N(CCCN1CCNCC1)CCCN1CCNCC1]
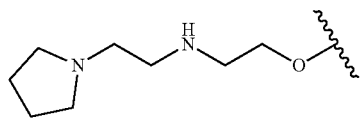 [SMILES: *OCCNCCN1CCCC1]
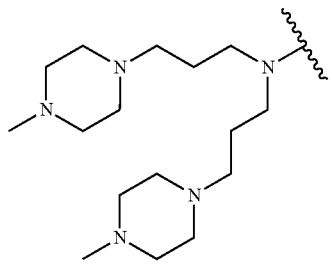 [SMILES: *N(CCCN1CCN(C)CC1)CCCN1CCN(C)CC1]
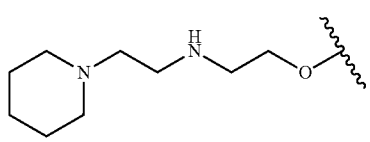 [SMILES: *OCCNCCN1CCCCC1]
—N(CH₂CH₂OCH₂CH₂OH)₂
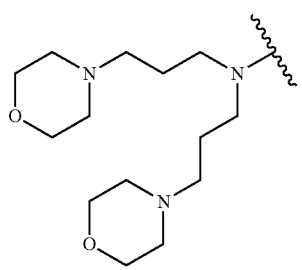 [SMILES: *N(CCCN1CCOCC1)CCCN1CCOCC1]
—N(CH₂CH₂OCH₂CH₂OMe)₂
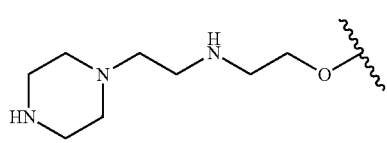 [SMILES: *OCCNCCN1CCNCC1]
—N(CH₂CH₂OCH₂CH₂OEt)₂
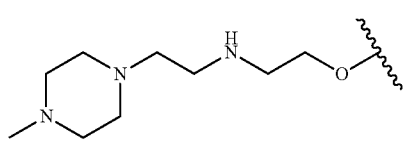 [SMILES: *OCCNCCN1CCN(C)CC1]
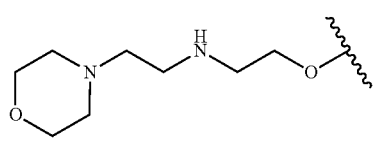 [SMILES: *OCCNCCN1CCOCC1]
—OCH₂CH₂NHCH₂CH₂CH₂OH
—OCH₂CH₂NHCH₂CH₂CH₂OMe
—OCH₂CH₂NHCH₂CH₂CH₂OEt
—OCH₂CH₂NHCH₂CH₂CH₂NH₂
—OCH₂CH₂NHCH₂CH₂CH₂NHMe
—N(CH₂CH₂OCH₂CH₂NH₂)₂
—N(CH₂CH₂OCH₂CH₂NHMe)₂
—N(CH₂CH₂OCH₂CH₂NMe₂)₂
—NMeCH₂CH₂OH
—NMeCH₂CH₂OMe -continued
—OCH₂CH₂NHCH₂CH₂NMe₂
—NMeCH₂CH₂OEt
—NMeCH₂CH₂NH₂
—NMeCH₂CH₂NHMe
—NMeCH₂CH₂NMe₂
—OCH₂CH₂CH₂NHCH₂CH₂OH
—OCH₂CH₂CH₂NHCH₂CH₂OMe
—OCH₂CH₂CH₂NHCH₂CH₂OEt
—OCH₂CH₂CH₂NHCH₂CH₂NH₂
—OCH₂CH₂CH₂NHCH₂CH₂NHMe
—OCH₂CH₂CH₂NHCH₂CH₂NMe₂
—NMeCH₂CH₂CH₂OH
—NMeCH₂CH₂CH₂OMe
—NMeCH₂CH₂CH₂OEt
—NMeCH₂CH₂CH₂NH₂
—NMeCH₂CH₂CH₂NHMe
—NMeCH₂CH₂CH₂NMe₂
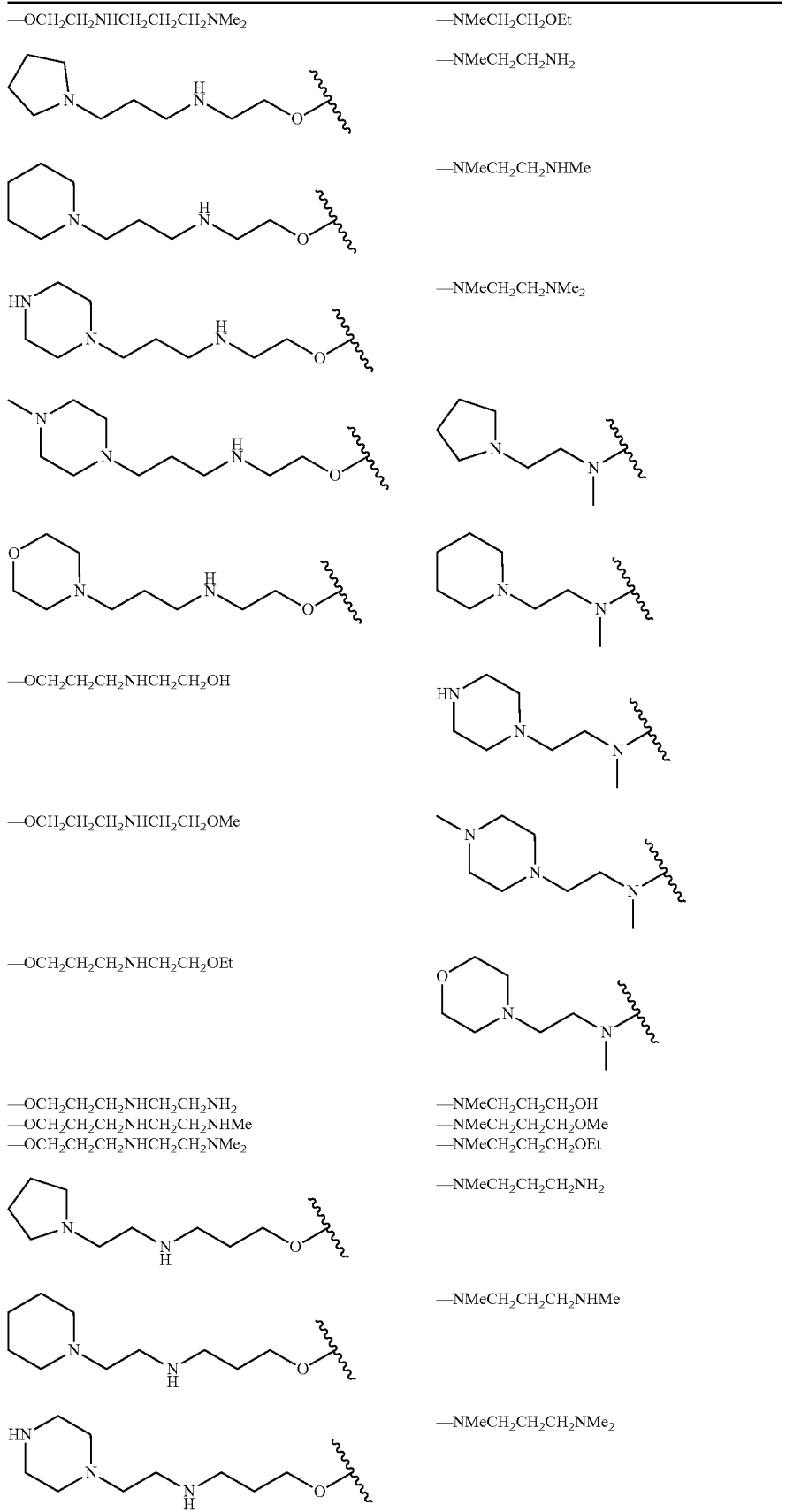

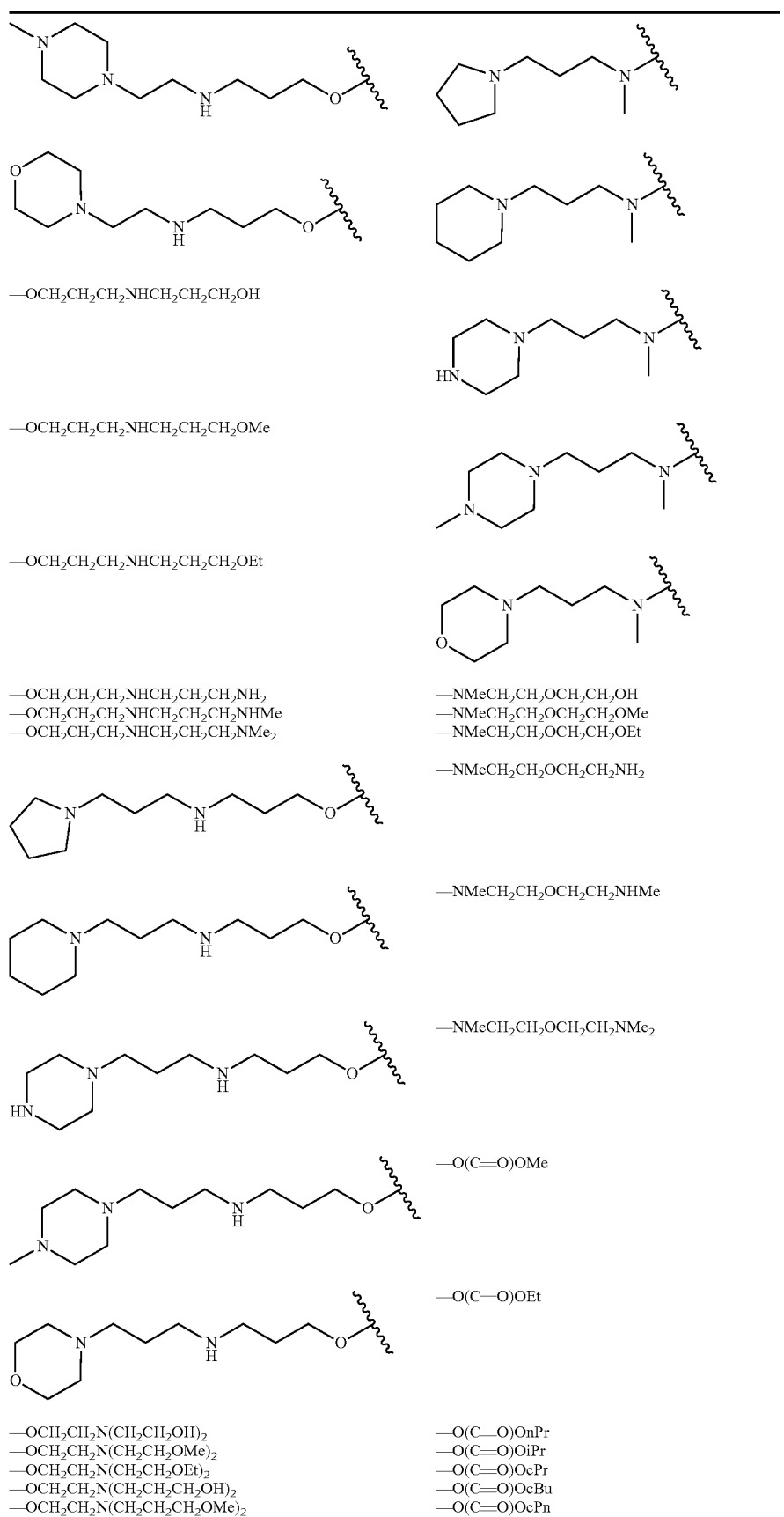

—OCH$_2$CH$_2$CH$_2$NHCH$_2$CH$_2$OH

—OCH$_2$CH$_2$CH$_2$NHCH$_2$CH$_2$OMe

—OCH$_2$CH$_2$CH$_2$NHCH$_2$CH$_2$OEt

—OCH$_2$CH$_2$CH$_2$NHCH$_2$CH$_2$NH$_2$
—OCH$_2$CH$_2$CH$_2$NHCH$_2$CH$_2$NHMe
—OCH$_2$CH$_2$CH$_2$NHCH$_2$CH$_2$NMe$_2$

—NMeCH$_2$CH$_2$OCH$_2$CH$_2$OH
—NMeCH$_2$CH$_2$OCH$_2$CH$_2$OMe
—NMeCH$_2$CH$_2$OCH$_2$CH$_2$OEt

—NMeCH$_2$CH$_2$OCH$_2$CH$_2$NH$_2$

—NMeCH$_2$CH$_2$OCH$_2$CH$_2$NHMe

—NMeCH$_2$CH$_2$OCH$_2$CH$_2$NMe$_2$

—O(C=O)OMe

—O(C=O)OEt

—OCH$_2$CH$_2$N(CH$_2$CH$_2$OH)$_2$
—OCH$_2$CH$_2$N(CH$_2$CH$_2$OMe)$_2$
—OCH$_2$CH$_2$N(CH$_2$CH$_2$OEt)$_2$
—OCH$_2$CH$_2$N(CH$_2$CH$_2$CH$_2$OH)$_2$
—OCH$_2$CH$_2$N(CH$_2$CH$_2$CH$_2$OMe)$_2$

—O(C=O)OnPr
—O(C=O)OiPr
—O(C=O)OcPr
—O(C=O)OcBu
—O(C=O)OcPn

-continued

—OCH$_2$CH$_2$N(CH$_2$CH$_2$OEt)$_2$
—OCH$_2$CH$_2$CH$_2$(HCH$_2$CH$_2$OH)$_2$
—OCH$_2$CH$_2$CH$_2$N(CH$_2$CH$_2$OMe)$_2$
—OCH$_2$CH$_2$CH$_2$N(CH$_2$CH$_2$OEt)$_2$
—OCH$_2$CH$_2$CH$_2$N(CH$_2$CH$_2$CH$_2$OH)$_2$
—OCH$_2$CH$_2$CH$_2$N(CH$_2$CH$_2$CH$_2$OMe)$_2$
—OCH$_2$CH$_2$CH$_2$N(CH$_2$CH$_2$CH$_2$OEt)$_2$
—OCH$_2$CH$_2$NMeCH$_2$CH$_2$OH
—OCH$_2$CH$_2$NMeCH$_2$CH$_2$OMe
—OCH$_2$CH$_2$NMeCH$_2$CH$_2$OEt
—OCH$_2$CH$_2$NMeCH$_2$CH$_2$NH$_2$
—OCH$_2$CH$_2$NMeCH$_2$CH$_2$NHMe
—OCH$_2$CH$_2$NMeCH$_2$CH$_2$NMe$_2$

—O(C═O)OcHex
—COOH
—CH$_2$(C═O)OH
—CH$_2$(C═O)OMe
—CH$_2$(C═O)OEt
—CH$_2$(C═O)ONPr
—CH$_2$(C═O)OiPr
—CH$_2$(C═O)OcPr
—CH$_2$(C═O)OcBu
—CH$_2$(C═O)OcPn
—CH$_2$(C═O)OcHex
—OCH$_2$(C═O)OH
—OCH$_2$(C═O)OMe

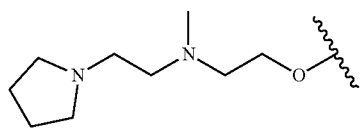 [SMILES: *OCCN(C)CCN1CCCC1]

—OCH$_2$(C═O)OEt

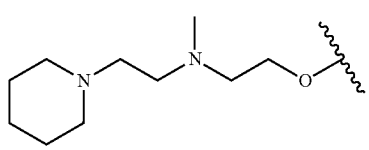 [SMILES: *OCCN(C)CCN1CCCCC1]

—OCH$_2$(C═O)OnPr

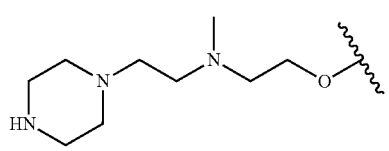 [SMILES: *OCCN(C)CCN1CCNCC1]

—OCH$_2$(C═O)OiPr

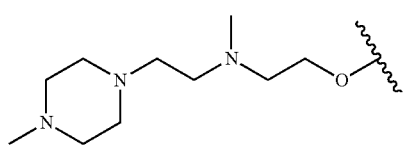 [SMILES: *OCCN(C)CCN1CCN(C)CC1]

—OCH$_2$(C═O)OcPr

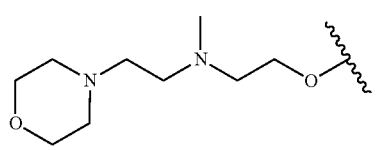 [SMILES: *OCCN(C)CCN1CCOCC1]

—OCH$_2$(C═O)OcBu

—OCH$_2$CH$_2$NMeCH$_2$CH$_2$CH$_2$OH
—OCH$_2$CH$_2$NMeCH$_2$CH$_2$CH$_2$OMe
—OCH$_2$CH$_2$NMeCH$_2$CH$_2$CH$_2$OEt
—OCH$_2$CH$_2$NMeCH$_2$CH$_2$CH$_2$NH$_2$
—OCH$_2$CH$_2$NMeCH$_2$CH$_2$CH$_2$NHMe
—OCH$_2$CH$_2$NMeCH$_2$CH$_2$CH$_2$NMe$_2$

—OCH$_2$(C═O)OcPn
—OCH$_2$(C═O)OcHex
—OCH$_2$(C═O)OH
—OCH$_2$(C═O)OMe
—OCH$_2$(C═O)OEt
—OCH$_2$(C═O)OnPr

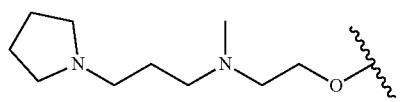 [SMILES: *OCCN(C)CCCN1CCCC1]

—OCH$_2$(C═O)OiPr

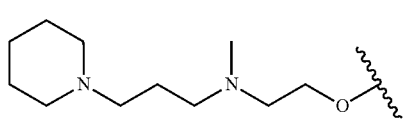 [SMILES: *OCCN(C)CCCN1CCCCC1]

—OCH$_2$(C═O)OcPr

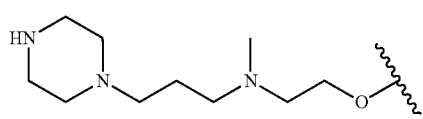

—OCH$_2$(C═O)OcBu

-continued

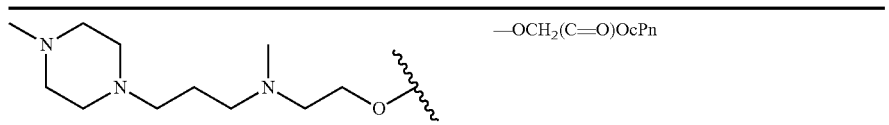
—OCH₂(C=O)OcPn

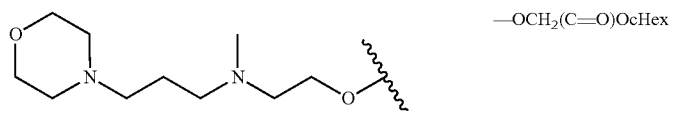
—OCH₂(C=O)OcHex

—OCH₂CH₂CH₂NMeCH₂CH₂OH —NHCH₂(C=O)OH
—OCH₂CH₂CH₂NMeCH₂CH₂OMe —NHCH₂(C=O)OMe
—OCH₂CH₂CH₂NMeCH₂CH₂OEt —NHCH₂(C=O)OEt
—OCH₂CH₂CH₂NMeCH₂CH₂NH₂ —NHCH₂(C=O)OnPr
—OCH₂CH₂CH₂NMeCH₂CH₂NHMe —NHCH₂(C=O)OiPr
—OCH₂CH₂CH₂NMeCH₂CH₂NMe₂ —NHCH₂(C=O)OcPr

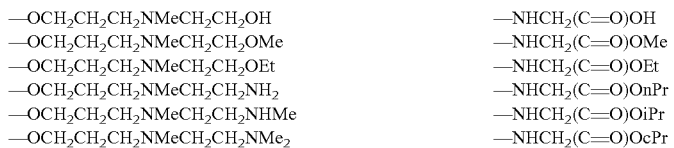
—NHCH₂(C=O)OcBu

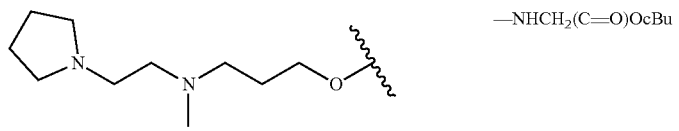
—NHCH₂(C=O)OcPn

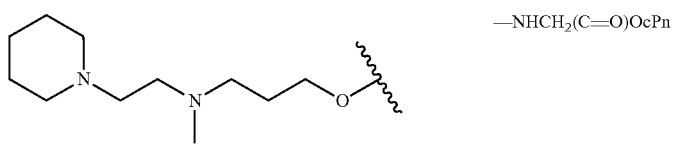
—NHCH₂(C=O)OcHex

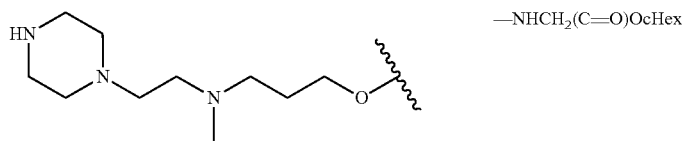
—NMeCH₂(C=O)OH

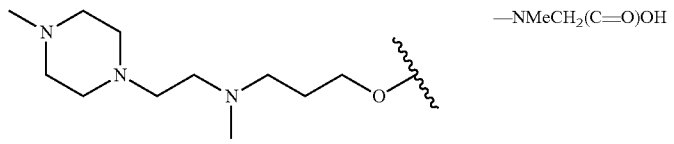
—NH(CH₂(C=O)OH)₂

—OCH₂CH₂CH₂NMeCH₂CH₂CH₂OH —CH₂CH₂(C=O)OH
—OCH₂CH₂CH₂NMeCH₂CH₂CH₂OMe —CH₂OCH₂(C=O)OH
—OCH₂CH₂CH₂NMeCH₂CH₂CH₂OEt —OCH₂CH₂(C=O)OH
—OCH₂CH₂CH₂NMeCH₂CH₂CH₂NH₂ —CH₂CH₂CH₂(C=O)OH
—OCH₂CH₂CH₂NMeCH₂CH₂CH₂NHMe —CH₂CH₂OCH₂(C=O)OH
—OCH₂CH₂CH₂NMeCH₂CH₂CH₂NMe₂ —CH₂OCH₂CH₂(C=O)OH

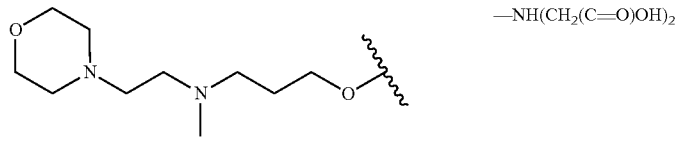
—OCH₂CH₂CH₂(C=O)OH

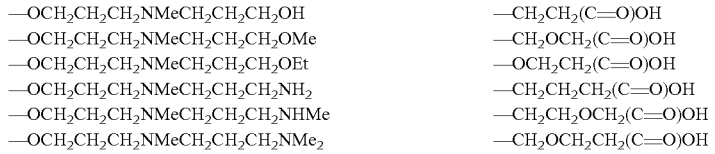
—OCH₂CH₂OCH₂(C=O)OH

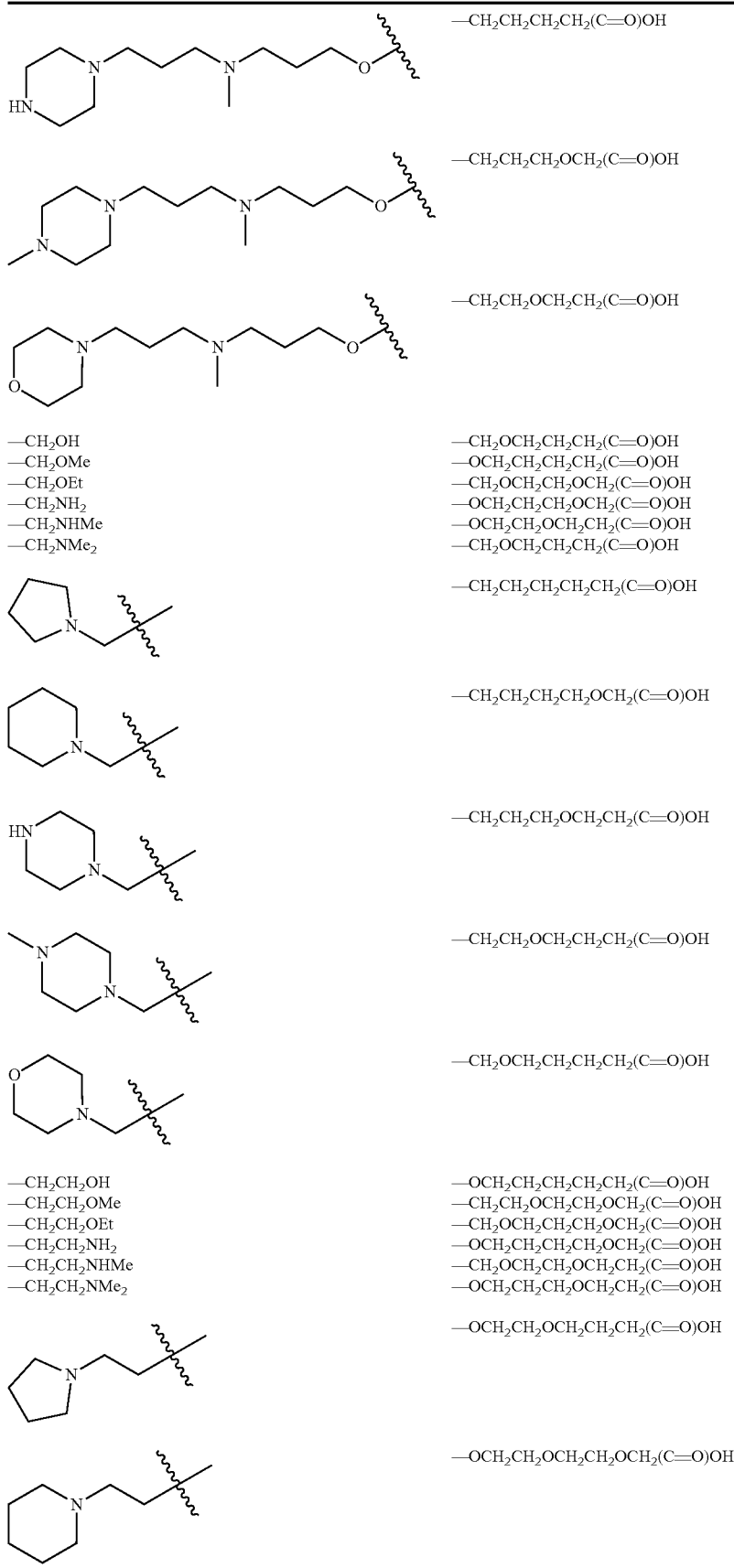

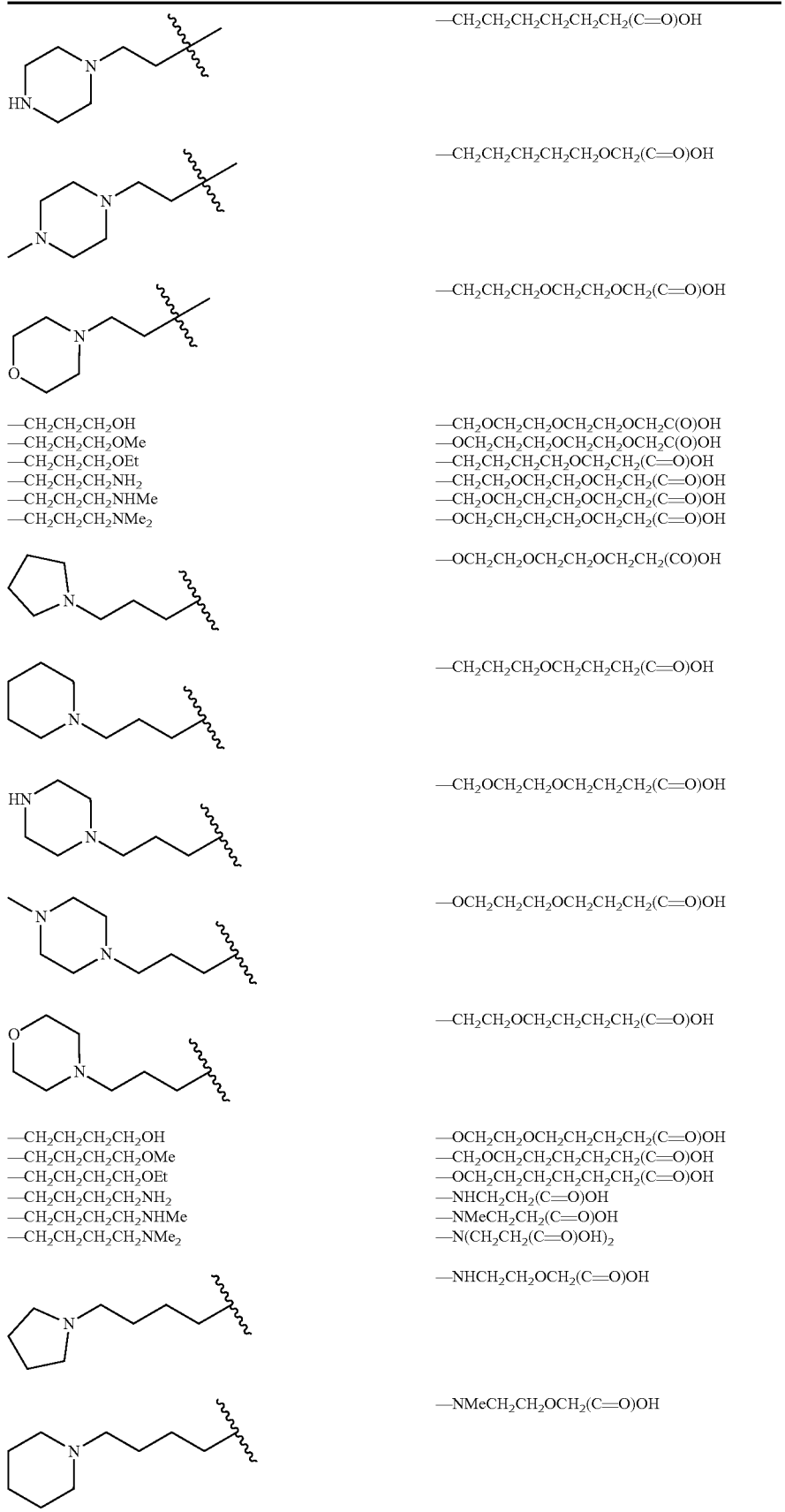

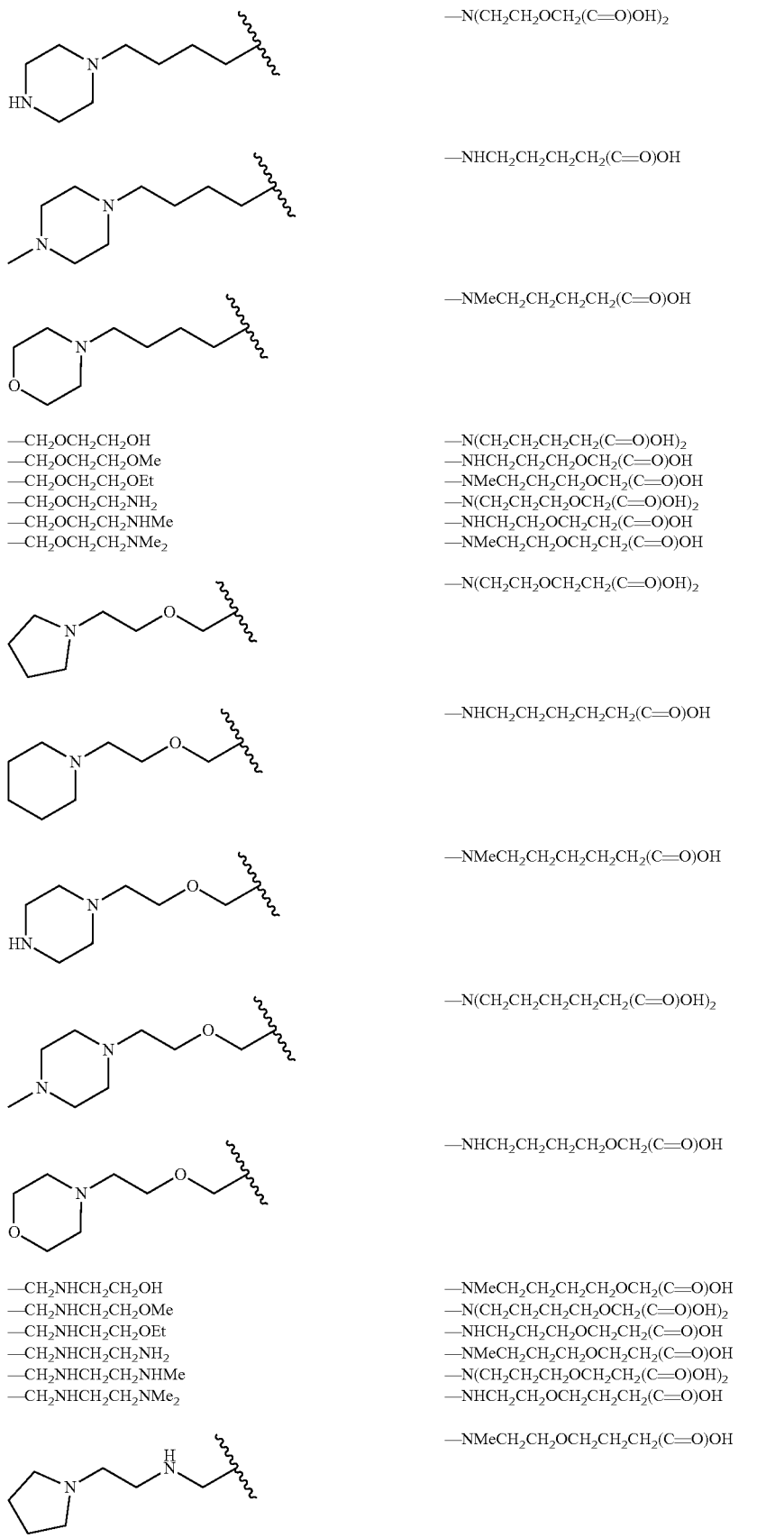

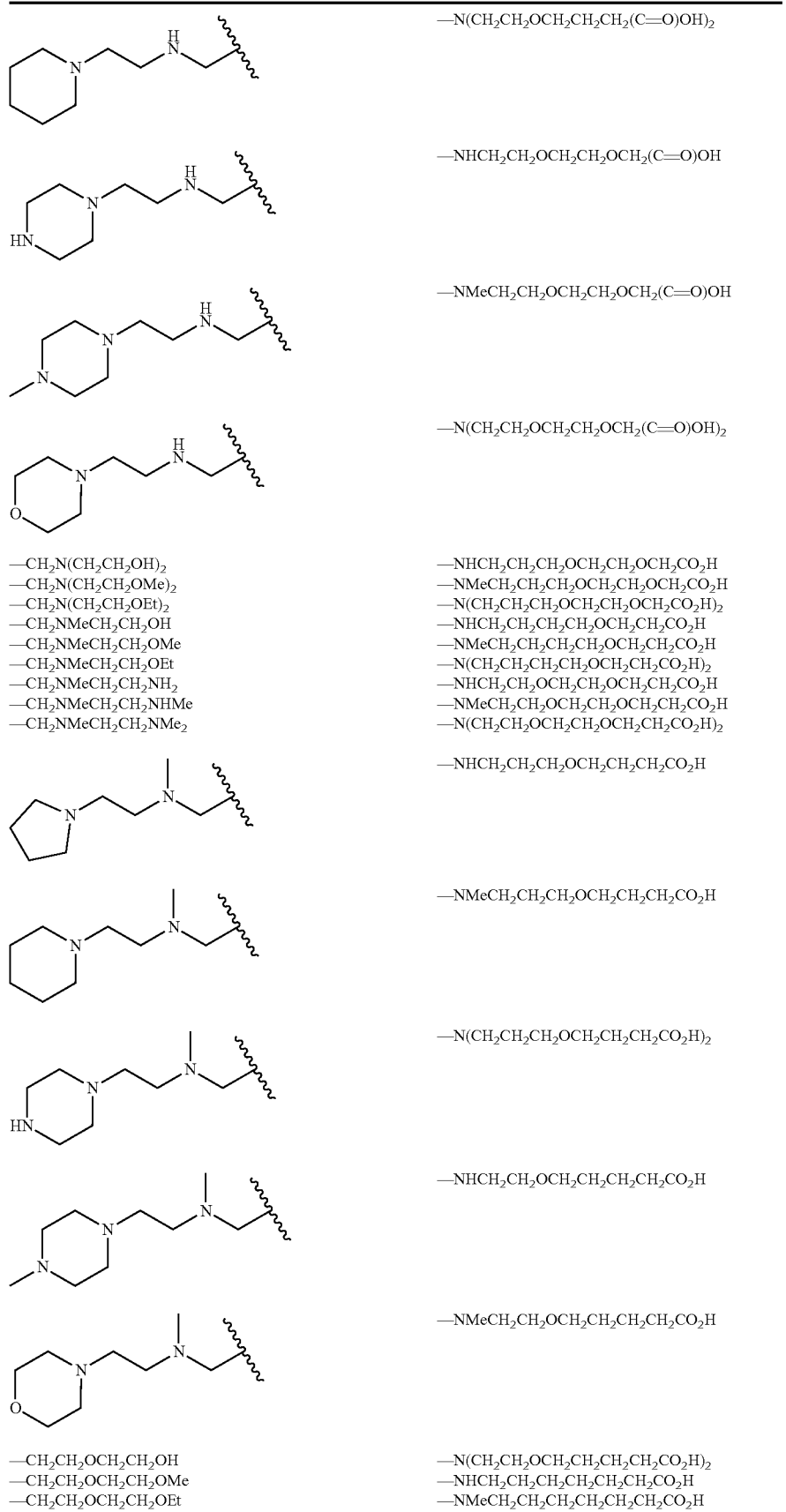

—N(CH$_2$CH$_2$OCH$_2$CH$_2$(C═O)OH)$_2$

—NHCH$_2$CH$_2$OCH$_2$CH$_2$OCH$_2$(C═O)OH

—NMeCH$_2$CH$_2$OCH$_2$CH$_2$OCH$_2$(C═O)OH

—N(CH$_2$CH$_2$OCH$_2$CH$_2$OCH$_2$(C═O)OH)$_2$

—CH$_2$N(CH$_2$CH$_2$OH)$_2$
—CH$_2$N(CH$_2$CH$_2$OMe)$_2$
—CH$_2$N(CH$_2$CH$_2$OEt)$_2$
—CH$_2$NMeCH$_2$CH$_2$OH
—CH$_2$NMeCH$_2$CH$_2$OMe
—CH$_2$NMeCH$_2$CH$_2$OEt
—CH$_2$NMeCH$_2$CH$_2$NH$_2$
—CH$_2$NMeCH$_2$CH$_2$NHMe
—CH$_2$NMeCH$_2$CH$_2$NMe$_2$

—NHCH$_2$CH$_2$CH$_2$OCH$_2$CH$_2$OCH$_2$CO$_2$H
—NMeCH$_2$CH$_2$OCH$_2$CH$_2$OCH$_2$CO$_2$H
—N(CH$_2$CH$_2$OCH$_2$CH$_2$OCH$_2$CO$_2$H)$_2$
—NHCH$_2$CH$_2$CH$_2$OCH$_2$CH$_2$CO$_2$H
—NMeCH$_2$CH$_2$CH$_2$OCH$_2$CH$_2$CO$_2$H
—N(CH$_2$CH$_2$CH$_2$OCH$_2$CH$_2$CO$_2$H)$_2$
—NHCH$_2$CH$_2$OCH$_2$CH$_2$OCH$_2$CO$_2$H
—NMeCH$_2$CH$_2$OCH$_2$CH$_2$OCH$_2$CO$_2$H
—N(CH$_2$CH$_2$OCH$_2$CH$_2$OCH$_2$CO$_2$H)$_2$

—NHCH$_2$CH$_2$OCH$_2$CH$_2$CH$_2$CO$_2$H

—NMeCH$_2$CH$_2$CH$_2$OCH$_2$CH$_2$CH$_2$CO$_2$H

—N(CH$_2$CH$_2$CH$_2$OCH$_2$CH$_2$CH$_2$CO$_2$H)$_2$

—NHCH$_2$CH$_2$OCH$_2$CH$_2$CH$_2$CH$_2$CO$_2$H

—NMeCH$_2$CH$_2$OCH$_2$CH$_2$CH$_2$CH$_2$CO$_2$H

—CH$_2$CH$_2$OCH$_2$CH$_2$OH
—CH$_2$CH$_2$OCH$_2$CH$_2$OMe
—CH$_2$CH$_2$OCH$_2$CH$_2$OEt

—N(CH$_2$CH$_2$OCH$_2$CH$_2$CH$_2$CH$_2$CO$_2$H)$_2$
—NHCH$_2$CH$_2$CH$_2$CH$_2$CH$_2$CH$_2$CO$_2$H
—NMeCH$_2$CH$_2$CH$_2$CH$_2$CH$_2$CH$_2$CO$_2$H

—CH$_2$CH$_2$OCH$_2$CH$_2$NH$_2$
—CH$_2$CH$_2$OCH$_2$CH$_2$NHMe;

—N(CH$_2$CH$_2$CH$_2$CH$_2$CH$_2$CH$_2$CO$_2$H)$_2$

L$^S$ is a bond, O, NR$^{c6}$, C$_{1-4}$ alkylene, C(O), NR$^{c6}$C(O), or C(O)NR$^{c6}$;

R$^{a1}$, R$^{b1}$, R$^{a2}$, R$^{b2}$, R$^{a3}$, R$^{b3}$, R$^{a4}$, R$^{b4}$, R$^{a5}$, R$^{b5}$, R$^{a6}$ and R$^{b6}$ are each independently selected from the group consisting of hydrogen, C$_{1-4}$ alkyl, C$_{2-4}$ alkenyl, C$_{2-4}$ alkynyl, C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, 5-10 membered heterocycloalkyl-C$_{1-4}$ alkylene, and C$_{1-4}$ alkoxy-C$_{1-4}$ alkylene,
  wherein each of said C$_{1-4}$ alkyl, C$_{2-4}$ alkenyl, C$_{2-4}$ alkynyl, and C$_{1-4}$ alkoxy-C$_{1-4}$ alkylene forming R$^{a1}$, R$^{b1}$, R$^{a2}$, R$^{b2}$, R$^{a3}$, R$^{b3}$, R$^{a4}$, R$^{b4}$, R$^{a5}$, R$^{b5}$, R$^{a6}$ or R$^{b6}$ is independently unsubstituted or substituted by 1, 2, 3, 4 or 5 groups independently selected from the group consisting of halogen, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$ and
  wherein said C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, and 5-10 membered heterocycloalkyl-C$_{1-4}$ alkylene, forming R$^{a1}$, R$^{b1}$, R$^{a2}$, R$^{b2}$, R$^{a3}$, R$^{b3}$, R$^{a4}$ or R$^{b4}$ is independently unsubstituted or substituted by 1, 2, 3, 4 or 5 groups independently selected from the group consisting of C$_{1-6}$ alkyl, halogen, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$;

R$^{c1}$, R$^{d1}$, R$^{c2}$, R$^{d2}$, R$^{c3}$, R$^{d3}$, R$^{c4}$, R$^{d4}$, R$^{c5}$, R$^{d5}$, R$^{c6}$, and R$^{d6}$ are each independently selected from the group consisting of hydrogen, C$_{1-4}$ alkyl, C$_{2-4}$ alkenyl, C$_{2-4}$ alkynyl, C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, 5-10 membered heterocycloalkyl-C$_{1-4}$ alkylene, and C$_{1-4}$ alkoxy-C$_{1-4}$ alkylene,
  wherein each of said C$_{1-4}$ alkyl, C$_{2-4}$ alkenyl, C$_{2-4}$ alkynyl, and C$_{1-4}$ alkoxy-C$_{1-4}$ alkylene forming R$^{c1}$, R$^{d1}$, R$^{c2}$, R$^{d2}$, R$^{c3}$, R$^{d3}$, R$^{c4}$, R$^{d4}$, R$^{c5}$, R$^{d5}$, R$^{c6}$, or R$^{d6}$ is independently unsubstituted or substituted by 1, 2, 3, 4 or 5 groups independently selected from the group consisting of halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$ and
  wherein each of said C$_{6-10}$ aryl, 5-10 membered heteroaryl, C$_{3-7}$ cycloalkyl, 5-10 membered heterocycloalkyl, C$_{6-10}$ aryl-C$_{1-4}$ alkylene, C$_{3-7}$ cycloalkyl-C$_{1-4}$ alkylene, 5-10 membered heteroaryl-C$_{1-4}$ alkylene, and 5-10 membered heterocycloalkyl-C$_{1-4}$ alkylene, forming R$^{c1}$, R$^{d1}$, R$^{c2}$, R$^{d2}$, R$^{c3}$, R$^{d3}$, R$^{c4}$, R$^{d4}$, R$^{c5}$, R$^{d5}$, R$^{c6}$, or R$^{d6}$ is independently unsubstituted or substituted by 1, 2, 3, 4 or 5 groups independently selected from the group consisting of C$_{1-6}$ alkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$, and S(O)$_2$NR$^{c7}$R$^{d7}$;
  or R$^{c1}$ and R$^{d1}$, R$^{c2}$ and R$^{d2}$, R$^{c3}$ and R$^{d3}$, R$^{c4}$ and R$^{d4}$, R$^{c5}$ and R$^{d5}$, or R$^{c6}$ and R$^{d6}$, attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from the group consisting of C$_{1-6}$ alkyl, halo, CN, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)NR$^{c7}$R$^{d7}$, NR$^{c7}$C(O)OR$^{a7}$, C(=NR$^{e7}$)NR$^{c7}$R$^{d7}$, NR$^{c7}$C(=NR$^{e7}$)NR$^{c7}$R$^{d7}$, S(O)R$^{b7}$, S(O)NR$^{c7}$R$^{d7}$, S(O)$_2$R$^{b7}$, NR$^{c7}$S(O)$_2$R$^{b7}$ and S(O)$_2$NR$^{c7}$R$^{d7}$;

R$^{a7}$, R$^{b7}$, R$^{c7}$ and R$^{d7}$ are each independently selected from the group consisting of H, C$_{1-6}$ alkyl, C$_{1-6}$ haloalkyl, C$_{2-6}$ alkenyl, C$_{2-6}$ alkynyl, C$_{6-10}$ aryl, 5-10 membered heteroaryl, C$_{3-7}$ cycloalkyl, 4-10 membered heterocycloalkyl, C$_{6-10}$ aryl-C$_{1-4}$ alkylene, 5-10 membered heteroaryl-C$_{1-4}$ alkylene, C$_{3-7}$ cycloalkyl-C$_{1-4}$ alkylene, and 4-10 membered heterocycloalkyl-C$_{1-3}$ alkylene,
  wherein said C$_{1-6}$ alkyl, C$_{1-6}$ haloalkyl, C$_{2-6}$ alkenyl, C$_{2-6}$ alkynyl, C$_{6-10}$ aryl, 5-10 membered heteroaryl, C$_{3-7}$ cycloalkyl, 4-10 membered heterocycloalkyl, C$_{6-10}$ aryl-C$_{1-4}$ alkylene, 5-10 membered heteroaryl-C$_{1-4}$ alkylene, C$_{3-7}$ cycloalkyl-C$_{1-4}$ alkylene, and 4-10 membered heterocycloalkyl-C$_{1-3}$ alkylene forming R$^{a7}$, R$^{b7}$, R$^{c7}$ and R$^{d7}$ are each optionally substituted with 1, 2 or 3 substituents independently selected from the group consisting of OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl, and C$_{1-6}$ haloalkoxy;
  or R$^{c7}$ and R$^{d7}$ attached to the same N atom, together with the N atom to which they are both attached, form a 4-, 5-, 6- or 7-membered heterocycloalkyl group or 5-membered heteroaryl group, each optionally substituted with 1, 2 or 3 substituents independently selected from the group consisting of OH, CN, amino, NH(C$_{1-6}$ alkyl), N(C$_{1-6}$ alkyl)$_2$, halo, C$_{1-6}$ alkyl, C$_{1-6}$ alkoxy, C$_{1-6}$ haloalkyl and C$_{1-6}$ haloalkoxy; and R$^{e1}$, R$^{e2}$, R$^{e3}$, R$^{e4}$, R$^{e5}$, R$^{e6}$ and R$^{e7}$ are each independently selected from the group consisting of H, C$_{1-4}$ alkyl, OH, and C$_{1-4}$ alkoxy.

25. A compound selected from the group consisting of:
2-fluoro-4-(4-(6-(2-(2-morpholinoethoxy)ethoxy)quinolin-2-yl)-1H-1,2,3-triazol-1-yl)phenol;
2-fluoro-4-(4-(5-(3-(2-methoxyethoxy)phenoxy)quinolin-2-yl)-1H-1,2,3-tri azol -1-yl)phenol;

3-((2-(1-(3-fluoro-4-hydroxyphenyl)-1H-1,2,3-triazol-4-yl)quinolin-5-yl)oxy)benzoic acid;

2-fluoro-4-(4-(5-(2-(2-morpholinoethoxy)ethoxy)quinolin-2-yl)-1H-1,2,3-triazol-1-yl)phenol;

2-((2-(1-(3-fluoro-4-hydroxyphenyl)-1H-1,2,3-triazol-4-yl)quinolin-6-yl)oxy)acetic acid;

2-fluoro-4-(4-(5-(3-(2-(2-morpholinoethoxy)ethoxy)phenoxy)quinolin-2-yl)-1H-1,2,3-triazol-1-yl)phenol;

4-((2-(1-(3-fluoro-4-hydroxyphenyl)-1H-1,2,3-triazol-4-yl)quinolin-7-yl)oxy)butanoic acid;

2-(2-((2-(1-(3-fluoro-4-hydroxyphenyl)-1H-1,2,3-triazol-4-yl)quinolin-6-yl)oxy)ethoxy)acetic acid, or a pharmaceutically acceptable salt thereof.

* * * * *